United States Patent
Calder et al.

(10) Patent No.: US 10,538,524 B2
(45) Date of Patent: *Jan. 21, 2020

(54) PYRAZOLOPYRIMIDINE DERIVATIVES USEFUL AS INHIBITORS OF BRUTON'S TYROSINE KINASE

(71) Applicant: Loxo Oncology, Inc., Stamford, CT (US)

(72) Inventors: Mathew Calder, Cheshire (GB); Nicolas Guisot, Cheshire (GB)

(73) Assignee: Loxo Oncology Inc., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/977,470

(22) Filed: May 11, 2018

(65) Prior Publication Data
US 2019/0119281 A1   Apr. 25, 2019

Related U.S. Application Data

(63) Continuation of application No. 15/317,323, filed as application No. PCT/GB2015/051719 on Jun. 11, 2015, now Pat. No. 9,975,897.

(30) Foreign Application Priority Data

Jun. 11, 2014 (GB) .................................. 1410430.1

(51) Int. Cl.
| | | |
|---|---|---|
| C07D 487/04 | (2006.01) | |
| A61K 31/519 | (2006.01) | |
| A61K 45/06 | (2006.01) | |
| A61P 35/00 | (2006.01) | |

(52) U.S. Cl.
CPC .......... *C07D 487/04* (2013.01); *A61K 31/519* (2013.01); *A61K 45/06* (2013.01); *A61P 35/00* (2018.01)

(58) Field of Classification Search
CPC ........................... C07D 487/04; A61K 31/519
See application file for complete search history.

(56) References Cited

U.S. PATENT DOCUMENTS

| | | |
|---|---|---|
| 6,660,744 B1 | 12/2003 | Hirst et al. |
| 7,718,662 B1 | 5/2010 | Chen et al. |
| 8,673,925 B1 | 3/2014 | Goldstein |
| 9,090,621 B2 | 7/2015 | Goldstein |
| 9,975,897 B2 | 5/2018 | Calder et al. |
| 2002/0156081 A1 | 10/2002 | Hirst et al. |
| 2003/0225098 A1 | 12/2003 | Hirst et al. |
| 2008/0076921 A1 | 3/2008 | Honiberg et al. |
| 2010/0144705 A1 | 6/2010 | Miller |
| 2010/0254905 A1 | 10/2010 | Honigberg et al. |
| 2011/0144068 A1 | 6/2011 | Pulici et al. |
| 2014/0221333 A1 | 8/2014 | De Man et al. |
| 2017/0129897 A1 | 5/2017 | Calder et al. |
| 2018/0298008 A1 | 10/2018 | Guisot |
| 2018/0362512 A1 | 12/2018 | Guisot |
| 2018/0362533 A1 | 12/2018 | Guisot |
| 2018/0362537 A1 | 12/2018 | Guisot |
| 2019/0000806 A1 | 1/2019 | Guisot |

FOREIGN PATENT DOCUMENTS

| | | |
|---|---|---|
| CN | 102159214 | 8/2011 |
| CN | 105085474 | 11/2015 |
| EP | 2548877 | 1/2013 |
| WO | WO 0119829 | 3/2001 |
| WO | WO 02080926 | 10/2002 |
| WO | WO 2008/039218 | 4/2008 |
| WO | WO 2008/054827 | 5/2008 |
| WO | WO 2008/121742 | 10/2008 |
| WO | WO 2009/158571 | 12/2009 |
| WO | WO 2011/046964 | 4/2011 |
| WO | WO 2011/090760 | 7/2011 |
| WO | WO 2011/153514 | 12/2011 |
| WO | WO 2012/158764 | 11/2012 |
| WO | WO 2012/158843 | 11/2012 |
| WO | WO 2013/010136 | 1/2013 |
| WO | WO 2013/102059 | 7/2013 |
| WO | WO 2013/191965 | 12/2013 |

(Continued)

OTHER PUBLICATIONS

Buggy et al., "Bruton Tyrosine Kinase (BTK) and Its Role in B-cell Malignancy," International Reviews of Immunology, Mar. 21, 2012, 31(2):119-132.

Dubovsky et al., "Ibrutinib is an irreversible molecular inhibitor of ITK driving a Th1-selective pressure in T lymphocytes," Blood, Oct. 10, 2013, 122(15):2539-2549.

Haleblian, "Characterization of habits and crystalline modification of solids and their pharmaceutical applications," J Pharm Sci, Aug. 1975, 64(8):1269-1288.

International Preliminary Report on Patentability in International Application No. PCT/GB2015/051719, dated Dec. 15, 2016, 8 pages.

International Search Report in International Application No. PCT/GB2015/051719, dated Jul. 23, 2015, 16 pages.

International Search Report in International Application No. PCT/GB2016/052897, dated Oct. 31, 2016, 10 pages.

(Continued)

Primary Examiner — Susanna Moore
(74) Attorney, Agent, or Firm — James B Myers

(57) ABSTRACT

This invention relates to compounds of formula (I). The compounds of the invention are tyrosine kinase inhibitors. Specifically, the compounds of the invention are useful as inhibitors of Bruton's tyrosine kinase (BTK). The invention also contemplates the use of the compounds for treating conditions treatable by the inhibition of Bruton's tyrosine kinase, for example cancer, lymphoma, leukemia and immunological diseases.

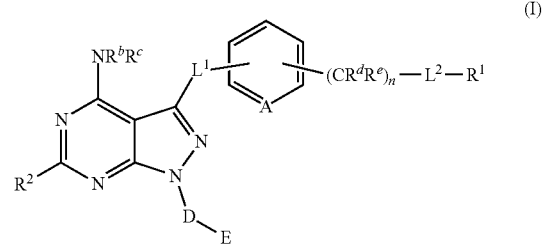

18 Claims, No Drawings

(56) References Cited

FOREIGN PATENT DOCUMENTS

| WO | WO 2014/022569 | 2/2014 |
|---|---|---|
| WO | WO 2014/068527 | 5/2014 |
| WO | WO 2014/082598 | 6/2014 |
| WO | WO 2014/188173 | 11/2014 |
| WO | WO 2015/048662 | 4/2015 |
| WO | WO 2015/095099 | 6/2015 |
| WO | WO 2015/127310 | 8/2015 |
| WO | WO 2015/140566 | 9/2015 |
| WO | WO 2017/046604 | 3/2017 |
| WO | WO 2017/103611 | 6/2017 |

OTHER PUBLICATIONS

International Search Report in International Application No. PCT/GB2016/053968, dated Mar. 14, 2017, 12 pages.

Kohrt et al., "Ibrutinib antagonizes rituximab-dependent NK cell-mediated cytotoxicity," Blood, Mar. 20, 2014, 123(12):1957-1960.

Maddocks et al., "Etiology of Ibrutinib Therapy Discontinuation and Outcomes in Patients With Chronic Lymphocytic Leukemia," JAMA Oncol., Apr. 2015, 1(1):80-87.

Search Report for Patent Application No. GB1410430.1, dated Feb. 13, 2015.

Whang et al., "Bruton's tyrosine kinase inhibitors for the treatment of rheumatoid arthritis," Drug Discov Today., Aug. 2014, 19(8):1200-1204.

Woyach et al., "Resistance mechanisms for the Bruton's tyrosine kinase inhibitor ibrutinib," N Engl J Med, Jun. 12, 2014, 370(24):2286-2294.

Zapf et al. "Covalent Inhibitors of Interleukin-2 Inducible T Cell Kinase (Itk) with Nanomolar Potency in a Whole-Blood Assay ," J. Med. Chem., Nov. 2012, 55(22):10047-10063.

Zhang et al., "Mechanisms of ibrutinib resistance in chronic lymphocytic leukaemia and non-Hodgkin lymphoma," Br J Haematol, Aug. 2015, 170(4):445-456.

PYRAZOLOPYRIMIDINE DERIVATIVES USEFUL AS INHIBITORS OF BRUTON'S TYROSINE KINASE

This invention relates to compounds. More specifically, the invention relates to compounds useful as kinase inhibitors, along with processes to prepare the compounds and uses of the compounds. Specifically, the invention relates to inhibitors of Bruton's tyrosine kinase (BTK).

BACKGROUND

Kinases are a class of enzyme that control the transfer of phosphate groups from phosphate donor groups, for example ATP, to specific substrates. Protein kinases are a subset of kinases and BTK is one such protein kinase.

BTK is a member of the src-related Tec family of cytoplasmic tyrosine kinases. BTK plays a key role in the signalling pathways of B-cells, affecting B-cell development, activation, signalling and survival. In certain malignancies, B-cells overexpress BTK. These malignant B-cells and the overexpression of BTK by the cells has been associated with the increased proliferation and survival of tumor cells. Inhibition of BTK affects the B-cell signalling pathways, preventing activation of B-cells and inhibiting the growth of malignant B-cells.

A number of clinical trials have shown that BTK inhibitors are affective against cancer.

BTK inhibitors that have been reported are Ibrutinib (PCI-32765) and CC-292. CC-292 is manufactured by Avila Pharmaceuticals who have filed applications for protein kinases published as WO 2011/090760 and WO 2009/158571. Ibrutinib is disclosed in at least US 2008/0076921. Studies on Ibrutinib have found that it possesses a number of undesirable pharmacological features. For example, Ibrutinib is poorly soluble and is a weak inhibitor of hERG. Furthermore, rat pharmacokinetic data has shown that Ibrutinib has a low estimated fraction absorbed, poor bioavailability and a high clearance rate from the body, with a terminal $T_{1/2}$ of 1.5 hours.

Since Ibrutinib was first disclosed there have been a number of patent applications concerned with structures closely related to Ibrutinib, for example see WO 2012/158843, WO 2012/158764, WO 2011/153514, WO 2011/046964, US 2010/0254905, US 2010/0144705, U.S. Pat. No. 7,718,662, WO, 2008/054827 and WO 2008/121742.

Most recently, WO 2013/010136 disclosed BTK inhibitors with a related structure to Ibrutinib.

Known BTK inhibitors, e.g. Ibrutinib, have presented gastrointestinal side effects. These side effects have been attributed to the EGFR inhibitory activity of the BTK inhibitors. It is therefore desirable to have a BTK inhibitor with high BTK inhibition and low EGFR inhibition to reduce or avoid the gastrointestinal side effects. Such high BTK inhibition and low EGFR inhibition is readily identified by a large "Fold Selectivity" value.

Therefore, an aim of the present invention is to provide BTK inhibitors. In addition the invention aims to provide BTK inhibitors with high selectivity for BTK inhibition over EGFR inhibition.

Furthermore, it is an aim of certain embodiments of this invention to provide new cancer treatments. In particular, it is an aim of certain embodiments of this invention to provide compounds which have comparable activity to existing cancer treatments, ideally they should have better activity. Certain embodiments of the invention also aim to provide improved solubility compared to prior art compounds and existing therapies. It is particularly attractive for certain compounds of the invention to provide better activity and better solubility over known compounds.

It is an aim of certain embodiments of this invention to provide compounds which exhibit reduced cytotoxicity relative to prior art compounds and existing therapies.

Another aim of certain embodiments of this invention is to provide compounds having a convenient pharmacokinetic profile and a suitable duration of action following dosing. A further aim of certain embodiments of this invention is to provide compounds in which the metabolised fragment or fragments of the drug after absorption are GRAS (Generally Regarded As Safe).

Certain embodiments of the present invention satisfy some or all of the above aims.

SUMMARY OF THE DISCLOSURE

In accordance with the present invention there is provided compounds as disclosed below. Furthermore, the invention provides compounds capable of inhibiting Bruton's tyrosine kinase (BTK) and the use of these compounds in inhibiting BTK. In accordance with the invention there is provided a method of treating conditions modulated by BTK. The invention provides compounds for use in treating a condition which is modulated by BTK.

In a first aspect of the invention there is provided a compound according to formula (I):

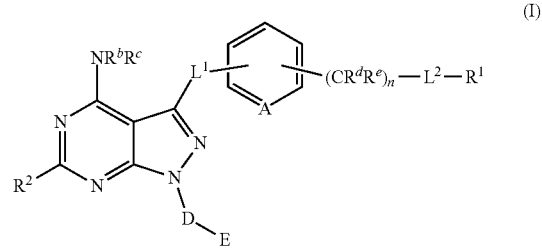

wherein
A is N or $CR^a$;
D is either a substituted or unsubstituted $C_{1-6}$ alkylene chain which is saturated or unsaturated and which may also contain, where chemically possible, 1, 2 or 3 N, O, or S atoms in the chain which are independently chosen at each occurrence;
or wherein D represents a substituted or unsubstituted carbocyclic or heterocyclic moiety which is saturated or unsaturated and which contains from 3 to 8 atoms in the carbocyclic or heterocyclic ring, wherein the ring is optionally substituted with —$NR^b$—, wherein —$NR^b$— is bonded to the ring; and wherein, when substituted, the alkylene chain or the carbocyclic or heterocyclic moiety includes 1 to 5 substituents independently selected at each occurrence from the group comprising: halo, —$OR^b$, —$SR^b$, —$NR^bR^c$, NO, =O, —CN, acyl, $C_{1-6}$ alkyl, $C_{1-6}$ haloalkyl, $C_{3-8}$ cycloalkyl, —$SO_2R^b$, and $SO_3R^b$, —C(O)$R^b$ and C(O)O$R^b$;
E is selected from: $C_{1-4}$ alkyl, or:

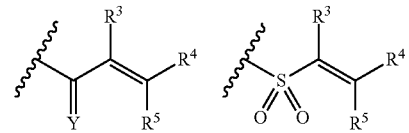

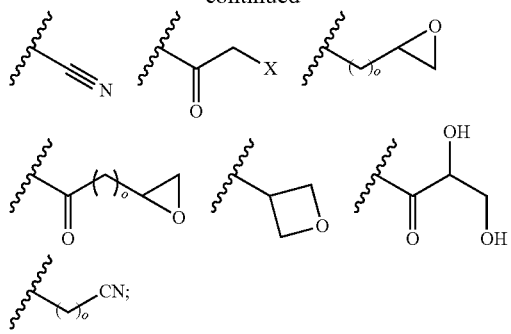

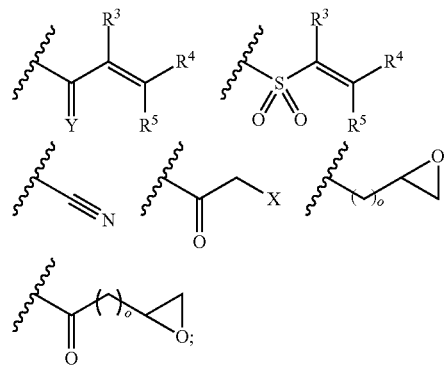

Y is either O or NR$^b$;
X is selected from H, methyl or CN;
L$^1$ is selected from a bond, —O—, —O(CR$^d$R$^e$)$_m$—, —NR$^b$— and —(CR$^d$R$^e$)$_m$—;
L$^2$ represents —NR$^b$C(O)—;
n is selected from 0, 1, 2, and 3;
m is selected from 1, 2, 3 and 4;
o is selected from 0, 1, 2, 3 and 4;
R$^a$ is selected from: H, halo, C$_{1-6}$ alkyl, C$_{1-6}$ haloalkyl, OH, SH, C$_{1-6}$ alkoxy, C$_{2-6}$ alkenyl, C$_{2-6}$ alkynyl, C$_{3-8}$ cycloalkyl, C$_{3-8}$ cycloalkenyl, NR$^b$R$^c$, —CN, acyl, —C(O)R$^b$, —C(O)OR$^b$, —SO$_2$R$^b$, and —SO$_3$R$^b$;
R$^b$ and R$^c$ are independently selected at each occurrence from: H, C$_{1-4}$ alkyl, C$_{1-4}$ haloalkyl, C$_{1-4}$ acyl, C$_{3-7}$ cycloalkyl, and C$_{3-7}$ halocycloalkyl;
R$^d$ and R$^e$ are independently selected at each occurrence from: H, halo, C$_{1-4}$ alkyl, C$_{1-4}$ haloalkyl, C$_{1-4}$ acyl, C$_{3-7}$ cycloalkyl, and C$_{3-7}$ halocycloalkyl;
R$^1$ is a group selected from a substituted or unsubstituted carbocyclic or heterocyclic moiety which either contains from 3 to 8 atoms in a single ring or 7 to 14 atoms in a fused polycyclic ring system, wherein, when substituted, R$^1$ contains 1 to 5 substituents independently selected at each occurrence from the group comprising: halo, —OR$^b$, —SR$^b$, —NR$^b$R$^c$, —NO$_2$, =O, —CN, acyl, C$_{1-6}$ alkyl, C$_{1-6}$ haloalkyl, C$_{3-8}$ cycloalkyl, C$_{3-8}$ heterocycloalkyl, —SO$_2$R$^b$, SO$_3$R$^b$, —C(O)R$^b$, —C(O)OR$^b$, C(O)NR$^b$R$^c$ and aryl optionally substituted by 1 or 2 halo atoms;
R$^2$ is selected from H, halo, —OR$^b$, C$_{1-6}$ alkoxy, C$_{1-6}$ alkyl, C$_{2-6}$ alkenyl, C$_{2-6}$ alkynyl, C$_{1-6}$ haloalkyl, C$_{3-8}$ cycloalkyl, C$_{3-8}$ heterocycloalkyl, C$_{3-8}$ cycloalkenyl, C$_{3-8}$ heterocycloalkenyl, —NR$^b$R$^c$, —CO$_2$R$^b$, —C(O)R$^b$ and —C(O)NR$^b$R$^c$; and
R$^3$, R$^4$, and R$^5$ are independently selected from H, halo, —OR$^b$, —CN, —NR$^b$R$^c$, —CH$_2$NR$^b$R$^c$, —CO$_2$R$^b$, —C(O)R$^b$, —C(O)NR$^b$R$^c$, C$_{1-6}$ alkoxy, C$_{1-6}$ alkyl, C$_{1-6}$ alkyl substituted with C$_{3-8}$ cycloalkyl, C$_{1-6}$ alkyl substituted with C$_{3-8}$ heterocycloalkyl, C$_{2-6}$ alkenyl, C$_{2-6}$ alkynyl, C$_{1-6}$ haloalkyl, C$_{3-8}$ cycloalkyl, C$_{3-8}$ heterocycloalkyl, C$_{3-8}$ cycloalkenyl, C$_{3-8}$ heterocycloalkenyl, aryl, heteroaryl, alkaryl and alkheteroaryl;
or R$^3$ and R$^4$ taken together with the carbon atoms to which they are attached form a C$_{3-8}$ cycloalkene and R$^5$ is independently selected as above;
or R$^4$ and R$^5$ taken together with the carbon atom to which they are attached form a C$_{3-8}$ cycloalkyl and R$^3$ is independently selected as above;
or R$^3$ and R$^5$ taken together with the carbon atoms to which they are attached form a C—C triple bond and R$^4$ is independently selected as above.

In an embodiment of the invention there is provided a compound according to formula (I):

wherein
A is N or CR$^a$;
D is either a substituted or unsubstituted C$_{1-6}$ alkylene chain which is saturated or unsaturated and which may also contain, where chemically possible, 1, 2 or 3 N, O, or S atoms in the chain which are independently chosen at each occurrence;
or wherein D represents a substituted or unsubstituted carbocyclic or heterocyclic moiety which is saturated or unsaturated and which contains from 3 to 8 atoms in the carbocyclic or heterocyclic ring, wherein the ring is optionally substituted with —NR$^b$—, wherein —NR$^b$— is bonded to the ring; and
wherein, when substituted, the alkylene chain or the carbocyclic or heterocyclic moiety includes 1 to 5 substituents independently selected at each occurrence from the group comprising: halo, —OR$^b$, —SR$^b$, —NR$^b$R$^c$, NO, =O, —CN, acyl, C$_{1-6}$ alkyl, C$_{1-6}$ haloalkyl, C$_{3-8}$ cycloalkyl, —SO$_2$R$^b$, and SO$_3$R$^b$, —C(O)R$^b$ and C(O)OR$^b$;
E is selected from: C$_{1-4}$ alkyl, or:

Y is either O or NR$^b$;
L$^1$ is selected from a bond, —O—, —O(CR$^d$R$^e$)$_m$—, —NR$^b$— and —(CR$^d$R$^e$)$_m$—;
L$^2$ represents —NR$^b$ C(O)—;
n is selected from 0, 1, 2, and 3;
m is selected from 1, 2, 3 and 4;
R$^a$ is selected from: H, halo, C$_{1-6}$ alkyl, C$_{1-6}$ haloalkyl, OH, SH, C$_{1-6}$ alkoxy, C$_{2-6}$ alkenyl, C$_{2-6}$ alkynyl, C$_{3-8}$ cycloalkyl, C$_{3-8}$ cycloalkenyl, NR$^b$R$^c$, —CN, acyl, —C(O)R$^b$, —C(O)OR$^b$, —SO$_2$R$^b$, and —SO$_3$R$^b$;
R$^b$ and R$^c$ are independently selected at each occurrence from: H, C$_{1-4}$ alkyl, C$_{1-4}$ haloalkyl, C$_{1-4}$ acyl, C$_{3-7}$ cycloalkyl, and C$_{3-7}$ halocycloalkyl;
R$^d$ and R$^e$ are independently selected at each occurrence from: H, halo, C$_{1-4}$ alkyl, C$_{1-4}$ haloalkyl, C$_{1-4}$ acyl, C$_{3-7}$ cycloalkyl, and C$_{3-7}$ halocycloalkyl;
R$^1$ is a group selected from a substituted or unsubstituted carbocyclic or heterocyclic moiety which either contains from 3 to 8 atoms in a single ring or 7 to 14 atoms in a fused polycyclic ring system, wherein, when substituted, $R^1$ contains 1 to 5 substituents independently selected at each occurrence from the group comprising: halo, —$OR^b$, —$SR^b$, —$NR^bR^c$, —$NO_2$, =O, —CN, acyl, $C_{1-6}$ alkyl, $C_{1-6}$ haloalkyl, $C_{3-8}$ cycloalkyl, $C_{3-8}$ heterocycloalkyl, —$SO_2R^b$, $SO_3R^b$, —$C(O)R^b$, —$C(O)OR^b$, —$C(O)NR^bR^c$ and aryl optionally substituted by 1 or 2 halo atoms;

$R^2$ is selected from H, halo, —$OR^b$, $C_{1-6}$ alkoxy, $C_{1-6}$ alkyl, $C_{2-6}$ alkenyl, $C_{2-6}$ alkynyl, $C_{1-6}$ haloalkyl, $C_{3-8}$ cycloalkyl, $C_{3-8}$ heterocycloalkyl, $C_{3-8}$ cycloalkenyl, $C_{3-8}$ heterocycloalkenyl, —$NR^bR^c$, —$CO_2R^b$, —$C(O)R^b$ and —$C(O)NR^bR^c$; and $R^3$, $R^4$, and $R^5$ are independently selected from H, halo, —$OR^b$, —CN, —$NR^bR^c$, —$CH_2NR^bR^c$, —$CO_2R^b$, —$C(O)R^b$, —$C(O)NR^bR^c$, $C_{1-6}$ alkoxy, $C_{1-6}$ alkyl, $C_{1-6}$ alkyl substituted with $C_{3-8}$ cycloalkyl, $C_{1-6}$ alkyl substituted with $C_{3-8}$ heterocycloalkyl, $C_{2-6}$ alkenyl, $C_{2-6}$ alkynyl, $C_{1-6}$ haloalkyl, $C_{3-8}$ cycloalkyl, $C_{3-8}$ heterocycloalkyl, $C_{3-8}$ cycloalkenyl, $C_{3-8}$ heterocycloalkenyl, aryl, heteroaryl, alkaryl and alkheteroaryl;

or $R^3$ and $R^4$ taken together with the carbon atoms to which they are attached form a $C_{3-8}$ cycloalkene and $R^5$ is independently selected as above;

or $R^4$ and $R^5$ taken together with the carbon atom to which they are attached form a $C_{3-8}$ cycloalkyl and $R^3$ is independently selected as above;

or $R^3$ and $R^5$ taken together with the carbon atoms to which they are attached form a C—C triple bond and $R^4$ is independently selected as above.

In embodiments, A may be an N atom. In embodiments A is $CR^a$. $R^a$ may be H, halo, e.g. fluoro or chloro, $C_{1-6}$ alkyl, $C_{1-6}$ haloalkyl, —OH, or $C_{1-6}$ alkoxy. In particular $R^a$ may be H, fluoro, chloro or $C_{1-4}$ haloalkyl. In particular A may be $CR^a$ and $R^a$ may be H, fluoro, chloro or $C_{1-4}$ haloalkyl, preferably H. Hence, in an embodiment A may be CH.

Thus, the compound of formula (I) may be a compound according to formula (Ia):

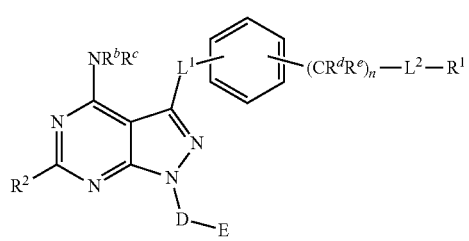

(Ia)

$L^2$ represents —$NR^bC(O)$—. Therefore, $L^2$ can be described as representing an amide, wherein the amide nitrogen is substituted by $R^b$. The amide, —$NR^bC(O)$—, may be oriented in one of two directions, as is evident to the skilled person. In other words: $L^2$ may represent an amide, —$NR^bC(O)$—, wherein the nitrogen is substituted by $R^b$ and the nitrogen is bonded to $(CR^dR^e)_n$, or the phenyl ring when n is 0, and the carbon is bonded to $R^1$ when oriented in a first direction; or the nitrogen is bonded to $R^1$ and the carbon is bonded to $(CR^dR^e)_n$, or the phenyl ring when n is 0, when oriented in a second direction. Thus, $L^2$ may represent —$NR^bC(O)$— or —$C(O)NR^b$—, wherein the groups are oriented in formula (I) as shown.

In all definitions of all other groups in the formulae of the invention the written representation of the groups is not necessarily indicative of the only orientation of the group when the relevant group may be oriented in other chemically possible ways.

In embodiments, where n is 1, the compound of formula (I) may be a compound according to formula (Ib) or in particular formula (Ic):

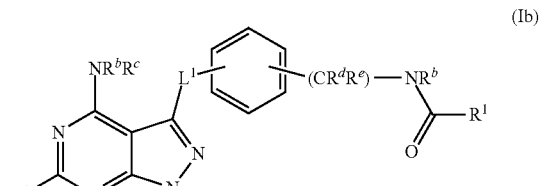

(Ib)

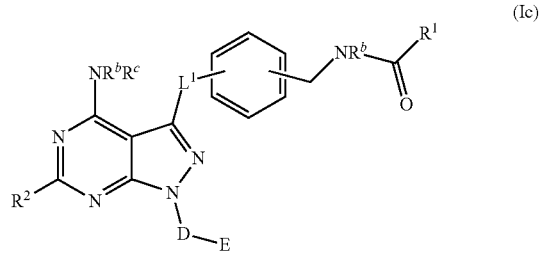

(Ic)

Furthermore, in embodiments where n is 1, the compound of formula (I) may be a compound according to formula (Id) or in particular formula (Ie):

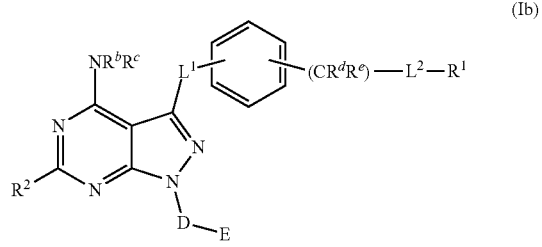

(Ib)

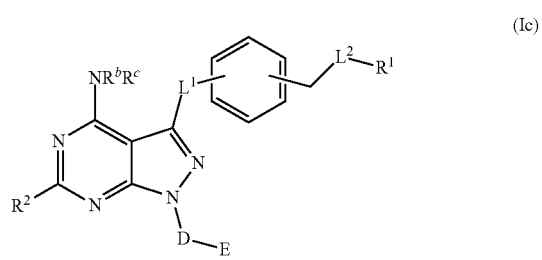

(Ic)

The groups, $L^1$ and $(CR^dR^e)_n$-$L^2$-$R^1$, on the phenyl ring of compounds of formula (I) and (Ia) may be substituted in any arrangement possible. For example the groups may be in a para, ortho or meta relationship. In an embodiment, the compound of formula (I) may be a compound according to formula (IIa), having a para relationship between the groups on the phenyl ring or (IIb), having a meta relationship between the groups on the phenyl ring:

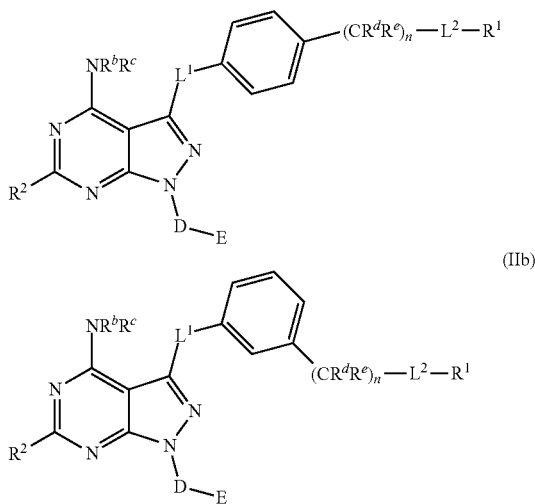

(IIa)

(IIb)

In embodiments where n is 1 the compound of formula (I) may be compounds according to formulae (IIc) and (IId).

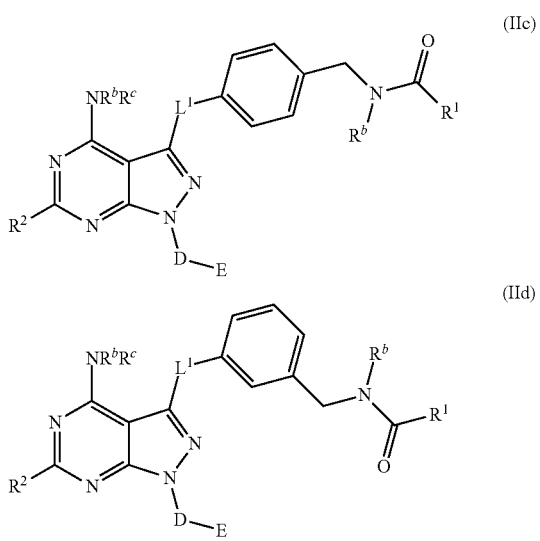

(IIc)

(IId)

The group $R^1$ may be a substituted or unsubstituted: cycloalkyl, aryl, heterocycloalkyl or heteroaryl, wherein the cycloalkyl and heterocycloalkyl groups may be saturated or unsaturated and the cycloalkyl, aryl, heterocycloalkyl or heteroaryl may contain either from 3 to 8 atoms in a single ring or 7 to 14 atoms in a fused polycyclic ring system.

The group $R^1$ may be a substituted or unsubstituted: $C_{3-8}$ cycloalkyl, $C_{6-14}$ aryl, $C_{3-8}$ heterocycloalkyl or $C_{5-14}$ heteroaryl, wherein the $C_{3-8}$ cycloalkyl and $C_{3-8}$ heterocycloalkyl groups may be saturated or unsaturated.

The group $R^1$ may be a substituted or unsubstituted: $C_{3-8}$ cycloalkyl (optionally $C_3$ or $C_{5-7}$ cycloalkyl), $C_{6-14}$ aryl (optionally $C_6$ $C_9$, or $C_{10}$ aryl) or $C_{5-14}$ heteroaryl (optionally $C_5$, $C_6$ or $C_{10}$ heteroaryl), wherein the $C_{3-8}$ cycloalkyl group may be saturated or unsaturated. When substituted, $R^1$ may contain 1, 2 or 3 substituents independently selected at each occurrence from the group comprising: halo, —$OR^b$, —$SR^b$, —$NR^bR^c$, NO, =O, —CN, acyl, $C_{1-6}$ alkyl, $C_{1-6}$ haloalkyl, $C_{3-8}$ cycloalkyl, $C_{3-8}$ heterocycloalkyl, —$SO_2R^b$, $SO_3R^b$, —$C(O)R^b$, —$C(O)OR^b$, —$C(O)NR^bR^c$ and aryl optionally substituted by 1 or 2 halo atoms.

In embodiments $R^1$ may be unsubstituted phenyl, unsubstituted pyridyl, substituted pyridyl or substituted phenyl.

Optionally, when $R^1$ is substituted it is substituted by 1, 2 or 3 substituents independently selected at each occurrence from the group comprising: halo, —$OR^b$, —CN, $C_{1-6}$ alkyl, $C_{1-6}$ haloalkyl, wherein $R^b$ is selected from H, $C_{1-4}$ alkyl and $C_{1-4}$ haloalkyl. Preferably the substituents are independently selected from fluoro, chloro, methoxy, —CN, methyl, ethyl, trifluoromethyl, trifluoroethyl, ethoxy or —$OCF_3$.

In embodiments $R^1$ may be unsubstituted phenyl or phenyl substituted with 1, 2 or 3 substituents independently selected at each occurrence from the group comprising: halo, —$OR^b$, —CN, $C_{1-6}$ alkyl, $C_{1-6}$ haloalkyl, wherein $R^b$ is selected from H, $C_{1-4}$ alkyl and $C_{1-4}$ haloalkyl. Preferably the substituents are independently selected from fluoro, chloro, methoxy, —CN, methyl, ethyl, trifluoromethyl, trifluoroethyl, ethoxy or —$OCF_3$.

In embodiments $R^1$ is selected from: phenyl, fluorophenyl, difluorophenyl, chlorophenyl, methylphenyl (also referred to as tolyl), methoxyphenyl, trifluoromethylphenyl, cyanophenyl, trifluoromethoxyphenyl, tert-butylphenyl, methyl-fluorophenyl (also referred to as fluorotolyl), fluoromethoxyphenyl, fluoro-trifluoromethylphenyl, fluoro-trifluoromethoxyphenyl, chloro-methoxyphenyl, methoxymethylphenyl (also referred to as methoxytolyl), methoxytrifluoromethylphenyl, chloro-trifluoromethylphenyl, ethoxy-trifluoromethylphenyl, dimethoxyphenyl, di(trifluoromethyl)phenyl, trifluorophenyl and chloro-methylphenyl (also referred to as chorotolyl).

In an embodiment, $R^2$ is hydrogen.

In an embodiment, $R^3$, $R^4$, and $R^5$ may be independently selected from hydrogen, fluorine, chlorine, bromine, iodine, —CN, —$C_2NR^bR^c$, $C_{1-6}$ alkyl, $C_{1-6}$ alkyl substituted with $C_{3-8}$ cycloalkyl, $C_{1-6}$ alkyl substituted with $C_{3-8}$ heterocycloalkyl, $C_{1-6}$ haloalkyl, aryl, heteroaryl, alkaryl and alkheteroaryl or $R^3$ and $R^5$ taken together with the carbon atoms to which they are attached form a C—C triple bond and $R^4$ is independently selected as above.

In an embodiment, $R^3$, $R^4$, and $R^5$ may be independently selected from hydrogen, fluorine, chlorine, bromine, iodine, —CN, —$C_2NR^bR^c$, $C_{1-6}$ alkyl, $C_{1-6}$ alkyl substituted with $C_{3-8}$ cycloalkyl, $C_{1-6}$ alkyl substituted with $C_{3-8}$ heterocycloalkyl, $C_{1-6}$ haloalkyl, aryl, heteroaryl, alkaryl and alkheteroaryl.

In another embodiment, $R^3$, $R^4$, and $R^5$ may be independently selected from hydrogen, fluorine, chlorine, bromine, iodine, —CN, —$C_2NR^bR^c$ and $C_{1-6}$ alkyl or $R^3$ and $R^5$ taken together with the carbon atoms to which they are attached form a C—C triple bond and $R^4$ is independently selected from hydrogen, fluorine, chlorine, bromine, iodine, —CN, —$CH_2NR^bR^c$ and $C_{1-6}$ alkyl, where $R^b$ and $R^c$ are independently selected from hydrogen and $C_{3-6}$ alkyl.

In another embodiment, $R^3$, $R^4$, and $R^5$ may be independently selected from hydrogen, fluorine, chlorine, bromine, iodine, —CN, —$C_2NR^bR^c$ and $C_{1-6}$ alkyl, where $R^b$ and $R^c$ are independently selected from hydrogen and $C_{1-6}$ alkyl.

In a more preferred embodiment, two of $R^3$, $R^4$, and $R^5$ may be hydrogen and the other may be fluorine, chlorine, bromine, iodine, —CN, —$CH_2NR^bR^c$ and $C_{1-6}$ alkyl or $R^3$ and $R^5$ taken together with the carbon atoms to which they are attached form a C—C triple bond and $R^4$ is $C_{1-6}$ alkyl, where $R^b$ and $R^c$ are independently selected from hydrogen and $C_{1-6}$ alkyl. For example, $R^3$ and $R^4$ may be hydrogen; or $R^4$ and $R^5$ may be hydrogen; or $R^3$ and $R^5$ may be hydrogen.

In a more preferred embodiment, two of R³, R⁴, and R⁵ may be hydrogen and the other may be fluorine, chlorine, bromine, iodine, —CN, —CH₂NR$^b$R$^c$ and $C_{1-6}$ alkyl, where R$^b$ and R$^c$ are independently selected from hydrogen and $C_{1-6}$ alkyl. For example, R³ and R⁴ may be hydrogen; or R⁴ and R⁵ may be hydrogen; or R³ and R⁵ may be hydrogen.

In a further preferred embodiment, R³, R⁴, and R⁵ are all hydrogen.

In an embodiment R³ is not —CN. Therefore, in an embodiment, R³ may be independently selected from hydrogen, fluorine, chlorine, bromine, iodine, —CH₂NR$^b$R$^c$, $C_{1-6}$ alkyl, $C_{1-6}$ alkyl substituted with $C_{3-8}$ cycloalkyl, $C_{1-8}$ alkyl substituted with $C_{3-8}$ heterocycloalkyl, $C_{1-6}$ haloalkyl, aryl, heteroaryl, alkaryl and alkheteroaryl. R⁴ and R⁵ may be as defined above.

In another embodiment, R³ may be independently selected from hydrogen, fluorine, chlorine, bromine, iodine, —CH₂NR$^b$R$^c$ and $C_{1-6}$ alkyl, where R$^b$ and R$^c$ are independently selected from hydrogen and $C_{1-6}$ alkyl. R⁴ and R⁵ may be as defined above.

In a more preferred embodiment, two of R³ may be hydrogen and the other may be fluorine, chlorine, bromine, iodine, —CH₂NR$^b$R$^c$ and $C_{1-6}$ alkyl, where R$^b$ and R$^c$ are independently selected from hydrogen and $C_{1-6}$ alkyl. R⁴ and R⁵ may be as defined above.

In an embodiment R³, R⁴, and R⁵ are not —CN.

In an embodiment, R$^b$ and R$^c$ are hydrogen or $C_{1-4}$ alkyl, preferably H or methyl.

In an embodiment R$^d$ and R$^e$ are independently selected at each occurrence from: H, halo, $C_{1-4}$ alkyl, $C_{1-4}$ haloalkyl or $C_{1-4}$ acyl. Preferably, R$^d$ and R$^e$ are independently selected at each occurrence from: H, halo (e.g. fluoro and chloro), $C_{1-4}$ alkyl (e.g. methyl or ethyl) or $C_{1-4}$ haloalkyl (e.g. trifluoromethyl or trifluoroethyl). Further preferably R$^d$ and R$^e$ are H.

In embodiments n is selected from 1, 2 or 3, preferably n is 1.

In one embodiment E is:

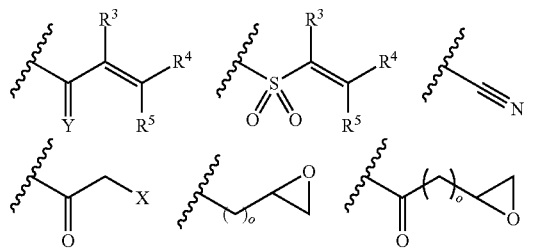

In one embodiment E is:

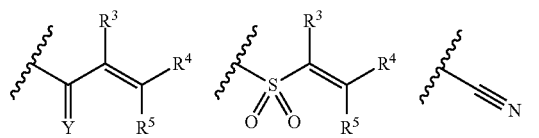

In one embodiment E is $C_{1-4}$ alkyl or:

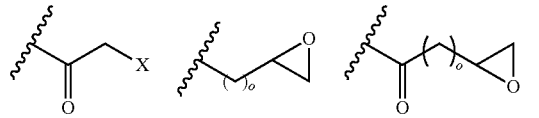

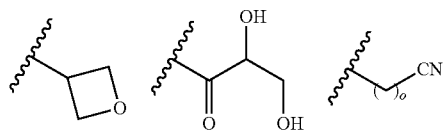

In one embodiment E is:

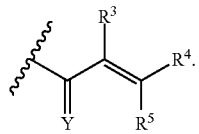

In all embodiments

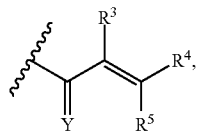

wherein Y is O or NR$^b$, may be selected from:

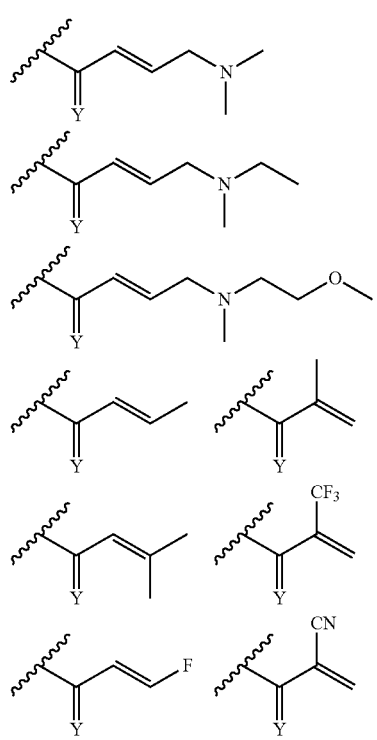

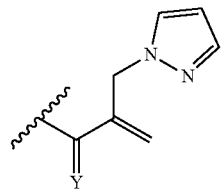

-continued
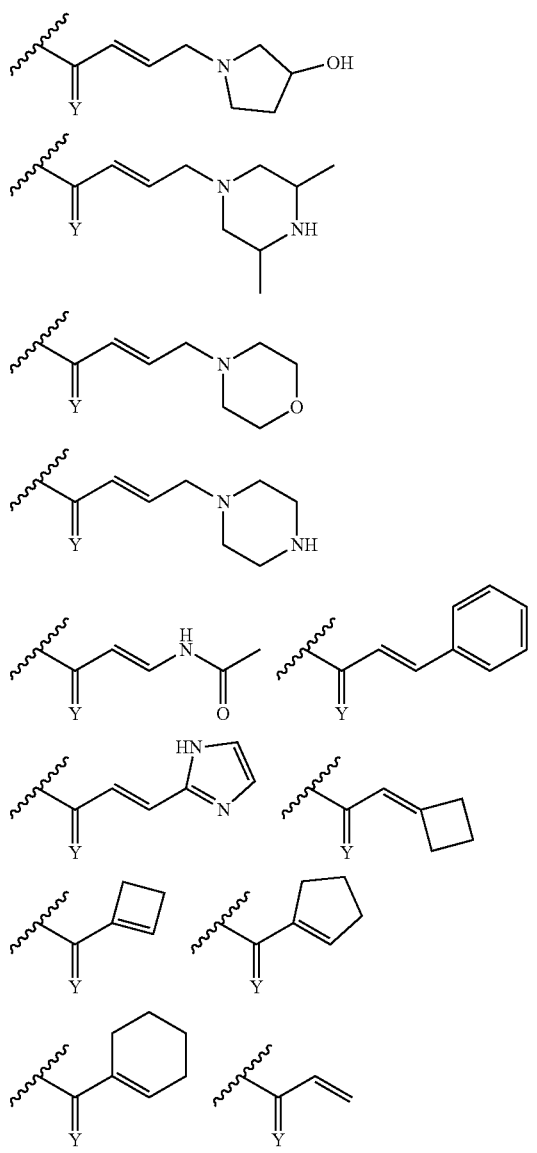
In another embodiment E is:
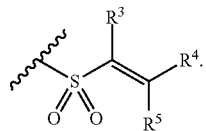
In all embodiments
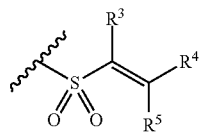
may be selected from:
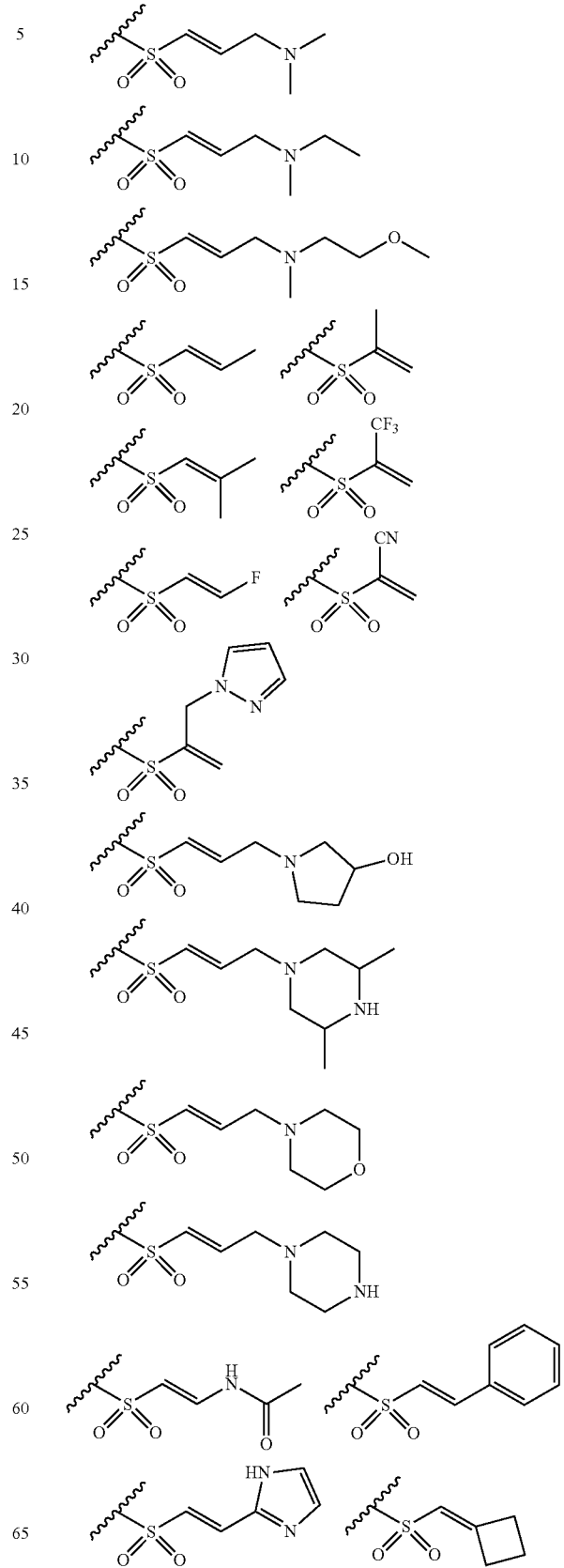

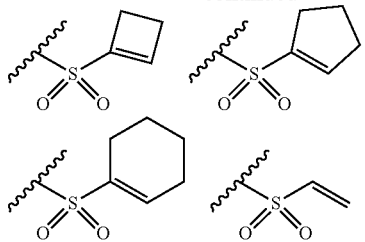

In a further embodiment E is:

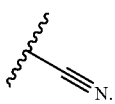

In a further embodiment E is:

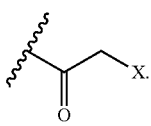

In a further embodiment E is:

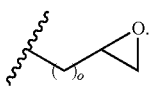

In a further embodiment E is:

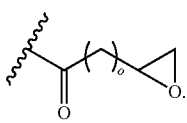

In an embodiment E is methyl or:

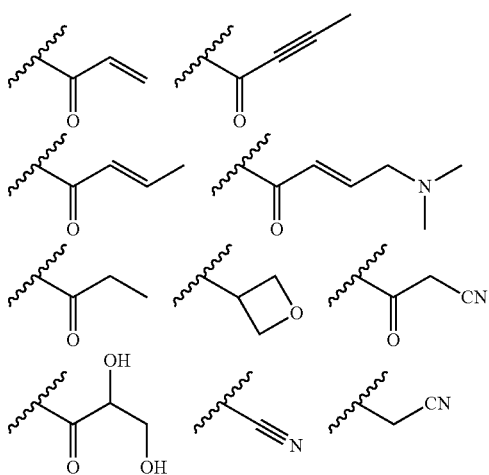

In embodiments Y is O. In alternative embodiments Y is $NR^a$ wherein $R^a$ is H or methyl.

In an embodiment o is 1 or 2.

In the statement of invention D may represent a substituted or unsubstituted carbocyclic or heterocyclic moiety which is saturated or unsaturated and which contains from 3 to 8 atoms in the carbocyclic or heterocyclic ring, wherein the ring is optionally substituted with —$NR^b$—. The group —$NR^b$— is bonded to two entities, as is evident to the skilled person. The two entities may be the heterocyclic or carbocyclic ring and E.

In an embodiment D is either a substituted or unsubstituted $C_{1-6}$ alkylene chain which is saturated or unsaturated and which may also contain, where chemically possible, 1, 2 or 3 N, O, or S atoms in the chain which are independently chosen at each occurrence;

or wherein D represents a substituted or unsubstituted carbocyclic or heterocyclic moiety which is saturated or unsaturated and which contains from 3 to 8 atoms in the carbocyclic or heterocyclic ring;

and wherein, when substituted, the alkylene chain or the carbocyclic or heterocyclic moiety includes 1 to 5 substituents independently selected at each occurrence from the group comprising: halo, —$OR^b$, —$SR^b$, —$NR^bR^c$, NO, =O, —CN, acyl, $C_{1-6}$ alkyl, $C_{1-6}$ haloalkyl, $C_{3-8}$ cycloalkyl, —$SO_2R^b$, and $SO_3R^b$, —$C(O)R^b$ and $C(O)OR^b$.

In an embodiment, D is selected from a substituted or unsubstituted saturated $C_{1-6}$ alkylene chain containing, where chemically possible, 1, 2 or 3, optionally 1 or 2, N, O or S atoms in the chain which are independently chosen at each occurrence;

or D represents a substituted or unsubstituted saturated heterocyclic moiety which contains from 3 to 8 atoms in the heterocyclic ring and contains, where chemically possible, 1, 2 or 3, optionally 1 or 2, N, O or S atoms in the ring which are independently chosen at each occurrence.

In embodiments the alkylene chain and the heterocyclic ring contain 1 heteroatom selected from N, O or S, optionally N. In embodiments the alkylene chain and the heterocyclic ring contain 1 nitrogen atom and the nitrogen atom is the point of connection with group E.

In an embodiment, D is selected from substituted or unsubstituted $C_{1-6}$ heteroalkyl, substituted or unsubstituted $C_{3-8}$ heterocycloalkyl and substituted or unsubstituted $C_{3-8}$ heterocycloalkenyl. In embodiments D may be selected from substituted or unsubstituted $C_{1-6}$ heteroalkyl, substituted or unsubstituted $C_{3-8}$ heterocycloalkyl and substituted or unsubstituted $C_{3-8}$ heterocycloalkenyl where N is the heteroatom and D comprises 1 or 2 nitrogen atoms. In an embodiment D is substituted or unsubstituted $C_{3-8}$ heterocycloalkyl, optionally $C_6$ heterocycloalkyl. D may be substituted or unsubsustituted piperidinyl, preferably unsubstituted.

In an embodiment D is unsubstituted. In an alternative embodiment D is substituted. In an embodiment D is substituted with halo, optionally fluoro.

In an embodiment, D may be selected from:

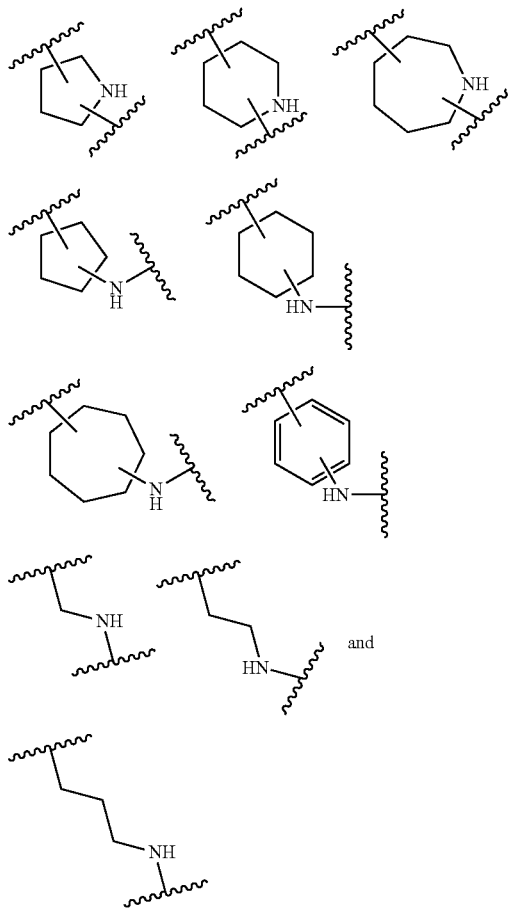

and D may be substituted or unsubstituted. In particular, D may be unsubstituted.

In an embodiment, D may be selected from:

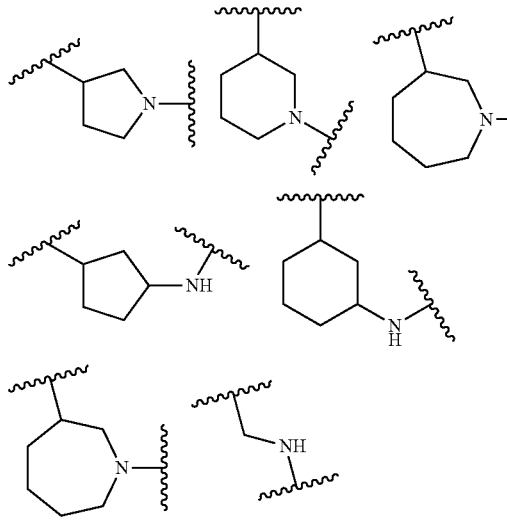

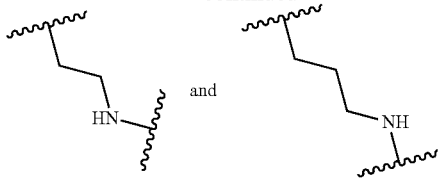

In an embodiment, D may be:

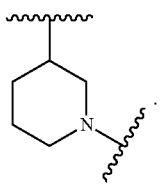 [SMILES: *C1CCCN(*)C1]

Optionally, D is substituted by a halo group, for example, fluoro.

In an embodiment D is cyclopentyl and E is not present.

In embodiments $L^1$ is selected from a bond, $-(CR^dR^e)_m-$, $-O-$ and $-NR^b-$. In embodiments m is 1 or 2, optionally m is 1. In embodiments $R^b$ is independently selected from hydrogen $C_{1-6}$ alkyl and $C_{1-6}$ haloalkyl and $R^d$ and $R^e$ are independently selected from hydrogen, fluorine, chlorine, bromine, iodine, $C_{1-6}$ alkyl and $C_{1-6}$ haloalkyl. In embodiments $R^b$, $R^d$ and $R^e$ are independently hydrogen or $C_{1-6}$ alkyl.

In embodiments $L^1$ is selected from a bond, $-CH_2-$, $-O-$ and $-NH-$, optionally a bond or $-CH_2-$.

The embodiments described above may be applied individually, or in any combination of one another, and independently, to the compounds of the invention, for example those compounds disclosed below.

In the case when D is:

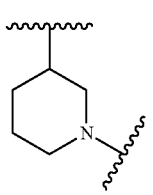 [SMILES: *C1CCCN(*)C1]

the compound of formula (I) is a compound according to formula (III):

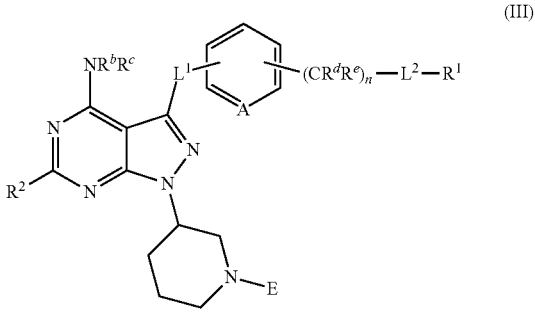

In any embodiment D may be the group shown below with the indicated stereochemistry:

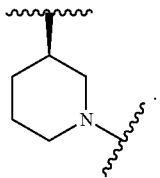 [SMILES: *[C@@H]1CCCN(*)C1]

Thus, the compound of formula (I) may be a compound according to formula (IIIa):

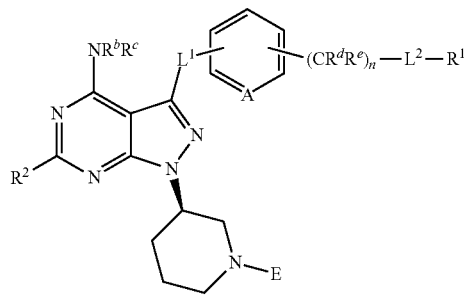

(IIIa)

In embodiments where there is a single enantiomer of the compounds of the invention, the compounds of the invention may have an enantiomeric purity of at least about 90% enantiomeric excess (ee), at least about 95% enantiomeric excess (ee), at least about 98% enantiomeric excess (ee), at least about 99% enantiomeric excess (ee), or 100% enantiomeric excess (ee). In embodiments where there is a mixture of enantiomers of the compounds of the invention, the compounds of the invention may be a racemic mixture or any other mixture of enantiomers, for example the compounds of the invention may have an enantiomeric purity of at least about 50% enantiomeric excess (ee), at least about 60% enantiomeric excess (ee), at least about 70% enantiomeric excess (ee), at least about 80% enantiomeric excess (ee), at least about 90% enantiomeric excess (ee), or at least about 95% enantiomeric excess (ee).

In an embodiment the compound of formula (I) is a compound according to formula (IVa) and (IVb):

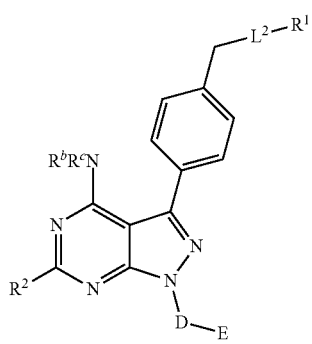

(IVa)

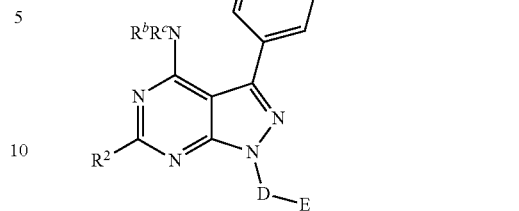

(IVb)

In an embodiment the compound of formula (I) is a compound according to formula (Va) and (Vb):

(Va)

(Vb)

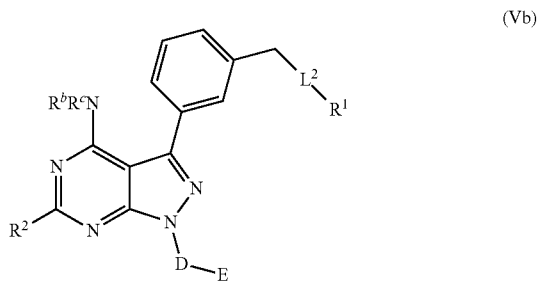

In an embodiment the compound of formula (I) is a compound according to formula (VIa) and (VIb):

(VIa)

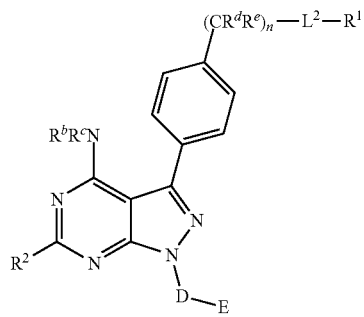

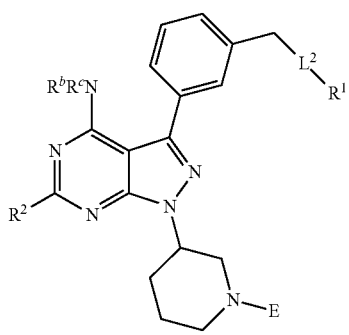
(VIb)
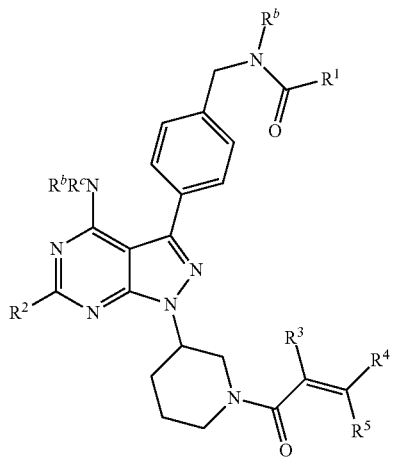
(VIIIa)
In an embodiment the compound of formula (I) is a compound according to formula (VIIa) and (VIIb):
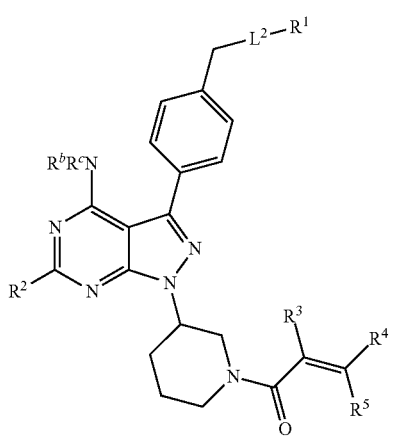
(VIIa)
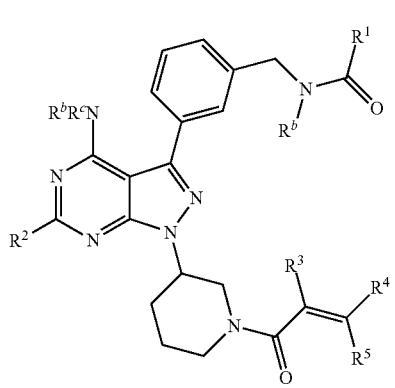
(VIIIb)
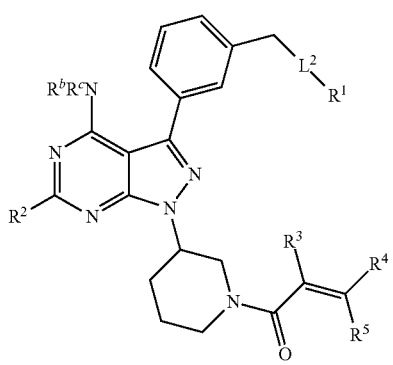
(VIIb)
Preferred compounds of the invention include:
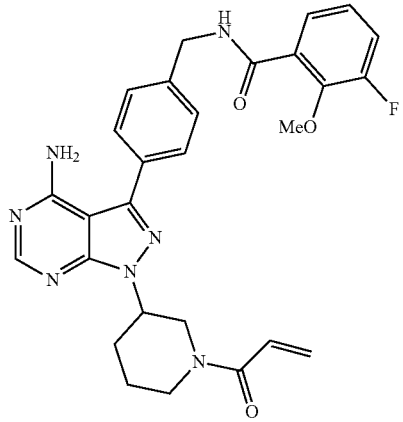
In an embodiment the compound of formula (I) is a compound according to formula (VIIIa) and (VIIIb):

21
-continued
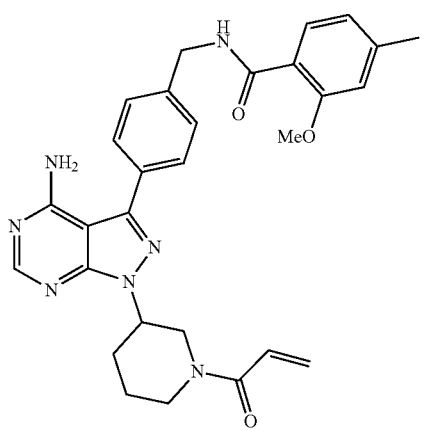
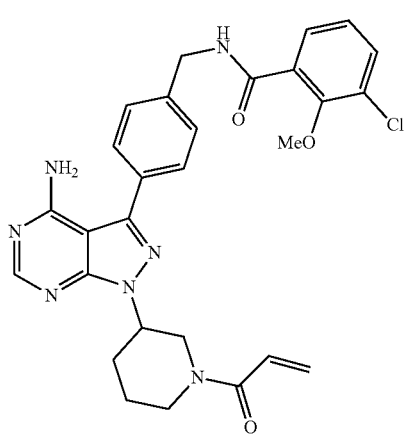
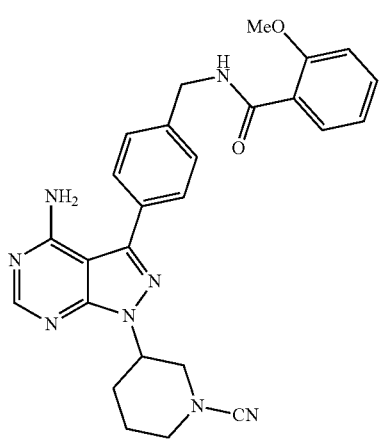
22
-continued
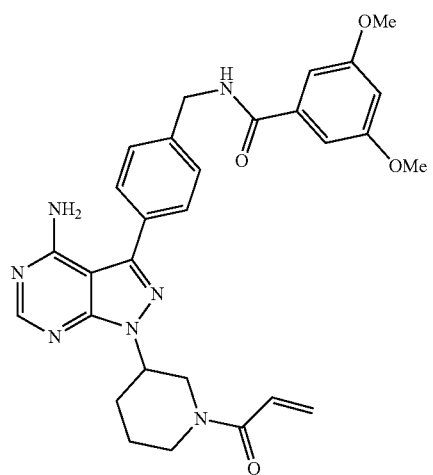
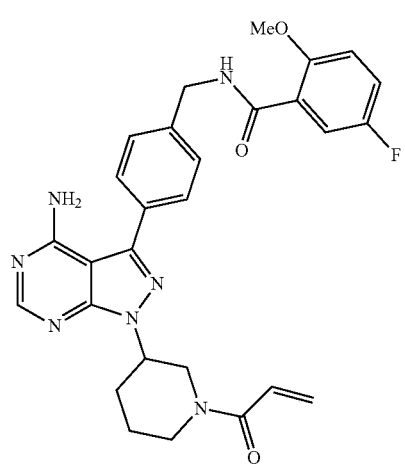
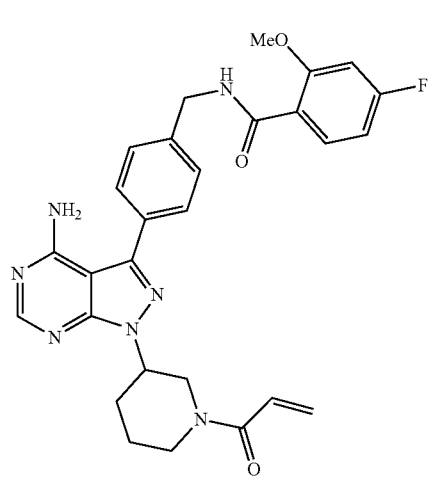

23
-continued
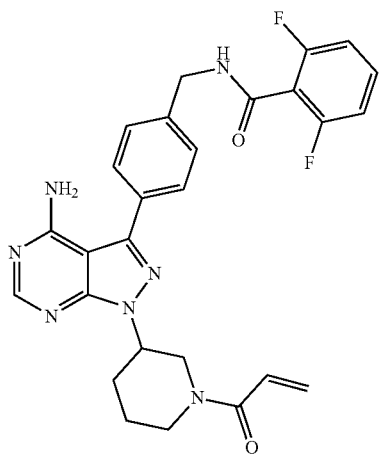
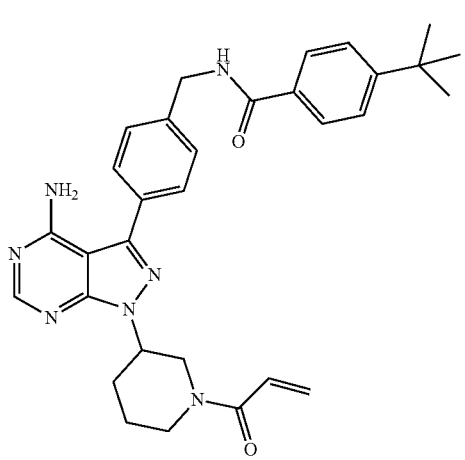
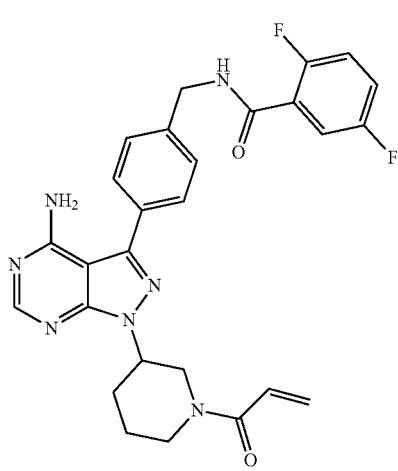
24
-continued
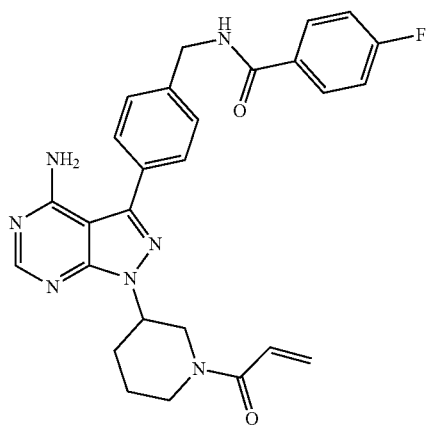
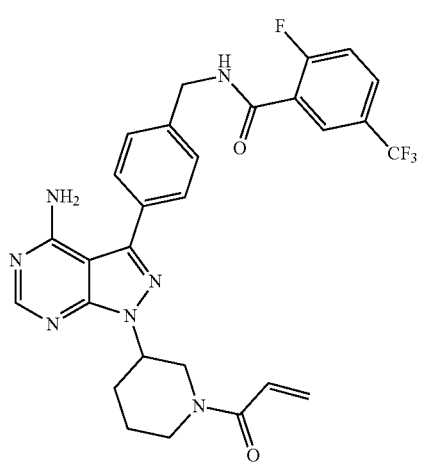
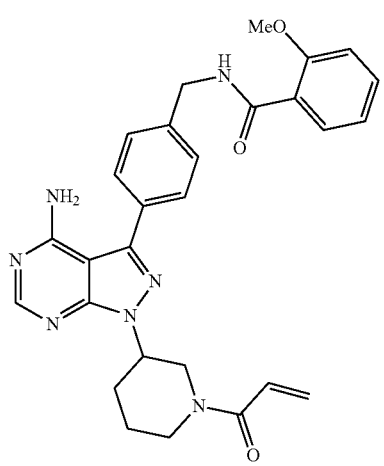

25
-continued
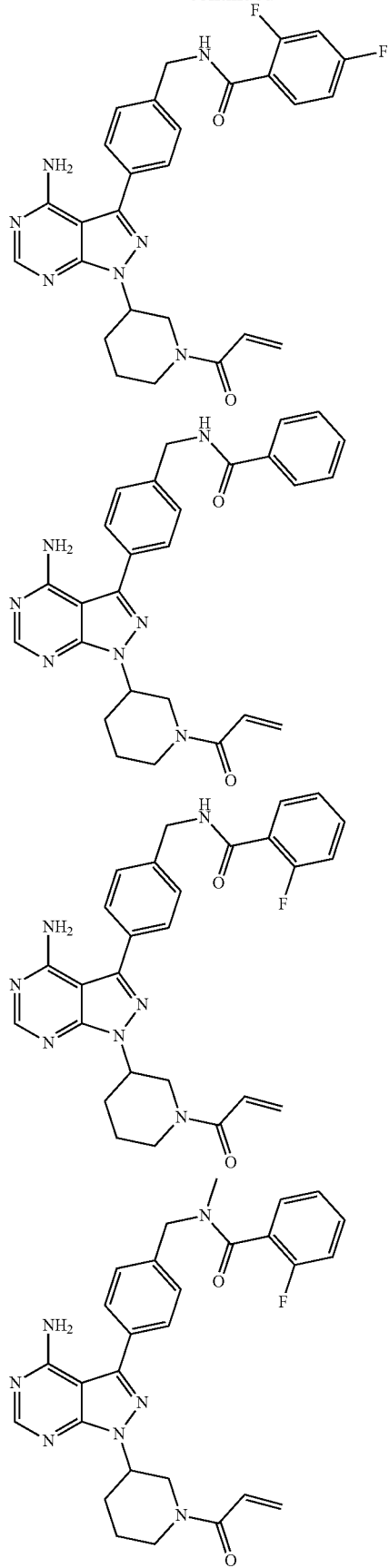
26
-continued
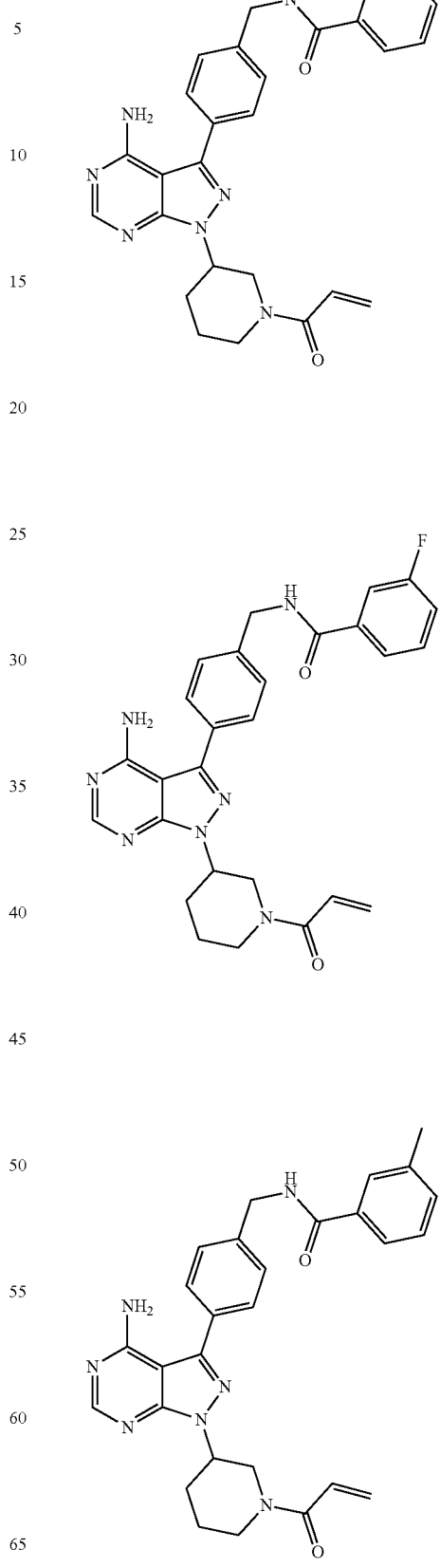

27
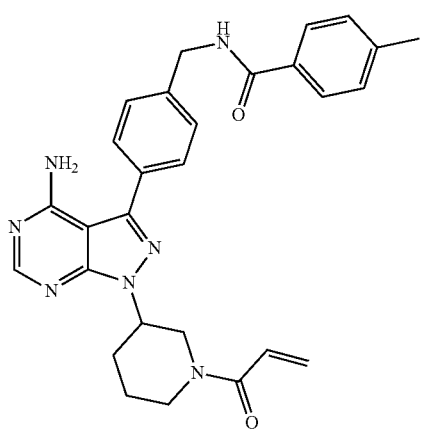
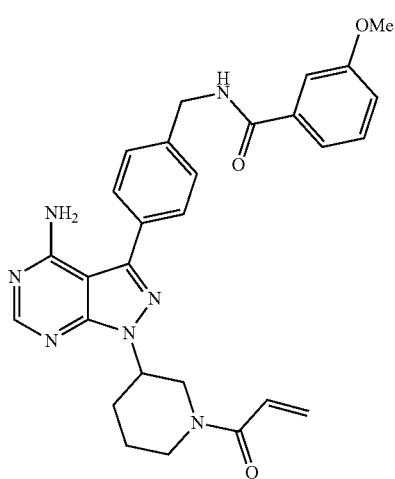
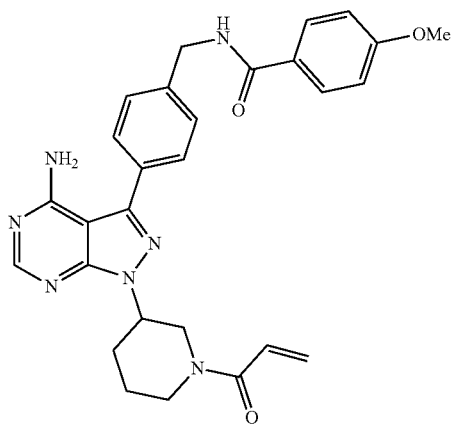
28
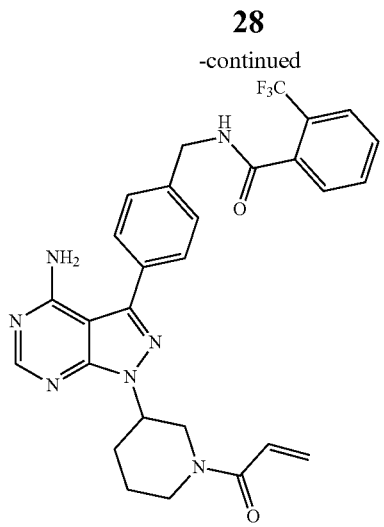
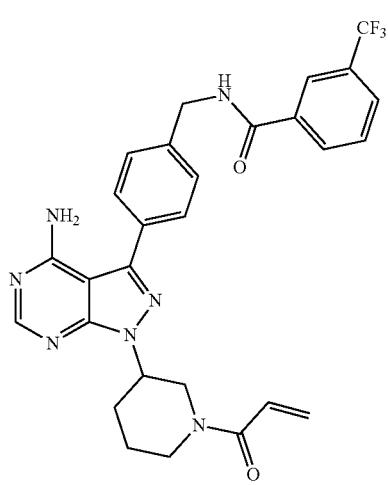
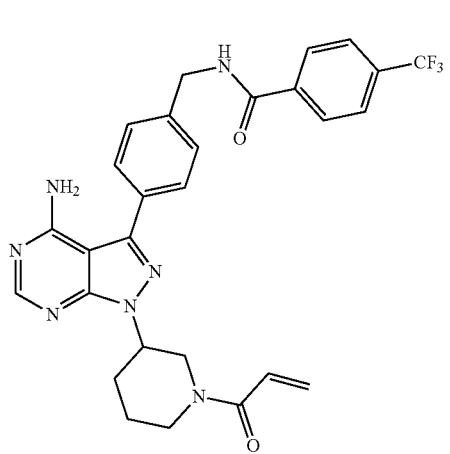

29
-continued
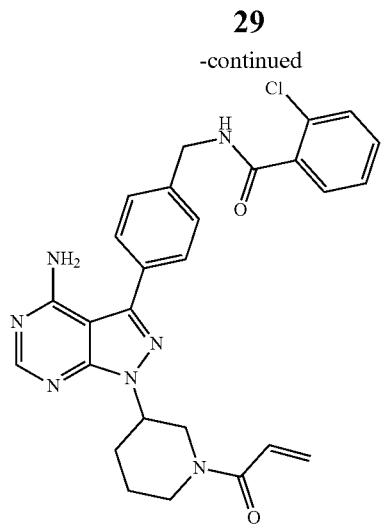
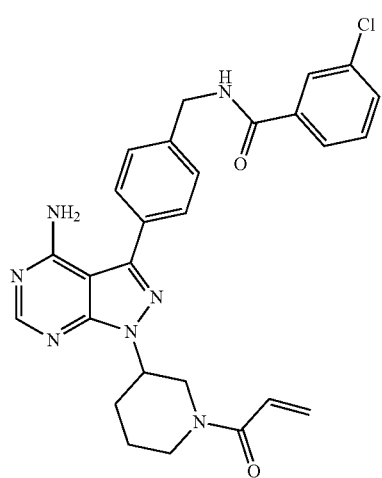
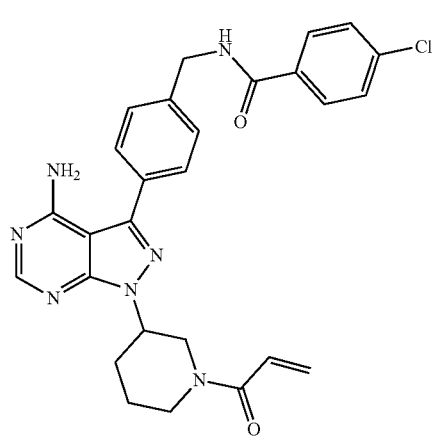
30
-continued
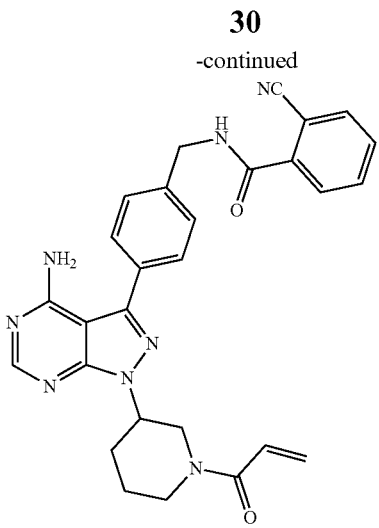
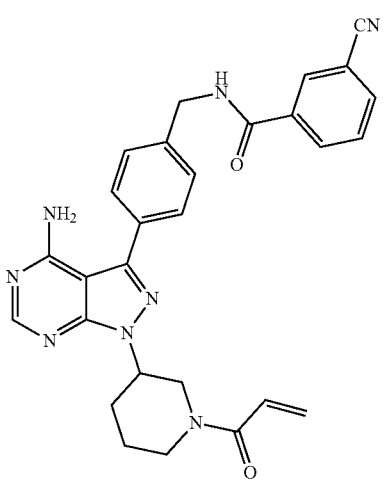
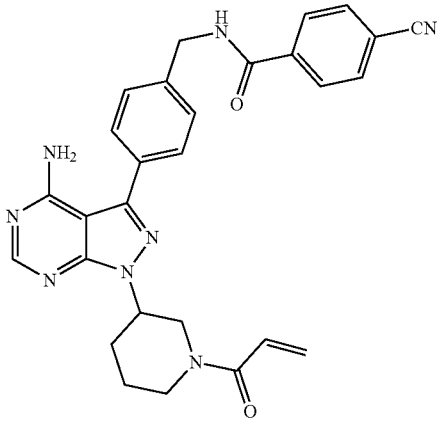

31
-continued
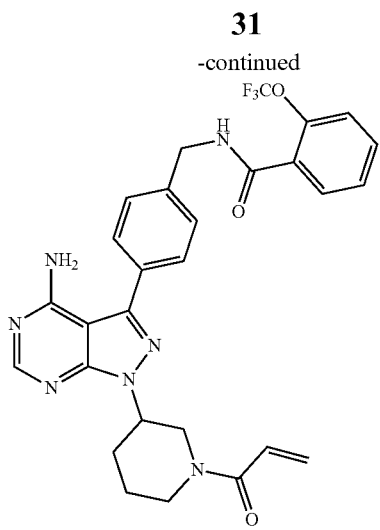
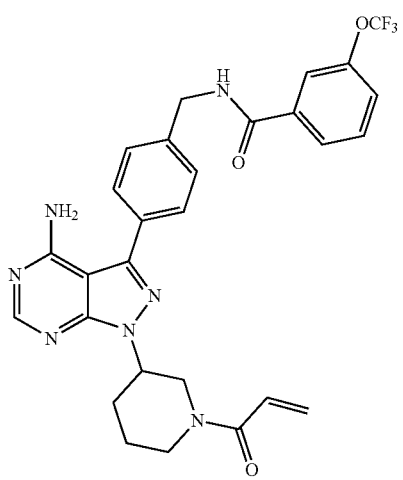
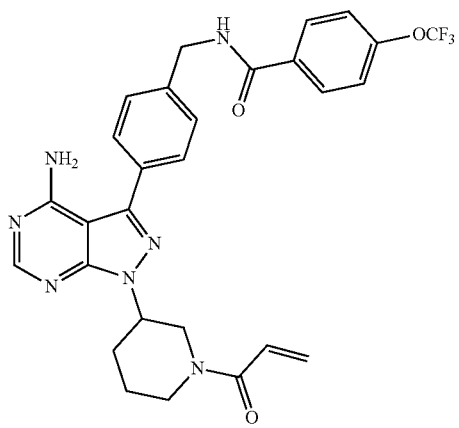
32
-continued
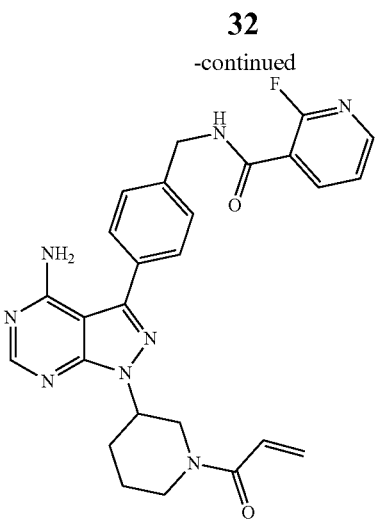
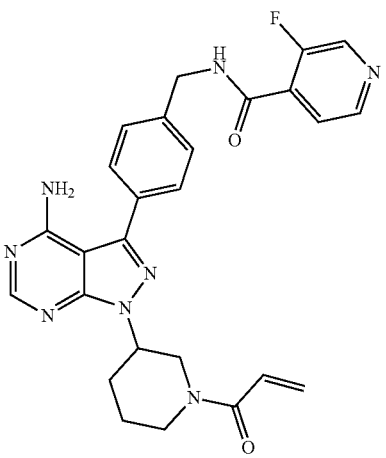
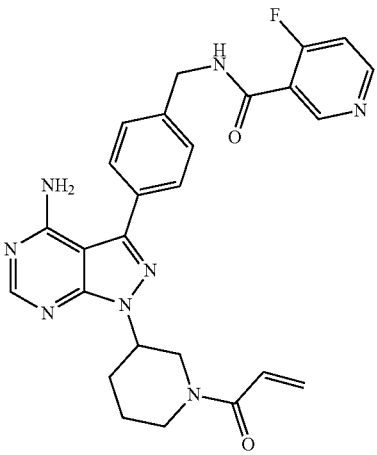

33
-continued
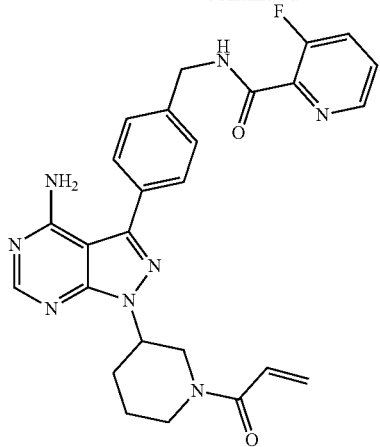
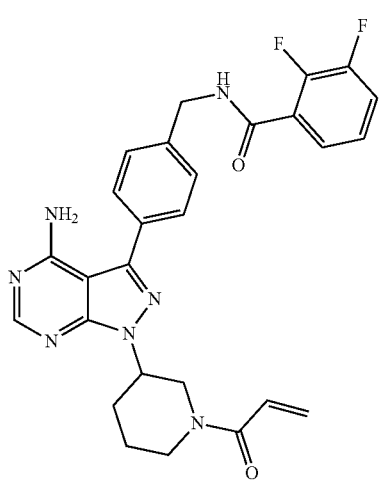
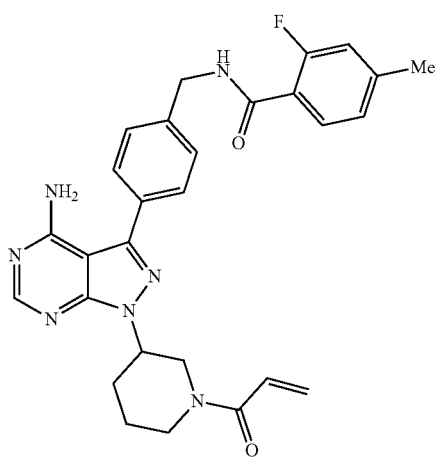
34
-continued
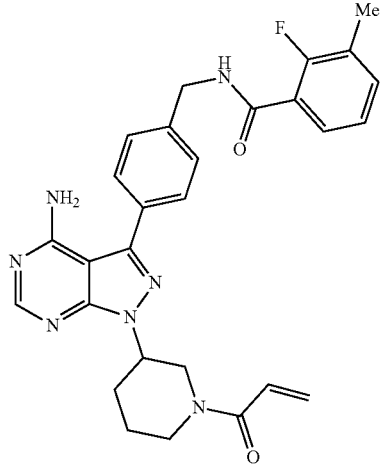
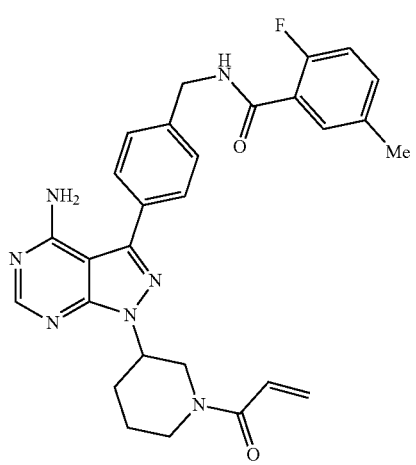
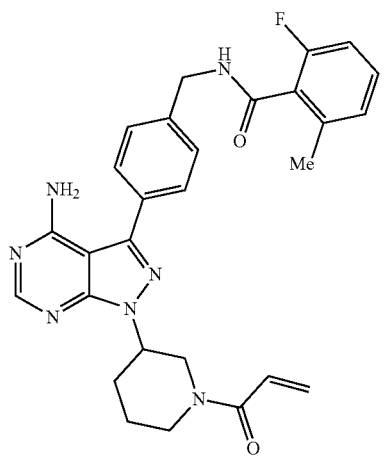

35
-continued
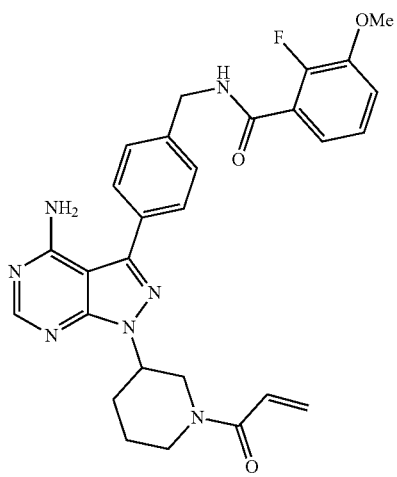
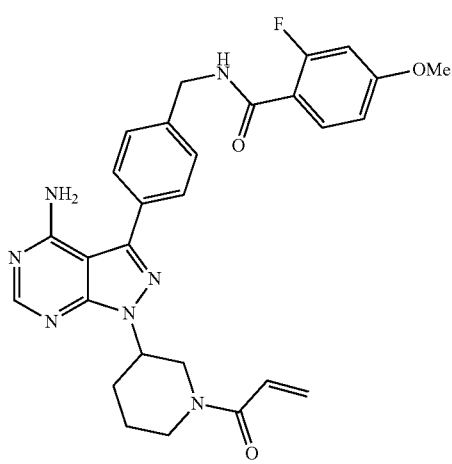
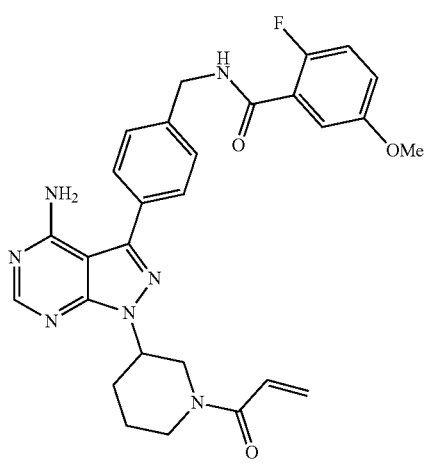
36
-continued
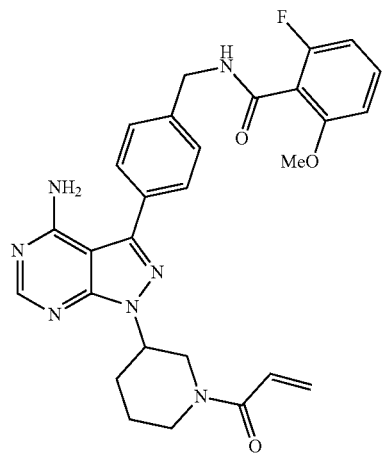
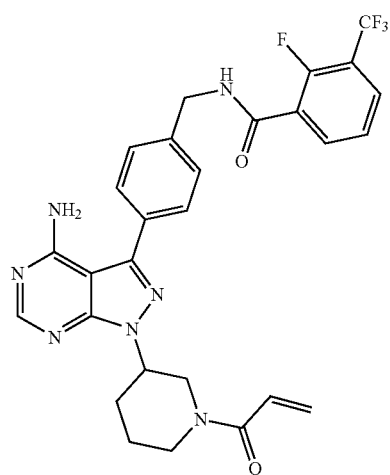

37
-continued
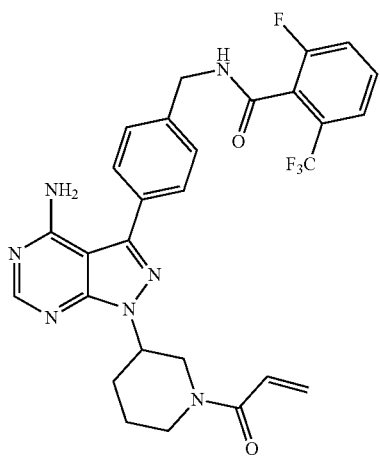
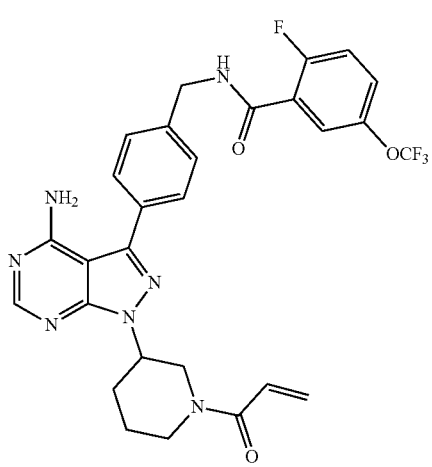
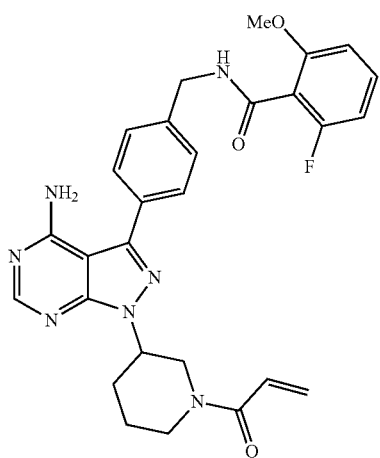
38
-continued
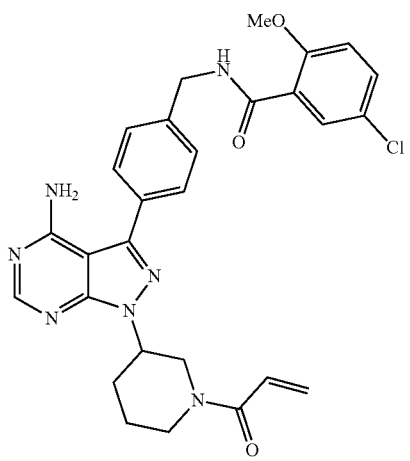
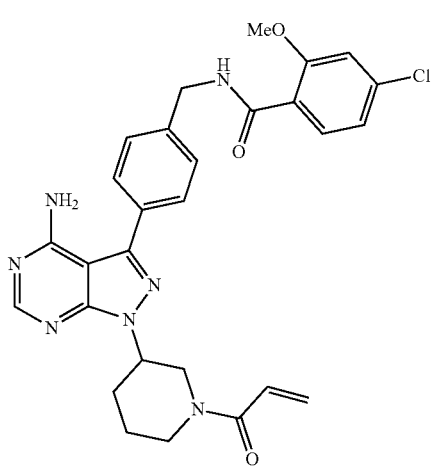
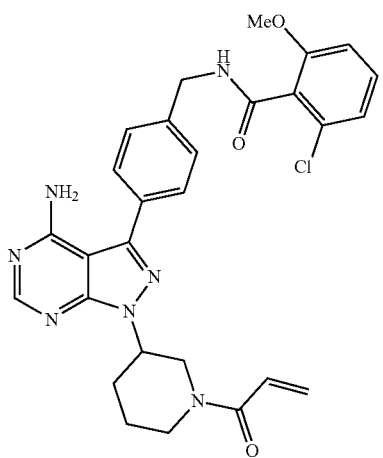

39
-continued
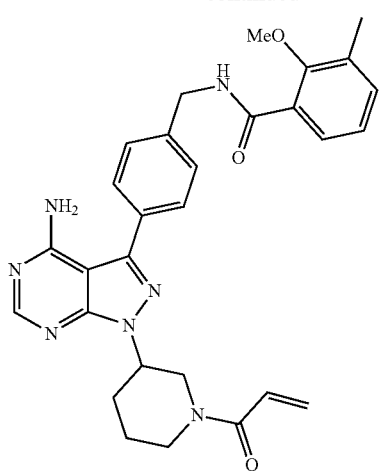
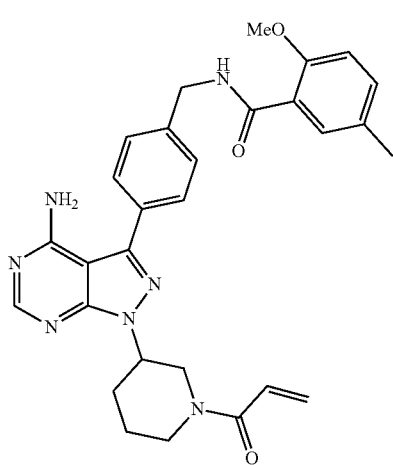
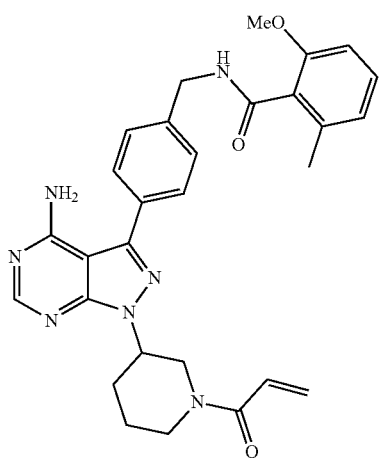
40
-continued
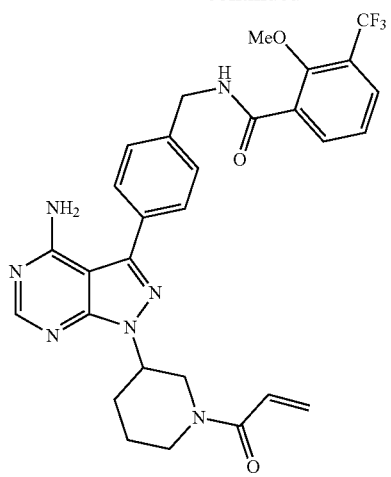
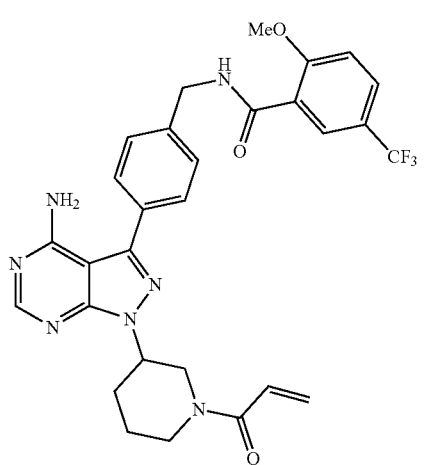
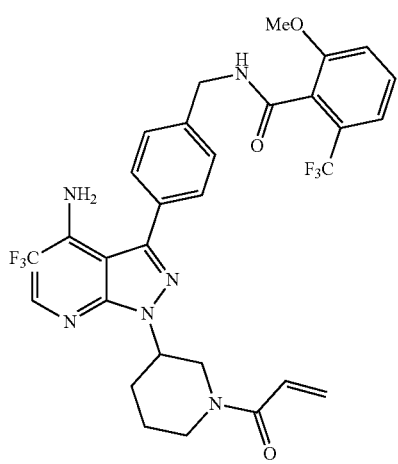

41
-continued
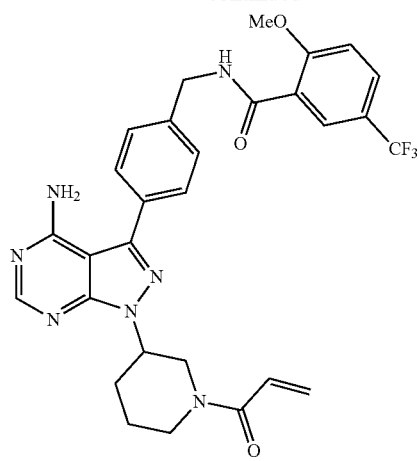
42
-continued
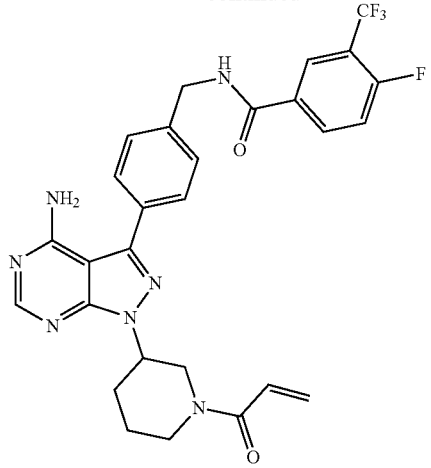
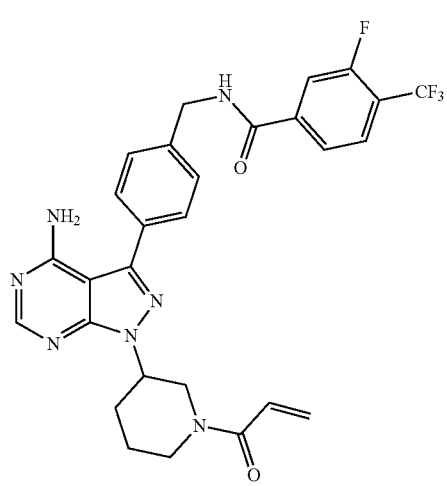
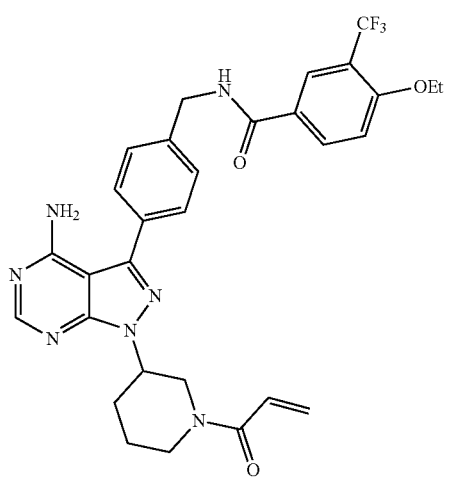
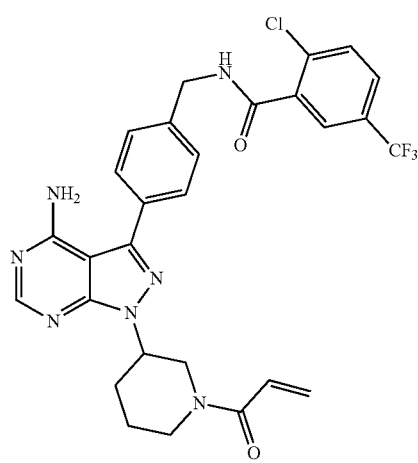
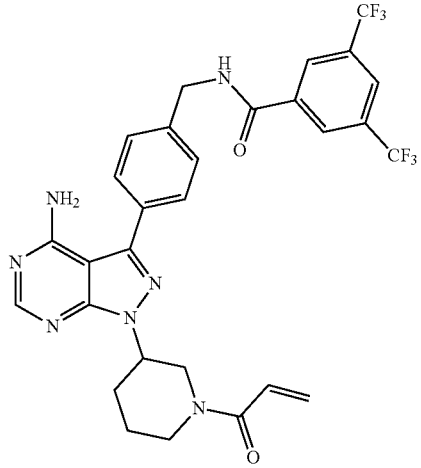

43
-continued
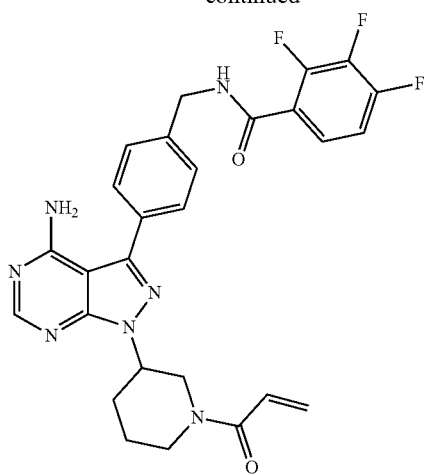
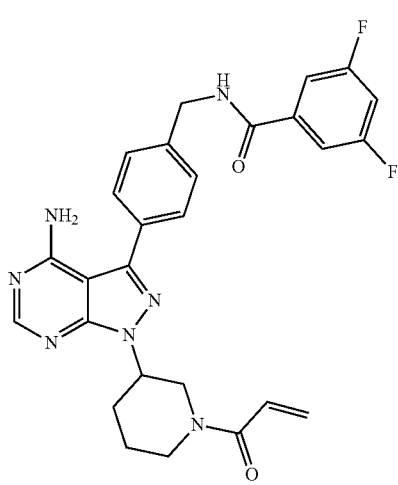
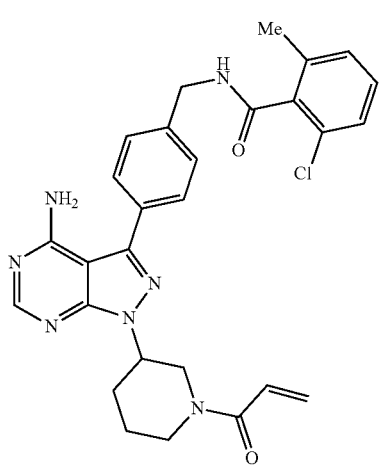
44
-continued
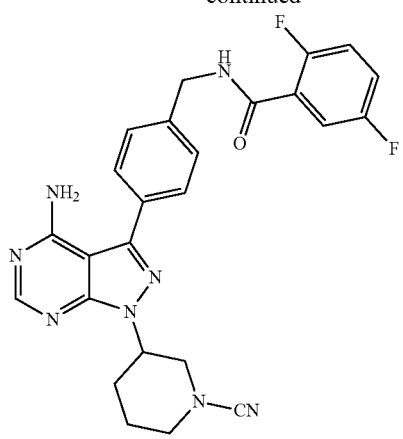
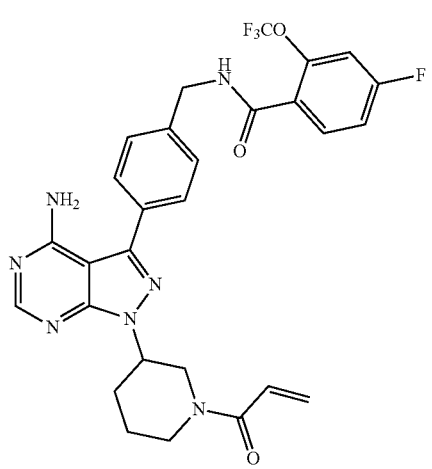
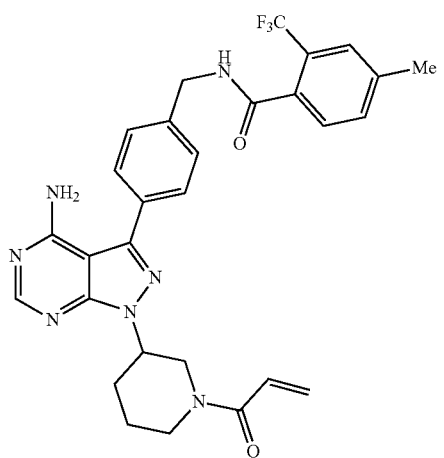

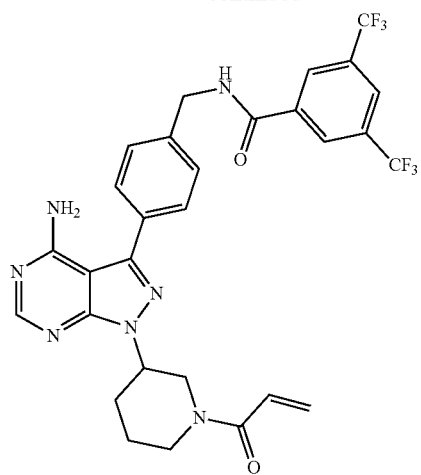
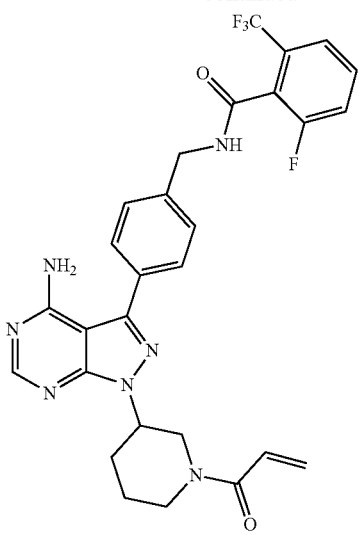
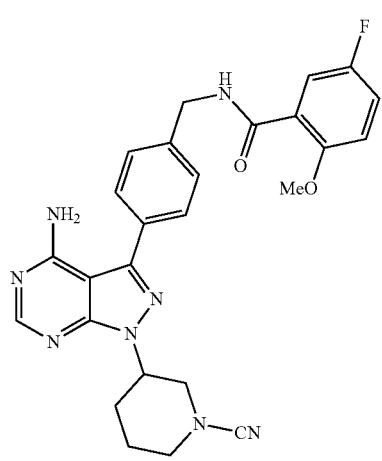
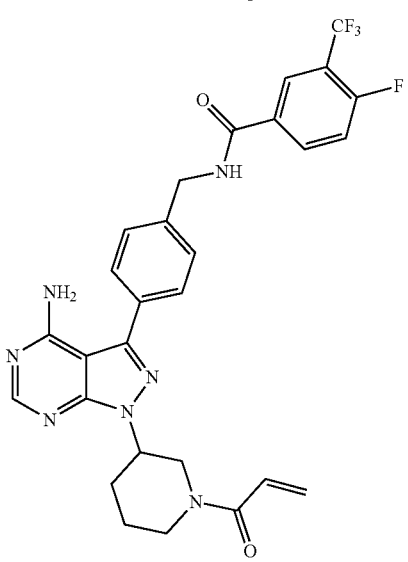
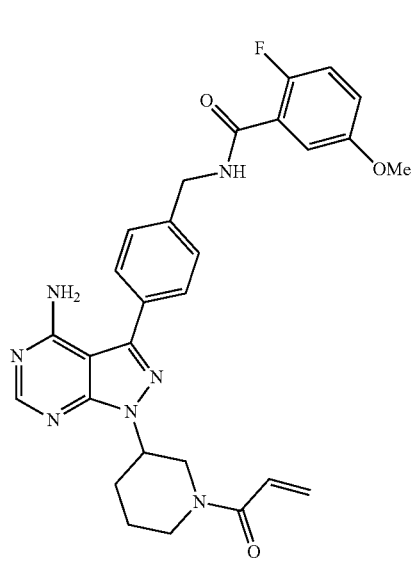
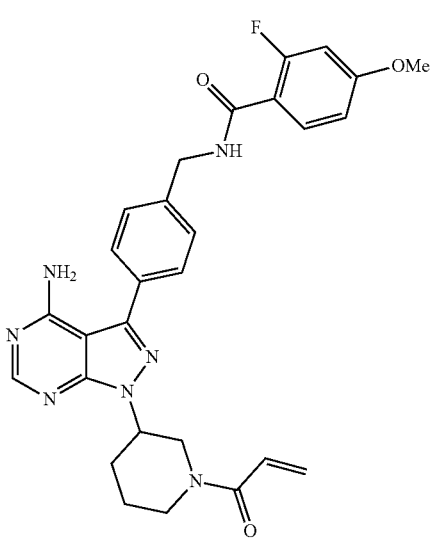

47
-continued
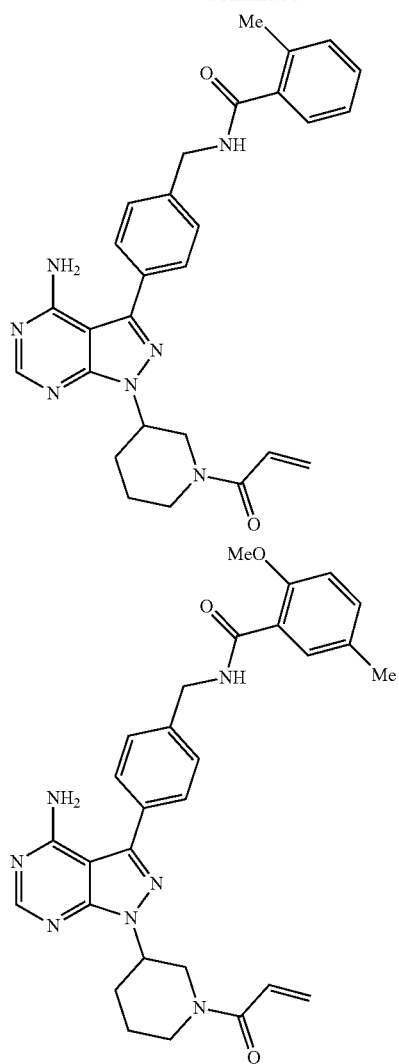
48
-continued
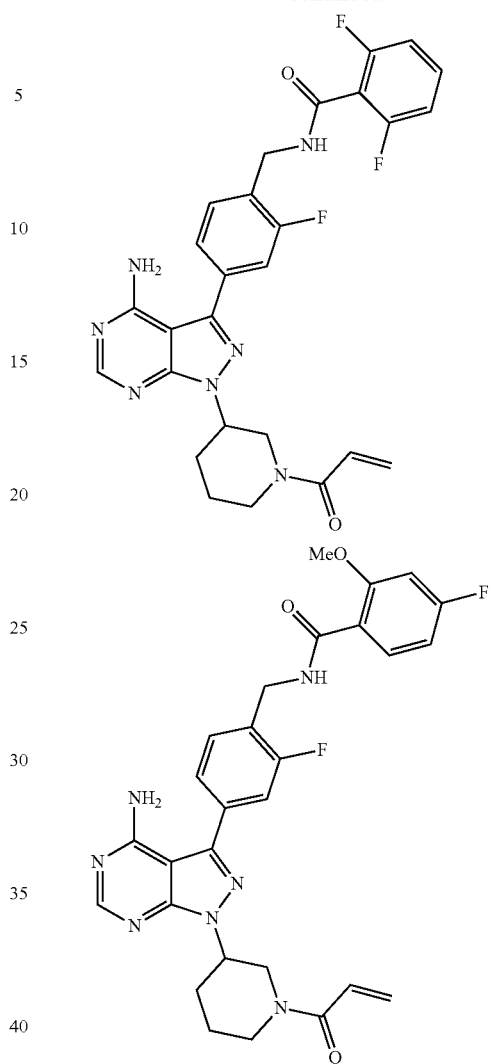
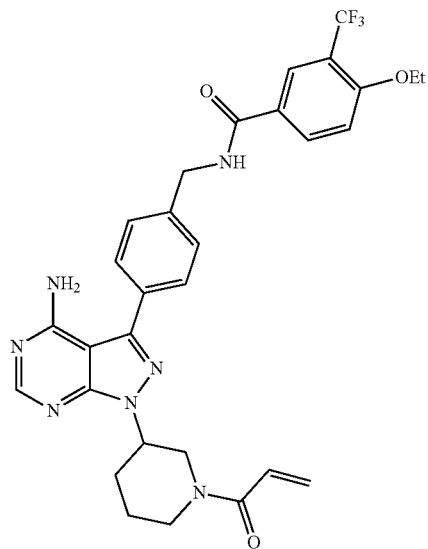
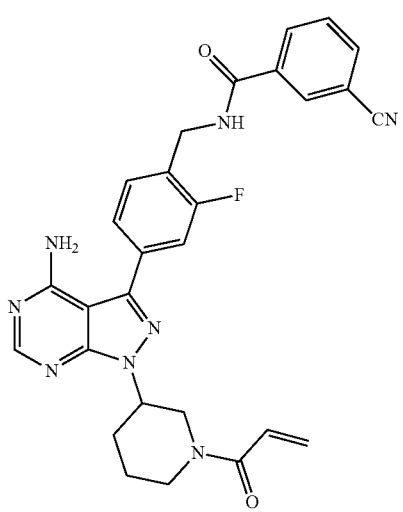

49
-continued
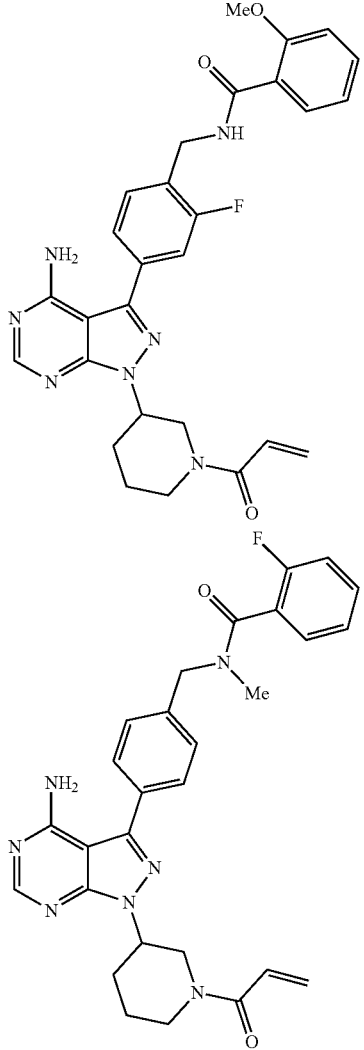
50
-continued
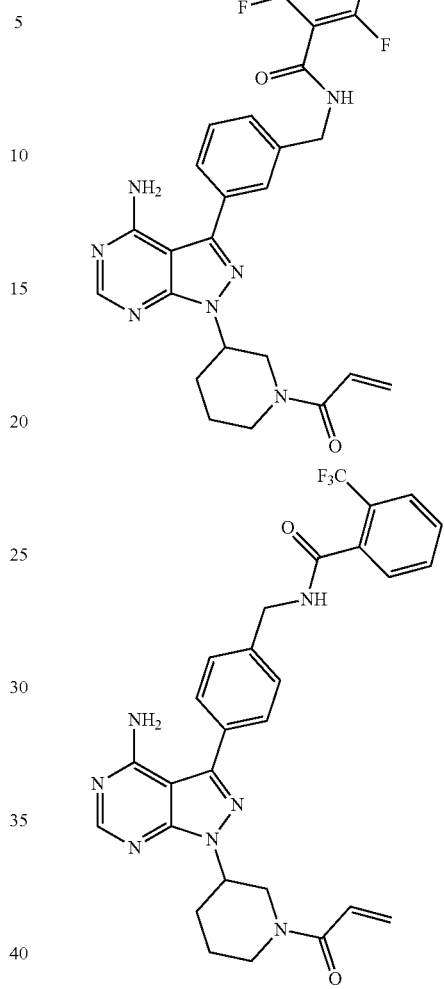
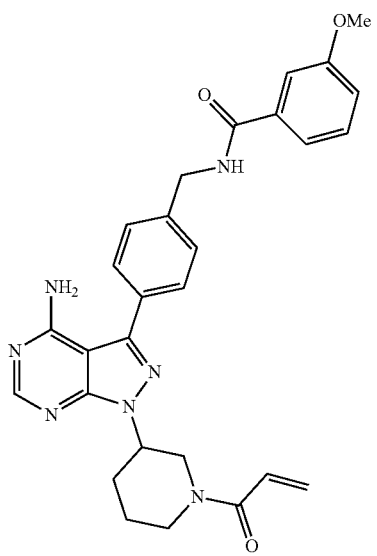
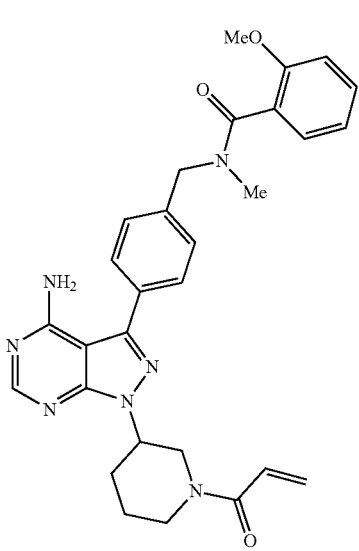

51
-continued
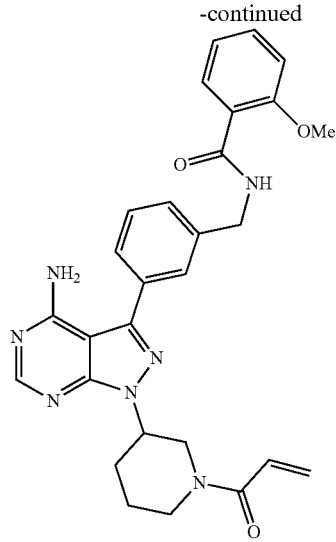
52
-continued
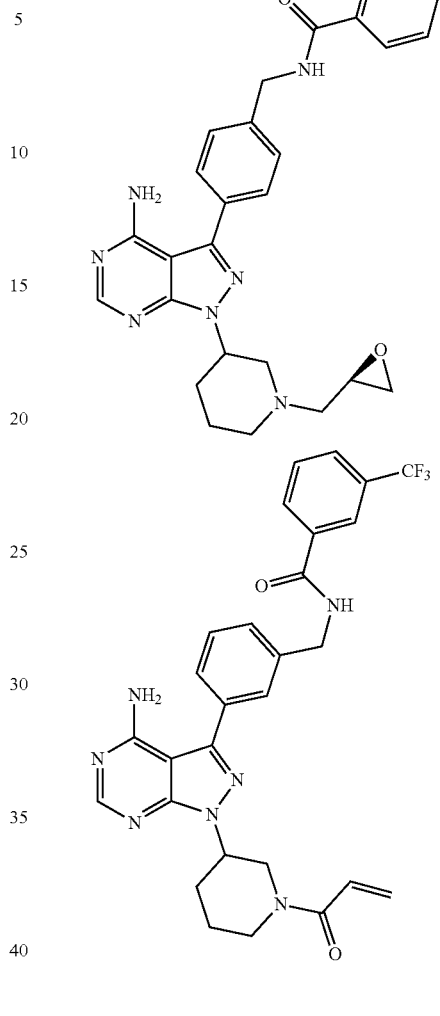
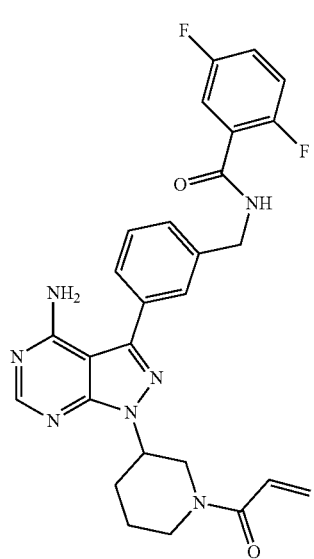
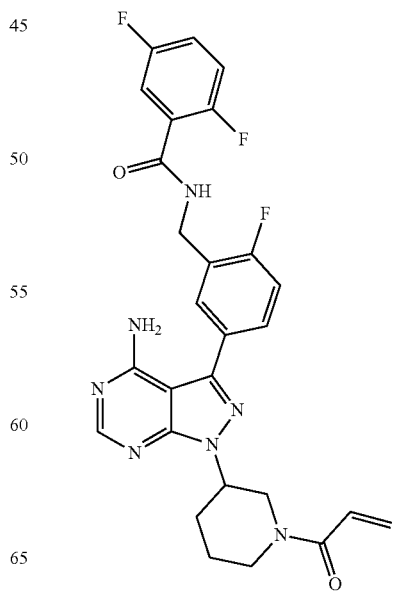

53
-continued
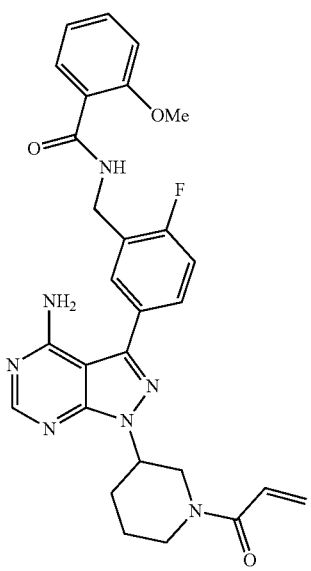
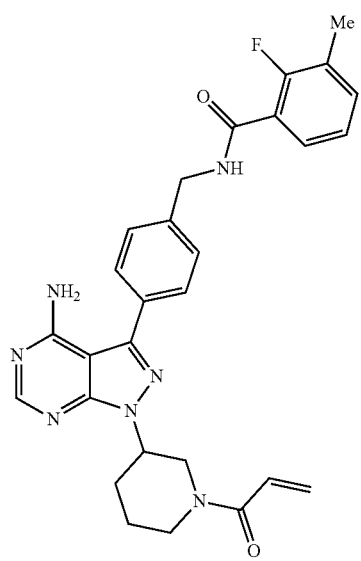
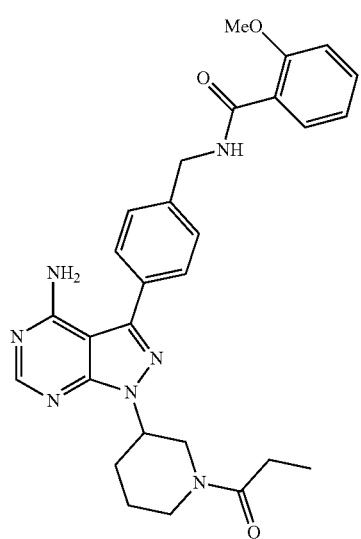
54
-continued
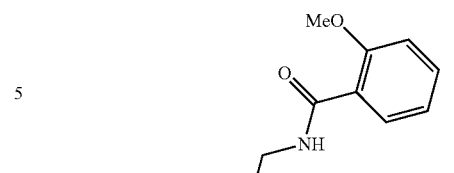
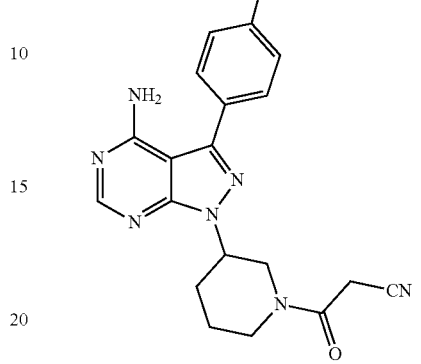
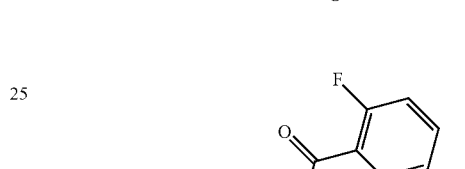
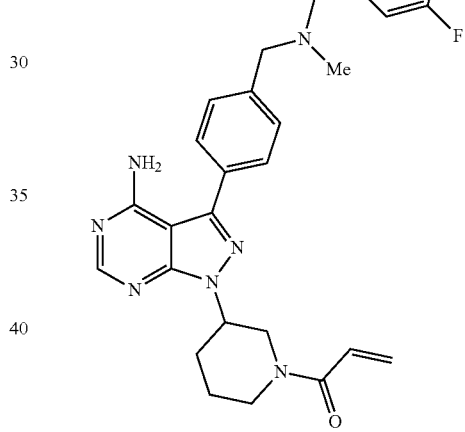
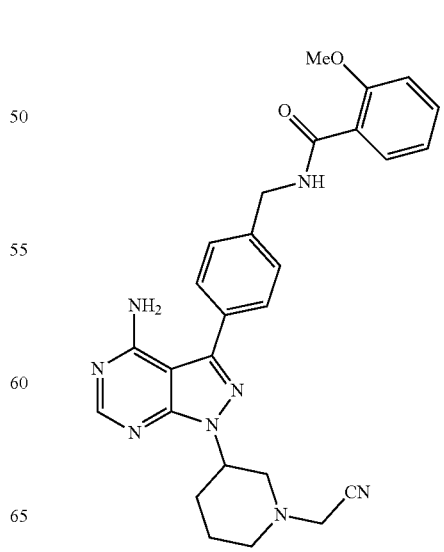

55
-continued
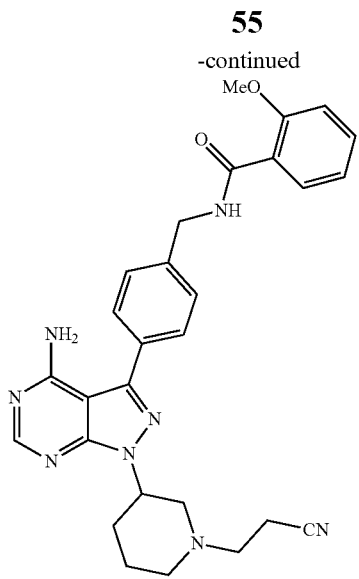
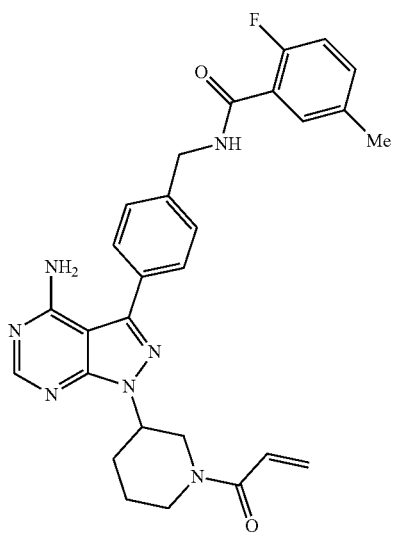
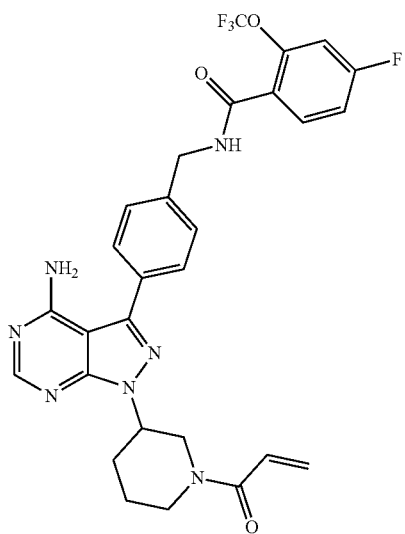
56
-continued
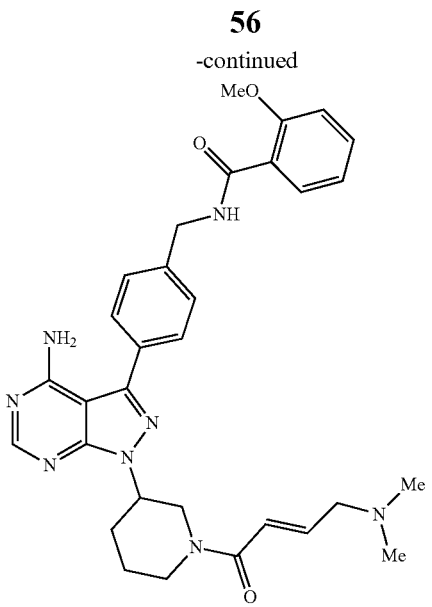
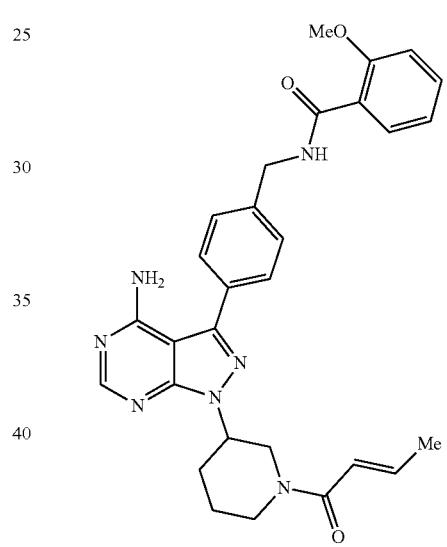
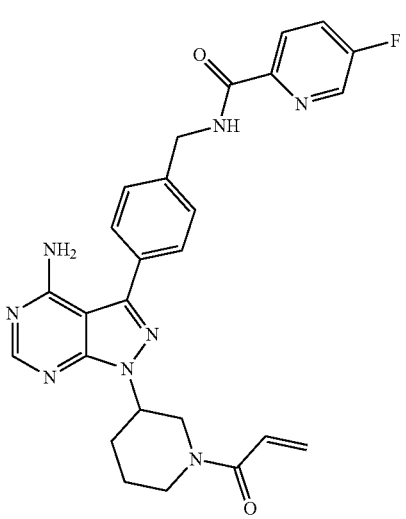

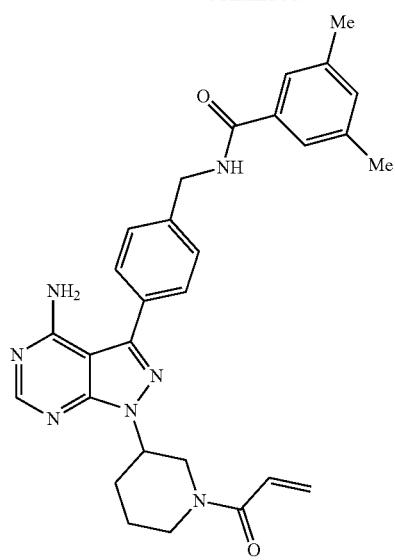
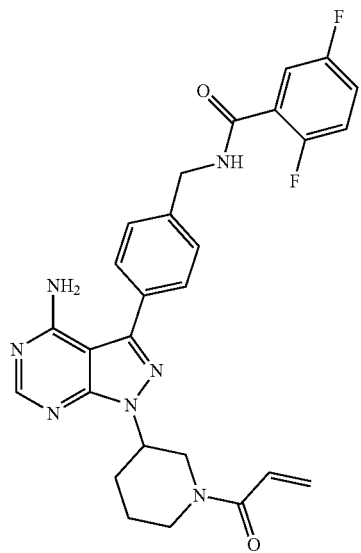
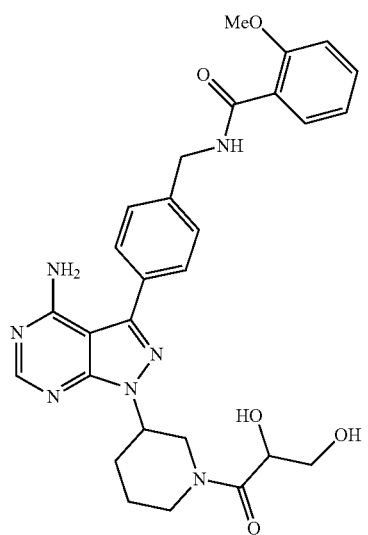
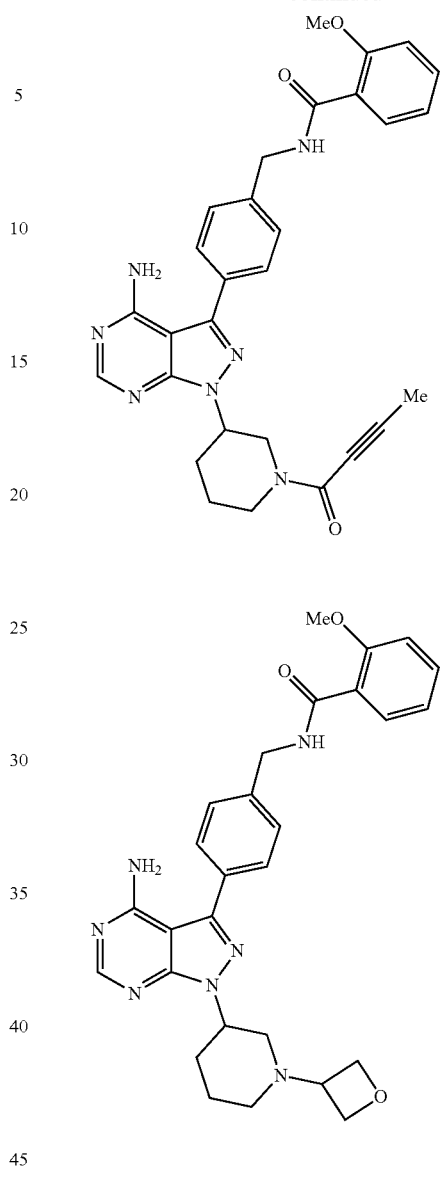
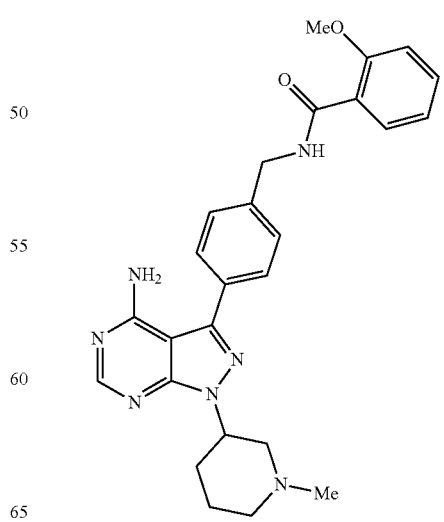

59
-continued
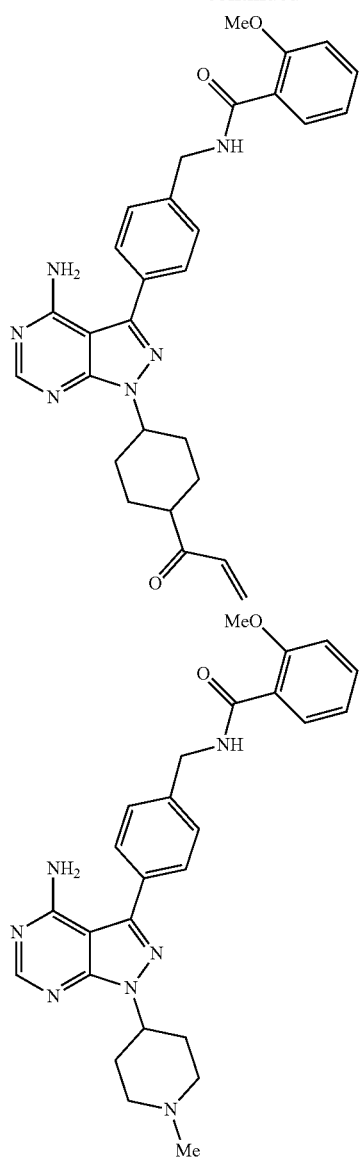
Particularly preferred compounds of the invention are:
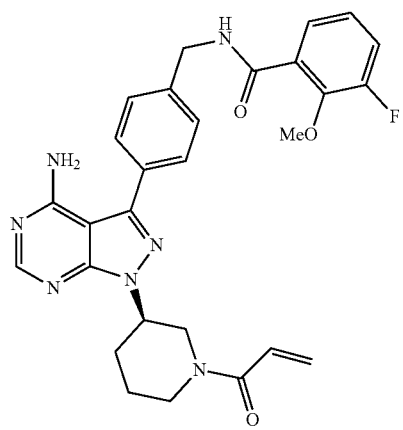
60
-continued
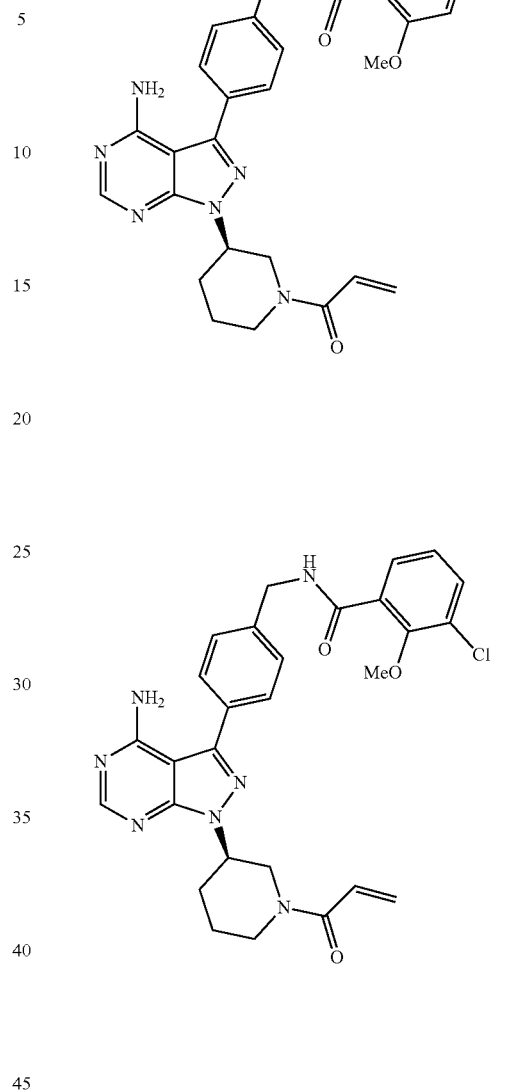
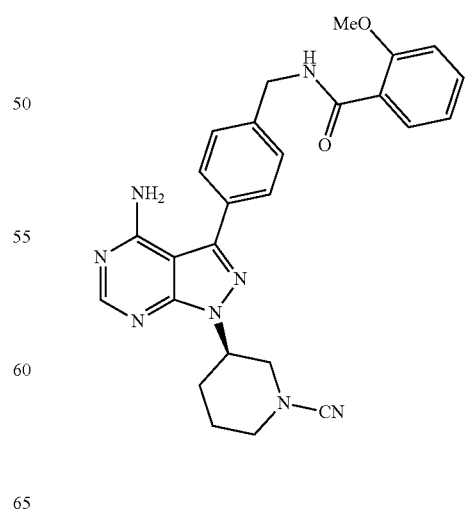

61
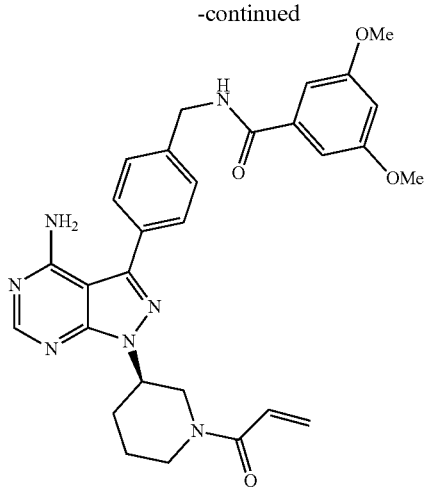
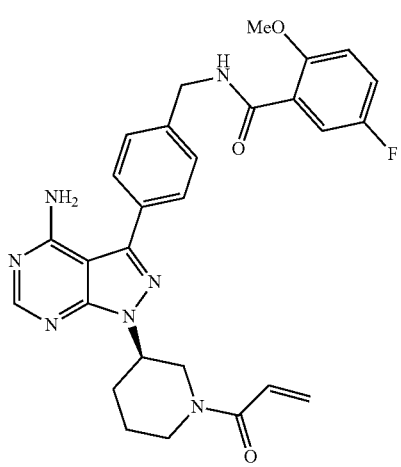
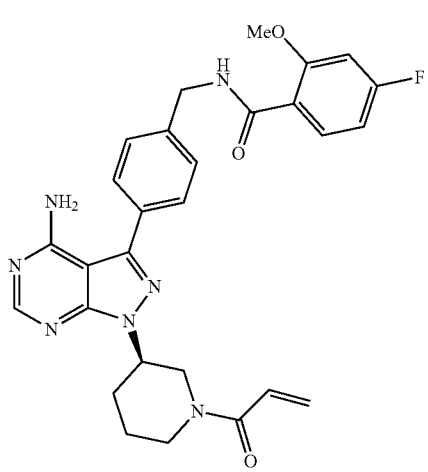
62
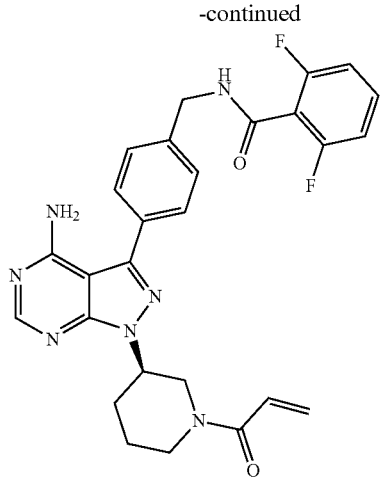
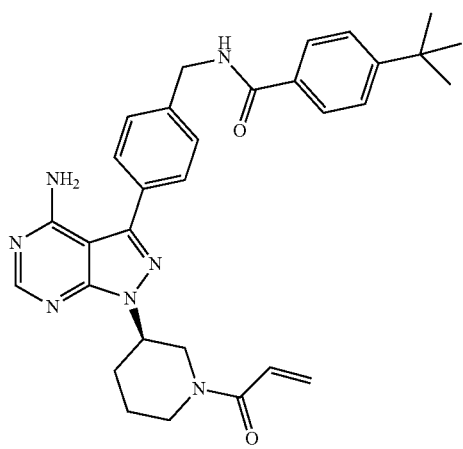
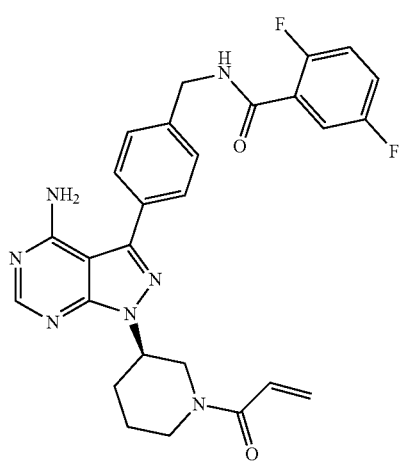

-continued
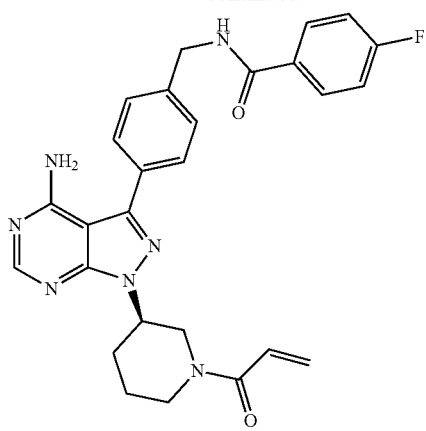
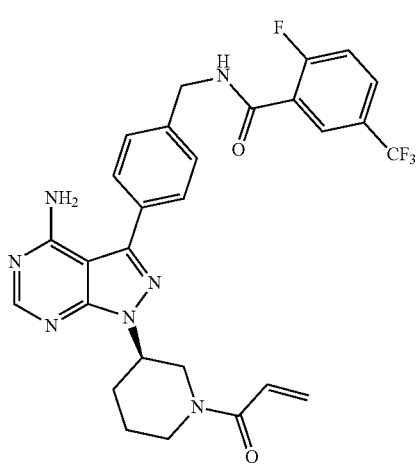
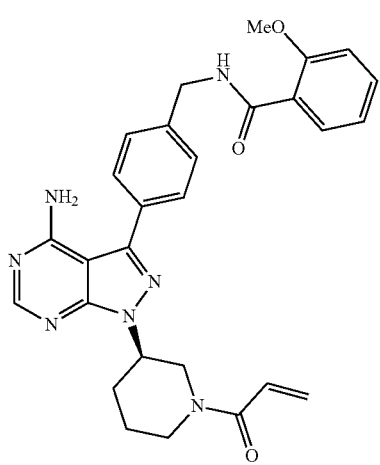
-continued
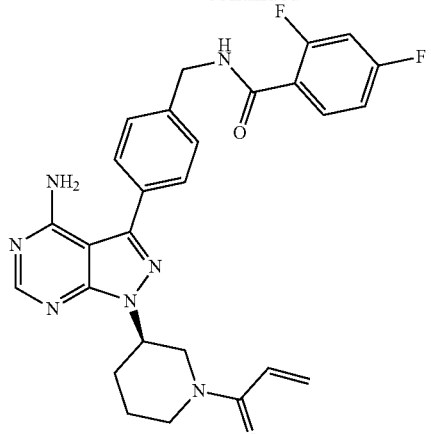
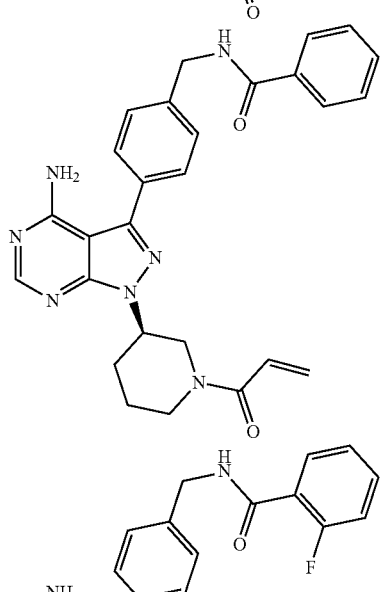
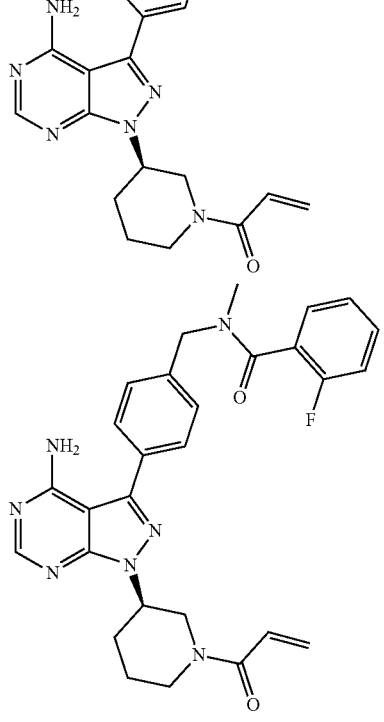

65
-continued
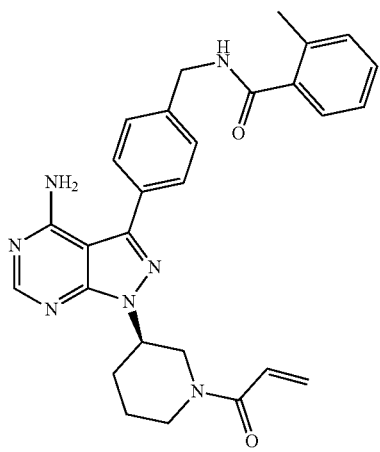
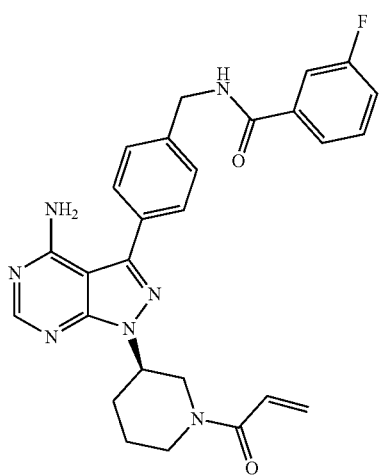
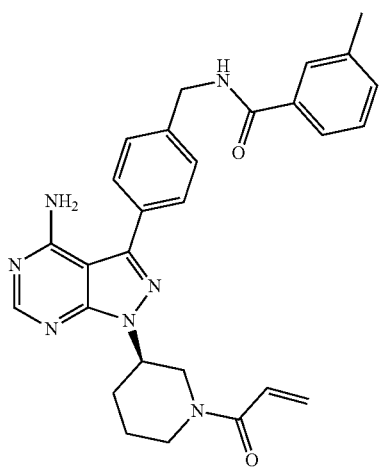
66
-continued
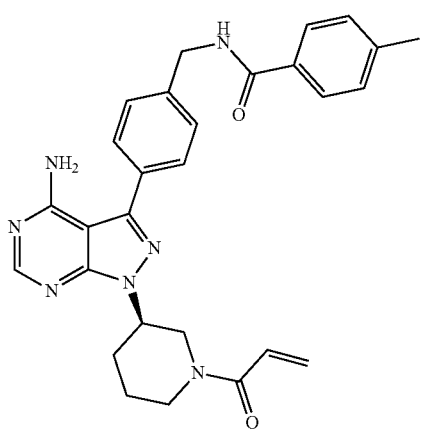
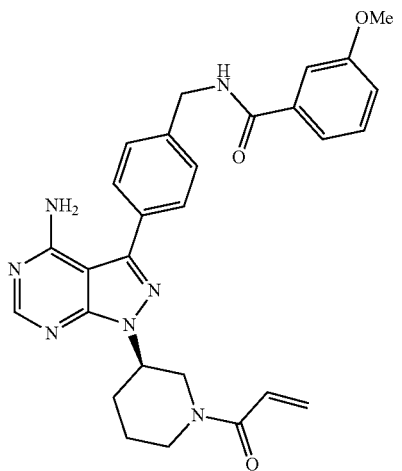
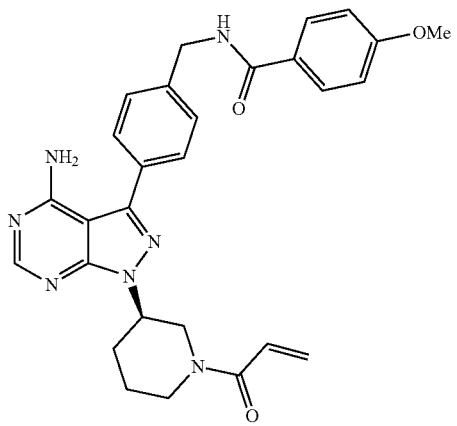

67
-continued
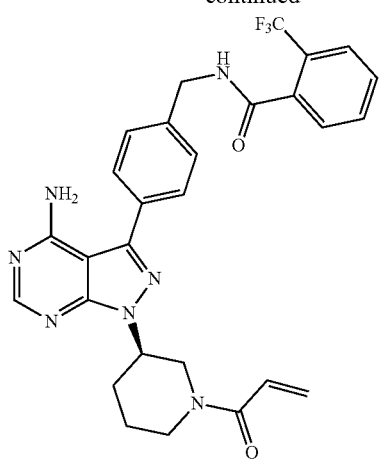
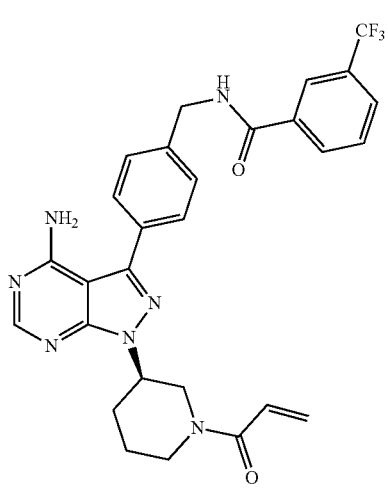
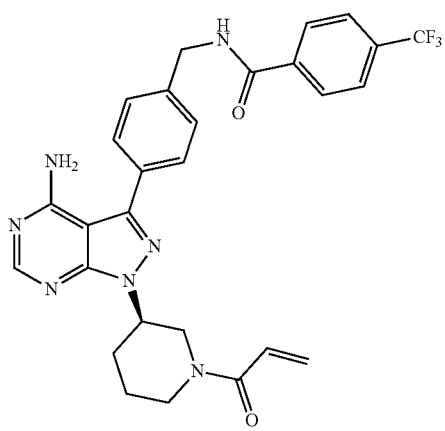
68
-continued
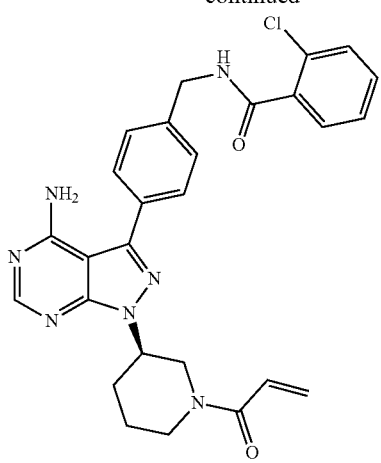
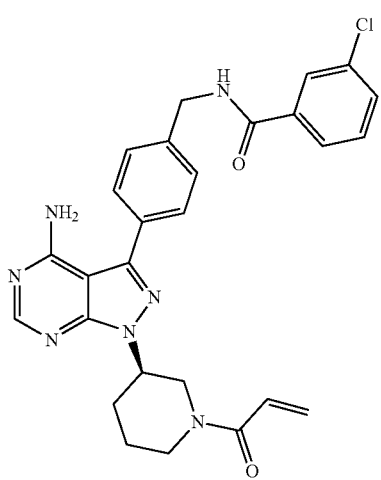
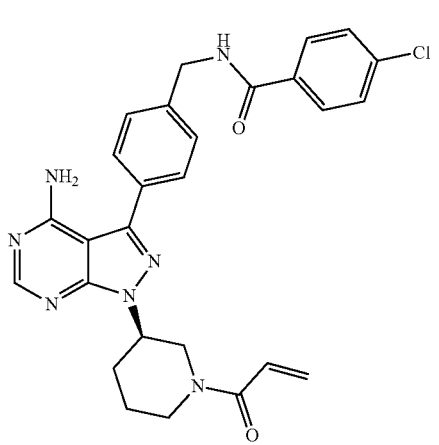

69
-continued
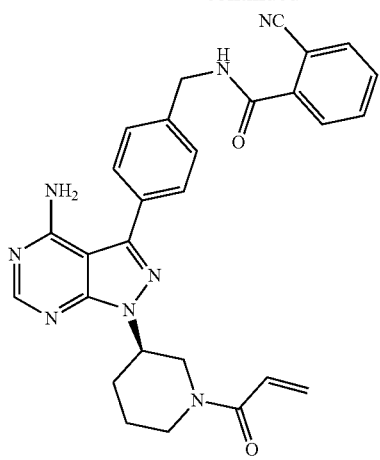
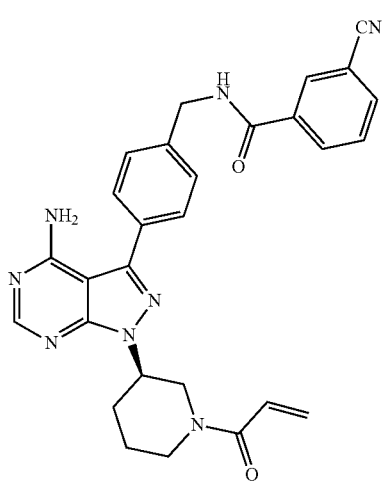
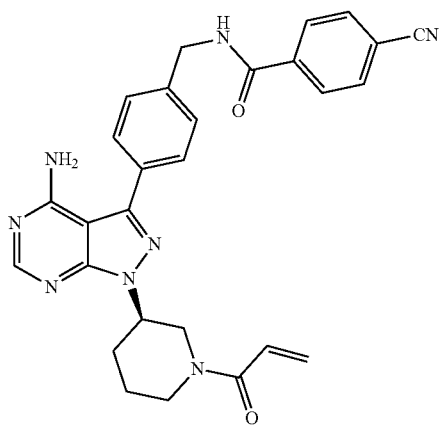
70
-continued
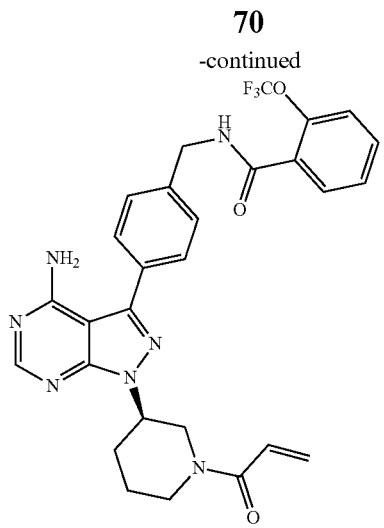
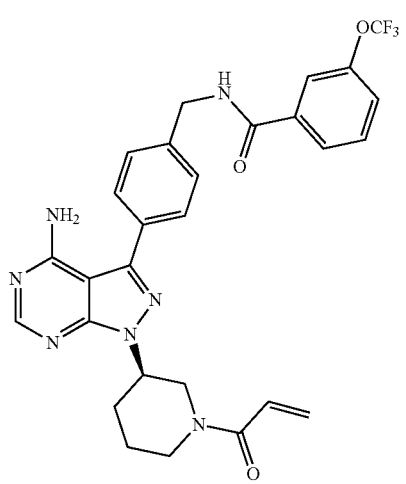
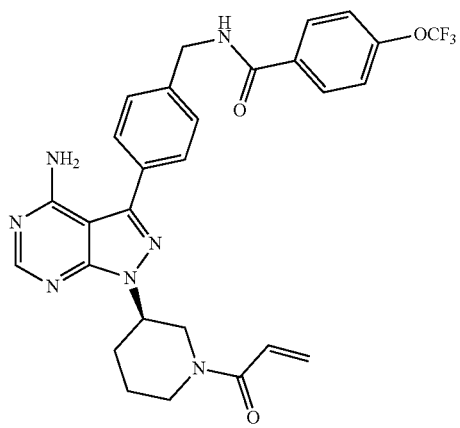

71
-continued
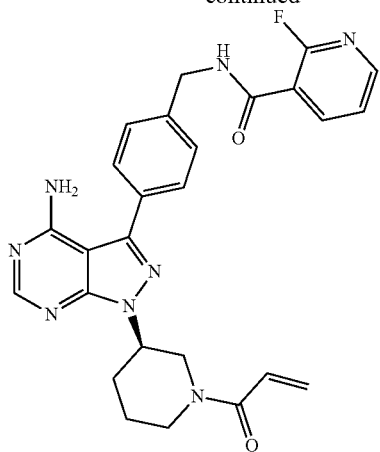
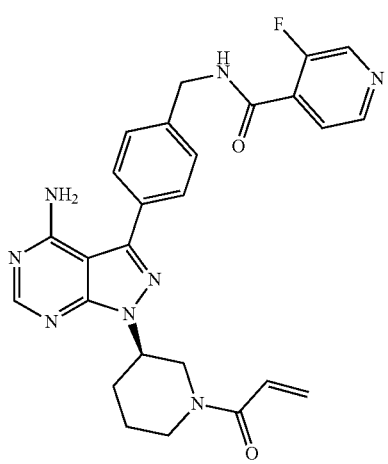
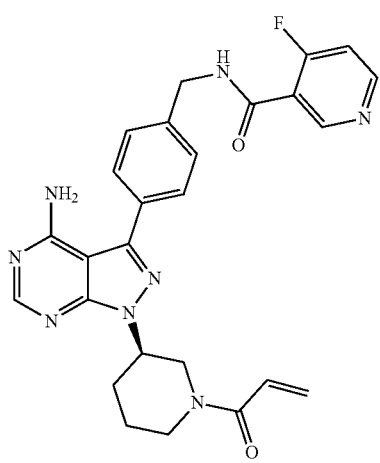
72
-continued
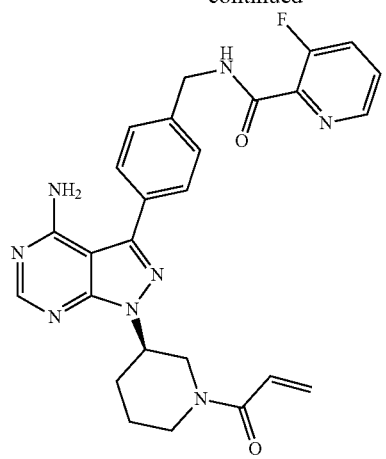
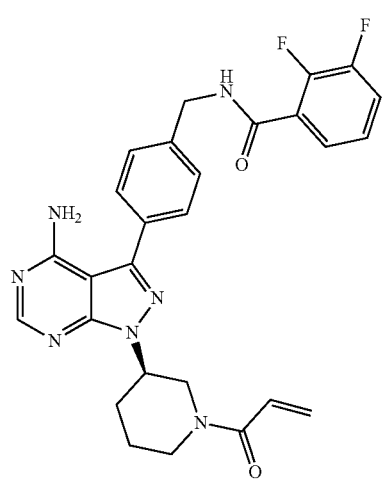
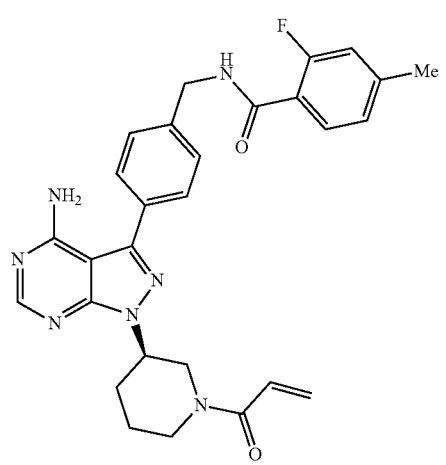

73
-continued
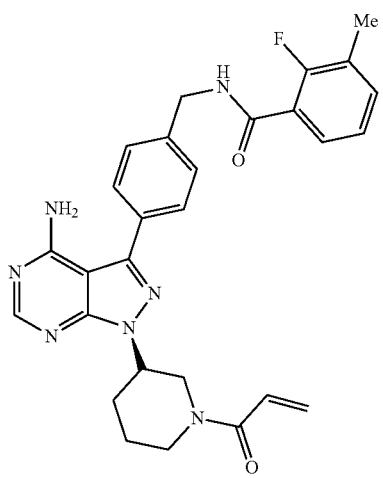
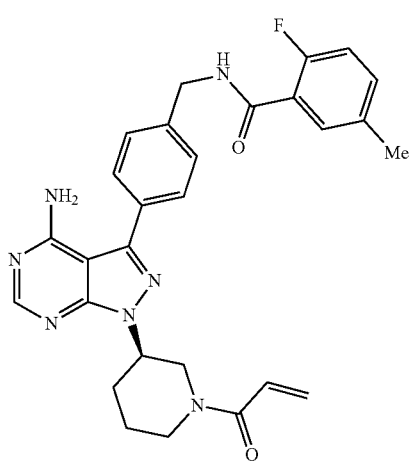
74
-continued
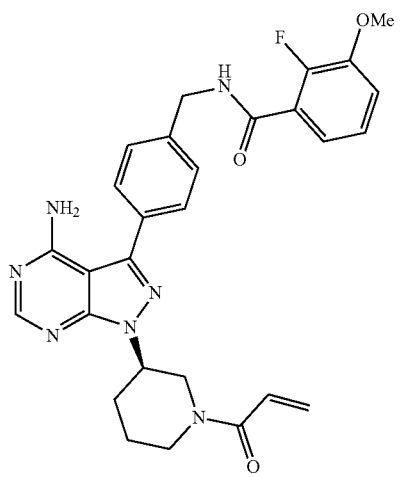
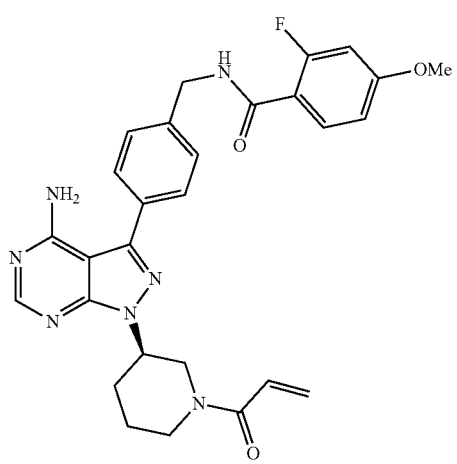

75
-continued
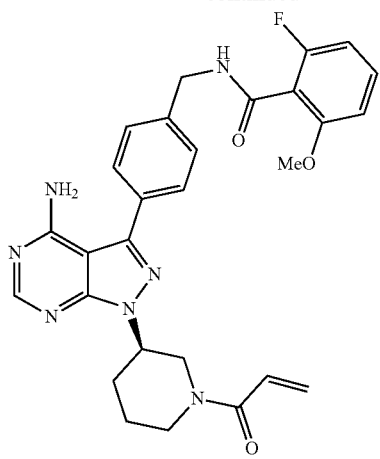
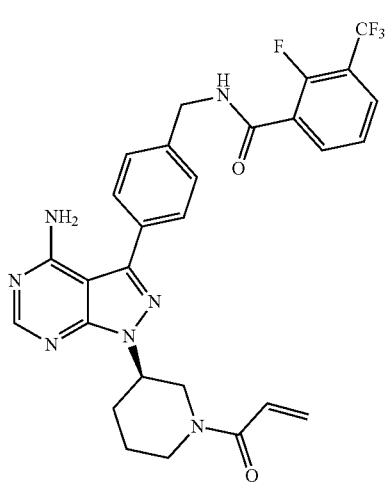
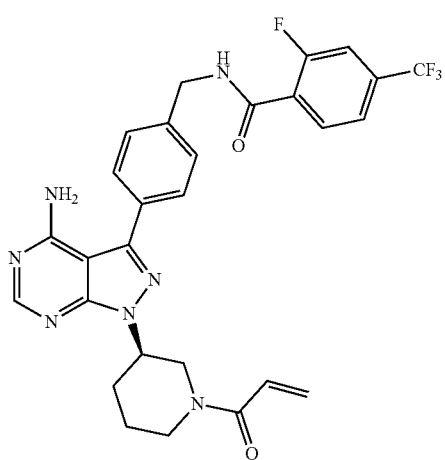
76
-continued
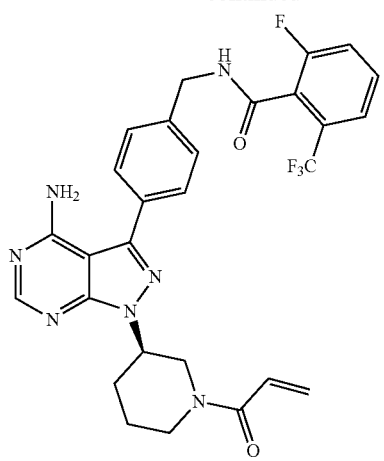
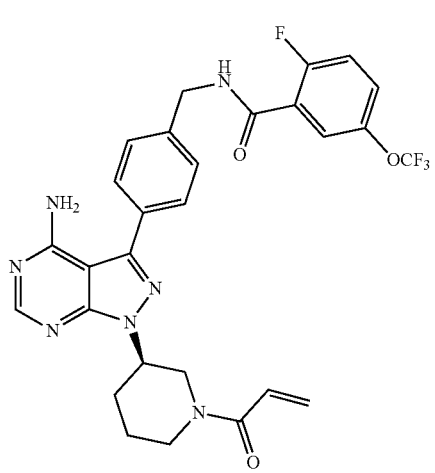
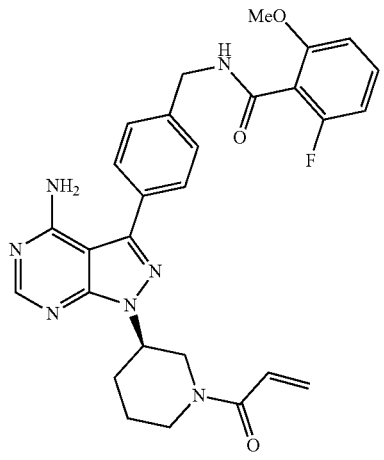

77
-continued
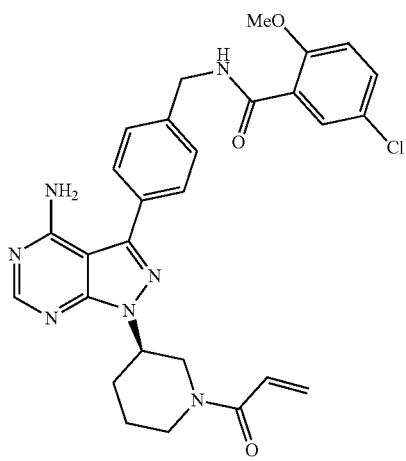
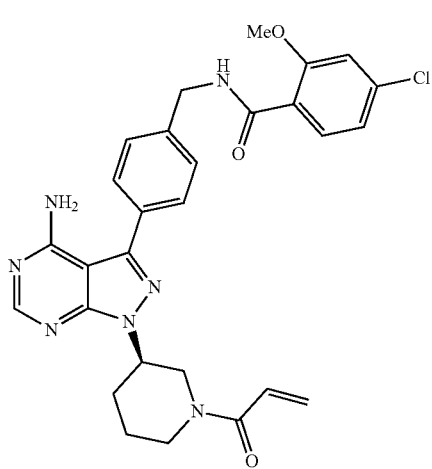
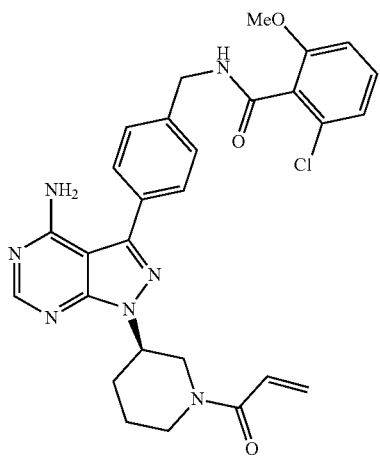
78
-continued
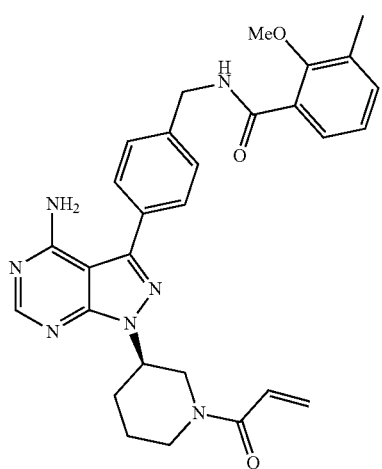
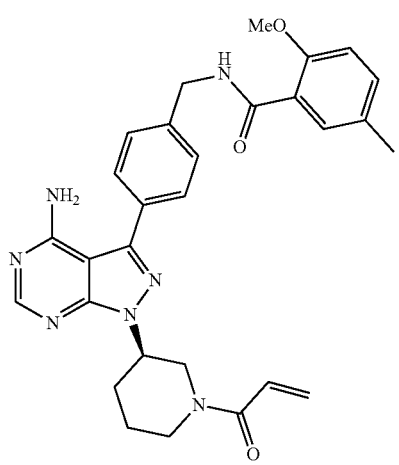
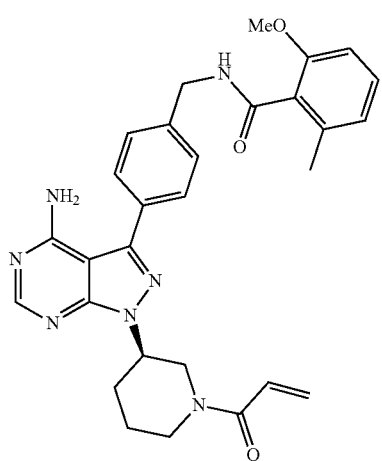

79
-continued
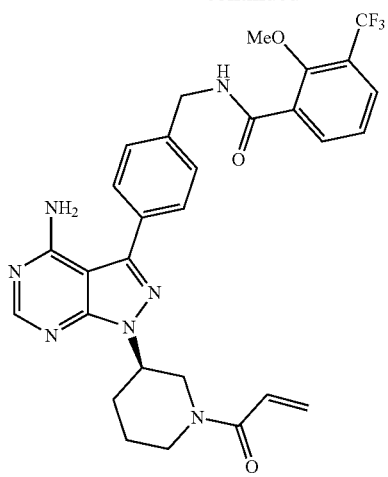
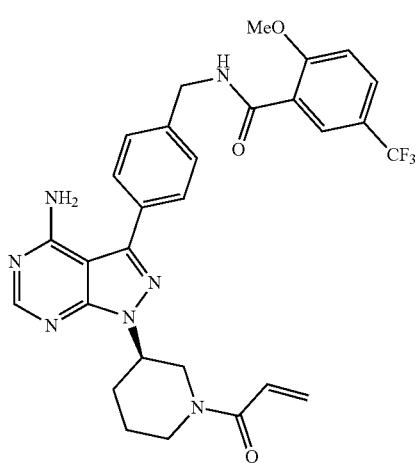
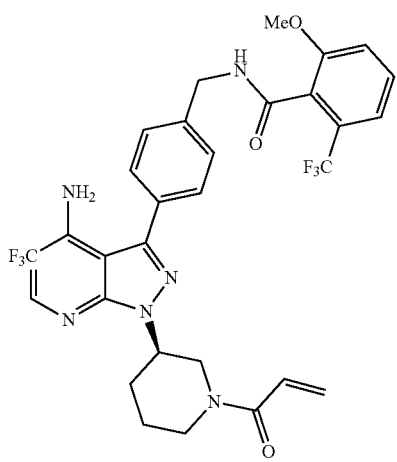
80
-continued
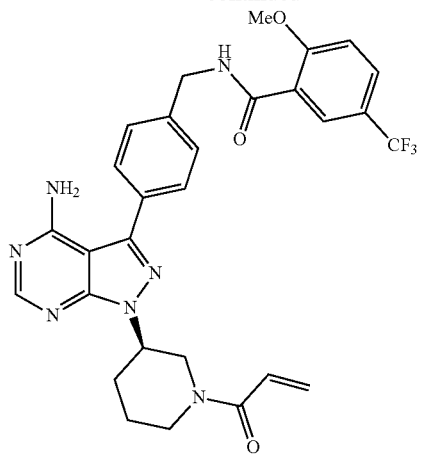
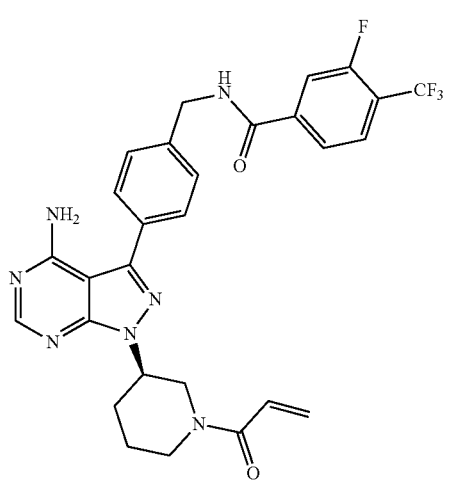
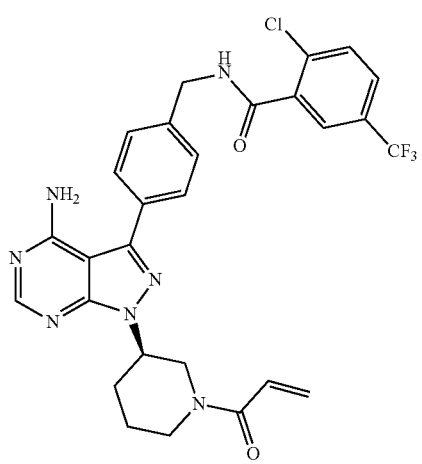

81
-continued
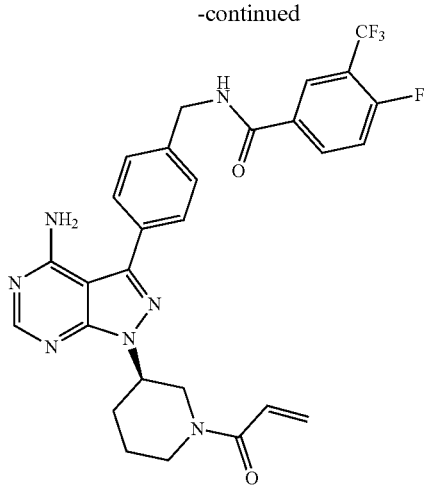
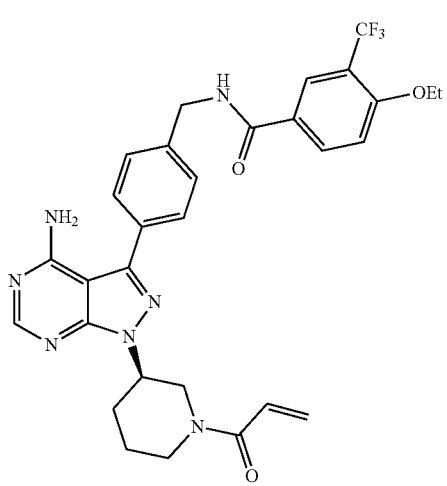
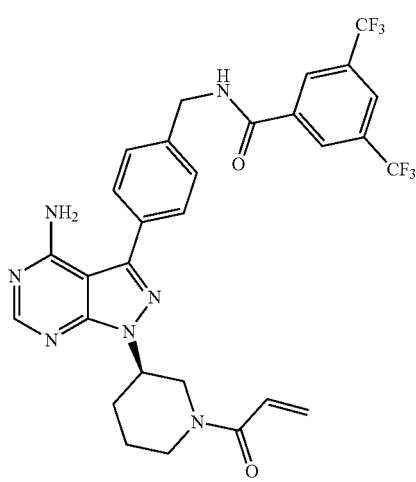
82
-continued
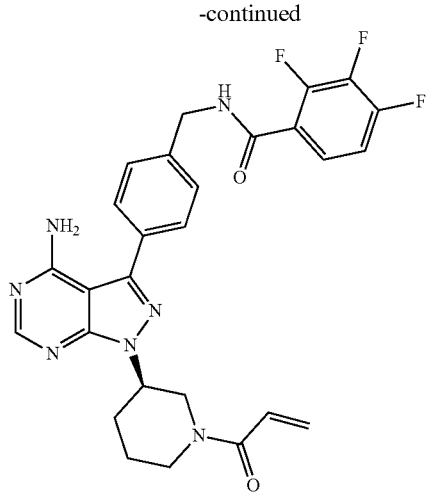
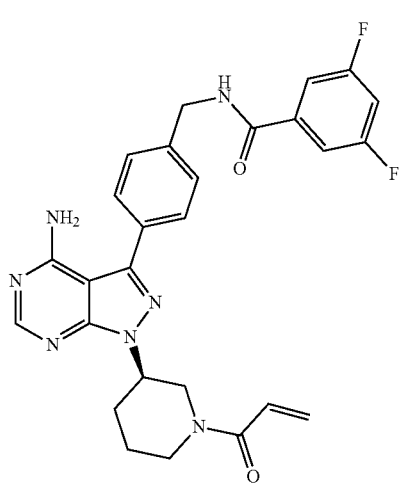
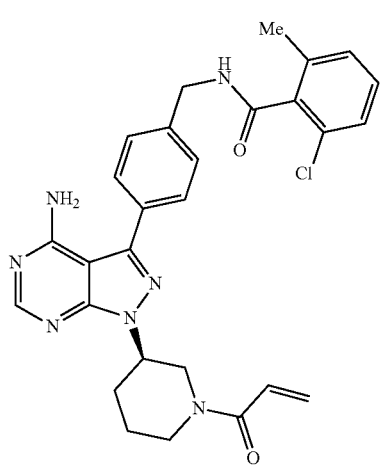

83
-continued
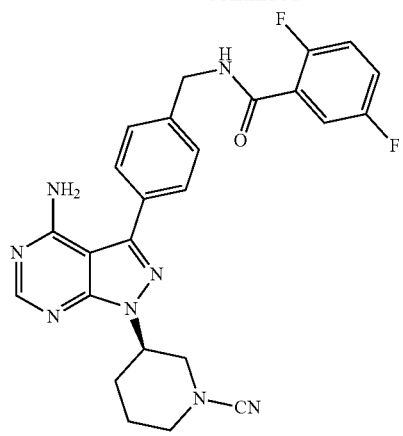
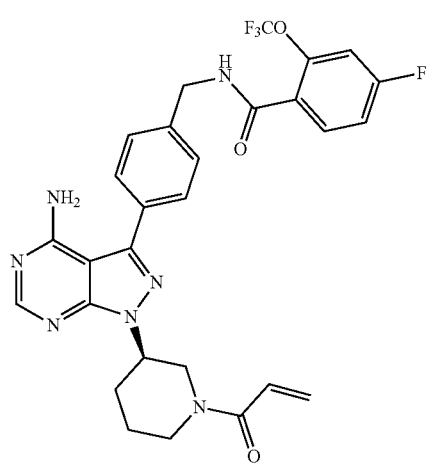
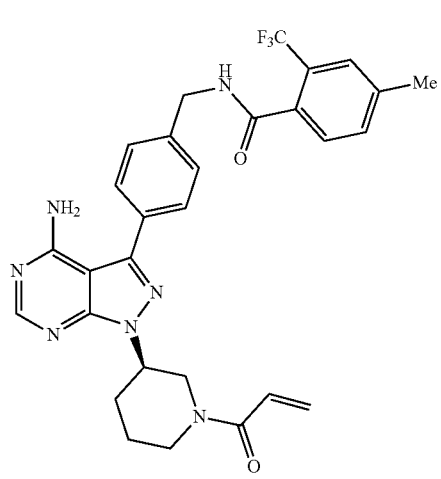
84
-continued
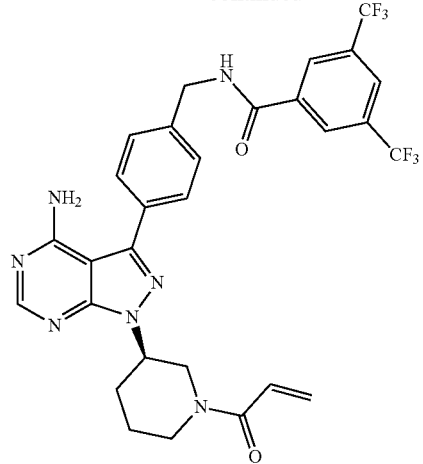
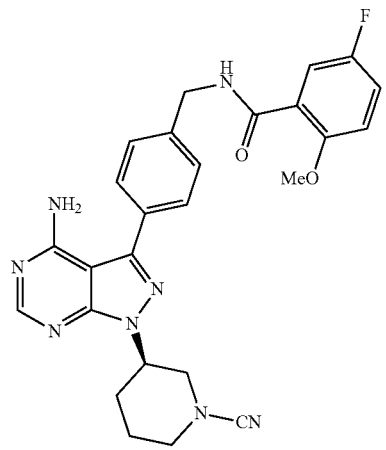
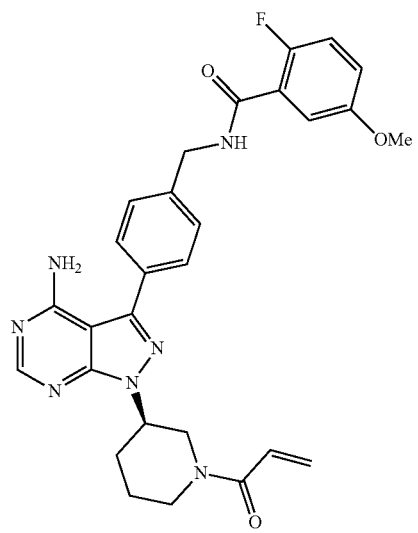

85
-continued
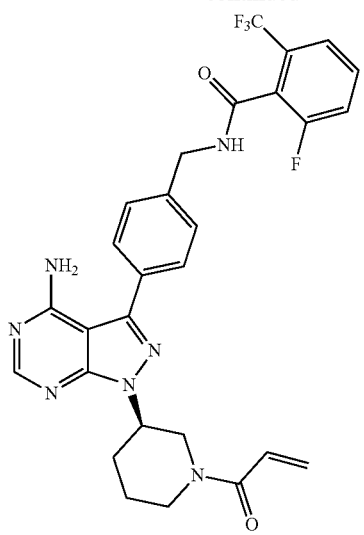
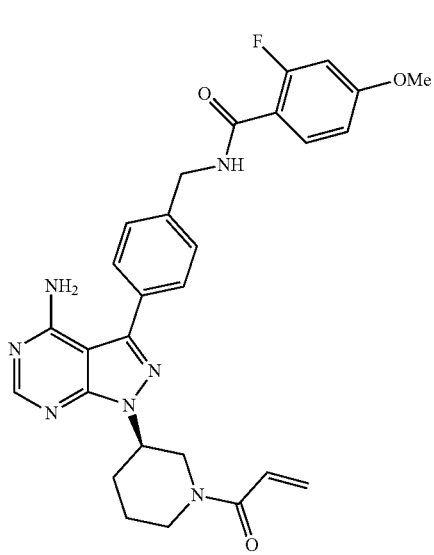
86
-continued
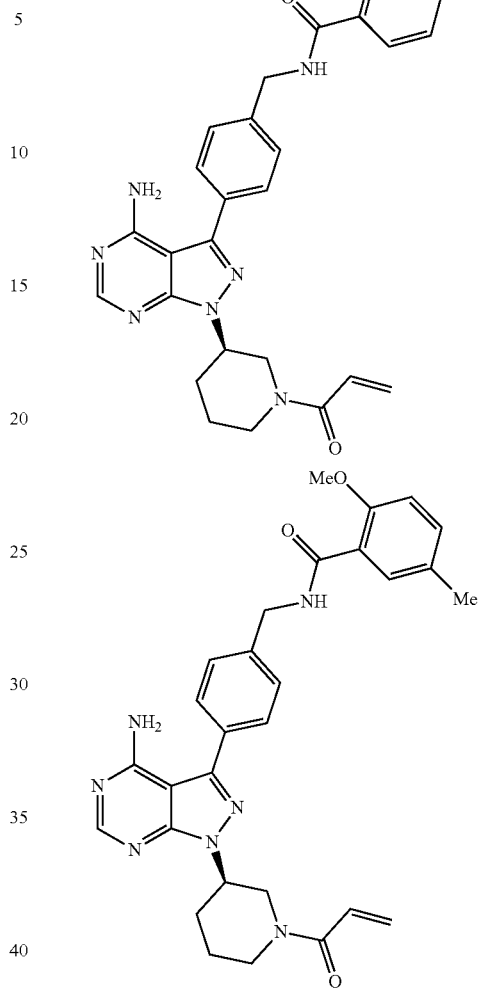
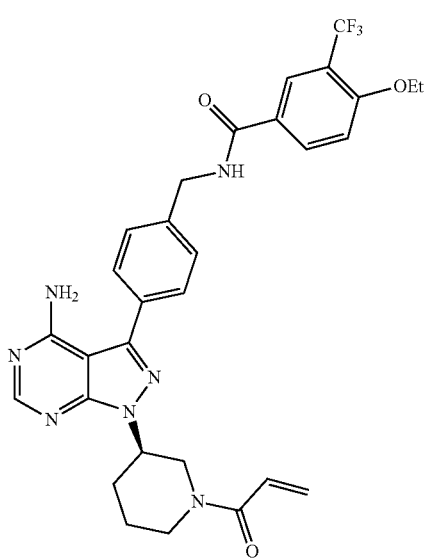

-continued
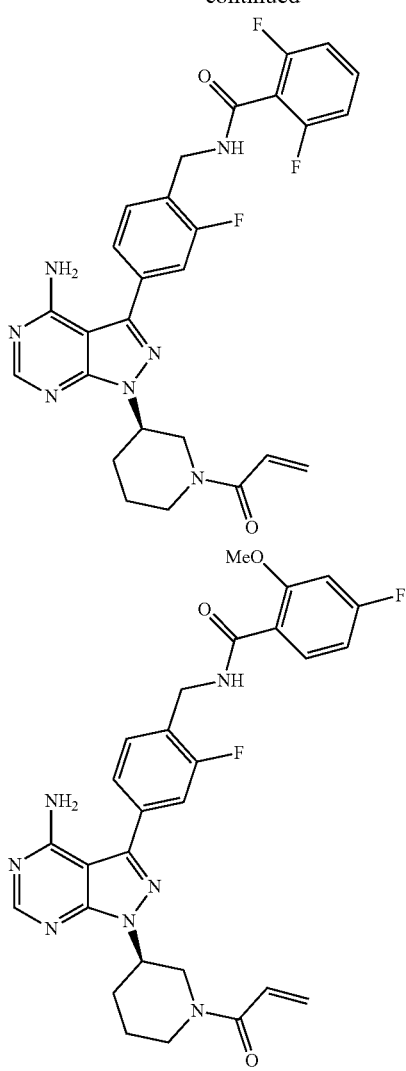
-continued
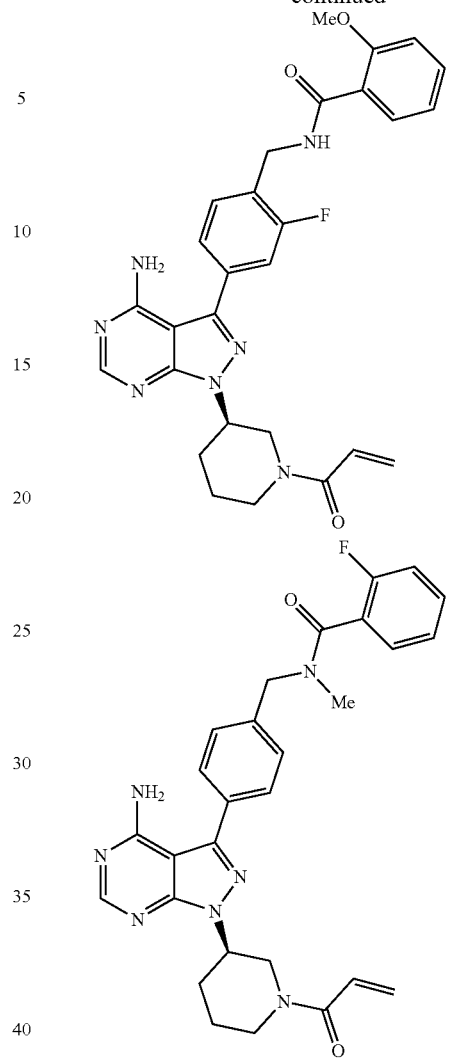
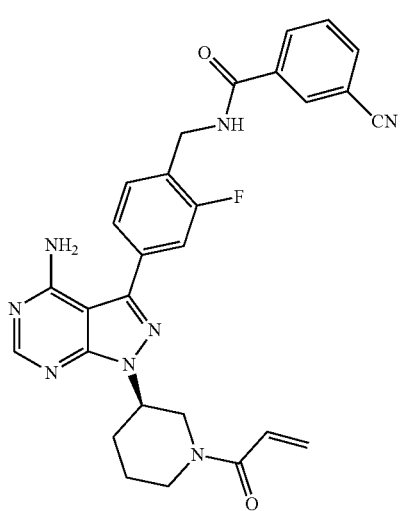
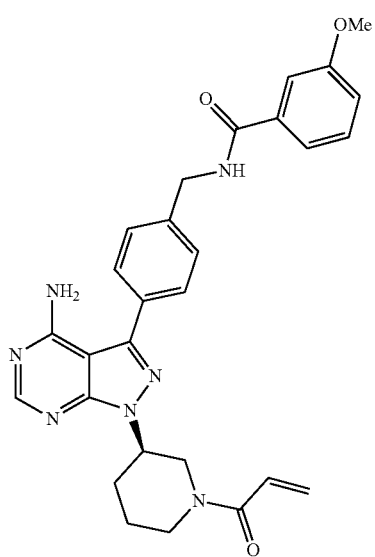

89
-continued
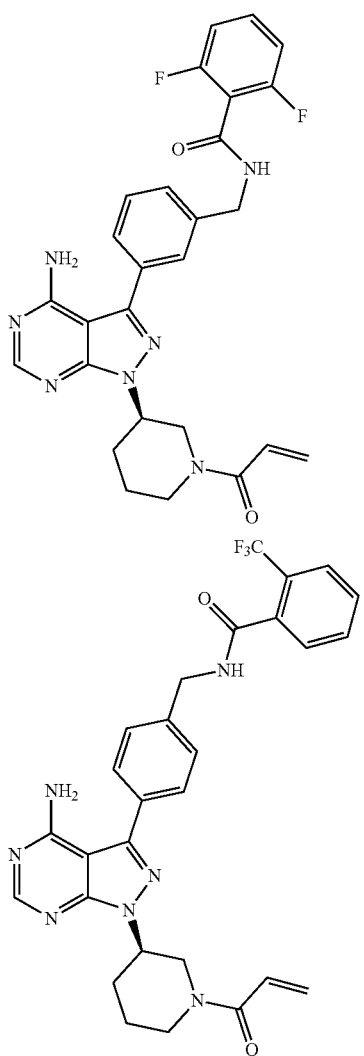
90
-continued
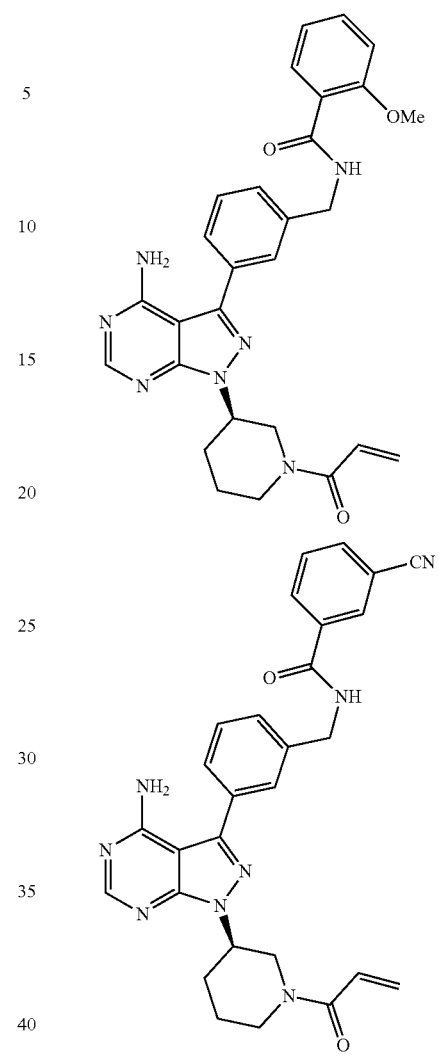
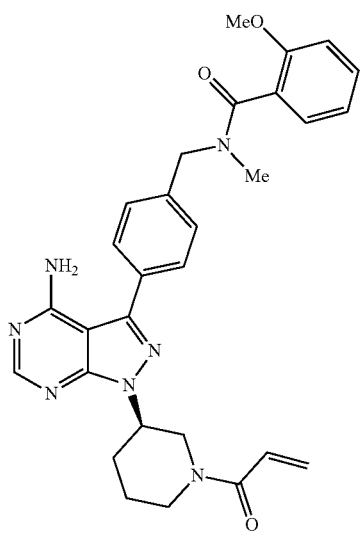
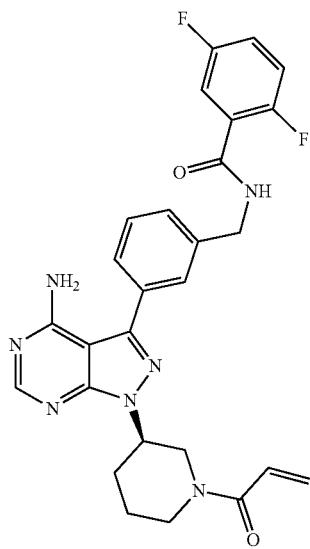

91
-continued
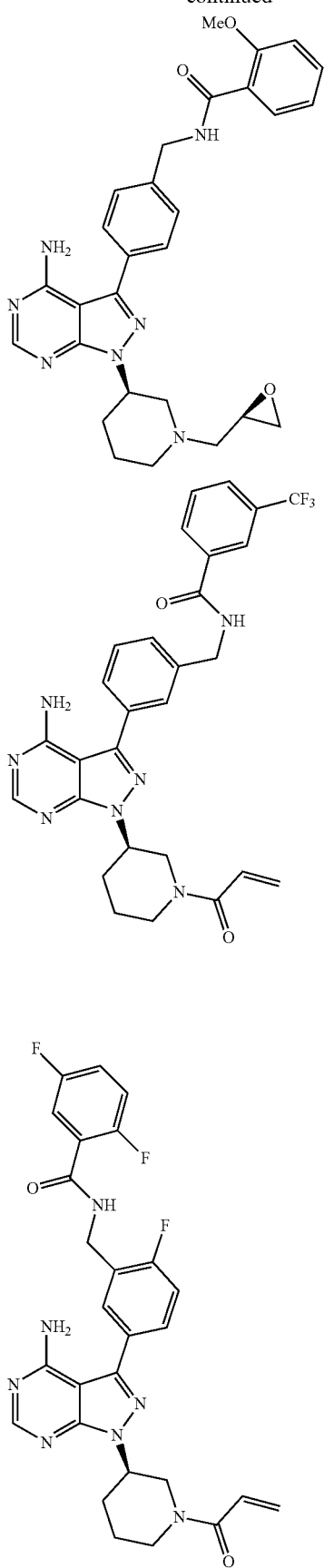
92
-continued
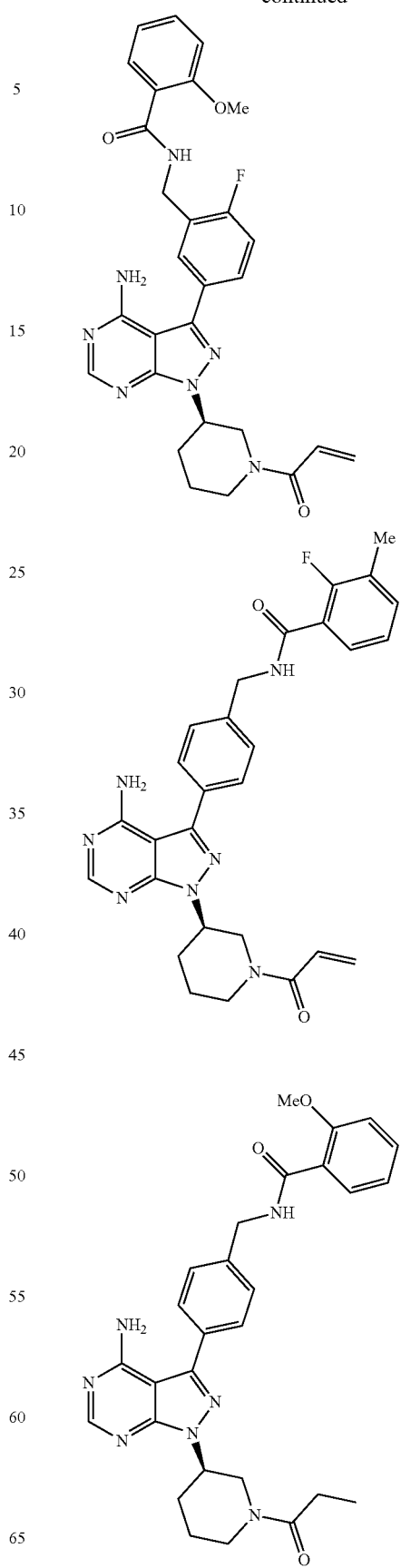

93
-continued
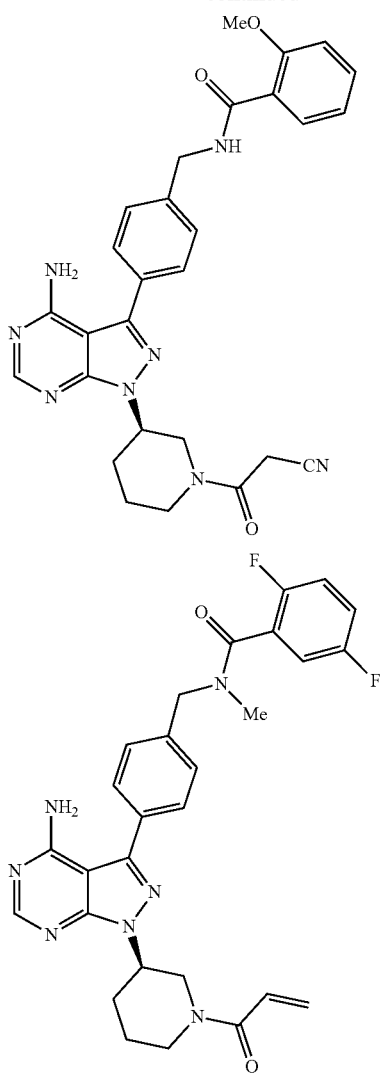
94
-continued
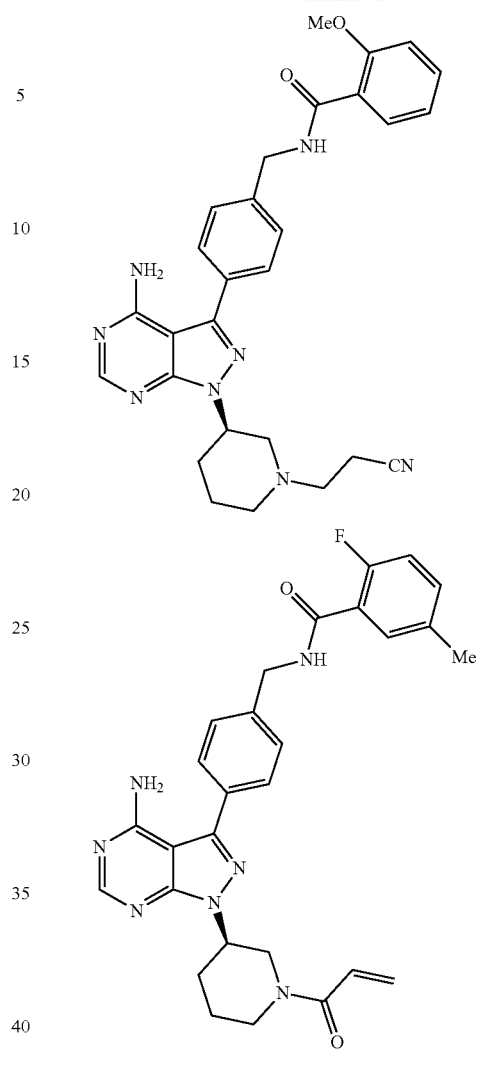
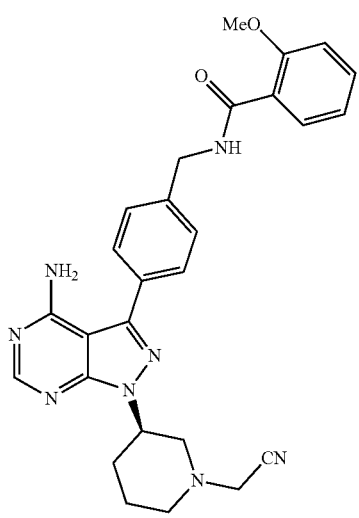
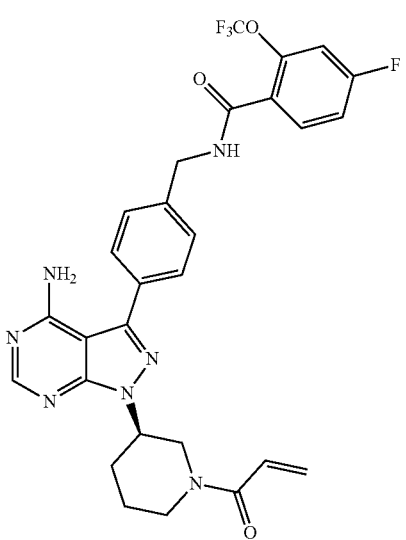

95
-continued
96
-continued
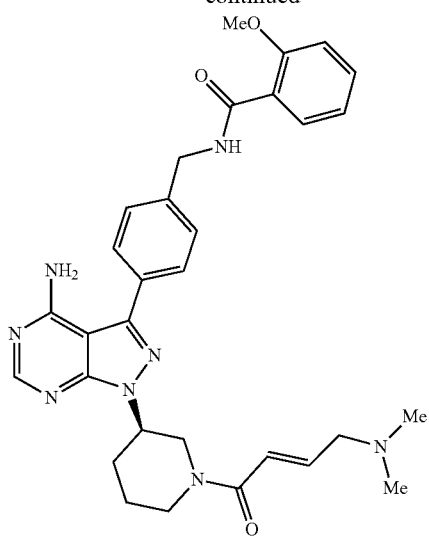
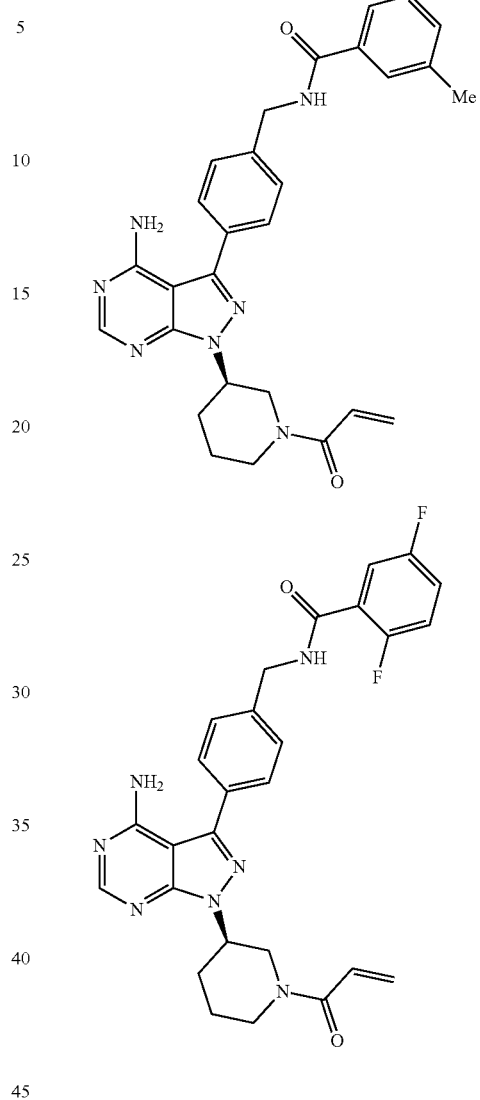
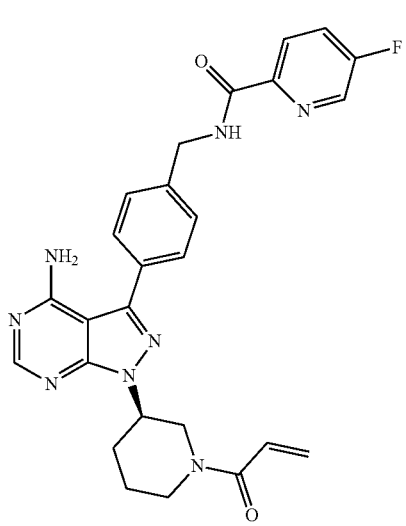
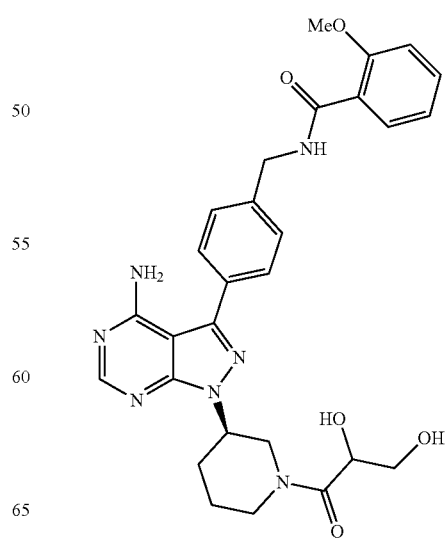

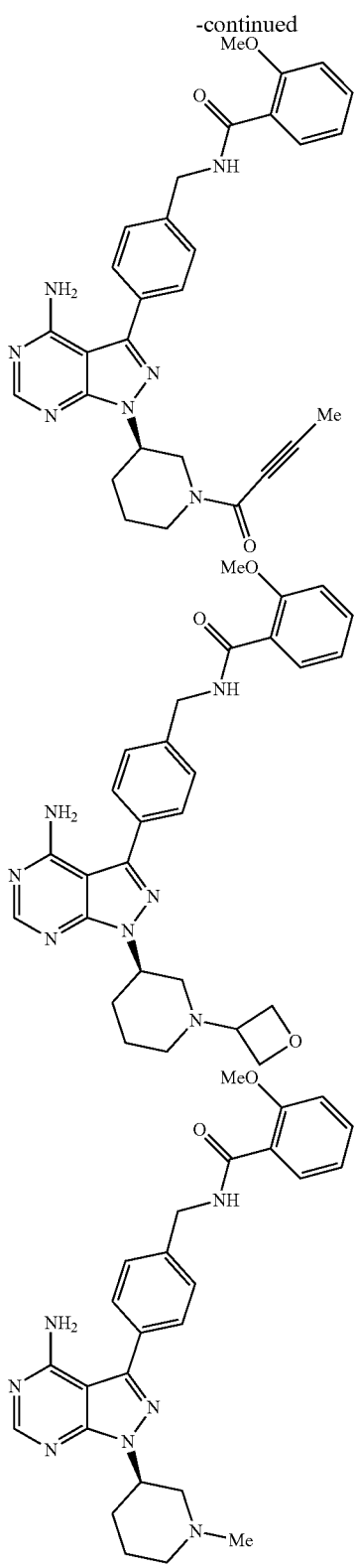

In another aspect of the invention there is provided a compound of formula (I) for use as a medicament.

In another aspect a compound of formula (I) is for use in the treatment of a condition which is modulated by Bruton's tyrosine kinase (BTK). Usually conditions that are modulated by BTK are conditions that would be treated by the inhibition of BTK using a compound of the present invention. A compound of formula (I) may be for use in the treatment of a condition treatable by the inhibition of Bruton's tyrosine kinase (BTK).

BTK inhibition is a novel approach for treating many different human diseases associated with the inappropriate activation of B-cells, including B-cell malignancies, immunological disease for example, autoimmune and inflammatory disorders. In embodiments the condition treatable by the inhibition of BTK may be selected from: cancer, lymphoma, leukemia, autoimmune diseases and inflammatory disorders. Specific conditions treatable by the inhibition of BTK may be selected from: B-cell malignancy, B-cell lymphoma, diffuse large B cell lymphoma, chronic lymphocyte leukemia, non-Hodgkin lymphoma for example ABC-DLBCL, mantle cell lymphoma, follicular lymphoma, hairy cell leukemia B-cell non-Hodgkin lymphoma, Waldenstrom's macroglobulinemia, multiple myeloma, bone cancer, bone metastasis, arthritis, multiple sclerosis osteoporosis, irritable bowel syndrome, inflammatory bowel disease, Crohn's disease and lupus.

B-cell malignancy, B-cell lymphoma, diffuse large B cell lymphoma, chronic lymphocyte leukemia, non-Hodgkin lymphoma for example ABC-DLBCL, mantle cell lymphoma, follicular lymphoma, hairy cell leukemia B-cell non-Hodgkin lymphoma, Waldenstrom's macroglobulinemia, multiple myeloma, bone cancer and bone metastasis are examples of cancer, lymphoma and leukemia treatable by BTK inhibition.

Arthritis, multiple sclerosis osteoporosis, irritable bowel syndrome, inflammatory bowel disease, Crohn's disease and lupus are examples of immunological diseases treatable by BTK inhibition. Arthritis is an example of an inflammatory disorder treatable by BTK inhibition. Lupus is an example of an autoimmune disease treatable by BTK inhibition.

In embodiments, a compound of the invention may be for use in the treatment of: cancer, lymphoma, leukemia, immunological diseases, autoimmune diseases and inflammatory disorders. The compound of the invention may be for use in the treatment of specific conditions selected from: B-cell malignancy, B-cell lymphoma, diffuse large B cell lymphoma, chronic lymphocyte leukemia, non-Hodgkin lymphoma for example ABC-DLBCL, mantle cell lymphoma, follicular lymphoma, hairy cell leukemia B-cell non-Hodgkin lymphoma, Waldenstrom's macroglobulinemia, multiple myeloma, bone cancer, bone metastasis, arthritis, multiple sclerosis osteoporosis, irritable bowel syndrome, inflammatory bowel disease, Crohn's disease and lupus. The compounds may also be used for the treatment of disorders associated with renal transplant.

In an embodiment the compound of the invention may be for use in the treatment of specific conditions selected from: B-cell malignancy, B-cell lymphoma, diffuse large B cell lymphoma, chronic lymphocyte leukemia, non-Hodgkin lymphoma for example ABC-DLBCL, mantle cell lymphoma, follicular lymphoma, hairy cell leukemia B-cell non-Hodgkin lymphoma, Waldenstrom's macroglobulinemia, multiple myeloma, lupus and arthritis.

In an aspect of the invention there is provided a method of treatment of a condition which is modulated by Bruton's tyrosine kinase, wherein the method comprises administering a therapeutic amount of a compound of the invention, to a patient in need thereof.

The method of treatment may be a method of treating a condition treatable by the inhibition of Bruton's tyrosine kinase.

The invention also provides a method of treating a condition selected from: cancer, lymphoma, leukemia, immunological diseases autoimmune diseases and inflammatory disorders, wherein the method comprises administering a therapeutic amount of a compound of the invention, to a patient in need thereof. The invention also provides a method of treating a specific condition selected from: B-cell malignancy, B-cell lymphoma, diffuse large B cell lymphoma, chronic lymphocyte leukemia, non-Hodgkin lymphoma for example ABC-DLBCL, mantle cell lymphoma, follicular lymphoma, hairy cell leukemia B-cell non-Hodgkin lymphoma, Waldenstrom's macroglobulinemia, multiple myeloma, bone cancer, bone metastasis, arthritis, multiple sclerosis osteoporosis, irritable bowel syndrome, inflammatory bowel disease, Crohn's disease and lupus, wherein the method comprises administering a therapeutic amount of a compound of formula (I), to a patient in need thereof. The method may also treat disorders associated with renal transplant.

In an embodiment the method may be for treating a specific condition selected from: B-cell malignancy, B-cell lymphoma, diffuse large B cell lymphoma, chronic lymphocyte leukemia, non-Hodgkin lymphoma for example ABC-DLBCL, mantle cell lymphoma, follicular lymphoma, hairy cell leukemia B-cell non-Hodgkin lymphoma, Waldenstrom's macroglobulinemia, multiple myeloma, arthritis and lupus.

In another aspect of the invention there is provided a pharmaceutical composition, wherein the composition comprises a compound of the invention and pharmaceutically acceptable excipients.

In an embodiment the pharmaceutical composition may be a combination product comprising an additional pharmaceutically active agent. The additional pharmaceutically active agent may be an anti-tumor agent described below.

DETAILED DESCRIPTION

Given below are definitions of terms used in this application. Any term not defined herein takes the normal meaning as the skilled person would understand the term.

The term "halo" refers to one of the halogens, group 17 of the periodic table. In particular the term refers to fluorine, chlorine, bromine and iodine. Preferably, the term refers to fluorine or chlorine.

The term "$C_{1-6}$ alkyl" refers to a linear or branched hydrocarbon chain containing 1, 2, 3, 4, 5 or 6 carbon atoms, for example methyl, ethyl, n-propyl, iso-propyl, n-butyl, sec-butyl, tert-butyl, n-pentyl and n-hexyl. Alkylene groups may likewise be linear or branched and may have two places of attachment to the remainder of the molecule. Furthermore, an alkylene group may, for example, correspond to one of those alkyl groups listed in this paragraph. The alkyl and alkylene groups may be unsubstituted or substituted by one or more substituents. Possible substituents are described below. Substituents for the alkyl group may be halogen, e.g. fluorine, chlorine, bromine and iodine, OH, $C_{1-6}$ alkoxy.

The term "$C_{1-6}$ alkoxy" refers to an alkyl group which is attached to a molecule via oxygen. This includes moieties where the alkyl part may be linear or branched and may contain 1, 2, 3, 4, 5 or 6 carbon atoms, for example methyl, ethyl, n-propyl, iso-propyl, n-butyl, sec-butyl, tert-butyl, n-pentyl and n-hexyl. Therefore, the alkoxy group may be methoxy, ethoxy, n-propoxy, iso-propoxy, n-butoxy, sec-butoxy, tert-butoxy, n-pentoxy and n-hexoxy. The alkyl part of the alkoxy group may be unsubstituted or substituted by one or more substituents. Possible substituents are described below. Substituents for the alkyl group may be halogen, e.g. fluorine, chlorine, bromine and iodine, OH, $C_{1-6}$ alkoxy.

The term "$C_{1-6}$ haloalkyl" refers to a hydrocarbon chain substituted with at least one halogen atom independently chosen at each occurrence, for example fluorine, chlorine, bromine and iodine. The halogen atom may be present at any position on the hydrocarbon chain. For example, $C_{1-6}$ haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl.

The term "$C_{2-6}$ alkenyl" refers to a branched or linear hydrocarbon chain containing at least one double bond and having 2, 3, 4, 5 or 6 carbon atoms. The double bond(s) may be present as the E or Z isomer. The double bond may be at any possible position of the hydrocarbon chain. For example, the "$C_{2-6}$ alkenyl" may be ethenyl, propenyl, butenyl, butadienyl, pentenyl, pentadienyl, hexenyl and hexadienyl.

The term "$C_{2-6}$ alkynyl" refers to a branded or linear hydrocarbon chain containing at least one triple bond and having 2, 3, 4, 5 or 6 carbon atoms. The triple bond may be at any possible position of the hydrocarbon chain. For example, the "$C_{2-6}$ alkynyl" may be ethynyl, propynyl, butynyl, pentynyl and hexynyl.

The term "$C_{1-6}$ heteroalkyl" refers to a branded or linear hydrocarbon chain containing 1, 2, 3, 4, 5, or 6 carbon atoms and at least one heteroatom selected from N, O and S positioned between any carbon in the chain or at an end of the chain. For example, the hydrocarbon chain may contain one or two heteroatoms. The $C_{1-6}$ heteroalkyl may be bonded to the rest of the molecule through a carbon or a heteroatom. For example, the "$C_{1-6}$ heteroalkyl" may be $C_{1-6}$ N-alkyl, $C_{1-6}$ N,N-alkyl, or $C_{1-6}$ O-alkyl.

The term "carbocyclic" refers to a saturated or unsaturated carbon containing ring system. A "carbocyclic" system may be monocyclic or a fused polycyclic ring system, for example, bicyclic or tricyclic. A "carbocyclic" moiety may contain from 3 to 14 carbon atoms, for example, 3 to 8 carbon atoms in a monocyclic system and 7 to 14 carbon atoms in a polycyclic system. "Carbocyclic" encompasses cycloalkyl moieties, cycloalkenyl moieties, aryl ring systems and fused ring systems including an aromatic portion.

The term "heterocyclic" refers to a saturated or unsaturated ring system containing at least one heteroatom selected from N, O or S. A "heterocyclic" system may contain 1, 2, 3 or 4 heteroatoms, for example 1 or 2. A "heterocyclic" system may be monocyclic or a fused polycyclic ring system, for example, bicyclic or tricyclic. A "heterocyclic" moiety may contain from 3 to 14 carbon atoms, for example, 3 to 8 carbon atoms in a monocyclic system and 7 to 14 carbon atoms in a polycyclic system. "Heterocyclic" encompasses heterocycloalkyl moieties, heterocycloalkenyl moieties and heteroaromatic moieties. For example, the heterocyclic group may be: oxirane, aziridine, azetidine, oxetane, tetrahydrofuran, pyrrolidine, imidazolidine, succinimide, pyrazolidine, oxazolidine, isoxazolidine, thiazolidine, isothiazolidine, piperidine, morpholine, thiomorpholine, piperazine, and tetrahydropyran.

The term "$C_{3-8}$ cycloalkyl" refers to a saturated hydrocarbon ring system containing 3, 4, 5, 6, 7 or 8 carbon atoms. For example, the "$C_{3-8}$ cycloalkyl" may be cyclopropyl, cyclobutyl, cyclopentyl, cyclohexyl, cycloheptyl and cyclooctyl.

The term "$C_{3-8}$ cycloalkenyl" refers to an unsaturated hydrocarbon ring system containing 3, 4, 5, 6, 7 or 8 carbon atoms that is not aromatic. The ring may contain more than one double bond provided that the ring system is not aromatic. For example, the "$C_{3-8}$ cycloalkyl" may be cyclopropenyl, cyclobutenyl, cyclopentenyl, cyclopentadienyl, cyclohexenyl, cyclohexadienly, cycloheptenyl, cycloheptadiene, cyclooctenyl and cycloatadienyl.

The term "$C_{3-8}$ heterocycloalkyl" refers to a saturated hydrocarbon ring system containing 3, 4, 5, 6, 7 or 8 carbon atoms and at least one heteroatom within the ring selected from N, O and S. For example there may be 1, 2 or 3 heteroatoms, optionally 1 or 2. The "$C_{3-8}$ heterocycloalkyl" may be bonded to the rest of the molecule through any carbon atom or heteroatom. The "$C_{3-8}$ heterocycloalkyl" may have one or more, e.g. one or two, bonds to the rest of the molecule: these bonds may be through any of the atoms in the ring. For example, the "$C_{3-8}$ heterocycloalkyl" may be oxirane, aziridine, azetidine, oxetane, tetrahydrofuran, pyrrolidine, imidazolidine, succinimide, pyrazolidine, oxazolidine, isoxazolidine, thiazolidine, isothiazolidine, piperidine, morpholine, thiomorpholine, piperazine, and tetrahydropyran.

The term "$C_{3-8}$ heterocycloalkenyl" refers to an unsaturated hydrocarbon ring system, that is not aromatic, containing 3, 4, 5, 6, 7 or 8 carbon atoms and at least one heteroatom within the ring selected from N, O and S. For example there may be 1, 2 or 3 heteroatoms, optionally 1 or 2. The "$C_{3-8}$ heterocycloalkenyl" may be bonded to the rest of the molecule through any carbon atom or heteroatom. The "$C_{3-8}$ heterocycloalkenyl" may have one or more, e.g. one or two, bonds to the rest of the molecule: these bonds may be through any of the atoms in the ring. For example, the "$C_{3-8}$ heterocycloalkyl" may be tetrahydropyridine, dihydropyran, dihydrofuran, pyrroline.

The term "aromatic" when applied to a substituent as a whole means a single ring or polycyclic ring system with 4n+2 electrons in a conjugated π system within the ring or ring system where all atoms contributing to the conjugated π system are in the same plane.

The term "aryl" refers to an aromatic hydrocarbon ring system. The ring system has 4n+2 electrons in a conjugated π system within a ring where all atoms contributing to the conjugated π system are in the same plane. For example, the "aryl" may be phenyl and naphthyl. The aryl system itself may be substituted with other groups.

The term "heteroaryl" refers to an aromatic hydrocarbon ring system with at least one heteroatom within a single ring or within a fused ring system, selected from O, N and S. The ring or ring system has 4n+2 electrons in a conjugated π system where all atoms contributing to the conjugated π system are in the same plane. For example, the "heteroaryl" may be imidazole, thiene, furane, thianthrene, pyrrol, benzimidazole, pyrazole, pyrazine, pyridine, pyrimidine and indole.

The term "alkaryl" refers to an aryl group, as defined above, bonded to a $C_{1-4}$ alkyl, where the $C_{1-4}$ alkyl group provides attachment to the remainder of the molecule.

The term "alkheteroaryl" refers to a heteroaryl group, as defined above, bonded to a $C_{1-4}$ alkyl, where the alkyl group provides attachment to the remainder of the molecule.

The term "halogen" herein includes reference to F, Cl, Br and I. Halogen may be Cl. Halogen may be F.

When —$NR^b$— is bonded to the carbocyclic or heterocyclic ring of D, the group E is bonded directly to —$NR^b$—.

A bond terminating in a "⌇" represents that the bond is connected to another atom that is not shown in the structure. A bond terminating inside a cyclic structure and not terminating at an atom of the ring structure represents that the bond may be connected to any of the atoms in the ring structure where allowed by valency.

Where a moiety is substituted, it may be substituted at any point on the moiety where chemically possible and consistent with atomic valency requirements. The moiety may be substituted by one or more substituents, e.g. 1, 2, 3 or 4 substituents; optionally there are 1 or 2 substituents on a group. Where there are two or more substituents, the substituents may be the same or different. The substituent(s) may be selected from: OH, $NHR^9$, amidino, guanidino, hydroxyguanidino, formamidino, isothioureido, ureido, mercapto, C(O)H, acyl, acyloxy, carboxy, sulfo, sulfamoyl, carbamoyl, cyano, azo, nitro, halo, $C_{1-6}$ alkyl, $C_{1-6}$ alkoxy, $C_{1-6}$ haloalkyl, $C_{3-8}$ cycloalkyl, $C_{2-6}$ alkenyl, $C_{2-6}$ alkynyl, aryl, heteroaryl or alkaryl. Where the group to be substituted is an alkyl group the substituent may be =O. Where the moiety is substituted with two or more substituents and two of the substituents are adjacent the adjacent substituents may form a $C_{4-8}$ ring along with the atoms of the moiety on which the substituents are substituted, wherein the $C_{4-8}$ ring is a saturated or unsaturated hydrocarbon ring with 4, 5, 6, 7, or 8 carbon atoms or a saturated or unsaturated hydrocarbon ring with 4, 5, 6, 7, or 8 carbon atoms and 1, 2 or 3 heteroatoms.

Substituents are only present at positions where they are chemically possible, the person skilled in the art being able to decide (either experimentally or theoretically) without inappropriate effort which substitutions are chemically possible and which are not.

Ortho, meta and para substitution are well understood terms in the art. For the absence of doubt, "ortho" substitution is a substitution pattern where adjacent carbons possess a substituent, whether a simple group, for example the fluoro group in the example below, or other portions of the molecule, as indicated by the bond ending in "⌇".

"Meta" substitution is a substitution pattern where two substituents are on carbons one carbon removed from each other, i.e. with a single carbon atom between the substituted carbons. In other words there is a substituent on the second atom away from the atom with another substituent. For example the groups below are meta substituted.

"Para" substitution is a substitution pattern where two substituents are on carbons two carbons removed from each other, i.e. with two carbon atoms between the substituted carbons. In other words there is a substituent on the third atom away from the atom with another substituent. For example the groups below are para substituted.

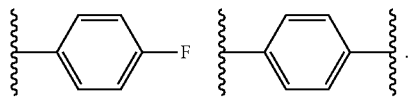

By "acyl" is meant an organic radical derived from, for example, an organic acid by the removal of the hydroxyl group, e.g. a radical having the formula R—C(O)—, where R may be selected from H, $C_{1-6}$ alkyl, $C_{3-8}$ cycloalkyl, phenyl, benzyl or phenethyl group, e.g. R is H or $C_{1-3}$ alkyl. In one embodiment acyl is alkyl-carbonyl. Examples of acyl groups include, but are not limited to, formyl, acetyl, propionyl and butyryl. A particular acyl group is acetyl.

Throughout the description the disclosure of a compound also encompasses pharmaceutically acceptable salts, solvates and stereoisomers thereof. Where a compound has a stereocentre, both (R) and (S) stereoisomers are contemplated by the invention, equally mixtures of stereoisomers or a racemic mixture are completed by the present application. Where a compound of the invention has two or more stereocentres any combination of (R) and (S) stereoisomers is contemplated. The combination of (R) and (S) stereoisomers may result in a diastereomeric mixture or a single diastereoisomer. The compounds of the invention may be present as a single stereoisomer or may be mixtures of stereoisomers, for example racemic mixtures and other enantiomeric mixtures, and diastereomeric mixtures. Where the mixture is a mixture of enantiomers the enantiomeric excess may be any of those disclosed above. Where the compound is a single stereoisomer the compounds may still contain other diastereoisomers or enantiomers as impurities. Hence a single stereoisomer does not necessarily have an enantiomeric excess (e.e.) or diastereomeric excess (d.e.) of 100% but could have an e.e. or d.e. of about at least 85%

The invention contemplates pharmaceutically acceptable salts of the compounds of formula (I). These may include the acid addition and base salts of the compounds. These may be acid addition and base salts of the compounds. In addition the invention contemplates solvates of the compounds. These may be hydrates or other solvated forms of the compound.

Suitable acid addition salts are formed from acids which form non-toxic salts. Examples include the acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) or by ring-opening a suitable cyclic precursor, for example, a lactone or lactam, using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of any formula include references to salts, solvates and complexes thereof and to solvates and complexes of salts thereof.

The compounds of the invention include compounds of a number of formula as herein defined, including all polymorphs and crystal habits thereof, prodrugs and isomers thereof (including optical, geometric and tautomeric isomers) as hereinafter defined and isotopically-labeled compounds of the invention.

Before purification, the compounds of the present invention may exist as a mixture of enantiomers depending on the synthetic procedure used. The enantiomers can be separated by conventional techniques known in the art. Thus the invention covers individual enantiomers as well as mixtures thereof.

For some of the steps of the process of preparation of the compounds of formula (I), it may be necessary to protect potential reactive functions that are not wished to react, and to cleave said protecting groups in consequence. In such a case, any compatible protecting radical can be used. In particular methods of protection and deprotection such as those described by T. W. GREENE (Protective Groups in Organic Synthesis, A. Wiley-Interscience Publication, 1981) or by P. J. Kocienski (Protecting groups, Georg Thieme Verlag, 1994), can be used. All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

Also, the compounds of the present invention as well as intermediates for the preparation thereof can be purified according to various well-known methods, such as for example crystallization or chromatography.

The method of treatment or the compound for use in the treatment of cancer, lymphoma, leukemia or immunological diseases as defined hereinbefore may be applied as a sole therapy or be a combination therapy with an additional active agent.

The method of treatment or the compound for use in the treatment of cancer, lymphoma or leukemia may involve, in addition to the compound of the invention, conventional surgery or radiotherapy or chemotherapy. Such chemotherapy may include one or more of the following categories of anti-tumor agents:

(i) antiproliferative/antineoplastic drugs and combinations thereof, such as alkylating agents (for example cisplatin, oxaliplatin, carboplatin, cyclophosphamide, nitrogen mustard, bendamustin, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, pemetrexed, cytosine arabinoside, and hydroxyurea); antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); proteasome inhibitors, for example carfilzomib and bortezomib; interferon therapy; and topoisomerase inhibitors (for example epipodophyllotoxins like etoposide and teniposide, amsacrine, topotecan, mitoxantrone and camptothecin);

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents, for example dasatinib and bosutinib (SKI-606), and metalloproteinase inhibitors, inhibitors of urokinase plasminogen activator receptor function or antibodies to Heparanase;

(iv) inhibitors of growth factor function: for example such inhibitors include growth factor antibodies and growth factor receptor antibodies, for example the anti-erbB2 antibody trastuzumab [Herceptin™], the anti-EGFR antibody panitumumab, the anti-erbB1 antibody cetuximab, tyrosine kinase inhibitors, for example inhibitors of the epidermal growth factor family (for example EGFR family tyrosine kinase inhibitors such as gefitinib, erlotinib and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib, tipifarnib and lonafarnib), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor, kinase inhibitors; aurora kinase inhibitors and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™); thalidomide; lenalidomide; and for example, a VEGF receptor tyrosine kinase inhibitor such as vandetanib, vatalanib, sunitinib, axitinib and pazopanib;

(vi) gene therapy approaches, including for example approaches to replace aberrant genes such as aberrant p53 or aberrant BRCA1 or BRCA2;

(vii) immunotherapy approaches, including for example antibody therapy such as alemtuzumab, rituximab, ibritumomab tiuxetan (Zevalin®) and ofatumumab; interferons such as interferon α; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); and toll-like receptor modulators for example TLR-7 or TLR-9 agonists; and (viii) cytotoxic agents for example fludaribine (fludara), cladribine, pentostatin (Nipent™);

(ix) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;

(x) targeted therapies, for example PI3Kd inhibitors, for example idelalisib and perifosine.

The method of treatment or the compound for use in the treatment of immunological diseases may involve, in addition to the compound of the invention, additional active agents. The additional active agents may be one or more active agents used to treat the condition being treated by the compound of formula (I) and additional active agent. The additional active agents may include one or more of the following active agents:

(i) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;

(ii) TNF inhibitors for example etanercept; monoclonal antibodies (e.g. infliximab (Remicade), adalimumab (Humira), certolizumab pegol (Cimzia), golimumab (Simponi)); fusion proteins (e.g. etanercept (Enbrel)); and 5-HT$_{2A}$ agonists (e.g. 2,5-dimethoxy-4-iodoamphetamine, TCB-2, lysergic acid diethylamide (LSD), lysergic acid dimethylazetidide);

(iii) anti-inflammatory drugs, for example non-steroidal anti-inflammatory drugs;

(iv) dihydrofolate reductase inhibitors/antifolates, for example methotrexate, trimethoprim, brodimoprim, tetroxoprim, iclaprim, pemetrexed, ralitrexed and pralatrexate; and (v) immunosuppressants for example cyclosporins, tacrolimus, sirolimus pimecrolimus, angiotensin II inhibitors (e.g. Valsartan, Telmisartan, Losartan, Irbesatan, Azilsartan, Olmesartan, Candesartan, Eprosartan) and ACE inhibitors e.g. sulfhydryl-containing agents (e.g. Captopril, Zofenopril), dicarboxylate-containing agents (e.g. Enalapril, Ramipril, Quinapril, Perindopril, Lisinopril, Benazepril, Imidapril, Zofenopril, Trandolapril), phosphate-containing agents (e.g. Fosinopril), casokinins, lactokinins and lactotripeptides.

Such combination treatment may be achieved by way of the simultaneous, sequential or separate dosing of the individual components of the treatment. Such combination products employ the compounds of this invention within a therapeutically effective dosage range described hereinbefore and the other pharmaceutically-active agent within its approved dosage range.

According to a further aspect of the invention there is provided a pharmaceutical product comprising a compound of formula (I), or a pharmaceutically acceptable salt thereof as defined hereinbefore and an additional active agent. The additional active agent may be an anti-tumour agent as defined hereinbefore for the combination treatment of a condition modulated by BTK.

According to a further aspect of the invention there is provided a method of treatment a condition modulated by BTK comprising administering a therapeutically effective amount of a compound of formula (I), or a pharmaceutically acceptable salt thereof simultaneously, sequentially or separately with an additional anti-tumor agent, as defined hereinbefore, to a patient in need thereof.

According to a further aspect of the invention there is provided a compound of formula (I), or a pharmaceutically acceptable salt thereof for use simultaneously, sequentially or separately with an additional anti-tumour agent as defined hereinbefore, in the treatment of a condition modulated by BTK.

According to another aspect of the invention there is provided a use of the compound of formula (I) in combination with an anti-tumor agent as hereinbefore described. The compound of formula (I) may be used simultaneously, sequentially or separately with the additional anti-tumor agent The use may be in a single combination product comprising the compound of formula (I) and the anti-tumor agent.

According to a further aspect there is provided a method of providing a combination product, wherein the method comprises providing a compound of formula (I) simultaneously, sequentially or separately with an anti-tumor agent, as defined hereinbefore. The method may comprise combining the compound of formula (I) and the anti-tumor agent in a single dosage form. Alternatively the method may comprise providing the anti-tumor agent as separate dosage forms.

According to a further aspect there is provided a method of providing a combination product, wherein the method comprises providing a compound of formula (I) simultaneously, sequentially or separately with an anti-tumor agent, as defined hereinbefore. The method may comprise combining the compound of formula (I) and the anti-tumor agent in a single dosage form. Alternatively the method may comprise providing the anti-tumor agent as separate dosage forms.

The condition modulated by BTK described above may be cancer, leukemia or cancer. More specifically the condition modulated by BTK may be selected from: B-cell malignancy, B-cell lymphoma, diffuse large B cell lymphoma, chronic lymphocyte leukemia, non-Hodgkin lymphoma for example ABC-DLBCL, mantle cell lymphoma, follicular lymphoma, hairy cell leukemia B-cell non-Hodgkin lymphoma, Waldenstrom's macroglobulinemia and multiple myeloma.

Compounds of the invention may exist in a single crystal form or in a mixture of crystal forms or they may be amorphous. Thus, compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

For the above-mentioned compounds of the invention the dosage administered will, of course, vary with the compound employed, the mode of administration, the treatment desired and the disorder indicated. For example, if the compound of the invention is administered orally, then the daily dosage of the compound of the invention may be in the range from 0.01 micrograms per kilogram body weight (μg/kg) to 100 milligrams per kilogram body weight (mg/kg).

A compound of the invention, or pharmaceutically acceptable salt thereof, may be used on their own but will generally be administered in the form of a pharmaceutical composition in which the compounds of the invention, or pharmaceutically acceptable salt thereof, is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration of the compounds of the invention, the pharmaceutical composition which is used to administer the compounds of the invention will preferably comprise from 0.05 to 99% w (percent by weight) compounds of the invention, more preferably from 0.05 to 80% w compounds of the invention, still more preferably from 0.10 to 70% w compounds of the invention, and even more preferably from 0.10 to 50% w compounds of the invention, all percentages by weight being based on total composition.

The pharmaceutical compositions may be administered topically (e.g. to the skin) in the form, e.g., of creams, gels, lotions, solutions, suspensions, or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); by rectal administration in the form of suppositories; or by inhalation in the form of an aerosol.

For oral administration the compounds of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compounds of the invention may be admixed with, for example, a vegetable oil or polyethylene glycol. Hard gelatine capsules may contain granules of the compound using either the above-mentioned excipients for tablets. Also liquid or semi-solid formulations of the compound of the invention may be filled into hard gelatine capsules. Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, sweetening agents (such as saccharine), preservative agents and/or carboxymethylcellulose as a thickening agent or other excipients known to those skilled in art.

For intravenous (parenteral) administration the compounds of the invention may be administered as a sterile aqueous or oily solution.

The size of the dose for therapeutic purposes of compounds of the invention will naturally vary according to the nature and severity of the conditions, the age and sex of the animal or patient and the route of administration, according to well-known principles of medicine.

Dosage levels, dose frequency, and treatment durations of compounds of the invention are expected to differ depending on the formulation and clinical indication, age, and co-morbid medical conditions of the patient. The standard duration of treatment with compounds of the invention is expected to vary between one and seven days for most clinical indications. It may be necessary to extend the duration of treatment beyond seven days in instances of recurrent infections or infections associated with tissues or implanted materials to which there is poor blood supply including bones/joints, respiratory tract, endocardium, and dental tissues.

EXAMPLES AND SYNTHESIS

As used herein the following terms have the meanings given: "Boc" refers to tert-butoxycarbonyl; "DCM" refers to dichloromethane; "DIPEA" refers to N,N-Diisopropylethylamine; "LCMS" refers to liquid chromatography/mass spectrometry; "MIM" refers to monoisotopic mass; "min" refers to minutes; "NMP" refers to N-methylpyrrolidinone; "TLC" refers to thin layer chromatography; "Rf" refers to Retention factor; "RT" refers to retention time; "SCX" refers to strong cation exchange; "TFA" refers to trifluoroacetic acid; "THF" refers to tetrahydrofuran; and "TBME" refers to tert-Butyl methyl ether.

Solvents, reagents and starting materials were purchased from commercial vendors and used as received unless otherwise described. All reactions were performed at room temperature unless otherwise stated. Compound identity and purity confirmations were performed by LCMS UV using a Waters Acquity SQ Detector 2 (ACQ-SQD2#LCA081). The diode array detector wavelength was 254 nM and the MS was in positive and negative electrospray mode (m/z: 150-800). A 2 µL aliquot was injected onto a guard column (0.2 µm×2 mm filters) and UPLC column (C18, 50×2.1 mm, <2 µm) in sequence maintained at 40° C. The samples were eluted at a flow rate of 0.6 mL/min with a mobile phase system composed of A (0.1% (v/v) Formic Acid in Water) and B (0.1% (v/v) Formic Acid in Acetonitrile) according to the gradients outlined in Table 1 below. Retention times RT are reported in minutes.

TABLE 1

| Time (min) | % A | % B |
|---|---|---|
| Long Acidic | | |
| 0 | 95 | 5 |
| 1.1 | 95 | 5 |
| 6.1 | 5 | 95 |
| 7 | 5 | 95 |
| 7.5 | 95 | 5 |
| 8 | 95 | 5 |
| Short Acidic | | |
| 0 | 95 | 5 |
| 0.3 | 95 | 5 |
| 2 | 5 | 95 |
| 2.6 | 95 | 5 |
| 3 | 95 | 5 |

NMR was also used to characterise final compounds. NMR spectra were obtained on a Bruker AVIII 400 Nanobay with 5 mm BBFO probe. Optionally, compound Rf values on silica thin layer chromatography (TLC) plates were measured.

Compound purification was performed by flash column chromatography on silica or by preparative LCMS. LCMS purification was performed using a Waters 3100 Mass detector in positive and negative electrospray mode (m/z: 150-800) with a Waters 2489 UV/Vis detector. Samples were eluted at a flow rate of 20 mL/min on a XBridge™ prep C18 5 µM OBD 19×100 mm column with a mobile phase system composed of A (0.1% (v/v) Formic Acid in Water) and B (0.1% (v/v) Formic Acid in Acetonitrile) according to the gradient outlined in Table 2 below.

TABLE 2

| Time (min) | % A | % B |
|---|---|---|
| 0 | 90 | 10 |
| 1.5 | 90 | 10 |
| 11.7 | 5 | 95 |
| 13.7 | 5 | 95 |
| 14 | 90 | 90 |
| 15 | 90 | 90 |

Chemical names in this document were generated using mol2nam—Structure to Name Conversion by OpenEye Scientific Software. Starting materials were purchased from commercial sources or synthesised according to literature procedures.

General Procedures

General Procedure A

To a suspension of 4-(aminomethyl)phenyl]boronic acid hydrochloride (1.1 eq.) and the corresponding benzoic acid (1.0 eq.) in anhydrous THF (0.49 M), under a nitrogen atmosphere, was added successively, N,N-diisopropylethylamine (5.0 eq.) and propylphosphonic anhydride (50% wt in EtOAc) (1.5 eq.). The reaction mixture was heated under reflux at 70° C. overnight with stirring. The mixture was diluted with water and DCM, then partitioned. The aqueous layer was extracted with DCM (×2). The combined organic extracts were filtered over a phase separator and concentrated under reduced pressure to afford the desired boronic acid. No further purification was attempted and the product was used directly in the next step.

General Procedure B

To a suspension of 4-(aminomethyl)phenyl]boronic acid hydrochloride (1.0 eq.) and DIPEA (3.0 eq.) in anhydrous THF (0.2 M) under a nitrogen atmosphere was added a solution of the corresponding benzoyl chloride derivative (1.1 eq.) in anhydrous THF (0.2 M). The reaction mixture was stirred overnight at room temperature, quenched with a saturated aqueous solution of ammonium chloride and then extracted into ethyl acetate (×3). The combined organics were washed with brine, dried over $Na_2SO_4$ and filtered then concentrated under reduced pressure to afford the desired boronic acid derivative. No further purification was attempted and the product was used directly in the next step.

General Procedure C

A mixture of tert-butyl (3R)-3-(4-amino-3-iodo-pyrazolo [3,4-d]pyrimidin-1-yl)piperidine-1-carboxylate (1.0 eq.), boronic acid or pinacol ester (1.5 eq.) and potassium carbonate (2.0 eq.) in 1,4-dioxane and water (3:1, 0.1 M) was degassed by bubbling nitrogen through it for 25 min. 1,1'-bis(diphenylphosphino)ferrocene-palladium(II) dichloride dichloromethane complex (0.05 eq.) was added and the mixture was degassed again by bubbling nitrogen through it for 30 min. The mixture was then heated at 120° C. for 14 h. The reaction mixture was filtered over Celite®. The cake was rinsed with DCM. Water was added to the filtrate and the layers were partitioned. The aqueous layer was extracted with DCM (2×). The combined organic extracts were filtered over phase separator and then concentrated under reduced pressure to give a dark solid. Further purification by flash column chromatography (DCM/MeOH 100:0 to 90:10) gave the desired compound.

General Procedure D

A mixture of tert-butyl (3R)-3-(4-amino-3-iodo-pyrazolo [3,4-d]pyrimidin-1-yl)piperidine-1-carboxylate (1.0 eq.), boronic acid or pinacol ester (1.5 eq.) and potassium carbonate (2.0 eq.) in 1,4-dioxane and water (3:1, 0.1 M) was degassed by bubbling nitrogen through it for 15 min. 1,1'-bis(diphenylphosphino)ferrocene-palladium(II) dichloride dichloromethane complex (0.05 eq.) was added and the mixture was degassed again by bubbling nitrogen through it for 15 min. The mixture was then heated under microwave irradiation at 120-140° C. for 60-90 minutes. The reaction mixture was either purified by SCX and used as such or purified using the following procedure, unless stated used crude. The mixture filtered over Celite®. The cake was rinsed with DCM. Water was added to the filtrate and the layers were partitioned. The aqueous layer was extracted with DCM (2×). The combined organic extracts were filtered over phase separator and then concentrated under reduced pressure to give a dark solid. Further purification by flash column chromatography (DCM/MeOH 100:0 to 90:10) gave the desired compound.

General Procedure E

To a solution of Boc-protected amine (1.0 eq.) in dry methanol (0.7 M) under a nitrogen atmosphere was added hydrogen chloride (20-30 eq.). The reaction mixture was stirred at room temperature overnight, and then concentrated under reduced pressure to give the crude product. Further purification by either SCX or flash column chromatography (dry loading, DCM/7N ammonia in MeOH 100:0 to 90:10) gave, after further drying, the desired compound.

General Procedure F

To a suspension of amine (1.0 eq.) and acrylic acid (1.0 eq.) in anhydrous THF (0.3 M) were added successively N,N-diisopropylethylamine (3.0 eq.) and propylphosphonic anhydride (1.5 eq.). The reaction mixture was stirred overnight at room temperature, diluted with water and DCM. The layers were partitioned. The aqueous layer was extracted with DCM (×2). The combined organic extracts were filtered over phase separator and concentrated to give a foam. Further purification by flash column chromatography gave the title compound.

General Procedure G

To a solution of amine (1.0 eq) in DCM (0.14 M) were added successively was added cyanogen bromide (4.0 eq) and triethylamine (4.0 eq). The reaction mixture was stirred at rt for 20 min, quenched with a 1M aqueous solution of NaOH and extracted with DCM. The combined organic extracts were filtered over a phase separator, concentrated in vacuo. Further purification by flash chromatography or preparative HPLC afforded the title product.

General Procedure H

To a stirred solution of benzaldehyde (1 eq) in EtOH (0.4 M) was added hydroxylamine hydrochloride (1.5 eq) under a nitrogen atmosphere. The reaction mixture was stirred for 1 h and then filtered. The filtrate was concentrated to dryness affording the desired oxime.

General Procedure I

To a stirred solution of oxime (1 eq) and triisopropylborate (2 eq) in THF (0.4 M) at −78° C. was added n-butyllithium solution (2.5 M, 3 eq) dropwise under nitrogen. The reaction was stirred for 90 min. Water was added and the mixture was brought to room temperature and concentrated in vacuo before 1 M HCl (aq) was added to bring the solution to pH 5. A white precipitate formed and was filtered to afford the corresponding boronic acid.

General Procedure J

To a stirred solution of imine (1 eq) and 12 M hydrochloric acid (2 eq) under nitrogen was added palladium (10 wt. % on carbon, 0.2 eq). The reaction was placed under a hydrogen atmosphere and allowed to stir at room temperature for 60 min. The reaction mixture was filtered through celite and the filtrate was concentrated to dryness. Acetone was added and the formed precipitate was filtered to afford the corresponding amine.

Example 1: N-[[4-[4-Amino-1-[(3R)-1-prop-2-enoyl-3-piperidyl]pyrazolo[3,4-d]pyrimidin-3-yl]phenyl]methyl]-2-fluoro-benzamide 2-Fluoro-N-[[4-(4,4,5,5-tetramethyl-1,3,2-dioxaborolan-2-yl)phenyl]methyl]benzamide Following general procedure A, 2-fluorobenzoic acid (182.6 mg, 1.30 mmol) and [4-(aminomethyl)phenyl]boronic acid hydrochloride (268.7 mg, 1.43 mmol) afforded crude [4-[[(2-fluorobenzoyl)amino]methyl]phenyl]boronic acid (236.8 mg, 0.87 mmol, 67% yield).
UPLC-MS (ES$^+$, Short acidic): 1.25 min, m/z 274.1 [M+H]$^+$ tert-Butyl (3R)-3-[4-amino-3-[4-[[(2-fluorobenzoyl)amino]methyl]phenyl]pyrazolo[3,4-d]pyrimidin-1-yl]piperidine-1-carboxylate Following general procedure D, [4-[[(2-fluorobenzoyl)amino]methyl]phenyl]boronic acid (161.1 mg, 0.59 mmol) and tert-butyl (3R)-3-(4-amino-3-iodo-pyrazolo[3,4-d]pyrimidin-1-yl)piperidine-1-carboxylate (165.0 mg, 0.37 mmol) gave tert-butyl (3R)-3-[4-amino-3-[4-[[(2-fluorobenzoyl)amino]methyl]phenyl]pyrazolo[3,4-d]pyrimidin-1-yl]piperidine-1-carboxylate (208.5 mg, 0.30 mmol, 82% yield) as a dark brown foam.
UPLC-MS (ES$^+$, Short acidic): 1.63 min, m/z 546.5 [M+H]$^+$ N-[[4-[4-Amino-1-[(3R)-3-piperidyl]pyrazolo[3,4-d]pyrimidin-3-yl]phenyl]methyl]-2-fluoro-benzamide Following general procedure E, tert-butyl (3R)-3-[4-amino-3-[4-[[(2-fluorobenzoyl)amino]methyl]phenyl]pyrazolo[3,4-d]pyrimidin-1-yl]piperidine-1-carboxylate (203.3 mg, 0.37 mmol) afforded N-[[4-[4-amino-1-[(3R)-3-piperidyl]pyrazolo[3,4-d]pyrimidin-3-yl]phenyl]methyl]-2-fluoro-benzamide (118.1 mg, 0.25 mmol, 68% yield) as a brown foam.
UPLC-MS (ES$^+$, Short acidic): 1.05 min, m/z 446.3 [M+H]$^+$ N-[[4-[4-Amino-1-[(3R)-1-prop-2-enoyl-3-piperidyl]pyrazolo[3,4-d]pyrimidin-3-yl]phenyl]methyl]-2-fluoro-benzamide Following general procedure F, N-[[4-[4-amino-1-[(3R)-3-piperidyl]pyrazolo[3,4-d]pyrimidin-3-yl]phenyl]methyl]-2-fluoro-benzamide (104.0 mg, 0.22 mmol) and acrylic acid (0.02 mL, 0.22 mmol) gave N-[[4-[4-amino-1-[(3R)-1-prop-2-enoyl-3-piperidyl]pyrazolo-[3,4-d]pyrimidin-3-yl]phenyl]methyl]-2-fluoro-benzamide (40.0 mg, 0.07 mmol, 33% yield) as an off-white foam.
UPLC-MS (ES$^+$, short acidic): 1.32 min, m/z 500.4 [M+H]$^+$
UPLC-MS (ES$^+$, long acidic): 2.98 min, m/z 500.4 [M+H]$^+$
$^1$H NMR (400 MHz, DMSO-d$_6$) δ (ppm, 1:1 mixture of conformers) 8.96-8.93 (m, 1H, NH), 8.27 (s, 1H, ArH), 7.70-7.68 (m, 1H, ArH), 7.65 (d, J 7.6 Hz, 2H, ArH), 7.58-7.54 (m, 1H, ArH), 7.51 (d, J 7.6 Hz, 2H, ArH), 7.34-7.28 (m, 2H, ArH), 6.87 (dd, $^3J_{trans}$ 16.4 Hz, $^3J_{cis}$ 10.4, 0.5H), 6.72 (dd, $^3J_{trans}$ 16.4 Hz, $^3J_{cis}$ 10.4, 0.5H), 6.14 (d, $^3J_{trans}$ 16.4 Hz, 0.5H), 6.07 (d, $^3J_{trans}$ 16.4 Hz, 0.5H), 5.72 (d, $^3J_{cis}$ 10.4 Hz, 0.5H) 5.69 (d, $^3J_{cis}$ 10.4 Hz, 0.5H), 4.78-4.71 (m, 1H), 4.56 (d, J 6.0 Hz, 2H), 4.55-4.51 (m, 0.5H), 4.22-4.19 (m, 1H), 4.09-4.06 (m, 0.5H), 3.74-3.68 (m, 0.5H), 3.25-3.17 (m, 1H), 3.05-2.98 (m, 0.5H), 2.28-2.23 (m, 1H), 2.14-2.11 (m, 1H), 1.95-1.92 (m, 1H), 1.62-1.56 (m, 1H).

Example 2: N-[[4-[4-Amino-1-[(3R)-1-prop-2-enoyl-3-piperidyl]pyrazolo[3,4-d]pyrimidin-3-yl]phenyl]methyl]benzamide

[4-(Benzamidomethyl)phenyl]boronic acid

Following general procedure A, a mixture of [4-(aminomethyl)phenyl]boronic acid hydrochloride (262.4 mg, 1.40 mmol) and benzoic acid (155.4 mg, 1.27 mmol) gave crude [4-(benzamidomethyl)phenyl]boronic acid (201.1 mg, 0.79 mmol, 62% yield) as an off-white solid.
UPLC-MS (ES$^+$, Short acidic): 1.22 min, m/z 256.1 [M+H]$^+$ tert-Butyl (3R)-3-[4-amino-3-[4-(benzamidomethyl)phenyl]pyrazolo[3,4-d]pyrimidin-1-yl]piperidine-1-carboxylate Following general procedure D, [4-(benzamidomethyl)phenyl]boronic acid (150.5 mg, 0.59 mmol) and tert-butyl (3R)-3-(4-amino-3-iodo-pyrazolo[3,4-d]pyrimidin-1-yl)piperidine-1-carboxylate (165.0 mg, 0.37 mmol) gave tert-butyl (3R)-3-[4-amino-3-[4-(benzamidomethyl)phenyl]pyrazolo[3,4-d]pyrimidin-1-yl]piperidine-1-carboxylate (168.0 mg, 0.29 mmol, 77% yield) as a brown foam.
UPLC-MS (ES$^+$, Short acidic): 1.60 min, m/z 528.4 [M+H]$^+$ N-[[4-[4-Amino-1-[(3R)-3-piperidyl]pyrazolo[3,4-d]pyrimidin-3-yl]phenyl]methyl]-benzamide Following general procedure E, tert-butyl (3R)-3-[4-amino-3-[4-(benzamidomethyl)phenyl]pyrazolo[3,4-d]pyrimidin-1-yl]piperidine-1-carboxylate (163.7 mg, 0.31 mmol) afforded N-[[4-[4-amino-1-[(3R)-3-piperidyl]pyrazolo[3,4-d]pyrimidin-3-yl]phenyl]methyl]-benzamide (104.0 mg, 0.23 mmol, 75% yield) as a yellow/brown foam.
UPLC-MS (ES$^+$, Short acidic): 1.03 min, m/z 428.3 [M+H]$^+$ N-[[4-[4-Amino-1-[(3R)-1-prop-2-enoyl-3-piperidyl]pyrazolo[3,4-d]pyrimidin-3-yl]phenyl]methyl]benzamide Following general procedure F, N-[[4-[4-amino-1-[(3R)-3-piperidyl]pyrazolo[3,4-d]pyrimidin-3-yl]phenyl]methyl]benzamide (104 mg, 0.23 mmol) and acrylic acid (0.02 mL, 0.23 mmol) gave N-[[4-[4-amino-1-[(3R)-1-prop-2-enoyl-3-piperidyl]pyrazolo[3,4-d]pyrimidin-3-yl]phenyl]methyl]benzamide (31.5 mg, 0.06 mmol, 26% yield) as an off-white foam.
UPLC-MS (ES$^+$, short acidic): 1.29 min, m/z 482.4 [M+H]$^+$
UPLC-MS (ES$^+$, long acidic): 2.91 min, m/z 482.4 [M+H]$^+$ ¹H NMR (400 MHz, DMSO-d₆) δ (ppm, 1:1 mixture of conformers) 9.12 (t, J 5.8 Hz, 1H, NH), 8.26 (s, 1H, ArH), 7.97-7.91 (m, 2H, ArH), 7.65 (d, J 7.6 Hz, 2H, ArH), 7.57-7.47 (m, 5H, ArH), 6.87 (dd, ³J$_{trans}$ 16.4 Hz, ³J$_{cis}$ 10.4, 0.5H) 6.71 (dd, ³J$_{trans}$ 16.4 Hz, ³J$_{cis}$ 10.4, 0.5H), 6.14 (d, ³J$_{trans}$ 16.4 Hz, 0.5H), 6.05 (d, ³J$_{trans}$ 16.4 Hz, 0.5H), 5.71 (d, ³J$_{cis}$ 10.4 Hz, 0.5H) 5.59 (d, ³J$_{cis}$ 10.4 Hz, 0.5H), 4.77-4.64 (m, 1H), 4.58 (d, J 6.0 Hz, 2H), 4.56-4.52 (m, 0.5H), 4.25-4.16 (m, 1H), 4.12-4.03 (m, 0.5H), 3.73-3.67 (m, 0.5H), 3.24-3.16 (m, 1H), 3.04-2.98 (m, 0.5H), 2.28-2.22 (m, 1H), 2.19-2.10 (m, 1H), 1.98-1.92 (m, 1H), 1.66-1.55 (m, 1H).

Example 3: N-[[4-[4-Amino-1-[(3R)-1-prop-2-enoyl-3-piperidyl]pyrazolo[3,4-d]pyrimidin-3-yl]phenyl]methyl]-2,4-difluoro-benzamide

[4-[[(2,4-Difluorobenzoyl)amino]methyl]phenyl]boronic acid

Following general procedure A, 4-difluorobenzoic acid (254.2 mg, 1.61 mmol) and [4-(aminomethyl)phenyl]boronic acid hydrochloride (331.5 mg, 1.77 mmol) gave [4-[[(2,4-difluorobenzoyl)amino]methyl]phenyl]boronic acid (287.0 mg, 0.64 mmol, 40% yield) as an off white solid.
UPLC-MS (ES⁺, Short acidic): 1.30 min, m/z 291.8 [M+H]⁺ tert-Butyl (3R)-3-[4-Amino-3-[4-[[(2,4-difluorobenzoyl)amino]methyl]phenyl]pyrazolo[3,4-d]pyrimidin-1-yl]piperidine-1-carboxylate Following general procedure D, [4-[[(2,4-difluorobenzoyl)amino]methyl]phenyl]boronic acid (262.0 mg, 0.54 mmol) and tert-butyl (3R)-3-(4-amino-3-iodo-pyrazolo[3,4-d]pyrimidin-1-yl)piperidine-1-carboxylate (150.0 mg, 0.34 mmol) gave tert-butyl (3R)-3-[4-amino-3-[4-[[(2,4-difluorobenzoyl)amino]methyl]phenyl]pyrazolo[3,4-d]pyrimidin-1-yl]piperidine-1-carboxylate (260.0 mg, 0.32 mmol, 96% yield) as a brown foam.
UPLC-MS (ES⁺, Short acidic): 1.66 min, m/z 564.4 [M+H]⁺

N-[[4-[4-Amino-1-[(3R)-3-piperidyl]pyrazolo[3,4-d]pyrimidin-3-yl]phenyl]methyl]-2,4-difluoro-benzamide Following general procedure E, tert-butyl (3R)-3-[4-amino-3-[4-[[(2,4-difluorobenzoyl)amino]methyl]phenyl]pyrazolo[3,4-d]pyrimidin-1-yl]piperidine-1-carboxylate (260.0 mg, 0.37 mmol) afforded N-[[4-[4-amino-1-[(3R)-3-piperidyl]pyrazolo[3,4-d]pyrimidin-3-yl]phenyl]methyl]-2,4-difluoro-benzamide (123.3 mg, 0.25 mmol, 68% yield) as a pale yellow foam.
UPLC-MS (ES⁺, Short acidic): 1.08 min, m/z 464.2 [M+H]⁺

N-[[4-[4-Amino-1-[(3R)-1-prop-2-enoyl-3-piperidyl]pyrazolo[3,4-d]pyrimidin-3-yl]phenyl]methyl]-2,4-difluoro-benzamide Following general procedure F, N-[[4-[4-amino-1-[(3R)-3-piperidyl]pyrazolo[3,4-d]pyrimidin-3-yl]phenyl]methyl]-2,4-difluoro-benzamide (123.3 mg, 0.27 mmol) gave N-[[4-[4-amino-1-[(3R)-1-prop-2-enoyl-3-piperidyl]-pyrazolo[3,4-d]pyrimidin-3-yl]phenyl]methyl]-2,4-difluoro-benzamide (33.0 mg, 0.06 mmol, 22% yield) as an off-white foam.

UPLC-MS (ES⁺, short acidic): 1.35 min, m/z 518.3 [M+H]⁺
UPLC-MS (ES⁺, long acidic): 3.07 min, m/z 518.3 [M+H]⁺
¹H NMR (400 MHz, DMSO-d₆) δ (ppm, 1:1 mixture of conformers) 8.95 (t, J 6.0 Hz, 1H, NH), 8.28 (s, 1H, ArH), 7.81-7.73 (m, 1H, ArH), 7.66 (d, J 8.0 Hz, 2H, ArH), 7.51 (d, J 8.0 Hz, 2H, ArH), 7.43-7.36 (m, 1H, ArH), 7.24-7.18 (m, 1H, ArH), 6.87 (dd, ³J$_{cis}$ 10.4, ³J$_{trans}$ 16.4 Hz, 0.5H) 6.71 (dd, ³J$_{cis}$ 10.4, ³J$_{trans}$ 16.4 Hz, 0.5H), 6.15 (d, ³J$_{trans}$ 16.4 Hz, 0.5H), 6.06 (d, ³J$_{trans}$ 16.4 Hz, 0.5H), 5.72 (d, ³J$_{cis}$ 10.4 Hz, 0.5H), 5.60 (d, ³J$_{cis}$ 10.4 Hz, 0.5H), 4.79-4.65 (m, 1H), 4.56 (d, J 6.0 Hz, 2H), 4.56-4.49 (m, 0.5H), 4.25-4.16 (m, 1H), 4.13-4.04 (m, 0.5H), 3.77-3.66 (m, 0.5H), 3.28-3.15 (m, 1H), 3.08-2.97 (m, 0.5H), 2.32-2.21 (m, 1H), 2.18-2.09 (m, 1H), 1.99-1.89 (m, 1H), 1.67-1.52 (m, 1H).

Example 4: N-[[4-[4-Amino-1-[(3R)-1-prop-2-enoyl-3-piperidyl]pyrazolo[3,4-d]pyrimidin-3-yl]phenyl]methyl]-2-methoxy-benzamide

[4-[[(2-Methoxybenzoyl)amino]methyl]phenyl]boronic acid

Following general procedure A, 2-methoxybenzoic acid (200 mg, 1.97 mmol) and [4-(aminomethyl)phenyl]boronic acid hydrochloride (406.5 mg, 2.17 mmol) afforded [4-[[(2-methoxybenzoyl)amino]methyl]phenyl]boronic acid (361.0 mg, 0.94 mmol, 48% yield) as a pale yellow solid.
UPLC-MS (ES⁺, short acidic):1.29 min, m/z 285.9 [M+H]⁺ tert-Butyl (3R)-3-[4-amino-3-[4-[[(2-methoxybenzoyl)amino]methyl]phenyl]pyrazolo[3,4-d]pyrimidin-1-yl]piperidine-1-carboxylate Following general procedure D, [4-[[(2-methoxybenzoyl)amino]methyl]phenyl]boronic acid (320.9 mg, 0.84 mmol) and tert-butyl (3R)-3-(4-amino-3-iodo-pyrazolo[3,4-d]pyrimidin-1-yl)piperidine-1-carboxylate (250 mg, 0.56 mmol) gave tert-butyl (3R)-3-[4-amino-3-[4-[[(2-methoxybenzoyl)amino]methyl]phenyl]pyrazolo[3,4-d]pyrimidin-1-yl]piperidine-1-carboxylate (168.0 mg, 0.24 mmol, 43% yield) as a brown foam.
UPLC-MS (ES⁺, Short acidic): 1.64 min, m/z 558.5 [M+H]⁺

N-[[4-[4-Amino-1-[(3R)-3-piperidyl]pyrazolo[3,4-d]pyrimidin-3-yl]phenyl]methyl]-2-methoxy-benzamide Following general procedure E, tert-butyl (3R)-3-[4-amino-3-[4-[[(2-methoxybenzoyl)amino]methyl]phenyl]pyrazolo[3,4-d]pyrimidin-1-yl]piperidine-1-carboxylate (430.0 mg, 0.77 mmol) afforded N-[[4-[4-amino-1-[(3R)-3-piperidyl]pyrazolo[3,4-d]pyrimidin-3-yl]phenyl]methyl]-2-methoxy-benzamide (187.0 mg, 0.36 mmol, 48% yield) as a brown foam.
UPLC-MS (ES⁺, Short acidic): 1.08 min, m/z 458.3 [M+H]⁺

N-[[4-[4-Amino-1-[(3R)-1-prop-2-enoyl-3-piperidyl]pyrazolo[3,4-d]pyrimidin-3-yl]phenyl]methyl]-2-methoxy-benzamide Following general procedure F, N-[[4-[4-amino-1-[(3R)-3-piperidyl]pyrazolo[3,4-d]pyrimidin-3-yl]phenyl]methyl]-

2-methoxy-benzamide (187.0 mg, 0.41 mmol) and acrylic acid (0.03 mL, 0.41 mmol) gave N-[[4-[4-amino-1-[(3R)-1-prop-2-enoyl-3-piperidyl]pyrazolo[3,4-d]pyrimidin-3-yl]phenyl]methyl]-2-methoxy-benzamide (90.0 mg, 0.16 mmol, 39% yield) as an off-white foam.

UPLC-MS (ES$^+$, short acidic): 1.34 min, m/z 512.4 [M+H]$^+$

UPLC-MS (ES$^+$, long acidic): 3.06 min, m/z 512.4 [M+H]$^+$ $^1$H NMR (400 MHz, DMSO-d$_6$) δ (ppm, 1:1 mixture of conformers) 8.78 (t, J 6.0 Hz, 1H, NH), 8.28 (s, 1H, ArH), 7.78 (dd, J 7.6, 1.8 Hz, 1H, ArH), 7.65 (d, J 8.0 Hz, 2H, ArH), 7.52 (d, J 8.0 Hz, 2H, ArH), 7.49-7.51 (m, 1H, ArH), 7.19-7.15 (m, 1H, ArH), 7.08-7.03 (m, 1H, ArH), 6.87 (dd, $^3J_{cis}$ 10.4, $^3J_{trans}$ 16.4 Hz, 0.5H), 6.73 (dd, $^3J_{cis}$ 10.4, $^3J_{trans}$ 16.4 Hz, 0.5H), 6.14 (d, $^3J_{trans}$ 16.4 Hz, 0.5H), 6.07 (d, $^3J_{trans}$ 16.4 Hz, 0.5H), 5.72 (d, $^3J_{cis}$ 10.4 Hz, 0.5H), 5.60 (d, $^3J_{cis}$ 10.4 Hz, 0.5H), 4.78-4.66 (m, 1H), 4.60 (d, J 6.4 Hz, 2H), 4.58-4.51 (m, 0.5H), 4.26-4.16 (m, 1H), 4.12-4.05 (m, 0.5H), 3.92 (s, 3H, CH$_3$), 3.75-3.66 (m, 0.5H), 3.25-3.15 (m, 1H), 3.07-2.96 (m, 0.5H), 2.33-2.22 (m, 1H), 2.17-2.08 (m, 1H), 1.98-1.89 (m, 1H), 1.67-1.52 (m, 1H).

Example 5: N-[[4-[4-Amino-1-[(3R)-1-prop-2-enoyl-3-piperidyl]pyrazolo[3,4-d]pyrimidin-3-yl]phenyl]methyl]-2-fluoro-5-(trifluoromethyl)benzamide

[4-[[[2-Fluoro-5-(trifluoromethyl)benzoyl]amino]methyl]phenyl]boronic acid

Following general procedure A, 2-fluoro-5-(trifluoromethyl)benzoic acid (302.7 mg, 1.45 mmol) and [4-(aminomethyl)phenyl]boronic acid hydrochloride (406.5 mg, 2.17 mmol) afforded [4-[[[2-fluoro-5-(trifluoromethyl)benzoyl]amino]methyl]phenyl]boronic acid (427.0 mg, 1.06 mmol, 73% yield) as a yellow oil.

UPLC-MS (ES$^+$, short acidic): 1.48 min, m/z 341.8 [M+H]$^+$ tert-Butyl (3R)-3-[4-amino-3-[4-[[[2-fluoro-5-(trifluoromethyl)benzoyl]amino]methyl]phenyl]pyrazolo[3,4-d]pyrimidin-1-yl]piperidine-1-carboxylate Following general procedure D, [4-[[[2-fluoro-5-(trifluoromethyl)benzoyl]amino]methyl]phenyl]boronic acid (316.7 mg, 0.74 mmol) and tert-butyl (3R)-3-(4-amino-3-iodo-pyrazolo[3,4-d]pyrimidin-1-yl)piperidine-1-carboxylate (220.0 mg, 0.50 mmol) gave tert-butyl (3R)-3-[4-amino-3-[4-[[[2-fluoro-5-(trifluoromethyl)benzoyl]amino]methyl]phenyl]pyrazolo[3,4-d]pyrimidin-1-yl]piperidine-1-carboxylate (304.1 mg, 0.42 mmol, 85% yield) as a brown/yellow foam.

UPLC-MS (ES$^+$, Short acidic): 1.78 min, m/z 614.4 [M+H]$^+$

N-[[4-[4-Amino-1-[(3R)-3-piperidyl]pyrazolo[3,4-d]pyrimidin-3-yl]phenyl]methyl]-2-fluoro-5-(trifluoromethyl)benzamide Following general procedure E, tert-butyl (3R)-3-[4-amino-3-[4-[[[2-fluoro-5-(trifluoromethyl)benzoyl]amino]methyl]phenyl]pyrazolo[3,4-d]pyrimidin-1-yl]piperidine-1-carboxylate (304.1 mg, 0.50 mmol) afforded N-[[4-[4-amino-1-[(3R)-3-piperidyl]pyrazolo[3,4-d]pyrimidin-3-yl]phenyl]methyl]-2-fluoro-5-(trifluoromethyl)benzamide (140.0 mg, 0.26 mmol, 52% yield) as an off white foam.

UPLC-MS (ES$^+$, Short acidic): 1.20 min, m/z 514.3 [M+H]$^+$

N-[[4-[4-Amino-1-[(3R)-1-prop-2-enoyl-3-piperidyl]pyrazolo[3,4-d]pyrimidin-3-yl]phenyl]methyl]-2-fluoro-5-(trifluoromethyl)benzamide Following general procedure F, N-[[4-[4-amino-1-[(3R)-3-piperidyl]pyrazolo[3,4-d]pyrimidin-3-yl]phenyl]methyl]-2-fluoro-5-(trifluoromethyl)benzamide (140 mg, 0.27 mmol) gave N-[[4-[4-amino-1-[(3R)-1-prop-2-enoyl-3-piperidyl]pyrazolo[3,4-d]pyrimidin-3-yl]phenyl]methyl]-2-fluoro-5-(trifluoromethyl)benzamide (50.0 mg, 0.08 mmol, 29% yield) as an off-white foam.

UPLC-MS (ES$^+$, short acidic): 1.49 min, m/z 568.3 [M+H]$^+$

UPLC-MS (ES$^+$, long acidic): 3.42 min, m/z 568.3 [M+H]$^+$ $^1$H NMR (400 MHz, DMSO-d$_6$) δ (ppm, 1:1 mixture of conformers) 9.18 (t, J 6.2 Hz, 1H, NH), 8.27 (s, 1H, ArH), 8.04-8.00 (m, 1H, ArH), 8.00-7.94 (m, 1H, ArH), 7.67 (d, J 8.5 Hz, 2H, ArH), 7.63-7.56 (m, 1H, ArH), 7.53 (d, J 8.5 Hz, 2H, ArH), 6.87 (dd, $^3J_{cis}$ 10.4, $^3J_{trans}$ 16.4 Hz, 0.5H) 6.72 (dd, $^3J_{cis}$ 10.4, $^3J_{trans}$ 16.4 Hz, 0.5H), 6.13 (d, $^3J_{trans}$ 16.4 Hz, 0.5H), 6.07 (d, $^3J_{trans}$ 16.4 Hz, 0.5H), 5.71 (d, $^3J_{cis}$ 10.4 Hz, 0.5H), 5.59 (d, $^3J_{cis}$ 10.4 Hz, 0.5H), 4.77-4.65 (m, 1H), 4.59 (d, J 6.0 Hz, 2H), 4.57-4.51 (m, 0.5H), 4.26-4.16 (m, 1H), 4.12-4.04 (m, 0.5H), 3.76-3.67 (m, 0.5H), 3.27-3.18 (m, 1H), 3.08-2.97 (m, 0.5H), 2.33-2.22 (m, 1H), 2.17-2.08 (m, 1H), 1.98-1.89 (m, 1H), 1.67-1.53 (m, 1H).

Example 6: N-[[4-[4-Amino-1-[(3R)-1-prop-2-enoyl-3-piperidyl]pyrazolo[3,4-d]pyrimidin-3-yl]phenyl]methyl]-4-fluoro-benzamide

[4-[[(4-Fluorobenzoyl)amino]methyl]phenyl]boronic acid

Following general procedure A, 4-fluorobenzoic acid (300.0 mg, 2.14 mmol) and [4-(aminomethyl)phenyl]boronic acid hydrochloride (441.5 mg, 2.36 mmol) afforded [4-[[(4-fluorobenzoyl)amino]methyl]phenyl]boronic acid (437.0 mg, 1.36 mmol, 63% yield) as a yellow oil.

UPLC-MS (ES$^+$, short acidic):1.27 min, m/z 273.8 [M+H]$^+$ tert-Butyl (3R)-3-[4-amino-3-[4-[[(4-fluorobenzoyl)amino]methyl]phenyl]pyrazole[3,4-d]pyrimidin-1-yl]piperidine-1-carboxylate Following general procedure D, [4-[[(4-fluorobenzoyl)amino]methyl]phenyl]boronic acid (282.7 mg, 0.83 mmol) and tert-butyl (3R)-3-(4-amino-3-iodo-pyrazolo[3,4-d]pyrimidin-1-yl)piperidine-1-carboxylate (230.0 mg, 0.52 mmol) gave tert-butyl (3R)-3-[4-amino-3-[4-[[(4-fluorobenzoyl)amino]methyl]phenyl]pyrazolo[3,4-d]pyrimidin-1-yl]piperidine-1-carboxylate (273.6 mg, 0.42 mmol, 82% yield) as a brown foam.

UPLC-MS (ES$^+$, Short acidic): 1.62 min, m/z 546.4 [M+H]$^+$

N-[[4-[4-Amino-1-[(3R)-3-piperidyl]pyrazolo[3,4-d]pyrimidin-3-yl]phenyl]methyl]-4-fluoro-benzamide Following general procedure E, tert-butyl (3R)-3-[4-amino-3-[4-[[(4-fluorobenzoyl)amino]methyl]phenyl]pyrazolo[3,4-d]pyrimidin-1-yl]piperidine-1-carboxylate (273.6 mg, 0.50 mmol) afforded N-[[4-[4-amino-1-[(3R)-3-piperidyl]pyrazolo[3,4-d]pyrimidin-3-yl]phenyl]methyl]-4-fluoro-benzamide (98.0 mg, 0.21 mmol, 42% yield) as an off-white foam.

UPLC-MS (ES+, Short acidic): 1.07 min, m/z 446.3 [M+H]+

N-[[4-[4-Amino-1-[(3R)-1-prop-2-enoyl-3-piperidyl]pyrazolo[3,4-d]pyrimidin-3-yl]phenyl]methyl]-4-fluoro-benzamide Following general procedure F, N-[[4-[4-amino-1-[(3R)-3-piperidyl]pyrazolo[3,4-d]pyrimidin-3-yl]phenyl]methyl]-4-fluoro-benzamide (98.0 mg, 0.22 mmol) gave N-[[4-[4-amino-1-[(3R)-1-prop-2-enoyl-3-piperidyl]pyrazolo-[3,4-d]pyrimidin-3-yl]phenyl]methyl]-4-fluoro-benzamide (25.0 mg, 0.05 mmol, 22% yield) as an off-white foam.

UPLC-MS (ES+, short acidic): 1.33 min, m/z 500.4 [M+H]+

UPLC-MS (ES+, long acidic): 3.01 min, m/z 500.4 [M+H]+

$^1$H NMR (400 MHz, DMSO-$d_6$) δ (ppm, 1:1 mixture of conformers): 9.14 (t, J 6.0 Hz, 1H, NH), 8.26 (s, 1H, ArH), 8.03-7.96 (m, 2H, ArH), 7.64 (d, J 8.0 Hz, 2H, ArH), 7.50 (d, J 8.0 Hz, 2H, ArH), 7.36-7.29 (m, 2H, ArH), 6.92-6.81 (dd, $^3J_{cis}$ 10.4, $^3J_{trans}$ 16.4 Hz, 0.5H) 6.77-6.66 (dd, $^3J_{cis}$ 10.4, $^3J_{trans}$ 16.4 Hz, 0.5H), 6.15-6.11 (d, $^3J_{trans}$ 16.4 Hz, 0.5H), 6.09-6.04 (d, $^3J_{trans}$ 16.4 Hz, 0.5H), 6.18-6.01 (d, $^3J_{cis}$ 10.4 Hz, 0.5H), 5.75-5.67 (d, $^3J_{cis}$ 10.4 Hz, 0.5H), 4.78-4.64 (m, 1H), 4.57 (d, J 6.0 Hz, 2H, CH$_2$), 4.57-4.50 (m, 0.5H), 4.24-4.14 (m, 1H), 4.12-4.03 (m, 0.5H), 3.75-3.65 (m, 0.5H), 3.26-3.14 (m, 1H), 3.07-2.96 (m, 0.5H), 2.32-2.20 (m, 1H), 2.16-2.10 (m, 1H), 1.97-1.89 (m, 1H), 1.66-1.51 (m, 1H).

Example 7: N-[[4-[4-Amino-1-[(3R)-1-prop-2-enoyl-3-piperidyl]pyrazolo[3,4-d]pyrimidin-3-yl]phenyl]methyl]-2,5-difluoro-benzamide

[4-[[(2,5-Difluorobenzoyl)amino]methyl]phenyl]boronic acid

Following general procedure B, a mixture of 2,5-difluorobenzoyl chloride (0.22 mL, 1.76 mmol) and [4-(aminomethyl)phenyl]boronic acid hydrochloride (300.0 mg, 1.60 mmol) was heated under reflux at 70° C. overnight with stirring. Further work-up afforded [4-[[(2,5-difluorobenzoyl)amino]methyl]phenyl]boronic acid (343.6 mg, 0.82 mmol, 52% yield) as a pale yellow solid.

UPLC-MS (ES+, short acidic): 1.30 min, m/z 291.8 [M+H]+ tert-Butyl (3R)-3-[4-amino-3-[4-[[(2,5-difluorobenzoyl)amino]methyl]phenyl]pyrazolo[3,4-d]pyrimidin-1-yl]piperidine-1-carboxylate Following general procedure D, [4-[[(2,5-difluorobenzoyl)amino]methyl]phenyl]boronic acid (350.0 mg, 0.84 mmol) and tert-butyl (3R)-3-(4-amino-3-iodo-pyrazolo[3,4-d]pyrimidin-1-yl)piperidine-1-carboxylate (210 mg, 0.47 mmol) gave tert-butyl (3R)-3-[4-amino-3-[4-[[(2,5-difluorobenzoyl)amino]methyl]phenyl]pyrazolo[3,4-d]pyrimidin-1-yl]piperidine-1-carboxylate (305.0 mg, 0.38 mmol, 80% yield) as a brown/yellow foam.

UPLC-MS (ES+, Short acidic): 1.66 min, m/z 564.4 [M+H]+

N-[[4-[4-Amino-1-[(3R)-3-piperidyl]pyrazolo[3,4-d]pyrimidin-3-yl]phenyl]methyl]-2,5-difluoro-benzamide Following general procedure E, tert-butyl (3R)-3-[4-amino-3-[4-[[(2,5-difluorobenzoyl)amino]methyl]phenyl]pyrazolo[3,4-d]pyrimidin-1-yl]piperidine-1-carboxylate (305.0 mg, 0.54 mmol) afforded N-[[4-[4-amino-1-[(3R)-3-piperidyl]pyrazolo[3,4-d]pyrimidin-3-yl]phenyl]methyl]-2,5-difluoro-benzamide (161.0 mg, 0.31 mmol, 58% yield) as an off white foam.

UPLC-MS (ES+, Short acidic): 1.08 min, m/z 464.3 [M+H]+

N-[[4-[4-Amino-1-[(3R)-1-prop-2-enoyl-3-piperidyl]pyrazolo[3,4-d]pyrimidin-3-yl]phenyl]methyl]-2,5-difluoro-benzamide Following general procedure F, N-[[4-[4-amino-1-[(3R)-3-piperidyl]pyrazolo[3,4-d]pyrimidin-3-yl]phenyl]methyl]-2,5-difluoro-benzamide (161.0 mg, 0.35 mmol) gave N-[[4-[4-amino-1-[(3R)-1-prop-2-enoyl-3-piperidyl]-pyrazolo[3,4-d]pyrimidin-3-yl]phenyl]methyl]-2,5-difluoro-benzamide (75.0 mg, 0.13 mmol, 38% yield) as an off-white foam.

UPLC-MS (ES+, short acidic): 1.36 min, m/z 518.4 [M+H]+

UPLC-MS (ES+, long acidic): 3.07 min, m/z 518.3 [M+H]+

$^1$H NMR (400 MHz, DMSO-$d_6$) δ (ppm, 1:1 mixture of conformers): 9.05 (t, J 5.7 Hz, 1H, NH), 8.27 (s, 1H, ArH), 7.66 (d, J 7.9 Hz, 2H, ArH), 7.52 (d, J 7.9 Hz, 2H, ArH), 7.51-7.47 (m, 1H, ArH), 7.43-7.38 (m, 2H, ArH), 6.87 (dd, $^3J_{cis}$ 10.4, $^3J_{trans}$ 16.4 Hz, 0.5H), 6.72 (dd, $^3J_{cis}$ 10.4, $^3J_{trans}$ 16.4 Hz, 0.5H), 6.14 (d, $^3J_{trans}$ 16.4 Hz, 0.5H), 6.07 (d, $^3J_{trans}$ 16.4 Hz, 0.5H), 5.72 (d, $^3J_{cis}$ 10.4 Hz, 0.5H), 5.59 (d, $^3J_{cis}$ 10.4 Hz, 0.5H), 4.78-4.65 (m, 1H), 4.56 (d, J 5.7 Hz, 2H, CH$_2$), 4.55-4.52 (m, 0.5H), 4.25-4.16 (m, 1H), 4.12-4.04 (m, 0.5H), 3.76-3.66 (m, 0.5H), 3.27-3.15 (m, 1H), 3.08-2.96 (m, 0.5H), 2.33-2.21 (m, 1H), 2.18-2.09 (m, 1H), 1.98-1.89 (m, 1H), 1.68-1.52 (m, 1H).

Example 8: N-[[4-[4-Amino-1-[(3R)-1-prop-2-enoyl-3-piperidyl]pyrazolo[3,4-d]pyrimidin-3-yl]phenyl]methyl]-4-tert-butyl-benzamide

[4-[[(4-tert-Butylbenzoyl)amino]methyl]phenyl]boronic acid

Following general procedure B, 4-tert-butylbenzoyl chloride (0.22 mL, 1.76 mmol) and [4-(aminomethyl)phenyl]boronic acid hydrochloride (300 mg, 1.6 mmol) afforded [4-[[(4-tert-butylbenzoyl)amino]methyl]phenyl]boronic acid (352.2 mg, 0.79 mmol, 50% yield) as a yellow/white solid.

UPLC-MS (ES+, short acidic):1.59 min, m/z 311.9 [M+H]+ tert-Butyl (3R)-3-[4-amino-3-[4-[[(4-tert-butylbenzoyl)amino]methyl]phenyl]pyrazolo[3,4-d]pyrimidin-1-yl]piperidine-1-carboxylate Following general procedure D, [4-[[(4-tert-butylbenzoyl)amino]methyl]phenyl]boronic acid (367.3 mg, 0.83 mmol) and tert-butyl (3R)-3-(4-amino-3-iodo-pyrazolo[3,4-d]pyrimidin-1-yl)piperidine-1-carboxylate (210.0 mg, 0.47 mmol) gave tert-butyl (3R)-3-[4-amino-3-[4-[[(4-tert-butylbenzoyl)amino]methyl]phenyl]pyrazolo[3,4-d]pyrimidin-1-yl]piperidine-1-carboxylate (320.0 mg, 0.38 mmol, 81% yield) as an brown foam.

UPLC-MS (ES$^+$, Short acidic): 1.87 min, m/z 584.5 [M+H]$^+$

N-[[4-[4-Amino-1-[(3R)-3-piperidyl]pyrazolo[3,4-d]pyrimidin-3-yl]phenyl]methy]-4-tert-butyl-benzamide Following general procedure E, tert-butyl (3R)-3-[4-amino-3-[4-[[(4-tert-butylbenzoyl)amino]methyl]phenyl]pyrazolo[3,4-d]pyrimidin-1-yl]piperidine-1-carboxylate (320.0 mg, 0.55 mmol) afforded N-[[4-[4-amino-1-[(3R)-3-piperidyl]pyrazolo[3,4-d]pyrimidin-3-yl]phenyl]methyl]-4-tert-butyl-benzamide (195.0 mg, 0.38 mmol, 70% yield) as an off brown foam.

UPLC-MS (ES$^+$, Short acidic): 1.29 min, m/z 484.5 [M+H]$^+$

N-[[4-[4-Amino-1-[(3R)-1-prop-2-enoyl-3-piperidyl]pyrazolo[3,4-d]pyrimidin-3-yl]phenyl]methyl]-4-tert-butyl-benzamide Following general procedure F, N-[[4-[4-amino-1-[(3R)-3-piperidyl]pyrazolo[3,4-d]pyrimidin-3-yl]phenyl]methyl]-4-tert-butyl-benzamide (195.0 mg, 0.40 mmol) gave N-[[4-[4-amino-1-[(3R)-1-prop-2-enoyl-3-piperidyl]-pyrazolo[3,4-d]pyrimidin-3-yl]phenyl]methyl]-4-tert-butyl-benzamide (49.0 mg, 0.08 mmol, 20% yield) as an off-white foam.

UPLC-MS (ES$^+$, short acidic): 1.58 min, m/z 538.4 [M+H]$^+$

UPLC-MS (ES$^+$, long acidic): 3.66 min, m/z 538.5 [M+H]$^+$ $^1$H NMR (400 MHz, DMSO-d$_6$) δ (ppm, 1:1 mixture of conformers) 9.04 (t, J 6.0 Hz, 1H, NH), 8.27 (s, 1H, ArH), 7.87 (d, J 7.8 Hz, 2H, ArH), 7.64 (d, J 7.8 Hz, 2H, ArH), 7.53-7.46 (m, 4H, ArH), 6.87 (dd, $^3J_{cis}$ 10.4, $^3J_{trans}$ 16.4 Hz, 0.5H), 6.72 (dd, $^3J_{cis}$ 10.4, $^3J_{trans}$ 16.4 Hz, 0.5H), 6.13 (d, $^3J_{trans}$ 16.4 Hz, 0.5H), 6.07 (d, $^3J_{trans}$ 16.4 Hz, 0.5H), 5.71 (d, $^3J_{cis}$ 10.4 Hz, 0.5H), 5.59 (d, $^3J_{cis}$ 10.4 Hz, 0.5H), 4.77-4.64 (m, 1H), 4.57 (d, J 6.0 Hz, 2H, CH$_2$), 4.56-4.51 (m, 0.5H), 4.26-4.16 (m, 1H), 4.12-4.03 (m, 0.5H), 3.75-3.66 (m, 0.5H), 3.27-3.14 (m, 1H), 3.06-2.96 (m, 0.5H), 2.33-2.20 (m, 1H), 2.17-2.08 (m, 1H), 1.98-1.88 (m, 1H), 1.66-1.51 (m, 1H), 1.31 (s, 9H).

Example 9: N-[[4-[4-Amino-1-[(3R)-1-prop-2-enoyl-3-piperidyl]pyrazolo[3,4-d]pyrimidin-3-yl]phenyl]methyl]-2,6-difluoro-benzamide

[4-[[(2,6-Difluorobenzoyl)amino]methyl]phenyl]boronic acid

Following general procedure B, 2,6-difluorobenzoyl chloride (0.22 mL, 1.76 mmol) and [4-(aminomethyl)phenyl]boronic acid hydrochloride (300.0 mg, 1.60 mmol) afforded [4-[[(2,6-difluorobenzoyl)amino]methyl]phenyl]boronic acid (338.3 mg, 0.81 mmol, 51% yield) as a white solid.

UPLC-MS (ES$^+$, short acidic):1.21 min, m/z 291.8 [M+H]$^+$ tert-Butyl (3R)-3-[4-amino-3-[4-[[(2,6-difluorobenzoyl)amino]methyl]phenyl]pyrazolo[3,4-d]pyrimidin-1-yl]piperidine-1-carboxylate Following general procedure D, [4-[[(2,6-difluorobenzoyl)amino]methyl]phenyl]boronic acid (338.3 mg, 0.82 mmol) and tert-butyl (3R)-3-(4-amino-3-iodo-pyrazolo[3,4-d]pyrimidin-1-yl)piperidine-1-carboxylate (205.0 mg, 0.46 mmol) gave tert-butyl (3R)-3-[4-amino-3-[4-[[(2,6-difluorobenzoyl)amino]methyl]phenyl]pyrazolo[3,4-d]pyrimidin-1-yl]piperidine-1-carboxylate (300.0 mg, 0.43 mmol, 92% yield) as an yellow foam.

UPLC-MS (ES$^+$, Short acidic): 1.60 min, m/z 564.4 [M+H]$^+$

N-[[4-[4-Amino-1-[(3R)-3-piperidyl]pyrazolo[3,4-d]pyrimidin-3-yl]phenyl]methyl]-2,6-difluoro-benzamide Following general procedure E, tert-butyl (3R)-3-[4-amino-3-[4-[[(2,6-difluorobenzoyl)amino]methyl]phenyl]pyrazolo[3,4-d]pyrimidin-1-yl]piperidine-1-carboxylate (300.0 mg, 0.53 mmol) afforded N-[[4-[4-amino-1-[(3R)-3-piperidyl]pyrazolo[3,4-d]pyrimidin-3-yl]phenyl]methyl]-2,6-difluoro-benzamide (145.0 mg, 0.28 mmol, 53% yield) as an off white foam.

UPLC-MS (ES$^+$, Short acidic): 1.01 min, m/z 464.3 [M+H]$^+$

N-[[4-[4-Amino-1-[(3R)-1-prop-2-enoyl-3-piperidyl]pyrazolo[3,4-d]pyrimidin-3-yl]phenyl]methyl]-2,6-difluoro-benzamide Following general procedure F, N-[[4-[4-amino-1-[(3R)-3-piperidyl]pyrazolo[3,4-d]pyrimidin-3-yl]phenyl]methyl]-2,6-difluoro-benzamide (145.0 mg, 0.31 mmol) gave N-[[4-[4-amino-1-[(3R)-1-prop-2-enoyl-3-piperidyl]pyrazolo[3,4-d]pyrimidin-3-yl]phenyl]methyl]-2,6-difluoro-benzamide (22.0 mg, 0.04 mmol, 12% yield) as an off-white foam.

UPLC-MS (ES$^+$, short acidic): 1.29 min, m/z 518.3 [M+H]$^+$

UPLC-MS (ES$^+$, long acidic): 2.91 min, m/z 518.4 [M+H]$^+$ $^1$H NMR (400 MHz, DMSO-d$_6$) δ (ppm, 1:1 mixture of conformers) 9.34 (t, J 6.0 Hz, 1H, NH), 8.27 (s, 1H, ArH), 7.68 (d, J 8.0 Hz, 2H, ArH), 7.60-7.52 (m, 1H, ArH), 7.51 (d, J 8.0 Hz, 2H, ArH), 7.24-7.17 (m, 2H, ArH), 6.88 (dd, $^3J_{cis}$ 10.4, $^3J_{trans}$ 16.4 Hz, 0.5H), 6.73 (dd, $^3J_{cis}$ 10.4, $^3J_{trans}$ 16.4 Hz, 0.5H), 6.14 (d, $^3J_{trans}$ 16.4 Hz, 0.5H), 6.07 (d, $^3J_{trans}$ 16.4 Hz, 0.5H), 5.72 (d, $^3J_{cis}$ 10.4 Hz, 0.5H), 5.60 (d, $^3J_{cis}$ 10.4 Hz, 0.5H), 4.78-4.65 (m, 1H), 4.58 (d, J 6.0 Hz, 2H, CH$_2$), 4.56-4.51 (m, 0.5H), 4.26-4.17 (m, 1H), 4.12-4.04 (m, 0.5H), 3.77-3.68 (m, 0.5H), 3.28-3.16 (m, 1H), 3.08-2.97 (m, 0.5H), 2.32-2.22 (m, 1H), 2.18-2.09 (m, 1H), 1.98-1.89 (m, 1H), 1.68-1.52 (m, 1H).

Example 10: N-[[4-[4-Amino-1-[(3R)-1-prop-2-enoyl-3-piperidyl]pyrazolo[3,4-d]pyrimidin-3-yl]phenyl]methyl]-4-fluoro-2-methoxy-benzamide

[4-[[(4-Fluoro-2-methoxy-benzoyl)amino]methyl]phenyl]boronic acid

Following general procedure A, [4-(aminomethyl)phenyl]boronic acid hydrochloride (363.5 mg, 1.94 mmol) and 4-fluoro-2-methoxybenzoic acid (300.0 mg, 1.76 mmol) gave [4-[[(4-fluoro-2-methoxy-benzoyl)amino]methyl]phenyl]boronic acid (361.0 mg, 0.89 mmol, 51% yield) as a yellow oil.

UPLC-MS (ES$^+$, short acidic):1.35 min, m/z 303.9 [M+H]$^+$ tert-Butyl (3R)-3-[4-amino-3-[4-[[(4-fluoro-2-methoxy-benzoyl)amino]methyl]phenyl]pyrazolo[3,4-d]pyrimidin-1-yl]piperidine-1-carboxylate Following general procedure D, [4-[[(4-fluoro-2-methoxy-benzoyl)amino]methyl]-phenyl]boronic acid (223.8 mg, 0.74 mmol) and tert-butyl (3R)-3-(4-amino-3-iodo-pyrazolo[3,4-d]pyrimidin-1-yl)piperidine-1-carboxylate (205.0 mg, 0.46 mmol) gave tert-butyl (3R)-3-[4-amino-3-[4-[[(4-fluoro-2-methoxy-benzoyl)amino]methyl]phenyl]pyrazolo-[3,4-d]pyrimidin-1-yl]piperidine-1-carboxylate (360.0 mg, 0.44 mmol, 95% yield) as a brown foam.

UPLC-MS (ES$^+$, Short acidic): 1.69 min, m/z 576.4 [M+H]$^+$

N-[[4-[4-Amino-1-[(3R)-3-piperidyl]pyrazolo[3,4-d]pyrimidin-3-yl]phenyl]methyl]-4-fluoro-2-methoxy-benzamide Following general procedure E, tert-butyl (3R)-3-[4-amino-3-[4-[[(4-fluoro-2-methoxy-benzoyl)amino]methyl]phenyl]pyrazolo[3,4-d]pyrimidin-1-yl]piperidine-1-carboxylate (360.0 mg, 0.44 mmol) afforded N-[[4-[4-amino-1-[(3R)-3-piperidyl]pyrazolo[3,4-d]-pyrimidin-3-yl]phenyl]methyl]-4-fluoro-2-methoxy-benzamide (165.0 mg, 0.31 mmol, 71% yield) as an off white foam.

UPLC-MS (ES$^+$, Short acidic): 1.13 min, m/z 476.2 [M+H]$^+$

N-[[4-[4-Amino-1-[(3R)-1-prop-2-enoyl-3-piperidyl]pyrazolo[3,4-d]pyrimidin-3-yl]phenyl]methyl]-4-fluoro-2-methoxy-benzamide Following general procedure F, N-[[4-[4-amino-1-[(3R)-3-piperidyl]pyrazolo[3,4-d]pyrimidin-3-yl]phenyl]methyl]-4-fluoro-2-methoxy-benzamide (165.0 mg, 0.35 mmol) gave N-[[4-[4-amino-1-[(3R)-1-prop-2-enoyl-3-piperidyl]pyrazolo[3,4-d]pyrimidin-3-yl]phenyl]methyl]-4-fluoro-2-methoxy-benzamide (26.4 mg, 0.05 mmol, 14% yield) as an off-white foam.

UPLC-MS (ES$^+$, short acidic): 1.39 min, m/z 530.4 [M+H]$^+$

UPLC-MS (ES$^+$, long acidic): 3.17 min, m/z 530.4 [M+H]$^+$ $^1$H NMR (400 MHz, DMSO-d$_6$) δ (ppm, 1:1 mixture of conformers) 8.73 (t, J 6.0 Hz, 1H, NH), 8.27 (s, 1H, ArH), 7.87-7.81 (m, 1H, ArH), 7.65 (d, J 8.0 Hz, 2H, ArH), 7.50 (d, J 8.0 Hz, 2H, ArH), 7.11-7.06 (m, 1H, ArH), 6.91-6.86 (m, 1H, ArH), 6.88-6.82 (m, 0.5H), 6.72 (dd, $^3J_{cis}$ 10.4, $^3J_{trans}$ 16.4 Hz, 0.5H), 6.13 (d, $^3J_{trans}$ 16.4 Hz, 0.5H), 6.07 (d, $^3J_{trans}$ 16.4 Hz, 0.5H), 5.71 (d, $^3J_{cis}$ 10.4 Hz, 0.5H), 5.59 (d, $^3J_{cis}$ 10.4 Hz, 0.5H), 4.77-4.65 (m, 1H), 4.58 (d, J 6.0 Hz, 2H), 4.57-4.51 (m, 0.5H), 4.26-4.16 (m, 1H), 4.13-4.04 (m, 0.5H), 3.94 (s, 3H, CH$_3$), 3.76-3.66 (m, 0.5H), 3.26-3.15 (m, 1H), 3.06-2.97 (m, 0.5H), 2.32-2.21 (m, 1H), 2.16-2.09 (m, 1H), 1.95-1.92 (m, 1H), 1.62-1.56 (m, 1H).

Example 11: N-[[4-[4-Amino-1-[(3R)-1-prop-2-enoyl-3-piperidyl]pyrazolo[3,4-d]pyrimidin-3-yl]phenyl]methyl]-5-fluoro-2-methoxy-benzamide

[4-[[(5-Fluoro-2-methoxy-benzoyl)amino]methyl]phenyl]boronic acid

Following general procedure A, 4-(aminomethyl)phenyl boronic acid hydrochloride (424.1 mg, 2.26 mmol) and 5-fluoro-2-methoxy-benzoic acid (350.0 mg, 2.06 mmol) gave [4-[[(5-fluoro-2-methoxy-benzoyl)amino]methyl]phenyl]boronic acid (361.0 mg, 0.89 mmol, 43% yield) as a yellow oil.

UPLC-MS (ES$^+$, short acidic): 1.35 min, [M+H]$^+$303.8 tert-Butyl (3R)-3-[4-amino-3-[4-[[(5-fluoro-2-methoxy-benzoyl)amino]methyl]phenyl]pyrazolo[3,4-d]pyrimidin-1-yl]piperidine-1-carboxylate Following general procedure D-2, [4-[[(5-fluoro-2-methoxy-benzoyl)amino]methyl]-phenyl]boronic acid (350.9 mg, 0.81 mmol) and tert-butyl (3R)-3-(4-amino-3-iodo-pyrazolo[3,4-d]pyrimidin-1-yl)piperidine-1-carboxylate (225.0 mg, 0.51 mmol) gave tert-butyl (3R)-3-[4-amino-3-[4-[[(5-fluoro-2-methoxy-benzoyl)amino]methyl]phenyl]-pyrazolo[3,4-d]pyrimidin-1-yl]piperidine-1-carboxylate (360.0 mg, 0.44 mmol, 86% yield) as a brown foam.

UPLC-MS (ES$^+$, Short acidic): 1.70 min, m/z 576.5 [M+H]$^+$

N-[[4-[4-Amino-1-[(3R)-3-piperidyl]pyrazolo[3,4-d]pyrimidin-3-yl]phenyl]methyl]-5-fluoro-2-methoxy-benzamide Following general procedure E, tert-butyl (3R)-3-[4-amino-3-[4-[[(5-fluoro-2-methoxy-benzoyl)amino]methyl]phenyl]pyrazolo[3,4-d]pyrimidin-1-yl]piperidine-1-carboxylate (383.0 mg, 0.47 mmol) afforded N-[[4-[4-amino-1-[(3R)-3-piperidyl]pyrazolo[3,4-d]pyrimidin-3-yl]phenyl]methyl]-5-fluoro-2-methoxy-benzamide (195.0 mg, 0.39 mmol, 84% yield) as a brown foam.

UPLC-MS (ES$^+$, Short acidic): 1.12 min, m/z 476.3 [M+H]$^+$

N-[[4-[4-Amino-1-[(3R)-1-prop-2-enoyl-3-piperidyl]pyrazolo[3,4-d]pyrimidin-3-yl]phenyl]methyl]-5-fluoro-2-methoxy-benzamide Following general procedure F, N-[[4-[4-amino-1-[(3R)-3-piperidyl]pyrazolo[3,4-d]pyrimidin-3-yl]phenyl]methyl]-5-fluoro-2-methoxy-benzamide (195.0 mg, 0.41 mmol) gave N-[[4-[4-amino-1-[(3R)-1-prop-2-enoyl-3-piperidyl]pyrazolo[3,4-d]pyrimidin-3-yl]phenyl]methyl]-5-fluoro-2-methoxy-benzamide (89.0 mg, 0.16 mmol, 39% yield) as an off-white foam.

UPLC-MS (ES$^+$, short acidic): 1.40 min, m/z 530.4 [M+H]$^+$

UPLC-MS (ES$^+$, long acidic): 3.17 min, m/z 530.4 [M+H]$^+$ $^1$H NMR (400 MHz, DMSO-d$_6$) δ (ppm, 1:1 mixture of conformers) 8.87 (t, J 6.0 Hz, 1H, NH), 8.27 (s, 1H, ArH), 7.65 (d, J 7.7 Hz, 2H, ArH), 7.56-7.48 (m, 3H, ArH), 7.38-7.31 (m, 1H, ArH), 7.23-7.17 (m, 1H, ArH), 6.87 (dd, $^3J_{cis}$ 10.4, $^3J_{trans}$ 16.4 Hz, 0.5H), 6.73 (dd, $^3J_{cis}$ 10.4, $^3J_{trans}$ 16.4 Hz, 0.5H), 6.14 (d, $^3J_{trans}$ 16.4 Hz, 0.5H), 6.07 (d, $^3J_{trans}$ 16.4 Hz, 0.5H), 5.71 (d, $^3J_{cis}$ 10.4 Hz, 0.5H), 5.59 (d, $^3J_{cis}$ 10.4 Hz, 0.5H), 4.77-4.65 (m, 1H), 4.59 (d, J 6.0 Hz, 2H, CH$_2$), 4.58-4.52 (m, 0.5H), 4.26-4.17 (m, 1H), 4.11-4.04 (m, 0.5H), 3.91 (s, 3H, CH$_3$), 3.75-3.67 (m, 0.5H), 3.26-3.15

(m, 1H), 3.07-2.97 (m, 0.5H), 2.34-2.21 (m, 1H), 2.17-2.08 (m, 1H), 1.98-1.88 (m, 1H), 1.66-1.52 (m, 1H).

Example 12: N-[[4-[4-Amino-1-[(3R)-1-prop-2-enoyl-3-piperidyl]pyrazolo[3,4-d]pyrimidin-3-yl]phenyl]methyl]-3,5-dimethoxy-benzamide

[4-[[(3,5-Dimethoxybenzoyl)amino]methyl]phenyl]boronic acid

To a solution of [4-(aminomethyl)phenyl]boronic acid (200.0 mg, 1.32 mmol), 3,5-dimethoxybenzoic acid (241.3 mg, 1.32 mmol) and (benzotriazol-1-yloxy)tris(dimethylamino)phosphonium hexafluorophosphate (644.5 mg, 1.46 mmol) in DMF (5 mL) was added N,N-diisopropylethylamine (0.35 mL, 1.99 mmol). The reaction mixture stirred at rt for 72 h, and then extracted into ethyl acetate (10 mL). The organic layer was washed with water twice and brine, dried over a phase separator and concentrated in vacuo to afford [4-[[(3,5-dimethoxybenzoyl)amino]methyl]phenyl]boronic acid (410.0 mg, 0.65 mmol, 49% yield) as a pale pink solid.
UPLC-MS (ES$^+$, Short acidic): 1.32 min, m/z 315.8 [M+H]$^+$ tert-Butyl (3R)-3-[4-amino-3-[4-[[3,5-dimethoxybenzoyl)amino]methyl]phenyl]pyrazolo[3,4-d]pyrimidin-1-yl]piperidine-1-carboxylate Following general procedure D, [4-[[(3,5-dimethoxybenzoyl)amino]methyl]phenyl]boronic acid (200.0 mg, 0.63 mmol) and tert-butyl (3R)-3-(4-amino-3-iodo-pyrazolo[3,4-d]pyrimidin-1-yl)piperidine-1-carboxylate (422.9 mg, 0.95 mmol) gave tert-butyl (3R)-3-[4-amino-3-[4-[[(3,5-dimethoxybenzoyl)amino]methyl]phenyl]pyrazolo[3,4-d]pyrimidin-1-yl]piperidine-1-carboxylate (200.0 mg, 0.34 mmol, 54% yield) as a brown foam.
UPLC-MS (ES$^+$, Short acidic): 1.67 min, m/z 588.5 [M+H]$^+$ N-[[4-[4-Amino-1-[(3R)-3-piperidyl]pyrazolo[3,4-d]pyrimidin-3-yl]phenyl]methyl]-3,5-dimethoxy-benzamide Following general procedure E, N-[[4-[4-amino-1-[(3R)-1-(3,3-dimethylbutanoyl)-3-piperidyl]pyrazolo[3,4-d]pyrimidin-3-yl]phenyl]methyl]-3,5-dimethoxy-benzamide (200.0 mg, 0.34 mmol) gave N-[[4-[4-amino-1-[(3R)-3-piperidyl]pyrazolo[3,4-d]pyrimidin-3-yl]phenyl]methyl]-3,5-dimethoxy-benzamide (120.0 mg, 0.25 mmol, 72% yield) as a white solid.
UPLC-MS (ES$^+$, Short acidic): 1.15 min, m/z 488.3 [M+H]$^+$ N-[[4-[4-amino-1-[(3R)-1-prop-2-enoyl-3-piperidyl]pyrazolo[3,4-d]pyrimidin-3-yl]phenyl]methyl]-3,5-dimethoxy-benzamide Following general procedure F, N-[[4-[4-amino-1-[(3R)-3-piperidyl]pyrazolo[3,4-d]pyrimidin-3-yl]phenyl]methyl]-3,5-dimethoxy-benzamide (100.0 mg, 0.21 mmol) gave N-[[4-[4-amino-1-[(3R)-1-prop-2-enoyl-3-piperidyl]pyrazolo[3,4-d]pyrimidin-3-yl]phenyl]methyl]-3,5-dimethoxy-benzamide (5.0 mg, 0.01 mmol, 5% yield)
UPLC-MS (ES$^+$, Short acidic): 1.38 min, m/z 542.2 [M+H]$^+$
UPLC-MS (ES$^+$, Long acidic): 3.10 min, m/z 542.4 [M+H]$^+$ $^1$H NMR (400 MHz, DMSO-d$_6$) δ (ppm, 1:1 mixture of conformers) 9.09 (t, $^3$J 6.0 Hz, 1H, NH), 8.26 (s, 1H, ArH), 7.64 (d, $^3$J 8.0 Hz, 2H, ArH), 7.49 (d, $^3$J 8.0 Hz, 2H, ArH), 7.09 (d, $^4$J 2.3 Hz, 2H, ArH), 6.86 (dd, $^3$J$_{trans}$ 16.1, $^3$J$_{cis}$ 10.7 Hz, 0.5H), 6.71 (dd, $^3$J$_{trans}$ 16.1, $^3$J$_{cis}$ 10.7 Hz, 0.5H), 6.66 (t, $^4$J 2.3 Hz, 1H, ArH), 6.13 (d, $^3$J$_{trans}$ 16.7 Hz, 0.5H), 6.06 (d, $^3$J$_{trans}$ 16.7 Hz, 0.5H), 5.71 (d, $^3$J$_{cis}$ 10.3 Hz, 0.5H), 5.58 (d, $^3$J$_{cis}$ 10.3 Hz, 0.5H), 4.77-4.64 (m, 1H, CH), 4.55 (d, $^3$J 6.0 Hz, 2H, CH$_2$), 4.55-4.50 (m, 0.5H), 4.24-4.15 (m, 1H), 4.11-4.03 (m, 0.5H), 3.79 (s, 6H, CH$_3$), 3.74-3.65 (m, 0.5H), 3.25-3.14 (m, 1H), 3.06-2.95 (m, 0.5H), 2.31-2.20 (m, 1H), 2.16-2.07 (m, 1H), 1.98-1.88 (m, 1H), 1.65-1.52 (m, 1H).

Example 13: N-[[4-[4-Amino-1-[(3R)-1-cyano-3-piperidyl]pyrazolo[3,4-d]pyrimidin-3-yl]phenyl]methyl]-2-methoxy-benzamide Following general procedure G, N-[[4-[4-amino-1-[(3R)-3-piperidyl]pyrazolo[3,4-d]pyrimidin-3-yl]phenyl]methyl]-2-methoxy-benzamide (63.8 mg, 0.14 mmol) afforded, after further purification by flash column chromatography, N-[[4-[4-amino-1-[(3R)-1-cyano-3-piperidyl]pyrazolo[3,4-d]pyrimidin-3-yl]phenyl]methyl]-2-methoxy-benzamide (23.0 mg, 0.05 mmol, 34% yield) as a white solid.
UPLC-MS (ES$^+$, Short acidic): 1.38 min, m/z 483.1 [M+H]$^+$
UPLC-MS (ES$^+$, Long acidic): 3.10 min, m/z 483.3 [M+H]$^+$
$^1$H NMR: (400 MHz, DMSO-d$_6$) δ 8.79 (t, J 6.1 Hz, 1H, NH), 8.29 (s, 1H, ArH), 7.79 (dd, J 7.7, J 1.8 Hz, 1H, ArH), 7.67 (d, J 8.3 Hz, 2H, ArH), 7.53 (d, J 8.3 Hz, 2H, ArH), 7.54-7.48 (m, 1H, ArH), 7.18 (d, J 8.5 Hz, 1H, ArH), 7.07 (td, J 7.5, J 1.0 Hz, 1H, ArH), 4.93-4.84 (m, 1H), 4.61 (d, J 6.1 Hz, 2H, CH$_2$), 3.93 (s, 3H, OCH$_3$), 3.65 (dd, J 12.5, J 4.2 Hz, 1H), 3.53 (dd, J 12.5, J 10.4 Hz, 1H), 3.45-3.38 (m, 1H), 3.22-3.14 (m, 1H), 2.25-2.06 (m, 2H), 1.97-1.78 (m, 2H).

Example 14: N-[[4-[4-Amino-1-[(3R)-1-prop-2-enoyl-3-piperidyl]pyrazolo[3,4-d]pyrimidin-3-yl]phenyl]methyl]-3-chloro-2-methoxy-benzamide

[4-[[(3-Chloro-2-methoxy-benzoyl)amino]methyl]phenyl]boronic acid

Following general procedure A, [4-(aminomethyl)phenyl]boronic acid hydrochloride (386.7 mg, 2.06 mmol) and 3-chloro-2-methoxy-benzoic acid (350.0 mg, 2.06 mmol) gave [4-[[(3-chloro-2-methoxy-benzoyl)amino]methyl]phenyl]boronic acid (467.0 mg, 0.95 mmol, 51% yield) as a yellow foam.
UPLC-MS (ES$^+$, Short acidic):1.42 min, m/z 319.8 [M+H]$^+$ tert-Butyl (3R)-3-[4-amino-3-[4-[[(3-chloro-2-methoxy-benzoyl)amino]methyl]phenyl]-pyrazolo[3,4-d]pyrimidin-1-yl]piperidine-1-carboxylate Following general procedure D, [4-[[(3-chloro-2-methoxy-benzoyl)amino]methyl]phenyl]boronic acid (442.9 mg, 0.90 mmol) and tert-butyl (3R)-3-(4-amino-3-iodo-pyrazolo[3,4-d]pyrimidin-1-yl)piperidine-1-carboxylate (230.0 mg, 0.52 mmol) gave tert-butyl (3R)-3-[4-amino-3-[4-[[(3-chloro-2-methoxy-benzoyl)amino]methyl]phenyl]-pyrazolo[3,4-d]pyrimidin-1-yl]piperidine-1-carboxylate (327.2 mg, 0.41 mmol, 80% yield) as a brown foam.

UPLC-MS (ES$^+$, Short acidic): 1.77 min, m/z 593.1 [M+H]$^+$

N-[[4-[4-Amino-1-[(3R)-3-piperidyl]pyrazolo[3,4-d]pyrimidin-3-yl]phenyl]methyl]-3-chloro-2-methoxy-benzamide Following general procedure E, tert-butyl (3R)-3-[4-amino-3-[4-[[(3-chloro-2-methoxy-benzoyl)amino]methyl]phenyl]pyrazolo[3,4-d]pyrimidin-1-yl]piperidine-1-carboxylate (327.0 mg, 0.41 mmol) afforded N-[[4-[4-amino-1-[(3R)-3-piperidyl]pyrazolo[3,4-d]pyrimidin-3-yl]phenyl]methyl]-3-chloro-2-methoxy-benzamide (173.4 mg, 0.33 mmol, 81% yield) as an orange solid.

UPLC-MS (ES$^+$, Short acidic): 1.20 min, m/z 492.2 [M+H]$^+$

N-[[4-[4-Amino-1-[(3R)-1-prop-2-enoyl-3-piperidyl]pyrazolo[3,4-d]pyrimidin-3-yl]phenyl]methyl]-3-chloro-2-methoxy-benzamide Following general procedure F, N-[[4-[4-amino-1-[(3R)-3-piperidyl]pyrazolo[3,4-d]pyrimidin-3-yl]phenyl]methyl]-3-chloro-2-methoxy-benzamide (173.4 mg, 0.35 mmol) gave N-[[4-[4-amino-1-[(3R)-1-prop-2-enoyl-3-piperidyl]pyrazolo[3,4-d]pyrimidin-3-yl]phenyl]methyl]-3-chloro-2-methoxy-benzamide (20.4 mg, 0.04 mmol, 10% yield) as an off-white foam.

UPLC-MS (ES$^+$, Short acidic): 1.46 min, m/z 547.0 [M+H]$^+$

UPLC-MS (ES$^+$, Long acidic): 3.35 min, m/z 547.0 [M+H]$^+$ $^1$H NMR (400 MHz, DMSO-d$_6$) δ (ppm, 1:1 mixture of conformers) 8.98 (t, $^3$J 6.0 Hz, 1H, NH), 8.27 (s, 1H, ArH), 7.67 (d, $^3$J 8.0 Hz, 2H, ArH), 7.63-7.59 (m, 1H, ArH), 7.57-7.52 (d, $^3$J 8.0 Hz, 2H, ArH), 7.54-7.50 (m, 1H, ArH), 7.24 (t, $^3$J 7.8 Hz, 1H, ArH), 6.88 (dd, $^3$J$_{cis}$ 10.4, $^3$J$_{trans}$ 16.4 Hz, 0.5H) 6.73 (dd, $^3$J$_{cis}$ 10.4, $^3$J$_{trans}$ 16.4 Hz, 0.5H), 6.14 (d, $^3$J$_{trans}$ 16.4 Hz, 0.5H), 6.07 (d, $^3$J$_{trans}$ 16.4 Hz, 0.5H), 5.72 (d, $^3$J$_{cis}$ 10.4 Hz, 0.5H), 5.60 (d, $^3$J$_{cis}$ 10.4 Hz, 0.5H), 4.78-4.66 (m, 1H, CH), 4.56 (d, $^3$J 6.0 Hz, 2H, CH$_2$), 4.57-4.50 (m, 0.5H), 4.26-4.17 (m, 1H), 4.12-4.04 (m, 0.5H), 3.82 (s, 3H, OCH$_3$), 3.76-3.67 (m, 0.5H), 3.27-3.16 (m, 1H), 3.07-2.97 (m, 0.5H), 2.33-2.22 (m, 1H), 2.17-2.09 (m, 1H), 1.98-1.90 (m, 1H), 1.67-1.52 (m, 1H).

Example 15: N-[[4-[4-Amino-1-[(3R)-1-prop-2-enoyl-3-piperidyl]pyrazolo[3,4-d]pyrimidin-3-yl]phenyl]methyl]-2-methoxy-4-methyl-benzamide

[4-[[(2-Methoxy-4-methyl-benzoyl)amino]methyl]phenyl]boronic acid

Following general procedure A, [4-(aminomethyl)phenyl]boronic acid hydrochloride (435.1 mg, 2.32 mmol) and 4-methyl-2-methoxy-benzoic acid (350.7 mg, 2.06 mmol) gave [4-[[(2-methoxy-4-methyl-benzoyl)amino]methyl]phenyl]boronic acid (464.0 mg, 1.16 mmol, 55% yield) as a yellow oil.

UPLC-MS (ES$^+$, Short acidic):1.39 min, m/z 299.8 [M+H]$^+$ tert-Butyl (3R)-3-[4-amino-3-[4-[[(2-methoxy-4-methyl-benzoyl)amino]methyl]phenyl]-pyrazolo[3,4-d]pyrimidin-1-yl]piperidine-1-carboxylate Following general procedure D, [4-[[(2-methoxy-4-methyl-benzoyl)amino]methyl]phenyl]-boronic acid (404.0 mg, 0.95 mmol) and tert-butyl (3R)-3-(4-amino-3-iodo-pyrazolo[3,4-d]pyrimidin-1-yl)piperidine-1-carboxylate (240.0 mg, 0.54 mmol) gave tert-butyl (3R)-3-[4-amino-3-[4-[[(2-methoxy-4-methyl-benzoyl)amino]methyl]phenyl]pyrazolo[3,4-d]pyrimidin-1-yl]piperidine-1-carboxylate (473.0 mg, 0.49 mmol, 92% yield) as a brown foam.

UPLC-MS (ES$^+$, Short acidic): 1.73 min, m/z 572.5 [M+H]$^+$

N-[[4-[4-Amino-1-[(3R)-3-piperidyl]pyrazolo[3,4-d]pyrimidin-3-yl]phenyl]methyl]-2-methoxy-4-methyl-benzamide Following general procedure E, tert-butyl (3R)-3-[4-amino-3-[4-[[(2-methoxy-4-methyl-benzoyl)amino]methyl]phenyl]pyrazolo[3,4-d]pyrimidin-1-yl]piperidine-1-carboxylate (473.0 mg, 0.54 mmol) afforded N-[[4-[4-amino-1-[(3R)-3-piperidyl]pyrazolo[3,4-d]pyrimidin-3-yl]phenyl]methyl]-2-methoxy-4-methyl-benzamide (223.5 mg, 0.45 mmol, 84% yield) as an off-white foam.

UPLC-MS (ES$^+$, Short acidic): 1.17 min, m/z 472.4 [M+H]$^+$

N-[[4-[4-Amino-1-[(3R)-1-prop-2-enoyl-3-piperidyl]pyrazolo[3,4-d]pyrimidin-3-yl]phenyl]methyl]-2-methoxy-4-methyl-benzamide Following general procedure F, N-[[4-[4-amino-1-[(3R)-3-piperidyl]pyrazolo[3,4-d]pyrimidin-3-yl]phenyl]methyl]-2-methoxy-4-methyl-benzamide (223.5 mg, 0.47 mmol) afforded the title compound (19.7 mg, 0.04 mmol, 8% yield) as an off-white foam.

UPLC-MS (ES$^+$, Short acidic): 1.44 min, m/z 526.4 [M+H]$^+$

UPLC-MS (ES$^+$, Long acidic): 3.28 min, m/z 526.4 [M+H]$^+$ $^1$H NMR (400 MHz, DMSO-d$_6$) δ (ppm, 1:1 mixture of conformers) 8.70 (t, J 6.0 Hz, 1H, NH), 8.27 (s, 1H, ArH), 7.73 (d, J 8.0 Hz, 1H, ArH), 7.64 (d, J 8.0 Hz, 2H, ArH), 7.50 (d, J 8.0 Hz, 2H, ArH), 7.00 (s, 1H, ArH), 6.91-6.84 (m, 0.5H), 6.89-6.86 (m, 1H, ArH), 6.73 (dd, $^3$J$_{trans}$ 16.4, $^3$J$_{cis}$ 10.4 Hz, 0.5H), 6.14 (d, $^3$J$_{trans}$ 16.4 Hz, 0.5H), 6.07 (d, $^3$J$_{trans}$ 16.4 Hz, 0.5H), 5.71 (d, $^3$J$_{cis}$ 10.4 Hz, 0.5H), 5.60-5.57 (d, $^3$J$_{cis}$ 10.4 Hz, 0.5H), 4.77-4.66 (m, 1H), 4.59 (d, J 6.0 Hz, 2H, CH$_2$), 4.58-4.51 (m, 0.5H), 4.27-4.16 (m, 1H), 4.13-4.04 (m, 0.5H), 3.92 (s, 3H, OCH$_3$), 3.75-3.66 (m, 0.5H), 3.27-3.15 (m, 1H), 3.06-2.96 (m, 0.5H), 2.36 (s, 3H, CH$_3$), 2.32-2.21 (m, 1H), 2.17-2.08 (m, 1H), 1.98-1.89 (m, 1H), 1.67-1.52 (m, 1H).

Example 16: N-[[4-[4-Amino-1-[(3R)-1-prop-2-enoyl-3-piperidyl]-pyrazolo[3,4-d]pyrimidin-3-yl]phenyl]methyl]-3-fluoro-2-methoxy-benzamide

[4-[[(3-Fluoro-2-methoxy-benzoyl)amino]methyl]phenyl]boronic acid

Following general procedure A, [4-(aminomethyl)phenyl]boronic acid hydrochloride (424.1 mg, 2.26 mmol) and 3-fluoro-2-methoxy-benzoic acid (350.0 mg, 2.06 mmol) gave [4-[[(3-fluoro-2-methoxy-benzoyl)amino]methyl]phenyl]boronic acid (554 mg, 1.10 mmol, 53% yield) as a deep red oil.

UPLC-MS (ES$^+$, Short acidic):1.35 min, m/z 303.8 [M+H]$^+$ tert-Butyl (3R)-3-[4-amino-3-[4-[[(3-fluoro-2-methoxy-benzoyl)amino]methyl]phenyl]pyrazolo[3,4-d]pyrimidin-1-yl]piperidine-1-carboxylate Following general procedure D, [4-[[(3-fluoro-2-methoxy-benzoyl)amino]methyl]phenyl]-boronic acid (554.0 mg, 1.83 mmol) and tert-butyl (3R)-3-(4-amino-3-iodo-pyrazolo[3,4-d]pyrimidin-1-yl)piperidine-1-carboxylate (240 mg, 0.54 mmol) gave tert-butyl (3R)-3-[4-amino-3-[4-[[(3-fluoro-2-methoxy-benzoyl)amino]methyl]phenyl]pyrazolo[3,4-d]pyrimidin-1-yl]piperidine-1-carboxylate (428.0 mg, 0.52 mmol, 96% yield) as a brown foam.

UPLC-MS (ES$^+$, Short acidic): 1.71 min, m/z 576.4 [M+H]

N-[[4-[4-Amino-1-[(3R)-3-piperidyl]pyrazolo[3,4-d]pyrimidin-3-yl]phenyl]methyl]-3-fluoro-2-methoxy-benzamide Following general procedure E, tert-butyl (3R)-3-[4-amino-3-[4-[[(3-fluoro-2-methoxy-benzoyl)amino]methyl]phenyl]pyrazolo[3,4-d]pyrimidin-1-yl]piperidine-1-carboxylate (428.0 mg, 0.52 mmol) afforded N-[[4-[4-amino-1-[(3R)-3-piperidyl]pyrazolo[3,4-d]pyrimidin-3-yl]phenyl]methyl]-3-fluoro-2-methoxy-benzamide (194.7 mg, 0.39 mmol, 75% yield) as a brown foam.

UPLC-MS (ES$^+$, Short acidic): 1.13 min, m/z 476.3 [M+H]$^+$

N-[[4-[4-Amino-1-[(3R)-1-prop-2-enoyl-3-piperidyl]pyrazolo[3,4-d]pyrimidin-3-yl]phenyl]methyl]-3-fluoro-2-methoxy-benzamide Following general procedure F, N-[[4-[4-amino-1-[(3R)-3-piperidyl]pyrazolo[3,4-d]pyrimidin-3-yl]phenyl]methyl]-3-fluoro-2-methoxy-benzamide (194.7 mg, 0.41 mmol) afforded the title compound (71.3 mg, 0.13 mmol, 31% yield) as an off-white foam.

UPLC-MS (ES$^+$, Short acidic): 1.41 min, m/z 530.4 [M+H]$^+$

UPLC-MS (ES$^+$, Long acidic): 3.21 min, m/z 530.4 [M+H]$^+$ $^1$H NMR (400 MHz, DMSO-d$_6$) δ (ppm, 1:1 mixture of conformers) 8.89 (t, J 6.0 Hz, 1H, NH), 8.27 (s, 1H, ArH), 7.67 (d, J 8.0 Hz, 2H, ArH), 7.54 (d, J 8.0 Hz, 2H, ArH), 7.45-7.38 (m, 2H, ArH), 7.24-7.16 (m, 1H, ArH), 6.88 (dd, $^3J_{trans}$ 16.4, $^3J_{cis}$ 10.4 Hz, 0.5H), 6.73 (dd, $^3J_{trans}$ 16.4, $^3J_{cis}$ 10.4 Hz, 0.5H), 6.14 (d, $^3J_{trans}$ 16.4 Hz, 0.5H), 6.07 (d, $^3J_{trans}$ 16.4 Hz, 0.5H), 5.72 (d, $^3J_{cis}$ 10.4 Hz, 0.5H), 5.60 (d, $^3J_{cis}$ 10.4 Hz, 0.5H), 4.77-4.67 (m, 1H), 4.57 (d, J 6.0 Hz, 2H, CH$_2$), 4.57-4.52 (m, 0.5H), 4.26-4.17 (m, 1H), 4.13-4.05 (m, 0.5H), 3.91 (s, 3H, OCH$_3$), 3.75-3.66 (m, 0.5H), 3.26-3.16 (m, 1H), 3.06-2.97 (m, 0.5H), 2.33-2.21 (m, 1H), 2.17-2.09 (m, 1H), 1.98-1.90 (m, 1H), 1.66-1.53 (m, 1H).

Example 17: N-[[4-[4-Amino-1-[(3R)-1-prop-2-enoyl-3-piperidyl]pyrazolo[3,4-d]pyrimidin-3-yl]phenyl]methyl]-3-cyano-benzamide

[4-[[(3-Cyanobenzoyl)amino]methyl]phenyl]boronic acid

To a solution of 3-cyanobenzoic acid (194.9 mg, 1.32 mmol), [4-(aminomethyl)phenyl]boronic acid (200.0 mg, 1.32 mmol) and (benzotriazol-1-yloxy)tris(dimethylamino)phosphonium hexafluorophosphate (644.5 mg, 1.46 mmol) in DMF (5 mL) was added N,N-diisopropylethylamine (0.4 mL, 1.99 mmol). The reaction mixture was then stirred under an N$_2$ atmosphere for 24 hours, extracted into ethyl acetate (10 mL). The organic layer was washed with brine (3×10 mL), dried over a phase separator and concentrated in vacuo to afford [4-[[(3-cyanobenzoyl)amino]methyl]phenyl]boronic acid (210.0 mg, 0.75 mmol, 56% yield) as a white solid.

UPLC-MS (ES$^+$, Short acidic): 1.21 min, m/z 280.8 [M+H]$^+$ tert-Butyl (3R)-3-[4-amino-3-[4-[[(3-cyanobenzoyl)amino]methyl]phenyl]pyrazolo[3,4-d]pyrimidin-1-yl]piperidine-1-carboxylate Following general procedure D, [4-[[(3-cyanobenzoyl)amino]methyl]phenyl]boronic acid (208.0 mg, 0.74 mmol), and tert-butyl (3R)-3-(4-amino-3-iodo-pyrazolo[3,4-d]pyrimidin-1-yl)piperidine-1-carboxylate (220.0 mg, 0.5 mmol) gave tert-butyl (3R)-3-[4-amino-3-[4-[[(3-cyanobenzoyl)amino]methyl]phenyl]pyrazolo[3,4-d]pyrimidin-1-yl]piperidine-1-carboxylate (200.0 mg, 0.36 mmol, 73% yield) as a yellow oil.

UPLC-MS (ES$^+$, Short acidic): 1.61 min, m/z 553.4 [M+H]$^+$

N-[[4-[4-Amino-1-[(3R)-3-piperidyl]pyrazolo[3,4-d]pyrimidin-3-yl]phenyl]methyl]-3-cyano-benzamide Following general procedure E, tert-butyl (3R)-3-[4-amino-3-[4-[[(3-cyanobenzoyl)amino]methyl]phenyl]pyrazolo[3,4-d]pyrimidin-1-yl]piperidine-1-carboxylate (200.0 mg, 0.36 mmol) gave N-[[4-[4-amino-1-[(3R)-3-piperidyl]pyrazolo[3,4-d]pyrimidin-3-yl]phenyl]methyl]-3-cyano-benzamide (80.0 mg, 0.17 mmol, 48% yield) as a white solid.

UPLC-MS (ES$^+$, Short acidic): 1.07 min, m/z 453.3 [M+H]$^+$

N-[[4-[4-Amino-1-[(3R)-1-prop-2-enoyl-3-piperidyl]pyrazolo[3,4-d]pyrimidin-3-yl]phenyl]methyl]-3-cyano-benzamide Following general procedure F, N-[[4-[4-amino-1-[(3R)-3-piperidyl]pyrazolo[3,4-d]pyrimidin-3-yl]phenyl]methyl]-3-cyano-benzamide (80.0 mg, 0.18 mmol) afforded N-[[4-[4-amino-1-[(3R)-1-prop-2-enoyl-3-piperidyl]pyrazolo[3,4-d]pyrimidin-3-yl]phenyl]methyl]-3-cyano-benzamide (21.0 mg, 0.04 mmol, 23% yield) as a colourless gum.

UPLC-MS (ES$^+$, Short acidic): 1.32 min, m/z 507.3 [M+H]$^+$

UPLC-MS (ES$^+$, Long acidic): 2.96 min, m/z 507.2 [M+H]$^+$ $^1$H NMR (400 MHz, DMSO-d$_6$) δ (ppm, 1:1 mixture of conformers) 9.37 (t, $^3$J 6.6 Hz, 1H, NH), 8.37 (s, 1H, ArH), 8.29-8.22 (m, 2H, ArH), 8.06-8.01 (m, 1H, ArH), 7.73 (t, $^3$J 8.3 Hz, 1H, ArH), 7.65 (d, $^3$J 8.3 Hz, 2H, ArH), 7.53 (d, $^3$J 8.3 Hz, 2H, ArH), 7.29 (br. s, 1H, NH$_2$), 6.87 (dd, $^3J_{trans}$ 16.6, $^3J_{cis}$ 10.8 Hz, 0.5H), 6.79-6.61 (m, 1.5H, NH$_2$+0.5H), 6.14 (d, $^3J_{trans}$ 16.6 Hz, 0.5H), 6.07 (d, $^3J_{trans}$ 16.6 Hz, 0.5H), 5.71 (d, $^3J_{cis}$ 10.8 Hz, 0.5H), 5.59 (d, $^3J_{cis}$ 10.8 Hz, 0.5H), 4.78-4.64 (m, 1H, CH), 4.59 (d, $^3$J 6.6 Hz, 2H, CH$_2$), 4.57-4.51 (m, 0.5H), 4.24-4.15 (m, 1H, CH), 4.12-4.03 (m, 0.5H), 3.76-3.65 (m, 0.5H), 3.27-3.14 (m, 1H, CH), 3.09-2.99 (m, 0.5H), 2.32-2.22 (m, 1H), 2.17-2.08 (m, 1H), 1.97-1.90 (m, 1H), 1.65-1.51 (m, 1H).

Example 18: N-[[4-[4-Amino-1-[(3R)-1-prop-2-enoyl-3-piperidyl]pyrazolo[3,4-d]pyrimidin-3-yl]phenyl]methyl]-4-methoxy-benzamide

[4-[[(4-Methoxybenzoyl)amino]methyl]phenyl]boronic acid

Following general procedure A, [4-(aminomethyl)phenyl]boronic acid (200.0 mg, 1.32 mmol) and 4-methoxybenzoyl chloride (226.0 mg, 1.32 mmol) afforded [4-[[(4-methoxybenzoyl)amino]methyl]phenyl]boronic acid (420.0 mg, 0.88 mmol, 66% yield) as white solid.

UPLC-MS (ES$^+$, Short acidic): 1.23 min, m/z 285.8 [M+H]$^+$ tert-Butyl (3R)-3-[4-amino-3-[4-[[(4-methoxybenzoyl)amino]methyl]phenyl]pyrazolo[3,4-d]pyrimidin-1-yl]piperidine-1-carboxylate Following general procedure D, [4-[[(4-methoxybenzoyl)amino]methyl]phenyl]boronic acid (211.7 mg, 0.74 mmol) and tert-butyl (3R)-3-(4-amino-3-iodo-pyrazolo[3,4-d]pyrimidin-1-yl)piperidine-1-carboxylate (220.0 mg, 0.50 mmol) gave tert-butyl (3R)-3-[4-amino-3-[4-[[(4-methoxybenzoyl)amino]methyl]phenyl]pyrazolo[3,4-d]pyrimidin-1-yl]piperidine-1-carboxylate (230.0 mg, 0.41 mmol, 83% yield) as a yellow solid.

UPLC-MS (ES$^+$, Short acidic): 1.62 min, m/z 558.4 [M+H]$^+$

N-[[4-[4-amino-1-[(3R)-3-piperidyl]pyrazolo[3,4-d]pyrimidin-3-yl]phenyl]methyl]-4-methoxy-benzamide Following general procedure E, tert-butyl (3R)-3-[4-amino-3-[4-[[(4-methoxybenzoyl)amino]methyl]phenyl]pyrazolo[3,4-d]pyrimidin-1-yl]piperidine-1-carboxylate (230.0 mg, 0.41 mmol) gave N-[[4-[4-amino-1-[(3R)-3-piperidyl]pyrazolo[3,4-d]pyrimidin-3-yl]phenyl]methyl]-4-methoxy-benzamide (120.0 mg, 0.26 mmol, 63% yield) as a white solid.

UPLC-MS (ES$^+$, Short acidic): 1.07 min, m/z 458.3 [M+H]$^+$

N-[[4-[4-Amino-1-[(3R)-1-prop-2-enoyl-3-piperidyl]pyrazolo[3,4-d]pyrimidin-3-yl]phenyl]methyl]-4-methoxy-benzamide Following general procedure F, N-[[4-[4-amino-1-[(3R)-3-piperidyl]pyrazolo[3,4-d]pyrimidin-3-yl]phenyl]methyl]-4-methoxy-benzamide (120.0 mg, 0.26 mmol) afforded N-[[4-[4-amino-1-[(3R)-1-prop-2-enoyl-3-piperidyl]pyrazolo[3,4-d]pyrimidin-3-yl]phenyl]methyl]-4-methoxy-benzamide (42.0 mg, 0.08 mmol, 31% yield) as a pale yellow gum.

UPLC-MS (ES$^+$, Short acidic): 1.33 min, m/z 512.4 [M+H]$^+$

UPLC-MS (ES$^+$, Long acidic): 2.99 min, m/z 512.4 [M+H]$^+$ $^1$H NMR (400 MHz, DMSO-d$_6$) δ (ppm, 1:1 mixture of conformers) 8.98 (t, $^3$J 7.1 Hz, 1H, NH), 8.27 (s, 1H, ArH), 7.92 (d, $^3$J 8.5 Hz, 2H, ArH), 7.65 (d, $^3$J 8.5 Hz, 2H, ArH), 7.50 (d, $^3$J 8.5 Hz, 2H, ArH), 7.29 (br. s, 1H, NH$_2$), 7.03 (d, $^3$J 8.5 Hz, 2H, ArH), 6.86 (dd, $^3$J$_{trans}$ 16.5, $^3$J$_{cis}$ 10.4 Hz, 0.5H), 6.77-6.64 (br. s, 1H, NH$_2$), 6.72 (dd, $^3$J$_{trans}$ 16.5, $^3$J$_{cis}$ 10.4 Hz, 0.5H), 6.13 (d, $^3$J$_{trans}$ 16.5 Hz, 0.5H), 6.07 (d, $^3$J$_{trans}$ 16.5 Hz, 0.5H), 5.71 (d, $^3$J$_{cis}$ 10.4 Hz, 0.5H), 5.59 (d, $^3$J$_{cis}$ 10.4 Hz, 0.5H), 4.76-4.67 (m, 1H, CH), 4.60-4.55 (m, 2.5H, 0.5H & CH$_2$), 4.25-4.16 (m, 1H, CH), 4.11-4.03 (m, 0.5H), 3.82 (s, 3H, OCH$_3$), 3.74-3.67 (m, 0.5H), 3.25-3.16 (m, 1H, CH), 3.05-2.98 (m, 0.5H), 2.32-2.18 (m, 1H, CH), 2.16-2.10 (m, 1H, CH), 1.95-1.90 (m, 1H, CH), 1.64-1.55 (m, 1H, CH).

Example 19: N-[[4-[4-Amino-1-[(3R)-1-prop-2-enoyl-3-piperidyl]pyrazolo[3,4-d]pyrimidin-3-yl]phenyl]methyl]-4-methyl-benzamide

[4-[[(4-Methylbenzoyl)amino]methyl]phenyl]boronic acid

General procedure A, [4-(aminomethyl)phenyl]boronic acid (200.0 mg, 1.32 mmol) and p-toluoyl chloride (0.18 mL, 1.32 mmol) gave [4-[[(4-methylbenzoyl)amino]methyl]phenyl]boronic acid (430.0 mg, 0.96 mmol, 72% yield) as white solid.

UPLC-MS (ES$^+$, Short acidic): 1.32 min, m/z 269.8 [M+H]$^+$ tert-Butyl (3R)-3-[4-amino-3-[4-[[(4-methylbenzoyl)amino]methyl]phenyl]pyrazolo[3,4-d]pyrimidin-1-yl]piperidine-1-carboxylate Following general procedure D, [4-[[(4-methylbenzoyl)amino]methyl]phenyl]boronic acid (218.1 mg, 0.81 mmol) and tert-butyl (3R)-3-(4-amino-3-iodo-pyrazolo[3,4-d]pyrimidin-1-yl)piperidine-1-carboxylate (240.0 mg, 0.54 mmol) gave tert-butyl (3R)-3-[4-amino-3-[4-[[(4-methylbenzoyl)amino]methyl]phenyl]pyrazolo[3,4-d]pyrimidin-1-yl]piperidine-1-carboxylate (260.0 mg, 0.48 mmol, 88% yield) as a yellow solid.

UPLC-MS (ES$^+$, Short acidic): 1.68 min, m/z 542.4 [M+H]$^+$

N-[[4-[4-Amino-1-[(3R)-3-piperidyl]pyrazolo[3,4-d]pyrimidin-3-yl]phenyl]methyl]-4-methyl-benzamide Following general procedure E, tert-butyl (3R)-3-[4-amino-3-[4-[[(4-methylbenzoyl)amino]methyl]phenyl]pyrazolo[3,4-d]pyrimidin-1-yl]piperidine-1-carboxylate gave N-[[4-[4-amino-1-[(3R)-3-piperidyl]pyrazolo[3,4-d]pyrimidin-3-yl]phenyl]methyl]-4-methyl-benzamide (90.0 mg, 0.20 mmol, 42% yield) as a white solid.

N-[[4-[4-Amino-1-[(3R)-1-prop-2-enoyl-3-piperidyl]pyrazolo[3,4-d]pyrimidin-3-yl]phenyl]methyl]-4-methyl-benzamide Following general procedure F, N-[[4-[4-amino-1-[(3R)-3-piperidyl]pyrazolo[3,4-d]pyrimidin-3-yl]phenyl]methyl]-4-methyl-benzamide (90.0 mg, 0.20 mmol) afforded N-[[4-[4-amino-1-[(3R)-1-prop-2-enoyl-3-piperidyl]pyrazolo[3,4-d]pyrimidin-3-yl]phenyl]methyl]-4-methyl-benzamide (78.0 mg, 0.16 mmol, 77% yield)

UPLC-MS (ES$^+$, Short acidic): 1.39 min, m/z 496.3 [M+H]$^+$

UPLC-MS (ES$^+$, Long acidic): 3.15 min, m/z 496.3 [M+H]$^+$ $^1$H NMR (400 MHz, DMSO-d$_6$) δ (ppm, 1:1 mixture of conformers) 9.04 (t, $^3$J 6.1 Hz, 1H, NH), 8.27 (s, 1H, ArH), 7.84 (d, $^3$J 7.9 Hz, 2H, ArH), 7.65 (d, $^3$J 7.9 Hz, 2H, ArH), 7.50 (d, $^3$J 7.9 Hz, 2H, ArH), 7.30 (d, $^3$J 7.9 Hz, 2H, ArH), 6.86 (dd, $^3$J$_{trans}$ 16.6, $^3$J$_{cis}$ 10.5 Hz, 0.5H), 6.72 (dd, $^3$J$_{trans}$ 16.6, $^3$J$_{cis}$ 10.5 Hz, 0.5H), 6.13 (d, $^3$J$_{trans}$ 16.6 Hz, 0.5H), 6.07 (d, $^3$J$_{trans}$ 16.6 Hz, 0.5H), 5.71 (d, $^3$J$_{cis}$ 10.5 Hz, 0.5H), 5.59 (d, $^3$J$_{cis}$ 10.5 Hz, 0.5H), 4.76-4.67 (m, 1H, CH), 4.56 (d, $^3$J 6.1 Hz, 2H, CH$_2$), 4.56-4.50 (m, 0.5H), 4.24-4.15 (m, 1H, CH), 4.11-4.03 (m, 0.5H), 3.73-3.65 (m, 0.5H), 3.26-3.16 (m, 1H, CH), 3.06-2.98 (m, 0.5H), 2.36 (s, 3H, CH$_3$), 2.31-2.21 (m, 1H, CH), 2.15-2.09 (m, 1H, CH), 1.96-1.90 (m, 1H, CH), 1.65-1.56 (m, 1H, CH).

Example 20: N-[[4-[4-Amino-1-[(3R)-1-prop-2-enoyl-3-piperidyl]pyrazolo[3,4-d]pyrimidin-3-yl]phenyl]methyl]-3-(trifluoromethyl)benzamide N-[[4-(4,4,5,5-Tetramethyl-1,3,2-dioxaborolan-2-yl)phenyl]methyl]-3-(trifluoromethyl)-benzamide To a solution of 3-(trifluoromethyl)benzamide (330.0 mg, 1.74 mmol) and 4-bromomethylphenylboronic acid pinacol ester (431.9 mg, 1.45 mmol), cooled to 0° C. under a nitrogen atmosphere, was added sodium hydride (87.2 mg, 2.18 mmol). The reaction mixture was stirred at this temperature for 1 h, then allowed to return to room temperature and stirred overnight. The reaction mixture was then diluted with EtOAc (20 mL) and quenched with a saturated aqueous solution of NH$_4$Cl (20 mL) and partitioned. The aqueous phase was extracted with EtOAc (3×10 mL). The combined organic extracts were washed successively with water (2×10 mL) and brine (20 mL), dried over Na$_2$SO$_4$, filtered and concentrated under reduced pressure to give crude N-[[4-(4,4,5,5-tetramethyl-1,3,2-dioxaborolan-2-yl)phenyl]methyl]-3-(trifluoromethyl)benzamide (644.0 mg, 0.79 mmol, 55% yield) as an off-white solid.

UPLC-MS (ES$^+$, Short acidic): 1.99 min, m/z 406.0 [M+H]$^+$ tert-Butyl (3R)-3-[4-amino-3-[4-[[[3-(trifluoromethyl)benzoyl]amino]methyl]phenyl]-pyrazolo[3,4-d]pyrimidin-1-yl]piperidine-1-carboxylate Following general procedure D, N-[[4-(4,4,5,5-tetramethyl-1,3,2-dioxaborolan-2-yl)phenyl]methyl]-3-(trifluoromethyl)benzamide (642.1 mg, 0.79 mmol) and tert-butyl (3R)-3-(4-amino-3-iodo-pyrazolo[3,4-d]pyrimidin-1-yl)piperidine-1-carboxylate (220.0 mg, 0.50 mmol) gave tert-butyl (3R)-3-[4-amino-3-[4-[[[3-(trifluoromethyl)benzoyl]amino]-methyl]phenyl]pyrazolo[3,4-d]pyrimidin-1-yl]piperidine-1-carboxylate (559.0 mg, 0.47 mmol, 95% yield) as a brown/yellow solid.

UPLC-MS (ES$^+$, Short acidic): 1.77 min, m/z 596.4 [M+H]$^+$

N-[[4-[4-Amino-1-[(3R)-3-piperidyl]pyrazolo[3,4-d]pyrimidin-3-yl]phenyl]methyl]-3-(trifluoromethyl)benzamide Following general procedure E, tert-butyl (3R)-3-[4-amino-3-[4-[[[3-(trifluoromethyl)benzoyl]amino]methyl]phenyl]pyrazolo[3,4-d]pyrimidin-1-yl]piperidine-1-carboxylate (559.0 mg, 0.47 mmol) afforded N-[[4-[4-amino-1-[(3R)-3-piperidyl]pyrazolo[3,4-d]pyrimidin-3-yl]phenyl]methyl]-3-(trifluoromethyl)benzamide (80.0 mg, 0.13 mmol, 28% yield) as a brown foam.

UPLC-MS (ES$^+$, Short acidic): 1.23 min, m/z 496.3 [M+H]$^+$

N-[[4-[4-Amino-1-[(3R)-1-prop-2-enoyl-3-piperidyl]pyrazolo[3,4-d]pyrimidin-3-yl]phenyl]methyl]-3-(trifluoromethylbenzamide Following general procedure F, N-[[4-[4-amino-1-[(3R)-3-piperidyl]pyrazolo[3,4-d]pyrimidin-3-yl]phenyl]methyl]-3-(trifluoromethyl)benzamide (80.0 mg, 0.16 mmol) gave N-[[4-[4-amino-1-[(3R)-1-prop-2-enoyl-3-piperidyl]-pyrazolo[3,4-d]pyrimidin-3-yl]phenyl]methyl]-3-(trifluoromethyl)benzamide (5.2 mg, 0.01 mmol, 6% yield) as an off-white powder.

UPLC-MS (ES$^+$, short acidic): 1.50 min, m/z 550.4 [M+H]$^+$

UPLC-MS (ES$^+$, long acidic): 3.44 min, m/z 550.3 [M+H]$^+$ $^1$H NMR (400 MHz, DMSO-d$_6$) δ (ppm, 1:1 mixture of conformers): 9.39 (t, $^3$J 5.4 Hz, 1H, NH), 8.29-8.22 (m, 3H, ArH), 7.97-7.92 (d, J 8.0 Hz, 1H, ArH), 7.79-7.73 (m, 1H, ArH), 7.68-7.62 (d, J 8.0 Hz, 2H, ArH), 7.55-7.49 (d, J 8.0 Hz, 2H, ArH), 6.87 (dd, $^3$J$_{trans}$ 16.4, $^3$J$_{cis}$ 10.4 Hz, 0.5H), 6.72 (dd, $^3$J$_{trans}$ 16.4, $^3$J$_{cis}$ 10.4 Hz, 0.5H), 6.13 (d, $^3$J$_{trans}$ 16.4 Hz, 0.5H), 6.06 (d, $^3$J$_{trans}$ 16.4 Hz, 0.5H), 5.71 (d, $^3$J$_{cis}$ 10.4 Hz, 0.5H), 5.59 (d, $^3$J$_{cis}$ 10.4 Hz, 0.5H), 4.77-4.64 (m, 1H), 4.60 (d, J 6.0 Hz, 2H, CH$_2$), 4.59-4.51 (m, 0.5H), 4.23-4.16 (m, 1H), 4.11-4.04 (m, 0.5H), 3.74-3.66 (m, 0.5H), 3.25-3.15 (m, 1H), 3.05-2.99 (m, 0.5H), 2.32-2.21 (m, 1H), 2.15-2.09 (m, 1H), 1.95-1.89 (m, 1H), 1.65-1.53 (m, 1H).

Example 21: N-[[4-[4-Amino-1-[(3R)-1-prop-2-enoyl-3-piperidyl]pyrazolo[3,4-d]pyrimidin-3-yl]phenyl]methyl]-4-cyano-benzamide

[4-[[(4-Cyanobenzoyl)amino]methyl]phenyl]boronic acid

Following general procedure A, 4-aminomethylphenylboronic acid (200.0 mg, 1.32 mmol) and 4-cyanobenzoyl chloride (0.16 mL, 1.32 mmol) afforded [4-[[(4-cyanobenzoyl)amino]methyl]phenyl]boronic acid (400.0 mg, 0.99 mmol, 75% yield) as a white solid.

UPLC-MS (ES$^+$, Short acidic): 1.21 min, m/z 280.8 [M+H]$^+$ tert-Butyl (3R)-3-[4-amino-3-[4-[[(4-cyanobenzoyl)amino]methyl]phenyl]pyrazolo[3,4-d]pyrimidin-1-yl]piperidine-1-carboxylate Following general procedure D, [4-[[(4-cyanobenzoyl)amino]methyl]phenyl]boronic acid (189.1 mg, 0.68 mmol) and tert-butyl (3R)-3-(4-amino-3-iodo-pyrazolo[3,4-d]pyrimidin-1-yl)piperidine-1-carboxylate (200.0 mg, 0.45 mmol) gave tert-butyl (3R)-3-[4-amino-3-[4-[[(4-cyanobenzoyl)amino]methyl]phenyl]pyrazolo[3,4-d]pyrimidin-1-yl]piperidine-1-carboxylate (90.0 mg, 0.16 mmol, 36% yield) as a yellow solid.

UPLC-MS (ES$^+$, Short acidic): 1.62 min, m/z 553.4 [M+H]$^+$

N-[[4-[4-Amino-1-[(3R)-3-piperidyl]pyrazolo[3,4-d]pyrimidin-3-yl]phenyl]methyl]-4-cyano-benzamide Following general procedure E tert-butyl (3R)-3-[4-amino-3-[4-[[(4-cyanobenzoyl)amino]methyl]phenyl]pyrazolo[3,4-d]pyrimidin-1-yl]piperidine-1-carboxylate (200.0 mg, 0.36 mmol) gave N-[[4-[4-amino-1-[(3R)-3-piperidyl]pyrazolo[3,4-d]pyrimidin-3-yl]phenyl]methyl]-4-cyano-benzamide (43.0 mg, 0.10 mmol, 26% yield) as an off white solid.

UPLC-MS (ES$^+$, Short acidic): 1.07 min, m/z 453.3 [M+H]$^+$

N-[[4-[4-Amino-1-[(3R)-1-prop-2-enoyl-3-piperidyl] pyrazolo[3,4-d]pyrimidin-3-yl]phenyl]methyl]-4-cyano-benzamide Following general procedure F, N-[[4-[4-amino-1-[(3R)-3-piperidyl]pyrazolo[3,4-d]pyrimidin-3-yl]phenyl]methyl]-4-cyano-benzamide (43.0 mg, 0.10 mmol) afforded N-[[4-[4-amino-1-[(3R)-1-prop-2-enoyl-3-piperidyl]pyrazolo[3,4-d]pyrimidin-3-yl]phenyl]methyl]-4-cyano-benzamide (10.0 mg, 0.02 mmol, 20% yield)

UPLC-MS (ES$^+$, Short acidic): 1.31 min, m/z 507.2 [M+H]$^+$

UPLC-MS (ES$^+$, long acidic): 2.94 min, m/z 507.3 [M+H]$^+$ $^1$H NMR (400 MHz, DMSO-d$_6$) δ (ppm, 1:1 mixture of conformers) 9.38 (t, $^3$J 5.9 Hz, 1H, NH), 8.27 (s, 1H, ArH), 8.08 (d, $^3$J 8.6 Hz, 2H, ArH), 8.00 (d, $^3$J 8.6 Hz, 2H, ArH), 7.65 (d, $^3$J 7.8 Hz, 2H, ArH), 7.51 (d, $^3$J 7.8 Hz, 2H, ArH), 6.87 (dd, $^3$J$_{trans}$ 16.5, $^3$J$_{cis}$ 10.6 Hz, 0.5H), 6.71 (dd, $^3$J$_{trans}$ 16.5, $^3$J$_{cis}$ 10.6 Hz, 0.5H), 6.13 (d, $^3$J$_{trans}$ 16.5 Hz, 0.5H), 6.06 (d, $^3$J$_{trans}$ 16.5 Hz, 0.5H), 5.71 (d, $^3$J$_{cis}$ 10.6 Hz, 0.5H), 5.59 (d, $^3$J$_{cis}$ 10.6 Hz, 0.5H), 4.76-4.65 (m, 1H), 4.59 (d, $^3$J 5.9 Hz, 2H), 4.56-4.51 (m, 0.5H), 4.24-4.15 (m, 1H), 4.11-4.05 (m, 0.5H), 3.74-3.66 (m, 0.5H), 3.25-3.16 (m, 1H), 3.06-2.97 (m, 0.5H), 2.32-2.22 (m, 1H), 2.16-2.08 (m, 1H), 1.97-1.89 (m, 1H), 1.65-1.56 (m, 1H).

Example 22: N-[[4-[4-Amino-1-[(3R)-1-prop-2-enoyl-3-piperidyl]pyrazolo[3,4-d]pyrimidin-3-yl]phenyl]methyl]-2-methoxy-5-methyl-benzamide

[4-[[(2-Methoxy-5-methyl-benzoyl)amino]methyl]phenyl]boronic acid

Following general procedure A, [4-(aminomethyl)phenyl]boronic acid hydrochloride (434.3 mg, 2.32 mmol) and 5-fluoro-2-methoxy-benzoic acid (350.0 mg, 2.06 mmol) gave [4-[[(2-methoxy-5-methyl-benzoyl)amino]methyl]phenyl]boronic acid (215.0 mg, 0.36 mmol, 17% yield) as an off-white solid.

UPLC-MS (ES$^+$, Short acidic):1.40 min, m/z 299.9 [M+H]$^+$ tert-Butyl (3R)-3-[4-amino-3-[4-[[(2-methoxy-5-methyl-benzoyl)amino]methyl]phenyl]pyrazolo[3,4-d]pyrimidin-1-yl]piperidine-1-carboxylate Following general procedure D, [4-[[(2-methoxy-5-methyl-benzoyl)amino]methyl]-phenyl]boronic acid (206.4 mg, 0.69 mmol) and tert-butyl (3R)-3-(4-amino-3-iodo-pyrazolo[3,4-d]pyrimidin-1-yl)piperidine-1-carboxylate (230.0 mg, 0.52 mmol) gave tert-butyl (3R)-3-[4-amino-3-[4-[[(2-methoxy-5-methyl-benzoyl)amino]methyl]phenyl]pyrazolo[3,4-d]pyrimidin-1-yl]piperidine-1-carboxylate (323.0 mg, 0.42 mmol, 82% yield) as a brown foam.

UPLC-MS (ES$^+$, Short acidic): 1.74 min, m/z 572.5 [M+H]$^+$

N-[[4-[4-Amino-1-[(3R)-3-piperidyl]pyrazolo[3,4-d]pyrimidin-3-yl]phenyl]methyl]-2-methoxy-5-methyl-benzamide Following general procedure E, tert-butyl (3R)-3-[4-amino-3-[4-[[(2-methoxy-5-methyl-benzoyl)amino]methyl]phenyl]pyrazolo[3,4-d]pyrimidin-1-yl]piperidine-1-carboxylate (323.0 mg, 0.42 mmol) afforded N-[[4-[4-amino-1-[(3R)-3-piperidyl]pyrazolo[3,4-d]pyrimidin-3-yl]phenyl]methyl]-2-methoxy-5-methyl-benzamide (147.0 mg, 0.28 mmol, 66% yield) as an off-white foam.

UPLC-MS (ES$^+$, Short acidic): 1.20 min, m/z 472.3 [M+H]$^+$

N-[[4-[4-Amino-1-[(3R)-1-prop-2-enoyl-3-piperidyl]pyrazolo[3,4-d]pyrimidin-3-yl]phenyl]methyl]-2-methoxy-5-methyl-benzamide Following general procedure F, N-[[4-[4-amino-1-[(3R)-3-piperidyl]pyrazolo[3,4-d]pyrimidin-3-yl]phenyl]methyl]-2-methoxy-5-methyl-benzamide (147.0 mg, 0.31 mmol) gave N-[[4-[4-amino-1-[(3R)-1-prop-2-enoyl-3-piperidyl]pyrazolo[3,4-d]pyrimidin-3-yl]phenyl]methyl]-2-methoxy-5-methyl-benzamide (22.2 mg, 0.04 mmol, 13% yield) as an off-white foam.

UPLC-MS (ES$^+$, short acidic): 1.45 min, m/z 526.5 [M+H]$^+$

UPLC-MS (ES$^+$, long acidic): 3.29 min, m/z 526.5 [M+H]$^+$ $^1$H NMR (400 MHz, DMSO-d$_6$) δ (ppm, 1:1 mixture of conformers): 8.75 (t, J 6.0 Hz, 1H, NH), 8.27 (s, 1H, ArH), 7.65 (d, J 8.0 Hz, 2H, ArH), 7.60 (d, J 2.0 Hz, 1H, ArH), 7.50 (d, J 8.0 Hz, 2H, ArH), 7.29 (ddd, J 8.4, J 2.4, J 0.6 Hz, 1H, ArH), 7.06 (d, J 8.4 Hz, 1H, ArH), 6.87 (dd, $^3$J$_{trans}$ 16.4, $^3$J$_{cis}$ 10.4 Hz, 0.5H), 6.73 (dd, $^3$J$_{trans}$ 16.4, $^3$J$_{cis}$ 10.4 Hz, 0.5H), 6.13 (d, $^3$J$_{trans}$ 16.4 Hz, 0.5H), 6.07 (d, $^3$J$_{trans}$ 16.4 Hz, 0.5H), 5.71 (d, $^3$J$_{cis}$ 10.4 Hz, 0.5H), 5.59 (d, $^3$J$_{cis}$ 10.4 Hz, 0.5H), 4.76-4.66 (m, 1H), 4.59 (d, J 6.0 Hz, 2H, CH$_2$), 4.59-4.52 (m, 0.5H), 4.25-4.17 (m, 1H), 4.10-4.06 (m, 0.5H), 3.88 (s, 3H, OCH$_3$), 3.74-3.68 (m, 0.5H), 3.25-3.17 (m, 1H), 3.04-2.98 (m, 0.5H), 2.27 (s, 3H, CH$_3$), 2.26-2.22 (m, 1H), 2.17-2.08 (m, 1H), 1.97-1.81 (m, 1H), 1.65-1.53 (m, 1H).

Example 23: N-[[4-[4-Amino-1-[(3R)-1-prop-2-enoyl-3-piperidyl]pyrazolo[3,4-d]pyrimidin-3-yl]phenyl]methyl]-4-chloro-benzamide

[4-[[(4-Chlorobenzoyl)amino]methyl]phenyl]boronic acid

Following general procedure A, [4-(aminomethyl)phenyl]boronic acid (200.0 mg, 1.32 mmol), 4-chlorobenzoyl chloride (0.20 mL, 1.32 mmol) afforded [4-[[(4-chlorobenzoyl)amino]methyl]phenyl]boronic acid (350.0 mg, 0.72 mmol, 54% yield) as a white solid.

UPLC-MS (ES$^+$, Short acidic): 1.39 min, m/z 290.5 [M+H]$^+$ tert-Butyl (3R)-3-[4-amino-3-[4-[[(4-chlorobenzoyl)amino]methyl]phenyl]pyrazolo[3,4-d]pyrimidin-1-yl]piperidine-1-carboxylate Following general procedure D, [4-[[(4-chlorobenzoyl)amino]methyl]phenyl]boronic acid (195.5 mg, 0.68 mmol) and tert-butyl (3R)-3-(4-amino-3-iodo-pyrazolo[3,4-d]pyrimidin-1-yl)piperidine-1-carboxylate (220.0 mg, 0.50 mmol) gave tert-butyl (3R)-3-[4-amino-3-[4-[[(4-chlorobenzoyl)amino]methyl]phenyl]pyrazolo[3,4-d]pyrimidin-1-yl]piperidine-1-carboxylate (200.0 mg, 0.35 mmol, 79% yield) as an off white solid.

UPLC-MS (ES$^+$, Short acidic): 1.74 min, m/z 563.0 [M+H]$^+$

N-[[4-[4-Amino-1-[(3R)-3-piperidyl]pyrazolo[3,4-d]pyrimidin-3-yl]phenyl]methyl]-4-chloro-benzamide Following general procedure E, tert-butyl (3R)-3-[4-amino-3-[4-[[(4-chlorobenzoyl)amino]methyl]phenyl]pyrazolo[3,4-d]pyrimidin-1-yl]piperidine-1-carboxylate (253.0 mg, 0.45 mmol) afforded N-[[4-[4-amino-1-[(3R)-3-piperidyl]pyrazolo[3,4-d]pyrimidin-3-yl]phenyl]methyl]-4-chloro-benzamide (130.0 mg, 0.28 mmol, 62% yield) as a white solid.

UPLC-MS (ES+, Short acidic): 1.07 min, m/z 462.3 [M+H]+

N-[[4-[4-Amino-1-[(3R)-1-prop-2-enoyl-3-piperidyl]pyrazolo[3,4-d]pyrimidin-3-yl]phenyl]methyl]-4-chloro-benzamide Following general procedure F, N-[[4-[4-amino-1-[(3R)-3-piperidyl]pyrazolo[3,4-d]pyrimidin-3-yl]phenyl]methyl]-4-chloro-benzamide (130.0 mg, 0.28 mmol) afforded N-[[4-[4-amino-1-[(3R)-1-prop-2-enoyl-3-piperidyl]pyrazolo[3,4-d]pyrimidin-3-yl]phenyl]methyl]-4-chloro-benzamide (12.0 mg, 0.02 mmol, 8% yield) as a white solid.

UPLC-MS (ES+, Short acidic): 1.44 min, m/z 516.2 [M+H]+

UPLC-MS (ES+, Long acidic): 3.27 min, m/z 516.1 [M+H]+

$^1$H NMR (400 MHz, DMSO-$d_6$) δ (ppm, 1:1 mixture of conformers) 9.21 (t, $^3$J 5.7 Hz, 1H, NH), 8.27 (s, 1H, ArH), 7.95 (d, $^3$J 8.6 Hz, 2H, ArH), 7.65 (d, $^3$J 7.9 Hz, 2H, ArH), 7.57 (d, $^3$J 8.6 Hz, 2H, ArH), 7.50 (d, $^3$J 7.9 Hz, 2H, ArH), 6.87 (dd, $^3J_{trans}$ 16.7, $^3J_{cis}$ 10.3 Hz, 0.5H), 6.72 (dd, $^3J_{trans}$ 16.7, $^3J_{cis}$ 10.3 Hz, 0.5H), 6.13 (d, $^3J_{trans}$ 16.7 Hz, 0.5H), 6.07 (d, $^3J_{trans}$ 16.7 Hz, 0.5H), 5.71 (d, $^3J_{cis}$ 10.3 Hz, 0.5H), 5.59 (d, $^3J_{cis}$ 10.3 Hz, 0.5H), 4.75-4.67 (m, 1H, CH), 4.57 (d, $^3$J 5.7 Hz, 2H, CH$_2$), 4.55-4.50 (m, 0.5H), 4.24-4.16 (m, 1H), 4.12-4.03 (m, 0.5H), 3.74-3.65 (m, 0.5H), 3.25-3.16 (m, 1H), 3.07-2.98 (m, 0.5H), 2.32-2.22 (m, 1H), 2.15-2.10 (m, 1H), 1.96-1.90 (m, 1H), 1.67-1.57 (m, 1H).

Example 24: N-[[4-[4-Amino-1-[(3R)-1-prop-2-enoyl-3-piperidyl]pyrazolo[3,4-d]pyrimidin-3-yl]phenyl]methyl]-4-chloro-2-methoxy-benzamide

[4-[[(4-Chloro-2-methoxy-benzoyl)amino]methyl]phenyl]boronic acid

Following general procedure A, [4-(aminomethyl)phenyl]boronic acid hydrochloride (386.7 mg, 2.06 mmol) and 4-chloro-2-methoxy-benzoic acid (350.0 mg, 1.87 mmol) gave [4-[[(4-chloro-2-methoxy-benzoyl)amino]methyl]phenyl]boronic acid (520.0 mg, 1.06 mmol, 56% yield) as a yellow oil.

UPLC-MS (ES+, Short acidic):1.45 min, m/z 319.8 [M+H]+ tert-Butyl (3R)-3-[4-amino-3-[4-[[(4-chloro-2-methoxy-benzoyl)amino]methyl]phenyl]pyrazolo[3,4-d]pyrimidin-1-yl]piperidine-1-carboxylate Following general procedure D, [4-[[(4-chloro-2-methoxy-benzoyl)amino]methyl]-phenyl]boronic acid (458.1 mg, 0.93 mmol) and tert-butyl (3R)-3-(4-amino-3-iodo-pyrazolo[3,4-d]pyrimidin-1-yl)piperidine-1-carboxylate (230 mg, 0.52 mmol) gave tert-butyl (3R)-3-[4-amino-3-[4-[[(4-chloro-2-methoxy-benzoyl)amino]methyl]phenyl]pyrazolo[3,4-d]pyrimidin-1-yl]piperidine-1-carboxylate (452.0 mg, 0.50 mmol, 96% yield) as a brown foam.

UPLC-MS (ES+, Short acidic): 1.79 min, m/z 593.1 [M+H]+

N-[[4-[4-Amino-1-[(3R)-3-piperidyl]pyrazolo[3,4-d]pyrimidin-3-yl]phenyl]methyl]-4-chloro-2-methoxy-benzamide Following general procedure E, tert-butyl (3R)-3-[4-amino-3-[4-[[(4-chloro-2-methoxy-benzoyl)amino]methyl]phenyl]pyrazolo[3,4-d]pyrimidin-1-yl]piperidine-1-carboxylate (452.0 mg, 0.50 mmol) afforded N-[[4-[4-amino-1-[(3R)-3-piperidyl]pyrazolo[3,4-d]pyrimidin-3-yl]phenyl]methyl]-4-chloro-2-methoxy-benzamide (199.8 mg, 0.39 mmol, 78% yield) as an off-white/brown foam.

UPLC-MS (ES+, Short acidic): 1.23 min, m/z 492.3 [M+H]+

N-[[4-[4-Amino-1-[(3R)-1-prop-2-enoyl-3-piperidyl]pyrazolo[3,4-d]pyrimidin-3-yl]phenyl]methyl]-4-chloro-2-methoxy-benzamide Following general procedure F, N-[[4-[4-amino-1-[(3R)-3-piperidyl]pyrazolo[3,4-d]pyrimidin-3-yl]phenyl]methyl]-4-chloro-2-methoxy-benzamide (199.8 mg, 0.41 mmol) gave N-[[4-[4-amino-1-[(3R)-1-prop-2-enoyl-3-piperidyl]pyrazolo[3,4-d]pyrimidin-3-yl]phenyl]methyl]-4-chloro-2-methoxy-benzamide (27.7 mg, 0.05 mmol, 12% yield).

UPLC-MS (ES+, short acidic): 1.49 min, m/z 547.1 [M+H]+

UPLC-MS (ES+, long acidic): 3.39 min, m/z 547.0 [M+H]+

$^1$H NMR (400 MHz, DMSO-$d_6$) δ (ppm, 1:1 mixture of conformers): 8.78 (t, J 6.0 Hz, 1H, NH), 8.27 (s, 1H, ArH), 7.77 (d, J 8.0 Hz, 1H, ArH), 7.65 (d, J 8.0 Hz, 2H, ArH), 7.51 (d, J 8.0 Hz, 2H, ArH), 7.26 (d, J 1.8 Hz, 1H, ArH), 7.12 (dd, J 8.2, J 1.8 Hz, 1H, ArH), 6.87 (dd, $^3J_{trans}$ 16.4, $^3J_{cis}$ 10.4 Hz, 0.5H), 6.72 (dd, $^3J_{trans}$ 16.4, $^3J_{cis}$ 10.4 Hz, 0.5H), 6.14 (d, $^3J_{trans}$ 16.4 Hz, 0.5H), 6.07 (d, $^3J_{trans}$ 16.4 Hz, 0.5H), 5.72 (d, $^3J_{cis}$ 10.4 Hz, 0.5H), 5.59 (d, $^3J_{cis}$ 10.4 Hz, 0.5H), 4.76-4.66 (m, 1H), 4.58 (d, J 6.0 Hz, 2H, CH$_2$), 4.55-4.50 (m, 0.5H), 4.25-4.17 (m, 1H), 4.12-4.05 (m, 0.5H), 3.95 (s, 3H, CH$_3$), 3.75-3.67 (m, 0.5H), 3.27-3.15 (m, 1H), 3.07-2.97 (m, 0.5H), 2.29-2.22 (m, 1H), 2.13-2.11 (m, 1H), 1.95-1.92 (m, 1H), 1.65-1.53 (m, 1H).

Example 25: N-[[4-[4-Amino-1-[(3R)-1-prop-2-enoyl-3-piperidyl]pyrazolo[3,4-d]pyrimidin-3-yl]phenyl]methyl]-2-(trifluoromethoxy)benzamide

[4-[[[2-(Trifluoromethoxy)benzoyl]amino]methyl]phenyl]boronic acid

Following general procedure A, [4-(aminomethyl)phenyl]boronic acid hydrochloride (300.0 mg, 1.6 mmol) and 2-(trifluoromethoxy)benzoyl chloride (395.4 mg, 1.76 mmol) gave [4-[[[2-(trifluoromethoxy)benzoyl]amino]methyl]phenyl]boronic acid (421.3 mg, 0.87 mmol, 54% yield) as an off white solid.

UPLC-MS (ES+, Short acidic): 1.59 min, m/z 311.9 [M+Na]+ tert-Butyl (3R)-3-[4-amino-3-[4-[[[2-(trifluoromethoxy)benzoyl]amino]methyl]phenyl]pyrazolo[3,4-d]pyrimidin-1-yl]piperidine-1-carboxylate Following general procedure D, [4-[[[2-(trifluoromethoxy)benzoyl]amino]methyl]phenyl]boronic acid (427.4 mg, 1.26 mmol) and tert-butyl (3R)-3-(4-amino-3-iodo-pyrazolo[3,4-d]pyrimidin-1-yl)piperidine-1-carboxylate (200.0 mg, 0.45 mmol) gave tert-butyl (3R)-3-[4-amino- 3-[4-[[[2-(trifluoromethoxy)benzoyl]amino]methyl]phenyl]pyrazolo[3,4-d]pyrimidin-1-yl]piperidine-1-carboxylate (350.0 mg, 0.40 mmol, 88% yield) as an orange solid.

UPLC-MS (ES⁺, Short acidic): 1.74 min, m/z 560.5 [M+H]⁺

N-[[4-[4-Amino-1-[(3R)-3-piperidyl]pyrazolo[3,4-d]pyrimidin-3-yl]phenyl]methyl]-2-(trifluoromethoxy)benzamide Following general procedure E, tert-butyl (3R)-3-[4-amino-3-[4-[[[2-(trifluoromethoxy)benzoyl]amino]methyl]phenyl]pyrazolo[3,4-d]pyrimidin-1-yl]piperidine-1-carboxylate (380.0 mg, 0.62 mmol) gave N-[[4-[4-amino-1-[(3R)-3-piperidyl]pyrazolo[3,4-d]pyrimidin-3-yl]phenyl]methyl]-2-fluoro-4-methyl-benzamide (200.0 mg, 0.44 mmol, 83% yield as a yellow foam.

UPLC-MS (ES⁺, Short acidic): 1.17 min, m/z 512.3 [M+H]⁺

N-[[4-[4-Amino-1-[(3R)-1-prop-2-enoyl-3-piperidyl]pyrazolo[3,4-d]pyrimidin-3-yl]phenyl]methyl]-2-(trifluoromethoxy)benzamide Following general procedure F, N-[[4-[4-amino-1-[(3R)-3-piperidyl]pyrazolo[3,4-d]pyrimidin-3-yl]phenyl]methyl]-2-(trifluoromethoxy)benzamide (184.0 mg, 0.36 mmol) afforded N-[[4-[4-amino-1-[(3R)-1-prop-2-enoyl-3-piperidyl]pyrazolo[3,4-d]pyrimidin-3-yl]phenyl]methyl]-2-(trifluoromethoxy)benzamide (22.0 mg, 0.04 mmol, 10% yield) as a white solid.

UPLC-MS (ES⁺, Short acidic): 1.44 min, m/z 566.3 [M+H]⁺

UPLC-MS (ES⁺, Long acidic): 3.27 min, m/z 566.3 [M+H]⁺

¹H NMR (400 MHz, DMSO-d₆) 9.07 (t, J 6.0 Hz, 1H, NH), 8.28 (s, 1H, ArH), 7.68-7.63 (m, 3H, ArH), 7.63-7.59 (m, 1H, ArH), 7.55-7.44 (m, 4H, ArH), 6.87 (dd, ³J$_{trans}$ 16.4, ³J$_{cis}$ 10.4 Hz, 0.5H), 6.72 (dd, ³J$_{trans}$ 16.4, ³J$_{cis}$ 10.4 Hz, 0.5H), 6.14 (d, ³J$_{trans}$ 16.4 Hz, 0.5H), 6.07 (d, ³J$_{trans}$ 16.4 Hz, 0.5H), 5.71 (d, ³J$_{cis}$ 10.4 Hz, 0.5H), 5.59 (d, ³J$_{cis}$ 10.4 Hz, 0.5H), 4.76-4.66 (m, 1H), 4.55 (d, J 6.0 Hz, 2H, CH₂), 4.59-4.50 (m, 0.5H), 4.25-4.17 (m, 1H), 4.12-4.05 (m, 0.5H), 3.75-3.67 (m, 0.5H), 3.29-3.15 (m, 1H), 3.07-2.97 (m, 0.5H), 2.33-2.22 (m, 1H), 2.18-2.09 (m, 1H), 1.98-1.89 (m, 1H), 1.65-1.53 (m, 1H).

Example 26: N-[[4-[4-Amino-1-[(3R)-1-prop-2-enoyl-3-piperidyl]pyrazolo[3,4-d]pyrimidin-3-yl]phenyl]methyl]-2-fluoro-4-methyl-benzamide

[4-[[(2-Fluoro-4-methyl-benzoyl)amino]methyl]phenyl]boronic acid

Following general procedure A, [4-(aminomethyl)phenyl]boronic acid hydrochloride (300.0 mg, 1.60 mmol) and 2-fluoro-4-methylbenzoyl chloride (303.8 mg, 1.76 mmol) afforded crude [4-[[(2-fluoro-4-methyl-benzoyl)amino]methyl]phenyl]boronic acid (651.5 mg, 1.59 mmol, 99% yield) as an off-white solid.

UPLC-MS (ES⁺, short acidic): 1.59 min, m/z 311.9 [M+H]⁺ tert-Butyl (3R)-3-[4-amino-3-[4-[[(2-fluoro-4-methyl-benzoyl)amino]methyl]phenyl]pyrazolo[3,4-d]pyrimidin-1-yl]piperidine-1-carboxylate Following general procedure D, [4-[[(3-fluorobenzoyl)amino]methyl]phenyl]boronic acid (368.8 mg, 1.35 mmol), and tert-butyl (3R)-3-(4-amino-3-iodo-pyrazolo[3,4-d]pyrimidin-1-yl)piperidine-1-carboxylate (200.0 mg, 0.45 mmol) gave tert-butyl (3R)-3-[4-amino-3-[4-[[(2-fluoro-4-methyl-benzoyl)amino]methyl]phenyl]pyrazolo[3,4-d]pyrimidin-1-yl]piperidine-1-carboxylate (250.0 mg, 0.45 mmol, 99% yield) as a brown solid.

UPLC-MS (ES⁺, Short acidic): 1.74 min, m/z 560.5 [M+H]⁺

N-[[4-[4-Amino-1-[(3R)-3-piperidyl]pyrazolo[3,4-d]pyrimidin-3-yl]phenyl]methyl]-2-fluoro-4-methyl-benzamide Following general procedure E, tert-butyl (3R)-3-[4-amino-3-[4-[[(2-fluoro-4-methyl-benzoyl)amino]methyl]phenyl]pyrazolo[3,4-d]pyrimidin-1-yl]piperidine-1-carboxylate (290.0 mg, 0.52 mmol) gave N-[[4-[4-amino-1-[(3R)-3-piperidyl]pyrazolo[3,4-d]pyrimidin-3-yl]phenyl]methyl]-2-fluoro-4-methyl-benzamide (200.0 mg, 0.44 mmol, 84% yield) as a yellow foam.

UPLC-MS (ES⁺, Short acidic): 1.16 min, m/z 460.3 [M+H]⁺

N-[[4-[4-Amino-1-[(3R)-1-prop-2-enoyl-3-piperidyl]pyrazolo[3,4-d]pyrimidin-3-yl]phenyl]methyl]-2-fluoro-4-methyl-benzamide Following general procedure F, N-[[4-[4-amino-1-[(3R)-3-piperidyl]pyrazolo[3,4-d]pyrimidin-3-yl]phenyl]methyl]-2-fluoro-4-methyl-benzamide (200.0 mg, 0.44 mmol) afforded N-[[4-[4-amino-1-[(3R)-1-prop-2-enoyl-3-piperidyl]pyrazolo[3,4-d]pyrimidin-3-yl]phenyl]methyl]-2-fluoro-4-methyl-benzamide (14.0 mg, 0.03 mmol, 6% yield).

UPLC-MS (ES⁺, Short acidic): 1.42 min, m/z 514.4 [M+H]⁺

UPLC-MS (ES⁺, Long acidic): 3.22 min, m/z 514.3 [M+H]⁺

¹H NMR (400 MHz, DMSO-d₆) 8.85-8.79 (m, 1H, NH), 8.27 (s, 1H, ArH), 7.80 (t, J 7.8 Hz, 1H, ArH), 7.66 (d, J 8.0 Hz, 2H, ArH), 7.63-7.56 (m, 1H, ArH), 7.51 (d, J 8.0 Hz, 2H, ArH), 7.18-7.08 (m, 1H, ArH), 6.87 (dd, ³J$_{trans}$ 16.4, ³J$_{cis}$ 10.4 Hz, 0.5H), 6.72 (dd, ³J$_{trans}$ 16.4, ³J$_{cis}$ 10.4 Hz, 0.5H), 6.14 (d, ³J$_{trans}$ 16.4 Hz, 0.5H), 6.07 (d, ³J$_{cis}$ 16.4 Hz, 0.5H), 5.71 (d, ³J$_{cis}$ 10.4 Hz, 0.5H), 5.59 (d, ³J$_{cis}$ 10.4 Hz, 0.5H), 4.78-4.65 (m, 1H), 4.56 (d, J 6.0 Hz, 2H, CH₂), 4.55-4.50 (m, 0.5H), 4.26-4.17 (m, 1H), 4.11-4.04 (m, 0.5H), 3.75-3.67 (m, 0.5H), 3.29-3.15 (m, 1H), 3.07-2.97 (m, 0.5H), 2.36 (s, 3H), 2.33-2.22 (m, 1H), 2.18-2.09 (m, 1H), 1.98-1.89 (m, 1H), 1.67-1.53 (m, 1H).

Example 27: N-[[4-[4-Amino-1-[(3R)-1-prop-2-enoyl-3-piperidyl]pyrazolo[3,4-d]pyrimidin-3-yl]phenyl]methyl]-2,4,5-trifluoro-benzamide

4-[[(2,4,5-Trifluorobenzoyl)amino]methyl]phenyl]boronic acid

Following general procedure B, 2,4,5-trifluorobenzoyl chloride (0.13 mL, 1.00 mmol) and [4-(aminomethyl)phenyl]boronic acid chloride (186.4 mg, 1.00 mmol) yielded the crude product [4-[[(2,4,5-trifluorobenzoyl)amino]methyl]phenyl]boronic acid (229.1 mg, 0.74 mmol, 74% yield) as a white solid.

UPLC-MS (ES⁺, Short acidic): 1.37 min, m/z 309.8 [M+H]⁺ tert-Butyl (3R)-3-[4-amino-3-[4-[[(2,4,5-trifluorobenzoyl)amino]methyl]phenyl]pyrazolo[3,4-d]pyrimidin-1-yl]piperidine-1-carboxylate Following general procedure D, [4-[[(2,4,5-trifluorobenzoyl)amino]methyl]phenyl]boronic acid (156.5 mg, 0.51 mmol) and tert-butyl (3R)-3-(4-amino-3-iodo-pyrazolo[3,4-d]pyrimidin-1-yl)piperidine-1-carboxylate (150.0 mg, 0.34 mmol), gave after further purification by flash column chromatography (DCM/MeOH 95:5), tert-butyl (3R)-3-[4-amino-3-[4-[[(2,4,5-trifluorobenzoyl)amino]methyl]phenyl]pyrazolo[3,4-d]pyrimidin-1-yl]piperidine-1-carboxylate (153.8 mg, 0.26 mmol, 78%).

UPLC-MS (ES$^+$, Short acidic): 1.74 min, m/z 582.4 [M+H]$^+$

N-[[4-[4-Amino-1-[(3R)-3-piperidyl]pyrazolo[3,4-d]pyrimidin-3-yl]phenyl]methyl]-2,4,5-trifluoro-benzamide Following general procedure E, tert-butyl (3R)-3-[4-amino-3-[4-[[(2,4,5-trifluorobenzoyl)amino]methyl]phenyl]pyrazolo[3,4-d]pyrimidin-1-yl]piperidine-1-carboxylate (153.8 mg, 0.26 mmol) gave, after purification by SCX column eluting NH$_3$/MeOH, N-[[4-[4-amino-1-[(3R)-3-piperidyl]pyrazolo[3,4-d]pyrimidin-3-yl]phenyl]methyl]-2,4,5-trifluoro-benzamide (106.0 mg, 0.22 mmol, 83% yield).

UPLC-MS (ES$^+$, Short acidic): 1.18 min, m/z 482.1 [M+H]$^+$

N-[[4-[4-Amino-1-[(3R)-1-prop-2-enoyl-3-piperidyl]pyrazolo[3,4-d]pyrimidin-3-yl]phenyl]methyl]-2,4,5-trifluoro-benzamide Following general procedure F, N-[[4-[4-amino-1-[(3R)-3-piperidyl]pyrazolo[3,4-d]pyrimidin-3-yl]phenyl]methyl]-2,4,5-trifluoro-benzamide (106 mg, 0.22 mmol) afforded N-[[4-[4-amino-1-[(3R)-1-prop-2-enoyl-3-piperidyl]pyrazolo[3,4-d]pyrimidin-3-yl]phenyl]methyl]-2,4,5-trifluoro-benzamide (40 mg, 0.07 mmol, 34% yield).

UPLC-MS (ES$^+$, Short acidic): 1.42 min, m/z 536.3 [M+H]$^+$

UPLC-MS (ES$^+$, Long acidic): 3.22 min, m/z 536.3 [M+H]$^+$ $^1$H NMR (400 MHz, DMSO-d$_6$): 9.07-9.01 (m, 1H, NH), 8.27 (s, 1H, ArH), 7.83-7.68 (m, 2H, ArH), 7.66 (d, J 8.0 Hz, 2H, ArH), 7.51 (d, J 8.0 Hz, 2H, ArH), 6.87 (dd, $^3J_{trans}$ 16.4, $^3J_{cis}$ 10.4 Hz, 0.5H), 6.72 (dd, $^3J_{trans}$ 16.4, $^3J_{cis}$ 10.4 Hz, 0.5H), 6.14 (d, $^3J_{trans}$ 16.4 Hz, 0.5H), 6.07 (d, $^3J_{cis}$ 16.4 Hz, 0.5H), 5.71 (d, $^3J_{cis}$ 10.4 Hz, 0.5H), 5.59 (d, $^3J_{cis}$ 10.4 Hz, 0.5H), 4.78-4.65 (m, 1H), 4.56 (d, J 6.0 Hz, 2H, CH$_2$), 4.55-4.49 (m, 0.5H), 4.25-4.16 (m, 1H), 4.12-4.04 (m, 0.5H), 3.75-3.67 (m, 0.5H), 3.29-3.15 (m, 1H), 3.07-2.97 (m, 0.5H), 2.33-2.22 (m, 1H), 2.18-2.09 (m, 1H), 1.98-1.89 (m, 1H), 1.67-1.53 (m, 1H).

Example 28: N-[[4-[4-Amino-1-[(3R)-1-prop-2-enoyl-3-piperidyl]pyrazolo[3,4-d]pyrimidin-3-yl]phenyl]methyl]-4-fluoro-2-(trifluoromethyl)benzamide

[4-[[[4-Fluoro-2-(trifluoromethyl)benzoyl]amino]methyl]phenyl]boronic acid

Following general procedure B, [4-(aminomethyl)phenyl]boronic acid chloride (186 mg, 1.00 mmol) and 4-fluoro-2-(trifluoromethyl)benzoyl chloride (0.15 mL, 1.00 mmol) gave [4-[[[4-fluoro-2-(trifluoromethyl)benzoyl]amino]methyl]phenyl]boronic acid (304 mg, 0.89 mmol, 89% yield) as a white solid.

UPLC-MS (ES$^+$, Short acidic): 1.38 min, m/z 341.8 [M+H]$^+$

Following general procedure D, [4-[[[4-fluoro-2-(trifluoromethyl)benzoyl]amino]methyl]phenyl]boronic acid (173 mg, 0.51 mmol) and tert-butyl (3R)-3-(4-amino-3-iodo-pyrazolo[3,4-d]pyrimidin-1-yl)piperidine-1-carboxylate (150 mg, 0.34 mmol) afforded crude tert-butyl (3R)-3-[4-amino-3-[4-[[[4-fluoro-2-(trifluoromethyl)benzoyl]amino]methyl]phenyl]pyrazolo[3,4-d]pyrimidin-1-yl]piperidine-1-carboxylate (284 mg, 0.46 mmol, assumed quantitative) as a crude product.

UPLC-MS (ES$^+$, Short acidic): 1.72 min, m/z 614.4 [M+H]$^+$

N-[[4-[4-Amino-1-[(3R)-3-piperidyl]pyrazolo[3,4-d]pyrimidin-3-yl]phenyl]methyl]-4-fluoro-2-(trifluoromethyl)benzamide Following general procedure E, tert-butyl (3R)-3-[4-amino-3-[4-[[[4-fluoro-2-(trifluoromethyl)benzoyl]amino]methyl]phenyl]pyrazolo[3,4-d]pyrimidin-1-yl]piperidine-1-carboxylate (141 mg, 0.23 mmol) afforded N-[[4-[4-amino-1-[(3R)-3-piperidyl]pyrazolo[3,4-d]pyrimidin-3-yl]phenyl]methyl]-4-fluoro-2-(trifluoromethyl)benzamide (91 mg, 0.18 mmol, 78% yield).

UPLC-MS (ES$^+$, Short acidic): 1.20 min, m/z 514.1 [M+H]$^+$

N-[[4-[4-Amino-1-[(3R)-1-prop-2-enoyl-3-piperidyl]pyrazolo[3,4-d]pyrimidin-3-yl]phenyl]methyl]-4-fluoro-2-(trifluoromethyl)benzamide Following general procedure F, N-[[4-[4-amino-1-[(3R)-3-piperidyl]pyrazolo[3,4-d]pyrimidin-3-yl]phenyl]methyl]-4-fluoro-2-(trifluoromethyl)benzamide (91.0 mg, 0.18 mmol) afforded N-[[4-[4-amino-1-[(3R)-1-prop-2-enoyl-3-piperidyl]pyrazolo[3,4-d]pyrimidin-3-yl]phenyl]methyl]-4-fluoro-2-(trifluoromethyl)benzamide (27.0 mg, 0.05 mmol, 27% yield).

UPLC-MS (ES$^+$, Short acidic): 1.43 min, m/z 568.3 [M+H]$^+$

UPLC-MS (ES$^+$, Long acidic): 3.24 min, m/z 568.2 [M+H]$^+$ $^1$H NMR (400 MHz, DMSO-d$_6$): 9.15 (t, J 6.0 Hz, 1H, NH), 8.27 (s, 1H, ArH), 7.74 (dd, J 9.4, J 2.4 Hz, 1H, ArH), 7.68-7.61 (m, 2H, ArH), 7.54-7.46 (m, 3H, ArH), 7.44-7.37 (m, 1H, ArH), 6.87 (dd, $^3J_{trans}$ 16.5, $^3J_{cis}$ 10.4 Hz, 0.5H), 6.78-6.65 (m, 0.5H), 6.13 (d, $^3J_{trans}$ 16.5 Hz, 0.5H), 6.06 (d, $^3J_{cis}$ 16.5 Hz, 0.5H), 5.71 (d, $^3J_{cis}$ 10.4 Hz, 0.5H), 5.59 (d, $^3J_{cis}$ 10.4 Hz, 0.5H), 4.81-4.62 (m, 1H), 4.53 (d, J 6.0 Hz, 2H, CH$_2$), 4.59-4.49 (m, 0.5H), 4.25-4.15 (m, 1H), 4.13-4.03 (m, 0.5H), 3.76-3.67 (m, 0.5H), 3.28-3.14 (m, 1H), 3.07-2.97 (m, 0.5H), 2.31-2.19 (m, 1H), 2.18-2.07 (m, 1H), 2.01-1.88 (m, 1H), 1.68-1.51 (m, 1H).

Example 29: N-[[4-[4-Amino-1-[(3R)-1-cyano-3-piperidyl]pyrazolo[3,4-d]pyrimidin-3-yl]phenyl]methyl]-2,5-difluoro-benzamide Following general procedure G, N-[[4-[4-amino-1-[(3R)-3-piperidyl]pyrazolo[3,4-d]pyrimidin-3-yl]phenyl]methyl]-2,5-difluoro-benzamide (92.0 mg, 0.20 mmol) afforded N-[[4-[4-amino-1-[(3R)-1-cyano-3-piperidyl]pyrazolo[3,4- d]pyrimidin-3-yl]phenyl]methyl]-2,5-difluoro-benzamide (21.0 mg, 0.04 mmol, 21% yield).

UPLC-MS (ES+, Short acidic): 1.40 min, m/z 489.3 [M+H]+

UPLC-MS (ES+, Long acidic): 3.13 min, m/z 489.3 [M+H]+

$^1$H NMR (400 MHz, DMSO-d$_6$) 9.10-9.01 (m, 1H, NH), 8.28 (s, 1H, ArH), 7.66 (d, J 8.2 Hz, 2H, ArH), 7.52 (d, J 8.2 Hz, 2H, ArH), 7.56-7.35 (m, 3H), 4.92-4.82 (m, 1H), 4.56 (d, J 6.0 Hz, 2H, CH$_2$), 3.64 (dd, J 12.5, 4.3 Hz, 1H), 3.55 (dd, J 12.5, 10.4 Hz, 1H), 3.45-3.38 (m, 1H), 3.22-3.11 (m, 1H), 2.24-2.05 (m, 2H), 1.96-1.72 (m, 2H).

Example 30: N-[[4-[4-Amino-1-[(3R)-1-prop-2-enoyl-3-piperidyl]pyrazolo[3,4-d]pyrimidin-3-yl]phenyl]methyl]-2-methoxy-3-(trifluoromethyl)benzamide

[4-[[[2-Methoxy-3-(trifluoromethyl)benzoyl]amino]methyl]phenyl]boronic acid

To a solution of 2-methoxy-3-(trifluoromethyl)benzoyl chloride (239.0 mg, 1.00 mmol) in THF (2 M) under a nitrogen atmosphere at 0° C. was added potassium phosphate (584.0 mg, 2.75 mmol), followed by 4-aminomethylphenylboronic acid hydrochloride (187.0 mg, 1.00 mmol). The reaction was allowed to return to rt and stirred overnight. Water was added, and the reaction mixture extracted with EtOAc (3×). The combined organics extracts were dried over anhydrous sodium sulfate, filtered, and concentrated in vacuo to afford [4-[[[2-Methoxy-3-(trifluoromethyl)benzoyl]amino]methyl]phenyl]boronic acid (211.0 mg, 0.60 mmol, 60% yield) as an off white solid.

UPLC-MS (ES+, short acidic): 1.48 min, m/z 353.8 [M+H]+ tert-Butyl (3R)-3-[4-amino-3-[4-[[[2-methoxy-3-(trifluoromethyl)benzoyl]amino]methyl]phenyl]pyrazolo[3,4-d]pyrimidin-1-yl]piperidine-1-carboxylate Following general procedure D, [4-[[[2-methoxy-3-(trifluoromethyl)benzoyl]amino]methyl]phenyl]boronic acid (191.0 mg, 0.54 mmol) and tert-butyl (3R)-3-(4-amino-3-iodo-pyrazolo[3,4-d]pyrimidin-1-yl)piperidine-1-carboxylate (160.0 mg, 0.36 mmol) gave tert-butyl (3R)-3-[4-amino-3-[4-[[[2-methoxy-3-(trifluoromethyl)benzoyl]amino]methyl]phenyl]pyrazolo[3,4-d]pyrimidin-1-yl]piperidine-1-carboxylate (157.0 mg, 0.25 mmol, 70% yield).

UPLC-MS (ES+, short acidic): 1.82 min, m/z 626.5 [M+H]+

N-[[4-[4-Amino-1-[(3R)-3-piperidyl]pyrazolo[3,4-d]pyrimidin-3-yl]phenyl]methyl]-2-methoxy-3-(trifluoromethyl)benzamide Following general procedure E, tert-butyl (3R)-3-[4-amino-3-[4-[[[2-methoxy-3-(trifluoromethyl)benzoyl]amino]methyl]phenyl]pyrazolo[3,4-d]pyrimidin-1-yl]piperidine-1-carboxylate (157.0 mg, 0.25 mmol) afforded N-[[4-[4-amino-1-[(3R)-3-piperidyl]pyrazolo[3,4-d]pyrimidin-3-yl]phenyl]methyl]-2-methoxy-3-(trifluoromethyl)benzamide (117.0 mg, 0.22 mmol, 89% yield).

UPLC-MS (ES+, Short acidic): 1.29 min, m/z 526.2 [M+H]+

N-[[4-[4-Amino-1-[(3R)-1-prop-2-enoyl-3-piperidyl]pyrazolo[3,4-d]pyrimidin-3-yl]phenyl]methyl]-2-methoxy-3-(trifluoromethyl)benzamide Following general procedure F, N-[[4-[4-amino-1-[(3R)-3-piperidyl]pyrazolo[3,4-d]pyrimidin-3-yl]phenyl]methyl]-2-methoxy-3-(trifluoromethyl)benzamide (84.0 mg, 0.16 mmol) afforded N-[[4-[4-amino-1-[(3R)-1-prop-2-enoyl-3-piperidyl]pyrazolo[3,4-d]pyrimidin-3-yl]phenyl]methyl]-2-methoxy-3-(trifluoromethyl)benzamide (44.0 mg, 0.04 mmol, 46% yield) as a white solid.

UPLC-MS (ES+, Short acidic): 1.52 min, m/z 580.3 [M+H]+

UPLC-MS (ES+, Long acidic): 3.47 min, m/z 580.3 [M+H]+

$^1$H NMR (400 MHz, DMSO-d$_6$): 9.11 (t, J 6.0 Hz, 1H, NH), 8.27 (s, 1H, ArH), 7.82-7.76 (m, 2H, ArH), 7.71-7.64 (m, 2H, ArH), 7.59-7.51 (m, 2H, ArH), 7.41-7.34 (m, 1H, ArH), 6.88 (dd, $^3J_{trans}$ 16.3, $^3J_{cis}$ 10.4 Hz, 0.5H), 6.72 (dd, $^3J_{trans}$ 16.3, $^3J_{cis}$ 10.4 Hz, 0.5H), 6.14 (d, $^3J_{trans}$ 16.3 Hz, 0.5H), 6.07 (d, $^3J_{cis}$ 10.4 Hz, 0.5H), 5.72 (d, $^3J_{cis}$ 10.4 Hz, 0.5H), 5.59 (d, $^3J_{cis}$ 10.4 Hz, 0.5H), 4.82-4.63 (m, 1H), 4.57 (d, J 6.0 Hz, 2H, CH$_2$), 4.60-4.50 (m, 0.5H), 4.27-4.15 (m, 1H), 4.13-4.04 (m, 0.5H), 3.70 (s, 3H, CH$_3$), 3.76-3.65 (m, 0.5H), 3.28-3.14 (m, 1H), 3.09-2.96 (m, 0.5H), 2.34-2.20 (m, 1H), 2.18-2.07 (m, 1H), 1.99-1.87 (m, 1H), 1.70-1.49 (m, 1H).

Example 31: N-[[4-[4-Amino-1-[(3R)-1-prop-2-enoyl-3-piperidyl]pyrazolo[3,4-d]pyrimidin-3-yl]phenyl]methyl]-2-fluoro-6-methoxybenzamide

[4-[[[2-Fluoro-6-methoxybenzoyl]amino]methyl]phenyl]boronic acid

To a solution of 2-fluoro-6-methoxybenzoyl chloride (189.0 mg, 1.00 mmol) in THF (2 M) under a nitrogen atmosphere at 0° C. was added potassium phosphate (584.0 mg, 2.75 mmol), followed by 4-aminomethylphenylboronic acid hydrochloride (187.0 mg, 1.00 mmol). The reaction was allowed to return to rt and stirred overnight. Water was added, and the reaction mixture extracted with EtOAc (3×). The combined organics extracts were dried over anhydrous sodium sulfate, filtered, and concentrated in vacuo to afford [4-[[(2-fluoro-6-methoxybenzoyl)amino]methyl]phenyl]boronic acid (245.0 mg, 0.81 mmol, 81% yield) as an off-white solid.

UPLC-MS (ES+, short acidic): 1.20 min, m/z 303.8 [M+H]+ tert-Butyl (3R)-3-[4-amino-3-[4-[[[2-fluoro-6-methoxybenzoyl]amino]methyl]phenyl]pyrazolo[3,4-d]pyrimidin-1-yl]piperidine-1-carboxylate Following general procedure D, [4-[[[2-fluoro-6-methoxybenzoyl]amino]methyl]phenyl]boronic acid (136.0 mg, 0.45 mmol) and tert-butyl (3R)-3-(4-amino-3-iodo-pyrazolo[3,4-d]pyrimidin-1-yl)piperidine-1-carboxylate (133.0 mg, 0.30 mmol) gave tert-butyl (3R)-3-[4-amino-3-[4-[[[2-fluoro-6-methoxybenzoyl]amino]methyl]phenyl]pyrazolo[3,4-d]pyrimidin-1-yl]piperidine-1-carboxylate (156.0 mg, 0.27 mmol, 90% yield).

UPLC-MS (ES+, short acidic): 1.60 min, m/z 576.4 [M+H]+

N-[[4-[4-Amino-1-[(3R)-3-piperidyl]pyrazolo[3,4-d]pyrimidin-3-yl]phenyl]methyl]-2-fluoro-6-methoxpenzamide Following general procedure E, tert-butyl (3R)-3-[4-amino-3-[4-[[[2-fluoro-6-methoxybenzoyl]amino]methyl]phenyl]pyrazolo[3,4-d]pyrimidin-1-yl]piperidine-1-carboxylate (150.0 mg, 0.26 mmol) afforded N-[[4-[4-amino-1-[(3R)-3-piperidyl]pyrazolo[3,4-d]pyrimidin-3-yl]phenyl]methyl]-2-fluoro-6-methoxybenzamide (108.0 mg, 0.23 mmol, 87% yield) as a white solid.

UPLC-MS (ES+, Short acidic): 1.07 min, m/z 476.2 [M+H]+

N-[[4-[4-Amino-1-[(3R)-1-prop-2-enoyl-3-piperidyl]pyrazolo[3,4-d]pyrimidin-3-yl]phenyl]methyl]-2-fluoro-6-methoxybenzamide Following general procedure F, N-[[4-[4-amino-1-[(3R)-3-piperidyl]pyrazolo[3,4-d]pyrimidin-3-yl]phenyl]methyl]-2-fluoro-6-methoxybenzamide (76.0 mg, 0.16 mmol) afforded N-[[4-[4-amino-1-[(3R)-1-prop-2-enoyl-3-piperidyl]pyrazolo[3,4-d]pyrimidin-3-yl]phenyl]methyl]-2-fluoro-6-methoxybenzamide (24.0 mg, 0.04 mmol, 27% yield) as a white solid.

UPLC-MS (ES+, Short acidic): 1.31 min, m/z 530.3 [M+H]+

UPLC-MS (ES+, Long acidic): 2.93 min, m/z 530.2 [M+H]+

$^1$H NMR (400 MHz, DMSO-$d_6$): 9.00 (t, J 6.0 Hz, 1H, NH), 8.28 (s, 1H, ArH), 7.70-7.63 (m, 2H, ArH), 7.55-7.50 (m, 2H, ArH), 7.45-7.37 (m, 1H), 7.03-6.66 (m, 4H), 6.14 (d, $^3J_{trans}$ 16.5 Hz, 0.5H), 6.07 (d, $^3J_{trans}$ 16.5 Hz, 0.5H), 5.72 (d, $^3J_{cis}$ 10.4 Hz, 0.5H), 5.60 (d, $^3J_{cis}$ 10.4 Hz, 0.5H), 4.79-4.64 (m, 1H), 4.54 (d, J 6.0 Hz, 2H, CH$_2$), 4.60-4.48 (m, 0.5H), 4.27-4.16 (m, 1H), 4.14-4.04 (m, 0.5H), 3.85 (s, 3H, CH$_3$), 3.77-3.65 (m, 0.5H), 3.29-3.14 (m, 1H), 3.09-2.95 (m, 0.5H), 2.32-2.21 (m, 1H), 2.18-2.07 (m, 1H), 1.99-1.89 (m, 1H), 1.68-1.50 (m, 1H).

Example 32: N-[[4-[4-Amino-1-[(3R)-1-prop-2-enoyl-3-piperidyl]pyrazolo[3,4-d]pyrimidin-3-yl]phenyl]methyl]-3-fluoro-benzamide

[4-[[(3-Fluorobenzoyl)amino]methyl]phenyl]boronic acid

Following general procedure A, [4-(aminomethyl)phenyl]boronic acid hydrochloride (300.0 mg, 1.6 mmol) and 3-fluorobenzoyl chloride (0.21 mL, 1.76 mmol) afforded [4-[[(3-fluorobenzoyl)amino]methyl]phenyl]boronic acid (438.8 mg, 1.12 mmol, 70% yield) as an off white solid.

UPLC-MS (ES+, short acidic): 1.59 min, m/z 311.9 [M+H]+ tert-Butyl (3R)-3-[4-amino-3-[4-[[(3-fluorobenzoyl)amino]methyl]phenyl]pyrazolo[3,4-d]pyrimidin-1-yl]piperidine-1-carboxylate Following general procedure D, [4-[[(3-fluorobenzoyl)amino]methyl]phenyl]boronic acid (368.8 mg, 1.35 mmol) and tert-butyl (3R)-3-(4-amino-3-iodo-pyrazolo[3,4-d]pyrimidin-1-yl)piperidine-1-carboxylate (200.0 mg, 0.45 mmol) gave tert-butyl (3R)-3-[4-amino-3-[4-[[(3-fluorobenzoyl)amino]methyl]phenyl]pyrazolo[3,4-d]pyrimidin-1-yl]piperidine-1-carboxylate (200.0 mg, 0.37 mmol, 81% yield) as yellow solid.

UPLC-MS (ES+, Short acidic): 1.66 min, m/z 546.4 [M+H]+

N-[[4-[4-Amino-1-[(3R)-3-piperidyl]pyrazolo[3,4-d]pyrimidin-3-yl]phenyl]methyl]-3-fluoro-benzamide Following general procedure E, tert-butyl (3R)-3-[4-amino-3-[4-[[(3-fluorobenzoyl)amino]methyl]phenyl]pyrazolo[3,4-d]pyrimidin-1-yl]piperidine-1-carboxylate (200.0 mg, 0.37 mmol) afforded N-[[4-[4-amino-1-[(3R)-3-piperidyl]pyrazolo[3,4-d]pyrimidin-3-yl]phenyl]methyl]-3-fluoro-benzamide (187.0 mg, 0.42 mmol, 114% yield)

UPLC-MS (ES+, Short acidic): 1.09 min, m/z 446.4 [M+H]+

N-[[4-[4-Amino-1-[(3R)-1-prop-2-enoyl-3-piperidyl]pyrazolo[3,4-d]pyrimidin-3-yl]phenyl]methyl]-3-fluoro-benzamide Following general procedure F, N-[[4-[4-amino-1-[(3R)-3-piperidyl]pyrazolo[3,4-d]pyrimidin-3-yl]phenyl]methyl]-3-fluoro-benzamide (187.0 mg, 0.42 mmol) afforded N-[[4-[4-amino-1-[(3R)-1-prop-2-enoyl-3-piperidyl]pyrazolo[3,4-d]pyrimidin-3-yl]phenyl]methyl]-3-fluoro-benzamide (18.0 mg, 0.04 mmol, 8% yield) as a white solid.

UPLC-MS (ES+, Short acidic): 1.36 min, m/z 500.3 [M+H]+

UPLC-MS (ES+, Long acidic): 3.05 min, m/z 500.3 [M+H]+

$^1$H NMR (400 MHz, DMSO-$d_6$): 9.22 (t, J 6.0 Hz, 1H, NH), 8.27 (s, 1H, ArH), 7.79 (dt, J 7.5, J 1.2 Hz, 1H, ArH), 7.75-7.70 (m, 1H ArH), 7.65 (d, J 7.8 Hz, 2H, ArH), 7.59-7.48 (m, 3H, ArH), 7.44-7.38 (m, 1H, ArH), 6.91-6.82 (m, 0.5H), 6.76-6.66 (m, 0.5H), 6.13 (d, J 16.8 Hz, 0.5H), 6.08 (d, J 16.8 Hz, 0.5H), 5.71 (d, J 10.4 Hz, 0.5H), 5.58 (d, J 10.4 Hz, 0.5H), 4.77-4.64 (m, 1H), 4.58 (d, J 6.0 Hz, 2H, CH$_2$), 4.58-4.51 (m, 0.5H), 4.25-4.16 (m, 1H), 4.11-4.04 (m, 0.5H), 3.75-3.66 (m, 0.5H), 3.27-3.14 (m, 1H), 3.07-2.97 (m, 0.5H), 2.33-2.20 (m, 1H), 2.16-2.08 (m, 1H), 1.97-1.89 (m, 1H), 1.65-1.52 (m, 1H).

Example 33: N-[[4-[4-Amino-1-[(3R)-1-prop-2-enoyl-3-piperidyl]pyrazolo[3,4-d]pyrimidin-3-yl]phenyl]methyl]-2-methoxy-4-(trifluoromethyl)benzamide

[4-[[[2-Methoxy-4-(trifluoromethyl)benzoyl]amino]methyl]phenyl]boronic acid Following general procedure A, 2-methoxy-4-(trifluoromethyl)benzoic acid (300.0 mg, 1.36 mmol) and [4-(aminomethyl)phenyl]boronic acid (226.3 mg, 1.50 mmol) afforded [4-[[[2-methoxy-4-(trifluoromethyl)benzoyl]amino]methyl]phenyl]boronic acid (360.0 mg, 0.71 mmol, 52% yield) as a yellow oil.

UPLC-MS (ES+, Short acidic): 1.46 min, m/z 353.8 [M+H]+ tert-Butyl (3R)-3-[4-amino-3-[4-[[[(2-methoxy-4-(trifluoromethyl)benzoyl]amino]methyl]phenyl]pyrazolo[3,4-d]pyrimidin-1-yl]piperidine-1-carboxylate Following general procedure D, [4-[[[2-methoxy-4-(trifluoromethyl)benzoyl]amino]methyl]phenyl]boronic acid and tert-butyl (3R)-3-(4-amino-3-iodo-pyrazolo[3,4-d]pyrimidin-1-yl)piperidine-1-carboxylate (200.0 mg, 0.45 mmol) gave tert-butyl (3R)-3-[4-amino-3-[4-[[[2-methoxy-4-(trifluoromethyl)benzoyl]amino]methyl]phenyl]pyrazolo[3,4-d]pyrimidin-1-yl]piperidine-1-carboxylate (330.0 mg, 0.37 mmol, 54% yield).

UPLC-MS (ES+, Short acidic): 1.85 min, m/z 626.4 [M+H]+

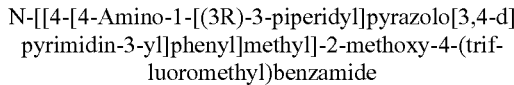

N-[[4-[4-Amino-1-[(3R)-3-piperidyl]pyrazolo[3,4-d]pyrimidin-3-yl]phenyl]methyl]-2-methoxy-4-(trifluoromethyl)benzamide Following general procedure E, tert-butyl (3R)-3-[4-amino-3-[4-[[[2-methoxy-4-(trifluoromethyl)benzoyl]amino]methyl]phenyl]pyrazolo[3,4-d]pyrimidin-1-yl]piperidine-1-carboxylate (330.0 mg, 0.53 mmol) gave N-[[4-[4-amino-1-[(3R)-3-piperidyl]pyrazolo[3,4-d]pyrimidin-3-yl]phenyl]methyl]-2-methoxy-4-(trifluoromethyl)benzamide (240.0 mg, 0.46 mmol, 86% yield) as a yellow foam.

UPLC-MS (ES+, Short acidic): 1.34 min, m/z 526.2 [M+H]+

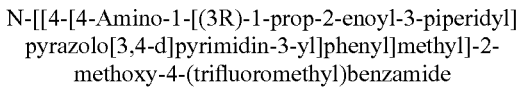

N-[[4-[4-Amino-1-[(3R)-1-prop-2-enoyl-3-piperidyl]pyrazolo[3,4-d]pyrimidin-3-yl]phenyl]methyl]-2-methoxy-4-(trifluoromethyl)benzamide Following general procedure F, N-[[4-[4-amino-1-[(3R)-3-piperidyl]pyrazolo[3,4-d]pyrimidin-3-yl]phenyl]methyl]-2-methoxy-4-(trifluoromethyl)benzamide (240.0 mg, 0.46 mmol) afforded N-[[4-[4-amino-1-[(3R)-1-prop-2-enoyl-3-piperidyl]pyrazolo[3,4-d]pyrimidin-3-yl]phenyl]methyl]-2-methoxy-4-(trifluoromethyl)benzamide (28.0 mg, 0.05 mmol, 11% yield) as a white solid.

UPLC-MS (ES+, Short acidic): 1.55 min, m/z 580.3 [M+H]+

UPLC-MS (ES+, long acidic): 3.55 min, m/z 580.2 [M+H]+

$^1$H NMR (400 MHz, DMSO-$d_6$): 8.92 (t, J 6.0 Hz, 1H, NH), 8.27 (s, 1H, ArH), 7.86 (d, J 7.8 Hz, 1H, ArH), 7.80 (d, J 7.8 Hz, 2H, ArH), 7.53 (d, J 7.8 Hz, 2H, ArH), 7.44 (s, 1H, ArH), 7.40 (d, J 7.8 Hz, 1H, ArH), 6.87 (dd, $^3J_{trans}$ 16.6, $^3J_{cis}$ 10.4 Hz, 0.5H), 6.72 (dd, $^3J_{trans}$ 16.6, $^3J_{cis}$ 10.4 Hz, 0.5H), 6.14 (d, J 16.8 Hz, 0.5H), 6.07 (d, J 16.8 Hz, 0.5H), 5.71 (d, J 10.4 Hz, 0.5H), 5.58 (d, J 10.4 Hz, 0.5H), 4.77-4.66 (m, 1H), 4.60 (d, J 6.0 Hz, 2H, CH$_2$), 4.58-4.53 (m, 0.5H), 4.25-4.16 (m, 1H), 4.11-4.04 (m, 0.5H), 3.99 (s, 3H, OCH$_3$), 3.75-3.68 (m, 0.5H), 3.27-3.14 (m, 1H), 3.06-2.97 (m, 0.5H), 2.33-2.22 (m, 1H), 2.16-2.09 (m, 1H), 1.97-1.89 (m, 1H), 1.65-1.52 (m, 1H).

Example 34: N-[[4-[4-Amino-1-[(3R)-1-prop-2-enoyl-3-piperidyl]pyrazolo[3,4-d]pyrimidin-3-yl]phenyl]methyl]-2-chloro-5-(trifluoromethyl)benzamide

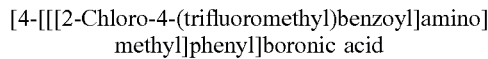

[4-[[[2-Chloro-4-(trifluoromethyl)benzoyl]amino]methyl]phenyl]boronic acid

To a stirred solution of 2-chloro-5-(trifluoromethyl)benzoyl chloride (0.16 mL, 1.00 mmol) in DCM (5 mL) was added triethylamine (0.56 mL, 4.00 mmol) and [4-(aminomethyl)phenyl]boronic acid (151.0 mg, 1.00 mmol). The resulting solution was stirred at room temperature overnight, quenched with water and then extracted with DCM. The combined organics were filtered over phase separator and concentrated in vacuo to yield [4-[[[2-chloro-4-(trifluoromethyl)benzoyl]amino]methyl]phenyl]boronic acid (437.8 mg, 1.22 mmol, 122% yield) as a white solid.

UPLC-MS (ES+, Short acidic): 1.52 min, m/z 357.9 [M+H]+

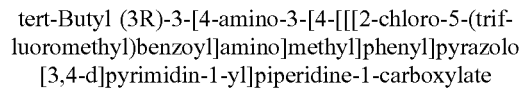

tert-Butyl (3R)-3-[4-amino-3-[4-[[[2-chloro-5-(trifluoromethyl)benzoyl]amino]methyl]phenyl]pyrazolo[3,4-d]pyrimidin-1-yl]piperidine-1-carboxylate Following general procedure D, [4-[[[2-chloro-5-(trifluoromethyl)benzoylamino]methyl]phenyl]boronic acid (241.4 mg, 0.68 mmol) and tert-butyl (3R)-3-(4-amino-3-iodo-pyrazolo[3,4-d]pyrimidin-1-yl)piperidine-1-carboxylate (200.0 mg, 0.45 mmol) gave tert-butyl (3R)-3-[4-amino-3-[4-[[[2-chloro-5-(trifluoromethyl)benzoyl]amino]methyl]phenyl]pyrazolo[3,4-d]pyrimidin-1-yl]piperidine-1-carboxylate (126.8 mg, 0.20 mmol, 45% yield) as a yellow solid.

UPLC-MS (ES+, Short acidic): 1.81 min, m/z 631.1 [M+H]+

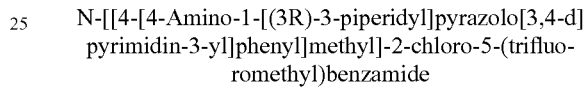

N-[[4-[4-Amino-1-[(3R)-3-piperidyl]pyrazolo[3,4-d]pyrimidin-3-yl]phenyl]methyl]-2-chloro-5-(trifluoromethyl)benzamide Following general procedure E, tert-butyl (3R)-3-[4-amino-3-[4-[[[2-chloro-5-(trifluoromethyl)benzoyl]amino]methyl]phenyl]pyrazolo[3,4-d]pyrimidin-1-yl]piperidine-1-carboxylate (126.8 mg, 0.20 mmol) gave N-[[4-[4-amino-1-[(3R)-3-piperidyl]pyrazolo[3,4-d]pyrimidin-3-yl]phenyl]methyl]-2-chloro-5-(trifluoromethyl)benzamide (66.4 mg, 0.13 mmol, 62% yield) as a dark yellow film.

UPLC-MS (ES+, Short acidic): 1.25 min, m/z 531.0 [M+H]+

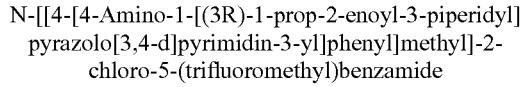

N-[[4-[4-Amino-1-[(3R)-1-prop-2-enoyl-3-piperidyl]pyrazolo[3,4-d]pyrimidin-3-yl]phenyl]methyl]-2-chloro-5-(trifluoromethyl)benzamide Following general procedure F, N-[[4-[4-amino-1-[(3R)-3-piperidyl]pyrazolo[3,4-d]pyrimidin-3-yl]phenyl]methyl]-2-chloro-5-(trifluoromethyl)benzamide (66.4 mg, 0.13 mmol) afforded N-[[4-[4-amino-1-[(3R)-1-prop-2-enoyl-3-piperidyl]pyrazolo[3,4-d]pyrimidin-3-yl]phenyl]methyl]-2-chloro-5-(trifluoromethyl)benzamide (21.0 mg, 0.04 mmol, 29% yield) as a white solid.

UPLC-MS (ES+, Short acidic): 1.52 min, m/z 580.4 [M+H]+

UPLC-MS (ES+, Long acidic): 3.45 min, m/z 580.4 [M+H]+

$^1$H NMR (400 MHz, DMSO-$d_6$): δ (ppm, 1:1 mixture of conformers) 9.23 (t, $^3$J 6.0 Hz, 1H, NH), 8.27 (d, $^3$J 1.6 Hz, 1H, ArH), 7.90-7.83 (m, 2H, ArH), 7.79 (d, $^3$J 8.3 Hz, 1H, ArH), 7.67 (d, $^3$J 8.0 Hz, 2H, ArH), 7.56 (d, $^3$J 8.0 Hz, 2H, ArH), 6.87 (dd, $^3J_{trans}$ 16.0, $^3J_{cis}$ 10.6 Hz, 0.5H), 6.73 (dd, $^3J_{trans}$ 16.0, $^3J_{cis}$ 10.6 Hz, 0.5H), 6.14 (d, $^3J_{trans}$ 16.0 Hz, 0.5H), 6.07 (d, $^3J_{trans}$ 16.0 Hz, 0.5H), 5.72 (d, $^3J_{cis}$ 10.6 Hz, 0.5H), 5.59 (d, $^3J_{cis}$ 10.6 Hz, 0.5H), 4.78-4.66 (m, 1H), 4.58 (d, $^3$J 6.0 Hz, 2H, CH$_2$), 4.58-4.52 (m, 1H), 4.25-4.17 (m, 0.5H), 4.12-4.05 (m, 0.5H), 3.76-3.67 (m, 0.5H), 3.28-3.18

(m, 1H), 3.07-2.98 (m, 0.5H), 2.33-2.21 (m, 1H), 2.17-2.09 (m, 1H), 1.98-1.90 (m, 1H), 1.67-1.55 (m, 1H).

Example 35: N-[[4-[4-Amino-1-[(3R)-1-prop-2-enoyl-3-piperidyl]pyrazolo[3,4-d]pyrimidin-3-yl]phenyl]methyl]-3-chloro-benzamide

[4-[[(3-Chlorobenzoyl)amino]methyl]phenyl]boronic acid

Following general procedure B, [4-(aminomethyl)phenyl]boronic acid hydrochloride (300.0 mg, 1.60 mmol) and 3-chlorobenzoyl chloride (0.23 mL, 1.76 mmol) gave [4-[[(3-chlorobenzoyl)amino]methyl]phenyl]boronic acid (519.9 mg, 1.17 mmol, 73% yield) as a pale yellow solid.
UPLC-MS (ES$^+$, Short acidic): 1.38 min, m/z 289.9 [M+H]$^+$ tert-Butyl (3R)-3-[4-amino-3-[4-[[(3-chlorobenzoyl)amino]methyl]phenyl]pyrazolo[3,4-d]pyrimidin-1-yl]piperidine-1-carboxylate Following general procedure D, [4-[[(3-chlorobenzoyl)amino]methyl]phenyl]boronic acid (146.6 mg, 0.51 mmol) and tert-butyl (3R)-3-(4-amino-3-iodo-pyrazolo[3,4-d]pyrimidin-1-yl)piperidine-1-carboxylate (150.0 mg, 0.36 mmol) gave tert-butyl (3R)-3-[4-amino-3-[4-[[(3-chlorobenzoyl)amino]methyl]phenyl]pyrazolo[3,4-d]pyrimidin-1-yl]piperidine-1-carboxylate (153.0 mg, 0.27 mmol, 81% yield) as a brown foam.
LC-MS (ES$^+$, Short acidic): 1.74 min, m/z 563.0 [M+H]$^+$ N-[[4-[4-Amino-1-[(3R)-3-piperidyl]pyrazolo[3,4-d]pyrimidin-3-yl]phenyl]methyl]-3-chloro-benzamide Following general procedure E, tert-butyl (3R)-3-[4-amino-3-[4-[[(3-chlorobenzoyl)amino]methyl]phenyl]pyrazolo[3,4-d]pyrimidin-1-yl]piperidine-1-carboxylate (153.0 mg, 0.27 mmol) afforded N-[[4-[4-amino-1-[(3R)-3-piperidyl]pyrazolo[3,4-d]pyrimidin-3-yl]phenyl]methyl]-3-chloro-benzamide (74.0 mg, 0.16 mmol, 59% yield) as a yellow oil.
LC-MS (ES$^+$, Short acidic): 1.18 min, m/z 462.2 [M+H]$^+$ N-[[4-[4-Amino-1-[(3R)-1-prop-2-enoyl-3-piperidyl]pyrazolo[3,4-d]pyrimidin-3-yl]phenyl]methyl]-3-chloro-benzamide Following general procedure F, N-[[4-[4-amino-1-[(3R)-3-piperidyl]pyrazolo[3,4-d]pyrimidin-3-yl]phenyl]methyl]-3-chloro-benzamide (74.0 mg, 0.16 mmol) gave N-[[4-[4-amino-1-[(3R)-1-prop-2-enoyl-3-piperidyl]pyrazolo[3,4-d]pyrimidin-3-yl]phenyl]methyl]-3-chloro-benzamide (36.0 mg, 0.07 mmol, 43% yield) as a white solid.
UPLC-MS (ES$^+$, Short acidic): 1.45 min, m/z 517.0 [M+H]$^+$
UPLC-MS (ES$^+$, Long acidic): 3.25 min, m/z 516.2 [M+H]$^+$
$^1$H-NMR (400 MHz, DMSO-d$_6$) δ (ppm, 1:1 mixture of conformers) 9.24 (t, $^3$J 6.0 Hz, 1H, ArH), 8.27 (s, 1H, ArH), 7.97 (t, $^3$J 1.8 Hz, 1H, ArH), 7.91-7.88 (m, 1H, ArH), 7.66-7.62 (m, 3H, ArH), 7.57-7.49 (m, 3H, ArH), 6.87 (dd, $^3$J$_{trans}$ 16.8, $^3$J$_{cis}$ 10.5 Hz, 0.5H), 6.72 (dd, $^3$J$_{trans}$ 16.8, $^3$J$_{cis}$ 10.5 Hz, 0.5H), 6.13 (d, $^3$J$_{trans}$ 16.8 Hz, 0.5H), 6.07 (d, $^3$J$_{trans}$ 16.8 Hz, 0.5H), 5.71 (d, $^3$J$_{cis}$ 10.5 Hz, 0.5H), 5.59 (d, $^3$J$_{cis}$ 10.5 Hz, 0.5H), 4.78-4.66 (m, 1H, CH), 4.57 (d, $^3$J 6.0 Hz, 2H, CH$_2$), 4.58-4.51 (m, 0.5H), 4.25-4.16 (m, 1H, CH), 4.11-4.04 (m, 0.5H), 3.75-3.66 (m, 0.5H), 3.27-3.17 (m, 1H), 3.07-2.97 (m, 0.5H), 2.33-2.21 (m, 1H), 2.17-2.08 (m, 1H), 1.97-1.90 (m, 1H), 1.66-1.52 (m, 1H).

Example 36: N-[[4-[4-Amino-1-[(3R)-1-prop-2-enoyl-3-piperidyl]pyrazolo[3,4-d]pyrimidin-3-yl]phenyl]methyl]-2-fluoro-4-(trifluoromethyl)benzamide

[4-[[[2-Fluoro-4-(trifluoromethyl)benzoyl]amino]methyl]phenyl]boronic acid

To 2-fluoro-4-(trifluoromethyl)benzoyl chloride (226 mg, 1 mmol) under a nitrogen atmosphere at 0° C. was added potassium phosphate (584 mg; 2.75 mmol.), followed by 4-aminomethylphenylboronic acid hydrochloride (187 mg, 1.00 mmol). The reaction was allowed to return to rt and stirred overnight. Water was added, and the reaction mixture extracted with EtOAc (3 times). The combined organics extracts were dried over anhydrous sodium sulfate, filtered, and concentrated in vacuo to afford [4-[[[2-fluoro-4-(trifluoromethyl)benzoyl]amino]methyl]phenyl]boronic acid (245 mg, 0.72 mmol, 72% yield) as yellow oil, which was used crude in the next step.
UPLC-MS (ES$^+$, short acidic): 1.42 min, m/z 341.9 [M+H]$^+$ tert-Butyl (3R)-3-[4-amino-3-[4-[[[2-fluoro-4-(trifluoromethyl)benzoyl]amino]methyl]phenyl]pyrazolo[3,4-d]pyrimidin-1-yl]piperidine-1-carboxylate Following general procedure D, [4-[[[2-fluoro-4-(trifluoromethyl)benzoylamino]methyl]phenyl]boronic acid (144 mg, 0.42 mmol) and tert-butyl (3R)-3-(4-amino-3-iodo-pyrazolo[3,4-d]pyrimidin-1-yl)piperidine-1-carboxylate (125 mg, 0.28 mmol) gave tert-butyl (3R)-3-[4-amino-3-[4-[[[2-fluoro-4-(trifluoromethyl)benzoyl]amino]methyl]phenyl]pyrazolo[3,4-d]pyrimidin-1-yl]piperidine-1-carboxylate (111 mg, 0.18 mmol, 64% yield).
UPLC-MS (ES$^+$, short acidic): 1.83 min, m/z 614.4 [M+H]$^+$ N-[[4-[4-Amino-1-[(3R)-3-piperidyl]pyrazolo[3,4-d]pyrimidin-3-yl]phenyl]methyl]-2-fluoro-4-(trifluoromethyl)benzamide Following general procedure E, tert-butyl (3R)-3-[4-amino-3-[4-[[[2-fluoro-4-(trifluoromethyl)benzoyl]amino]methyl]phenyl]pyrazolo[3,4-d]pyrimidin-1-yl]piperidine-1-carboxylate (111 mg, 0.18 mmol) afforded N-[[4-[4-amino-1-[(3R)-3-piperidyl]pyrazolo[3,4-d]pyrimidin-3-yl]phenyl]methyl]-2-fluoro-4-(trifluoromethyl)benzamide (76 mg, 0.15 mmol, 82% yield) as an off-white solid.
UPLC-MS (ES$^+$, Short acidic): 1.30 min, m/z 514.2 [M+H]$^+$ N-[[4-[4-Amino-1-[(3R)-1-prop-2-enoyl-3-piperidyl]pyrazolo[3,4-d]pyrimidin-3-yl]phenyl]methyl]-2-fluoro-4-(trifluoromethyl)benzamide Following general procedure F, N-[[4-[4-amino-1-[(3R)-3-piperidyl]pyrazolo[3,4-d]pyrimidin-3-yl]phenyl]methyl]-2-fluoro-4-(trifluoromethyl)benzamide (73 mg, 0.14 mmol) afforded N-[[4-[4-amino-1-[(3R)-1-prop-2-enoyl-3-piperidyl]pyrazolo[3,4-d]pyrimidin-3-yl]phenyl]methyl]-2-fluoro-4-(trifluoromethyl)benzamide (64 mg, 0.11 mmol, 79% yield) as a white solid UPLC-MS (ES⁺, Short acidic): 1.53 min, m/z 568.2 [M+H]⁺

UPLC-MS (ES⁺, Long acidic): 3.47 min, m/z 568.3 [M+H]⁺

$^1$H NMR (400 MHz, DMSO-d$_6$) δ (ppm, 1:1 mixture of conformers) 9.19 (t, $^3$J 6.0 Hz, 1H, NH), 8.27 (s, 1H, ArH), 7.91-7.82 (m, 2H, ArH), 7.73-7.63 (m, 3H, ArH), 7.53 (d, $^3$J 8.3 Hz, 2H, ArH), 6.88 (dd, $^3$J$_{trans}$ 16.2, $^3$J$_{cis}$ 10.5 Hz, 0.5H), 6.72 (dd, $^3$J$_{trans}$ 16.2, $^3$J$_{cis}$ 10.5 Hz, 0.5H), 6.14 (d, $^3$J$_{trans}$ 16.2 Hz, 0.5H), 6.07 (d, $^3$J$_{trans}$ 16.2 Hz, 0.5H), 5.72 (d, $^3$J$_{cis}$ 10.5 Hz, 0.5H), 5.59 (d, $^3$J$_{cis}$ 10.5 Hz, 0.5H), 4.78-4.65 (m, 1H), 4.59 (d, $^3$J 6.0 Hz, 2H, CH$_2$), 4.58-4.50 (m, 0.5H), 4.26-4.16 (m, 1H), 4.12-4.04 (m, 0.5H), 3.75-3.67 (m, 0.5H), 3.30-3.15 (m, 1H), 3.08-2.98 (m, 0.5H), 2.32-2.21 (m, 1H), 2.18-2.08 (m, 1H), 1.98-1.89 (m, 1H), 1.66-1.53 (m, 1H).

Example 37: N-[[4-[4-Amino-1-[(3R)-1-prop-2-enoyl-3-piperidyl]pyrazolo[3,4-d]pyrimidin-3-yl]phenyl]methyl]-3-fluoro-pyridine-4-carboxamide

[4-[[(3-Fluoropyridine-4-carbonyl)amino]methyl]phenyl]boronic acid

Following general procedure A, [4-(aminomethyl)phenyl]boronic acid (294.2 mg, 1.95 mmol) and 2-fluoronicotinic acid (250.0 mg, 1.77 mmol) afforded [4-[[(3-fluoropyridine-4-carbonyl)amino]methyl]phenyl]boronic acid (160.0 mg, 0.58 mmol, 33% yield) as a yellow oil.

UPLC-MS (ES⁺, Short acidic): 1.03 min, m/z 274.8 [M+H]⁺ tert-Butyl (3R)-3-[4-amino-3-[4-[[(3-fluoropyridine-4-carbonyl)amino]methyl]phenyl]pyrazolo[3,4-d]pyrimidin-1-yl]piperidine-1-carboxylate Following general procedure D, [4-[[(3-fluoropyridine-4-carbonyl)amino]methyl]phenyl]boronic acid (166.6 mg, 0.61 mmol), tert-butyl (3R)-3-(4-amino-3-iodo-pyrazolo[3,4-d]pyrimidin-1-yl)piperidine-1-carboxylate (200.0 mg, 0.45 mmol) gave tert-butyl (3R)-3-[4-amino-3-[4-[[(3-fluoropyridine-4-carbonyl)amino]methyl]phenyl]pyrazolo[3,4-d]pyrimidin-1-yl]piperidine-1-carboxylate (160.0 mg, 0.20 mmol, 51% yield) as a brown foam.

UPLC-MS (ES⁺, Short acidic): 1.50 min, m/z 547.4 [M+H]⁺

N-[[4-[4-Amino-1-[(3R)-3-piperidyl]pyrazolo[3,4-d]pyrimidin-3-yl]phenyl]methyl]-3-fluoro-pyridine-4-carboxamide Following general procedure E, tert-butyl (3R)-3-[4-amino-3-[4-[[(3-fluoropyridine-4-carbonyl)amino]methyl]phenyl]pyrazolo[3,4-d]pyrimidin-1-yl]piperidine-1-carboxylate (160.0 mg, 0.29 mmol) afforded N-[[4-[4-amino-1-[(3R)-3-piperidyl]pyrazolo[3,4-d]pyrimidin-3-yl]phenyl]methyl]-3-fluoro-pyridine-4-carboxamide (100.0 mg, 0.22 mmol, 77% yield) as a yellow solid.

UPLC-MS (ES⁺, Short acidic): 0.97 min, m/z 447.2 [M+H]⁺

N-[[4-[4-Amino-1-[(3R)-1-prop-2-enoyl-3-piperidyl]pyrazolo[3,4-d]pyrimidin-3-yl]phenyl]methyl]-3-fluoro-pyridine-4-carboxamide Following general procedure F, N-[[4-[4-amino-1-[(3R)-3-piperidyl]pyrazolo[3,4-d]pyrimidin-3-yl]phenyl]methyl]-3-fluoro-pyridine-4-carboxamide (100.0 mg, 0.22 mmol) afforded, after purification by preparative HPLC and salt removal by SCX cartridge, N-[[4-[4-amino-1-[(3R)-1-prop-2-enoyl-3-piperidyl]pyrazolo[3,4-d]pyrimidin-3-yl]phenyl]methyl]-3-fluoro-pyridine-4-carboxamide (7.0 mg, 0.01 mmol, 5% yield).

UPLC-MS (ES⁺, Short acidic): 1.19 min, m/z 501.4 [M+H]⁺

UPLC-MS (ES⁺, Long acidic): 2.65 min, m/z 501.3 [M+H]⁺

$^1$H-NMR (400 MHz, DMSO-d$_6$) δ (ppm, 1:1 mixture of conformers): 9.26 (t, $^3$J 6.0 Hz, 1H, NH), 8.72 (d, $^3$J 1.6 Hz, 1H, ArH), 8.56 (dd, $^3$J 5.0, $^4$J 1.3 Hz, 1H, ArH), 8.27 (s, 1H, ArH), 7.67-7.63 (m, 3H, ArH), 7.52 (d, $^3$J 8.5 Hz, 2H, ArH), 6.87 (dd, $^3$J$_{trans}$ 16.2, $^3$J$_{cis}$ 10.5 Hz, 0.5H), 6.71 (dd, $^3$J$_{trans}$ 16.2, $^3$J$_{cis}$ 10.5 Hz, 0.5H), 6.13 (d, $^3$J$_{trans}$ 16.2 Hz, 0.5H), 6.06 (d, $^3$J$_{trans}$ 16.2 Hz, 0.5H), 5.71 (d, $^3$J$_{cis}$ 10.5 Hz, 0.5H), 5.58 (d, $^3$J$_{cis}$ 10.5 Hz, 0.5H), 4.77-4.64 (m, 1H), 4.58 (d, $^3$J 6.0 Hz, 2H, CH$_2$), 4.56-4.51 (m, 0.5H), 4.24-4.16 (m, 1H), 4.11-4.04 (m, 0.5H), 3.75-3.67 (m, 0.5H), 3.25-3.15 (m, 1H), 3.07-2.98 (m, 0.5H), 2.32-2.21 (m, 1H), 2.16-2.09 (m, 1H), 1.98-1.89 (m, 1H), 1.66-1.53 (m, 1H).

Example 38: N-[[4-[4-Amino-1-[(3R)-1-prop-2-enoyl-3-piperidyl]pyrazolo[3,4-d]pyrimidin-3-yl]phenyl]methyl]-3-fluoro-pyridine-2-carboxamide

[4-[[(3-Fluoropyridine-2-carbonyl)amino]methyl]phenyl]boronic acid

Following general procedure A, [4-(aminomethyl)phenyl]boronic acid (294.2 mg, 1.95 mmol) and 3-fluoropyridine-2-carboxylic acid (250.0 mg, 1.77 mmol) afforded [4-[[(3-fluoropyridine-2-carbonyl)amino]methyl]phenyl]boronic acid (190.0 mg, 0.69 mmol, 39% yield) as a yellow foam.

UPLC-MS (ES⁺, Short acidic): 0.94 min, m/z 274.7 [M+H]⁺ tert-Butyl (3R)-3-[4-amino-3-[4-[[(3-fluoropyridine-2-carbonyl)amino]methyl]phenyl]pyrazolo[3,4-d]pyrimidin-1-yl]piperidine-1-carboxylate Following general procedure D, [[4-[[(3-fluoropyridine-2-carbonyl)amino]methyl]phenyl]boronic acid (185.1 mg, 0.68 mmol), tert-butyl (3R)-3-(4-amino-3-iodo-pyrazolo[3,4-d]pyrimidin-1-yl)piperidine-1-carboxylate (200.0 mg, 0.45 mmol) gave tert-butyl (3R)-3-[4-amino-3-[4-[[(3-fluoropyridine-2-carbonyl)amino]methyl]phenyl]pyrazolo[3,4-d]pyrimidin-1-yl]piperidine-1-carboxylate (230.0 mg, 0.42 mmol, 93% yield) as a yellow foam.

UPLC-MS (ES⁺, Short acidic): 1.55 min, m/z 547.5 [M+H]⁺

N-[[4-[4-Amino-1-[(3R)-3-piperidyl]pyrazolo[3,4-d]pyrimidin-3-yl]phenyl]methyl]-3-fluoro-pyridine-2-carboxamide Following general procedure E, tert-butyl (3R)-3-[4-amino-3-[4-[[(3-fluoropyridine-2-carbonyl)amino]methyl]phenyl]pyrazolo[3,4-d]pyrimidin-1-yl]piperidine-1-carboxylate (230.0 mg, 0.42 mmol) afforded N-[[4-[4-amino-1-[(3R)-3-piperidyl]pyrazolo[3,4-d]pyrimidin-3-yl]phenyl]methyl]-3-fluoro-pyridine-2-carboxamide (110.0 mg, 0.25 mmol, 59% yield) as a yellow foam.

UPLC-MS (ES⁺, Short acidic): 0.98 min, m/z 447.2 [M+H]⁺

N-[[4-[4-Amino-1-[(3R)-1-prop-2-enoyl-3-piperidyl]pyrazolo[3,4-d]pyrimidin-3-yl]phenyl]methyl]-3-fluoro-pyridine-2-carboxamide Following general procedure F, N-[[4-[4-amino-1-[(3R)-3-piperidyl]pyrazolo[3,4-d]pyrimidin-3-yl]phenyl]methyl]-3-fluoro-pyridine-2-carboxamide (100.0 mg, 0.22 mmol) afforded, after purification by preparative HPLC and salt removal by SCX cartridge, N-[[4-[4-amino-1-[(3R)-1-prop-2-enoyl-3-piperidyl]pyrazolo[3,4-d]pyrimidin-3-yl]phenyl]methyl]-3-fluoro-pyridine-2-carboxamide (13.0 mg, 0.03 mmol, 11% yield) as a thin film.

UPLC-MS (ES$^+$, Short acidic): 1.24 min, m/z 501.3 [M+H]$^+$

UPLC-MS (ES$^+$, Long acidic): 2.75 min, m/z 501.3 [M+H]$^+$ $^1$H-NMR (400 MHz, DMSO-d$_6$) δ (ppm, 1:1 mixture of conformers): 9.30 (t, $^3$J 6.4 Hz, 1H, NH), 8.51 (dt, J 4.6, J 1.5 Hz, 1H, ArH), 8.26 (s, 1H, ArH), 7.91-7.86 (m, 1H, ArH), 7.71-7.67 (m, 1H, ArH), 7.64 (d, $^3$J 8.0 Hz, 2H, ArH), 7.51 (d, $^3$J 8.3 Hz, 2H, ArH), 6.86 (dd, $^3$J$_{trans}$ 16.2, $^3$J$_{cis}$ 10.5 Hz, 0.5H), 6.71 (dd, $^3$J$_{trans}$ 16.2, $^3$J$_{cis}$ 10.5 Hz, 0.5H), 6.12 (d, $^3$J$_{trans}$ 16.2 Hz, 0.5H), 6.06 (d, $^3$J$_{trans}$ 16.2 Hz, 0.5H), 5.71 (d, $^3$J$_{cis}$ 10.5 Hz, 0.5H), 5.58 (d, $^3$J$_{cis}$ 10.5 Hz, 0.5H), 4.77-4.64 (m, 1H), 4.56 (d, $^3$J 6.0 Hz, 2H, CH$_2$), 4.55-4.51 (m, 0.5H), 4.25-4.16 (m, 1H), 4.11-4.03 (m, 0.5H), 3.74-3.65 (m, 0.5H), 3.26-3.15 (m, 1H), 3.04-2.96 (m, 0.5H), 2.31-2.22 (m, 1H), 2.16-2.07 (m, 1H), 1.97-1.89 (m, 1H), 1.66-1.52 (m, 1H).

Example 39: N-[[4-[4-Amino-1-[(3R)-1-prop-2-enoyl-3-piperidyl]pyrazolo[3,4-d]pyrimidin-3-yl]phenyl]methyl]-2-fluoro-3-methoxy-benzamide

[4-[[(2-Fluoro-3-methoxy-benzoyl)amino]methyl]phenyl]boronic acid

To a solution of 2-fluoro-3-methoxy-benzoyl chloride (0.29 mL, 1.66 mmol) in THF (2 M) under a nitrogen atmosphere at 0° C. was added potassium phosphate tribasic (878.8 mg, 4.14 mmol), followed by [4-(aminomethyl)phenyl]boronic acid (250.0 mg, 1.66 mmol). The reaction was allowed to return to rt and stirred overnight. Water was added, and the reaction mixture extracted with EtOAc (3×). The combined organics extracts were dried over anhydrous sodium sulfate, filtered, and concentrated in vacuo to afford crude [4-[[(2-fluoro-3-methoxy-benzoyl)amino]methyl]phenyl]boronic acid (200.0 mg, 0.67 mmol, 40% yield) as a white solid.

UPLC-MS (ES$^+$, Short acidic): 1.26 min, m/z 303.9 [M+H]$^+$ tert-Butyl (3R)-3-[4-amino-3-[4-[[(2-fluoro-3-methoxy-benzoyl)amino]methyl]phenyl]pyrazolo[3,4-d]pyrimidin-1-yl]piperidine-1-carboxylate Following general procedure D, [4-[[(2-fluoro-3-methoxy-benzoyl)amino]methyl]phenyl]boronic acid (204.7 mg, 0.68 mmol) and tert-butyl (3R)-3-(4-amino-3-iodo-pyrazolo[3,4-d]pyrimidin-1-yl)piperidine-1-carboxylate (200.0 mg, 0.45 mmol) gave tert-butyl (3R)-3-[4-amino-3-[4-[[(2-fluoro-3-methoxy-benzoyl)amino]methyl]phenyl]pyrazolo[3,4-d]pyrimidin-1-yl]piperidine-1-carboxylate (200.0 mg, 0.35 mmol, 77% yield) as a yellow foam.

UPLC-MS (ES$^+$, Short acidic): 1.64 min, m/z 576.5 [M+H]$^+$

N-[[4-[4-Amino-1-[(3R)-3-piperidyl]pyrazolo[3,4-d]pyrimidin-3-yl]phenyl]methyl]-2-fluoro-3-methoxy-benzamide Following general procedure E, tert-butyl (3R)-3-[4-amino-3-[4-[[(2-fluoro-3-methoxy-benzoyl)amino]methyl]phenyl]pyrazolo[3,4-d]pyrimidin-1-yl]piperidine-1-carboxylate (200.0 mg, 0.35 mmol) afforded N-[[4-[4-amino-1-[(3R)-3-piperidyl]pyrazolo[3,4-d]pyrimidin-3-yl]phenyl]methyl]-2-fluoro-3-methoxy-benzamide (130.0 mg, 0.27 mmol, 78% yield) as a pale foam.

UPLC-MS (ES$^+$, Short acidic): 1.07 min, m/z 476.4 [M+H]$^+$

N-[[4-[4-Amino-1-[(3R)-1-prop-2-enoyl-3-piperidyl]pyrazolo[3,4-d]pyrimidin-3-yl]phenyl]methyl]-2-fluoro-3-methoxy-benzamide Following general procedure F, N-[[4-[4-amino-1-[(3R)-3-piperidyl]pyrazolo[3,4-d]pyrimidin-3-yl]phenyl]methyl]-2-fluoro-3-methoxy-benzamide (130.0 mg, 0.27 mmol) afforded, after purification by preparative HPLC and salt removal by SCX cartridge, N-[[4-[4-amino-1-[(3R)-1-prop-2-enoyl-3-piperidyl]pyrazolo[3,4-d]pyrimidin-3-yl]phenyl]methyl]-2-fluoro-3-methoxy-benzamide (16.0 mg, 0.03 mmol, 11% yield) as a thin film.

UPLC-MS (ES$^+$, Short acidic): 1.35 min, m/z 530.3 [M+H]$^+$

UPLC-MS (ES$^+$, Long acidic): 3.03 min, m/z 530.2 [M+H]$^+$ $^1$H-NMR (400 MHz, DMSO-d$_6$) δ (ppm, 1:1 mixture of conformers): 8.95 (t, $^3$J 6.1 Hz, 1H, NH), 8.26 (s, 1H, ArH), 7.65 (d, $^3$J 7.6 Hz, 2H, ArH), 7.50 (d, $^3$J 7.6 Hz, 2H, ArH), 7.32-7.26 (m, 1H, ArH), 7.23-7.18 (m, 1H, ArH), 7.17-7.13 (m, 1H, ArH), 6.86 (dd, $^3$J$_{trans}$ 16.5, $^3$J$_{cis}$ 10.5 Hz, 0.5H), 6.71 (dd, $^3$J$_{trans}$ 16.5, $^3$J$_{cis}$ 10.5 Hz, 0.5H), 6.13 (d, $^3$J$_{trans}$ 16.5 Hz, 0.5H), 6.06 (d, $^3$J$_{trans}$ 16.5 Hz, 0.5H), 5.70 (d, $^3$J$_{cis}$ 10.5 Hz, 0.5H), 5.58 (d, $^3$J$_{cis}$ 10.5 Hz, 0.5H), 4.76-4.64 (m, 1H), 4.55 (d, $^3$J 6.0 Hz, 2H, CH$_2$), 4.57-4.50 (m, 0.5H), 4.25-4.15 (m, 1H), 4.11-4.06 (m, 0.5H), 3.87 (s, 3H, OCH$_3$), 3.74-3.66 (m, 0.5H), 3.27-3.15 (m, 1H), 3.04-2.96 (m, 0.5H), 2.32-2.21 (m, 1H), 2.16-2.07 (m, 1H), 1.99-1.88 (m, 1H), 1.65-1.53 (m, 1H).

Example 40: N-[[4-[4-Amino-1-[(3R)-1-prop-2-enoyl-3-piperidyl]pyrazolo-[3,4-d]pyrimidin-3-yl]phenyl]methyl]-2-chloro-benzamide

[4-[[(2-Chlorobenzoyl)amino]methyl]phenyl]boronic acid

Following general procedure B, [4-(aminomethyl)phenyl]boronic acid hydrochloride (300.0 mg, 1.6 mmol) and 2-chlorobenzoyl chloride (308.1 mg, 1.76 mmol) gave [4-[[(2-chlorobenzoyl)amino]methyl]phenyl]boronic acid (368.2 mg, 0.95 mmol, 60% yield) as an off-white solid.

UPLC-MS (ES$^+$, Short acidic): 1.25 min, m/z 289.8 [M+H]$^+$ tert-Butyl (3R)-3-[4-amino-3-[4-[[(2-chlorobenzoyl)amino]methyl]phenyl]pyrazolo[3,4-d]pyrimidin-1-yl]piperidine-1-carboxylate Following general procedure D, [4-[[(2-chlorobenzoyl)amino]methyl]phenyl]boronic acid (367.5 mg, 0.95 mmol) and tert-butyl (3R)-3-(4-amino-3-iodo-pyrazolo[3,4-d]pyrimidin-1-yl)piperidine-1-carboxylate (235 mg, 0.53 mmol)

gave tert-butyl (3R)-3-[4-amino-3-[4-[[(2-chlorobenzoyl)amino]methyl]phenyl]pyrazolo[3,4-d]pyrimidin-1-yl]piperidine-1-carboxylate (450 mg, 0.52 mmol, 98% yield) as a brown foam.

UPLC-MS (ES$^+$, Short acidic): 1.65 min, m/z 563.1 [M+H]$^+$

N-[[4-[4-Amino-1-[(3R)-3-piperidyl]pyrazolo[3,4-d]pyrimidin-3-yl]phenyl]methyl]-2-chloro-benzamide Following general procedure E, tert-butyl (3R)-3-[4-amino-3-[4-[[(2-chlorobenzoyl)amino]-methyl]phenyl]pyrazolo[3,4-d]pyrimidin-1-yl]piperidine-1-carboxylate (450.0 mg, 0.52 mmol) afforded N-[[4-[4-amino-1-[(3R)-3-piperidyl]pyrazolo[3,4-d]pyrimidin-3-yl]phenyl]methyl]-2-chloro-benzamide (192 mg, 0.37 mmol, 72% yield) as an off-white/brown foam.

UPLC-MS (ES$^+$, Short acidic): 1.07 min, m/z 462.2 [M+H]$^+$

N-[[4-[4-Amino-1-[(3R)-1-prop-2-enoyl-3-piperidyl]pyrazolo[3,4-d]pyrimidin-3-yl]-phenyl]methyl]-2-chloro-benzamide Following general procedure F, N-[[4-[4-amino-1-[(3R)-3-piperidyl]pyrazolo[3,4-d]pyrimidin-3-yl]phenyl]methyl]-2-chloro-benzamide (192.0 mg, 0.42 mmol) gave N-[[4-[4-amino-1-[(3R)-1-prop-2-enoyl-3-piperidyl]pyrazolo-[3,4-d]pyrimidin-3-yl]phenyl]methyl]-2-chloro-benzamide (22.4 mg, 0.04 mmol, 10% yield) as an off-white foam.

UPLC-MS (ES$^+$, Short acidic): 1.34 min, m/z 517.1 [M+H]$^+$ (96%)

UPLC-MS (ES$^+$, Long acidic): 2.99 min, m/z 517 [M+H]$^+$ (97%)

$^1$H-NMR (400 MHz, DMSO-d$_6$) δ (ppm, 1:1 mixture of conformers) 9.06 (t, J 6.0 Hz, 1H, NH), 8.27 (s, 1H, ArH), 7.66 (d, J 8.0 Hz, 2H, ArH), 7.55 (d, J 8.0 Hz, 2H, ArH), 7.53-7.48 (m, 2H, ArH), 7.48-7.40 (m, 2H, ArH), 6.88 (dd, $^3J_{trans}$ 16.4, $^3J_{cis}$ 10.4 Hz, 0.5H), 6.73 (dd, $^3J_{trans}$ 16.4, $^3J_{cis}$ 10.4 Hz, 0.5H), 6.14 (d, $^3J_{trans}$ 16.4 Hz, 0.5H), 6.07 (d, $^3J_{trans}$ 16.4 Hz, 0.5H), 5.72 (d, $^3J_{cis}$ 10.4 Hz, 0.5H), 5.59 (d, $^3J_{cis}$ 10.4 Hz, 0.5H), 4.78-4.65 (m, 1H), 4.55 (d, J 6.0 Hz, 2H, CH$_2$), 4.57-4.50 (m, 0.5H), 4.27-4.17 (m, 1H), 4.13-4.04 (m, 0.5H), 3.76-3.67 (m, 0.5H), 3.27-3.15 (m, 1H), 3.07-2.97 (m, 0.5H), 2.31-2.22 (m, 1H), 2.18-2.09 (m, 1H), 1.98-1.90 (m, 1H), 1.67-1.52 (m, 1H).

Example 41: N-[[4-[4-Amino-1-[(3R)-1-prop-2-enoyl-3-piperidyl]pyrazolo[3,4-d]pyrimidin-3-yl]phenyl]methyl]-3-methyl-benzamide

[4-[[(3-Methylbenzoyl)amino]methyl]phenyl]boronic acid

Following general procedure B, 3-methylbenzoylchloride (0.2 mL, 1.76 mmol) and [4-(aminomethyl)phenyl]boronic acid hydrochloride (300.0 mg, 1.60 mmol) afforded [4-[[(3-methylbenzoyl)amino]methyl]phenyl]boronic acid (393.8 mg, 0.97 mmol, 60% yield) as an off-white solid.

UPLC-MS (ES$^+$, Short acidic): 1.33 min, m/z 269.8 [M] (66%)

tert-Butyl (3R)-3-[4-amino-3-[4-[[(3-methylbenzoyl)amino]methyl]phenyl]pyrazolo[3,4-d]pyrimidin-1-yl]piperidine-1-carboxylate Following general procedure D-2, [4-[[(3-methylbenzoyl)amino]methyl]phenyl]boronic acid (181.7 mg, 0.68 mmol) and tert-butyl (3R)-3-(4-amino-3-iodo-pyrazolo[3,4-d]pyrimidin-1-yl)piperidine-1-carboxylate (200.0 mg, 0.45 mmol) gave, after further purification by flash column chromatography (DCM/MeOH 100:0 to 90:10) to give tert-butyl (3R)-3-[4-amino-3-[4-[[(3-methylbenzoyl)amino]methyl]phenyl]pyrazolo[3,4-d]pyrimidin-1-yl]piperidine-1-carboxylate (161.0 mg, 0.24 mmol, 53% yield) as a dark brown gum UPLC-MS (ES$^+$, Short acidic): 1.70 min, m/z 542.5 [M+H]$^+$ (82%)

N-[[4-[4-Amino-1-[(3R)-3-piperidyl]pyrazolo[3,4-d]pyrimidin-3-yl]phenyl]methyl]-3-methyl-benzamide Following general procedure E, tert-butyl (3R)-3-[4-amino-3-[4-[[(3-methylbenzoyl)amino]methyl]phenyl]pyrazolo[3,4-d]pyrimidin-1-yl]piperidine-1-carboxylate (161.0 mg, 0.30 mmol) gave, after further purification by flash column chromatography (DCM/7N NH$_3$ in MeOH 100:0 to 90:10), N-[[4-[4-amino-1-[(3R)-3-piperidyl]pyrazolo[3,4-d]pyrimidin-3-yl]phenyl]methyl]-3-methyl-benzamide (100.8 mg, 0.21 mmol, 69% yield) as a yellow solid.

UPLC-MS (ES$^+$, Short acidic): 1.15 min, m/z 442.3 [M+H]$^+$ (98%)

N-[[4-[4-Amino-1-[(3R)-1-prop-2-enoyl-3-piperidyl]pyrazolo[3,4-d]pyrimidin-3-yl]phenyl]methyl]-3-methyl-benzamide Following general procedure F, N-[[4-[4-amino-1-[(3R)-3-piperidyl]pyrazolo[3,4-d]pyrimidin-3-yl]phenyl]methyl]-3-methyl-benzamide (100.8 mg, 0.23 mmol) gave, purification by flash column chromatography (DCM/MeOH 100:0 to 90:10), N-[[4-[4-amino-1-[(3R)-1-prop-2-enoyl-3-piperidyl]pyrazolo[3,4-d]pyrimidin-3-yl]phenyl]methyl]-3-methyl-benzamide (34.7 mg, 0.06 mmol, 28% yield) as a cream solid.

UPLC-MS (ES$^+$, Short acidic): 1.39 min, m/z 496.5 [M+H]$^+$

UPLC-MS (ES$^+$, Long acidic): 3.14 min, m/z 496.4 [M+H]$^+$ $^1$H NMR (400 MHz, DMSO-d$_6$) δ (ppm, 1:1 mixture of conformers) 9.06 (t, J 6.0 Hz, 1H, NH), 8.27 (s, 1H, ArH), 7.77-7.74 (m, 1H, ArH), 7.73-7.70 (m, 1H, ArH), 7.67-7.62 (m, 2H, ArH), 7.52-7.48 (m, 2H, ArH), 7.40-7.35 (m, 2H, ArH), 6.87 (dd, $^3J_{trans}$ 16.2, $^3J_{cis}$ 10.4 Hz, 0.5H), 6.72 (dd, $^3J_{trans}$ 16.2, $^3J_{cis}$ 10.4 Hz, 0.5H), 6.13 (d, $^3J_{trans}$ 16.2 Hz, 0.5H), 6.07 (d, $^3J_{trans}$ 16.2 Hz, 0.5H), 5.71 (d, $^3J_{cis}$ 10.4 Hz, 0.5H), 5.59 (d, $^3J_{cis}$ 10.4 Hz, 0.5H), 4.78-4.65 (m, 1H), 4.56 (d, J 6.0 Hz, 2H, CH$_2$), 4.57-4.51 (m, 0.5H), 4.25-4.16 (m, 1H), 4.12-4.04 (m, 0.5H), 3.76-3.66 (m, 0.5H), 3.26-3.15 (m, 1H), 3.07-2.97 (m, 0.5H), 2.38 (s, 3H, CH$_3$), 2.31-2.21 (m, 1H), 2.17-2.09 (m, 1H), 1.98-1.89 (m, 1H), 1.67-1.52 (m, 1H).

Example 42: N-[[4-[4-Amino-1-[(3R)-1-prop-2-enoyl-3-piperidyl]pyrazolo[3,4-d]pyrimidin-3-yl]phenyl]methyl]-4-(trifluoromethoxy)benzamide

[4-[[[4-(Trifluoromethoxy)benzoyl]amino]methyl]phenyl]boronic acid

Following general procedure B, 4-(trifluoromethoxy)benzoyl chloride (0.3 mL, 1.76 mmol) and [4-(aminomethyl)phenyl]boronic acid hydrochloride (300.0 mg, 1.60 mmol)

gave [4-[[[4-(trifluoromethoxy)benzoyl]amino]methyl]phenyl]boronic acid (547.9 mg, 1.21 mmol, 76% yield) as an off-white solid.

UPLC-MS (ES+, Short acidic): 1.51 min, m/z 339.8 [M+H]+ tert-Butyl (3R)-3-[4-Amino-3-[4-[[[4-(trifluoromethoxy)benzoyl]amino]methyl]phenyl]pyrazolo[3,4-d]pyrimidin-1-yl]piperidine-1-carboxylate Following general procedure D, [4-[[[4-(trifluoromethoxy)benzoyl]amino]methyl]phenyl]boronic acid (229.0 mg, 0.68 mmol) and tert-butyl (3R)-3-(4-amino-3-iodo-pyrazolo[3,4-d]pyrimidin-1-yl)piperidine-1-carboxylate (200.0 mg, 0.45 mmol) gave, after further purification by flash column chromatography (DCM/MeOH 100:0 to 90:10), tert-butyl (3R)-3-[4-amino-3-[4-[[[4-(trifluoromethoxy)benzoyl]amino]methyl]phenyl]pyrazolo[3,4-d]pyrimidin-1-yl]piperidine-1-carboxylate (161.0 mg, 0.21 mmol, 47% yield) as a yellow-brown solid UPLC-MS (ES+, Short acidic): 1.83 min, m/z 612.5 [M+H]+

N-[[4-[4-Amino-1-[(3R)-3-piperidyl]pyrazolo[3,4-d]pyrimidin-3-yl]phenyl]methyl]-4-(trifluoromethoxy)benzamide Following general procedure E, tert-butyl (3R)-3-[4-amino-3-[4-[[[4-(trifluoromethoxy)benzoyl]amino]methyl]phenyl]pyrazolo[3,4-d]pyrimidin-1-yl]piperidine-1-carboxylate (133.4 mg, 0.22 mmol) gave, after further purification by flash column chromatography (DCM/7N NH3 in MeOH 100:0 to 90:10), N-[[4-[4-amino-1-[(3R)-3-piperidyl]pyrazolo[3,4-d]pyrimidin-3-yl]phenyl]methyl]-4-(trifluoromethoxy)benzamide (76.0 mg, 0.13 mmol, 61% yield) as a yellow solid.

UPLC-MS (ES+, Short acidic): 1.31 min, m/z 512.3 [M+H]+

N-[[4-[4-Amino-1-[(3R)-1-prop-2-enoyl-3-piperidyl]pyrazolo[3,4-d]pyrimidin-3-yl]phenyl]methyl]-4-(trifluoromethoxy)benzamide Following general procedure F, N-[[4-[4-amino-1-[(3R)-3-piperidyl]pyrazolo[3,4-d]pyrimidin-3-yl]phenyl]methyl]-4-(trifluoromethoxy)benzamide (76.0 mg, 0.15 mmol) gave, purification by flash column chromatography (DCM/MeOH 100:0 to 90:10), N-[[4-[4-amino-1-[(3R)-1-prop-2-enoyl-3-piperidyl]pyrazolo[3,4-d]pyrimidin-3-yl]phenyl]methyl]-4-(trifluoromethoxy)benzamide (39.7 mg, 0.06 mmol, 43% yield) as a pale brown solid.

UPLC-MS (ES+, Short acidic): 1.53 min, m/z 566.4 [M+H]+

UPLC-MS (ES+, Long acidic): 3.48 min, m/z 566.3 [M+H]+

$^1$H NMR (400 MHz, DMSO-$d_6$) δ (ppm, 1:1 mixture of conformers) 9.24 (t, J 6.0 Hz, 1H, NH), 8.27 (s, 1H, ArH), 8.07-8.03 (m, 2H, ArH), 7.68 (d, J 7.7 Hz, 2H, ArH), 7.53-7.48 (m, 4H, ArH), 6.87 (dd, $^3J_{trans}$ 16.2, $^3J_{cis}$ 10.4 Hz, 0.5H), 6.72 (dd, $^3J_{trans}$ 16.2, $^3J_{cis}$ 10.4 Hz, 0.5H), 6.13 (d, $^3J_{trans}$ 16.2 Hz, 0.5H), 6.06 (d, $^3J_{trans}$ 16.2 Hz, 0.5H), 5.71 (d, $^3J_{cis}$ 10.4 Hz, 0.5H), 5.59 (d, $^3J_{cis}$ 10.4 Hz, 0.5H), 4.78-4.65 (m, 1H), 4.58 (d, J 6.0 Hz, 2H, CH2), 4.57-4.51 (m, 0.5H), 4.25-4.16 (m, 1H), 4.12-4.04 (m, 0.5H), 3.75-3.66 (m, 0.5H), 3.26-3.15 (m, 1H), 3.07-2.97 (m, 0.5H), 2.31-2.21 (m, 1H), 2.17-2.09 (m, 1H), 1.98-1.89 (m, 1H), 1.67-1.52 (m, 1H).

Example 43: N-[[4-[4-Amino-1-[(3R)-1-prop-2-enoyl-3-piperidyl]pyrazolo[3,4-d]pyrimidin-3-yl]phenyl]methyl]-2-methoxy-5-(trifluoromethyl)benzamide

[4-[[[2-Methoxy-5-(trifluoromethyl)benzoyl]amino]methyl]phenyl]boronic acid

Following general procedure B, [4-(aminomethyl)phenyl]boronic acid hydrochloride (300.0 mg, 1.6 mmol) and 2-methoxy-5-(trifluoromethyl)benzoyl chloride (0.35 mL, 1.76 mmol) gave [4-[[[2-methoxy-5-(trifluoromethyl)benzoyl]amino]methyl]phenyl]boronic acid as a pale yellow solid.

UPLC-MS (ES+, Short acidic): 1.51 min, m/z 353.9 [M+H]+ tert-Butyl (3R)-3-[4-amino-3-[4-[[[2-methoxy-5-(trifluoromethyl)benzoyl]amino]methyl]phenyl]pyrazolo[3,4-d]pyrimidin-1-yl]piperidine-1-carboxylate Following general procedure D, [4-[[[2-methoxy-5-(trifluoromethyl)benzoyl]amino]methyl]phenyl]boronic acid (238.4 mg, 0.68 mmol) and tert-butyl (3R)-3-(4-amino-3-iodo-pyrazolo[3,4-d]pyrimidin-1-yl)piperidine-1-carboxylate (200.0 mg, 0.45 mmol) gave tert-butyl (3R)-3-[4-amino-3-[4-[[[2-methoxy-5-(trifluoromethyl)benzoyl]amino]methyl]phenyl]pyrazolo[3,4-d]pyrimidin-1-yl]piperidine-1-carboxylate (354.8 mg, 0.57 mmol, 126% yield) as a brown foam.

UPLC-MS (ES+, Short acidic): 1.82 min, m/z 626.5 [M+H]+

N-[[4-[4-Amino-1-[(3R)-3-piperidyl]pyrazolo[3,4-d]pyrimidin-3-yl]phenyl]methyl]-2-methoxy-5-(trifluoromethyl)benzamide Following general procedure E, tert-butyl (3R)-3-[4-amino-3-[4-[[[2-methoxy-5-(trifluoromethyl)benzoyl]amino]methyl]phenyl]pyrazolo[3,4-d]pyrimidin-1-yl]piperidine-1-carboxylate (354.8 mg, 0.57 mmol) gave N-[[4-[4-amino-1-[(3R)-3-piperidyl]pyrazolo[3,4-d]pyrimidin-3-yl]phenyl]methyl]-2-methoxy-5-(trifluoromethyl)benzamide (191.0 mg, 0.36 mmol, 64% yield) as a pale yellow film.

UPLC-MS (ES+, Short acidic): 1.31 min, m/z 526.3 [M+H]+

N-[[4-[4-Amino-1-[(3R)-1-prop-2-enoyl-3-piperidyl]pyrazolo[3,4-d]pyrimidin-3-yl]phenyl]methyl]-2-methoxy-5-(trifluoromethyl)benzamide Following general procedure F, N-[[4-[4-amino-1-[(3R)-3-piperidyl]pyrazolo[3,4-d]pyrimidin-3-yl]phenyl]methyl]-2-methoxy-5-(trifluoromethyl)benzamide (191.0 mg, 0.36 mmol) afforded N-[[4-[4-amino-1-[(3R)-1-prop-2-enoyl-3-piperidyl]pyrazolo[3,4-d]pyrimidin-3-yl]phenyl]methyl]-2-methoxy-5-(trifluoromethyl)benzamide (88.4 mg, 0.15 mmol, 42% yield) as an off white solid.

UPLC-MS (ES+, Short acidic): 1.54 min, m/z 580.4 [M+H]+

UPLC-MS (ES+, Long acidic): 3.51 min, m/z 580.4 [M+H]+

$^1$H NMR (400 MHz, DMSO-$d_6$) δ (ppm, 1:1 mixture of conformers)

8.92 (t, J 6.0 Hz, 1H, NH), 8.27 (s, 1H, ArH), 8.05 (d, J 2.2 Hz, 1H, ArH), 7.87 (dd, J 8.7, J 2.2 Hz, 1H, ArH), 7.66 (d, J 7.9 Hz, 2H, ArH), 7.52 (d, J 7.9 Hz, 2H, ArH), 7.38 (d, J 8.7 Hz, 1H, ArH), 6.87 (dd, $^3J_{trans}$ 16.2, $^3J_{cis}$ 10.5 Hz, 0.5H), 6.72 (dd, $^3J_{trans}$ 16.2, $^3J_{cis}$ 10.5 Hz, 0.5H), 6.14 (d, $^3J_{trans}$ 16.2 Hz, 0.5H), 6.07 (d, $^3J_{trans}$ 16.2 Hz, 0.5H), 5.71 (d, $^3J_{cis}$ 10.5 Hz, 0.5H), 5.59 (d, $^3J_{cis}$ 10.5 Hz, 0.5H), 4.78-4.65 (m, 1H), 4.58 (d, J 6.0 Hz, 2H, CH$_2$), 4.57-4.52 (m, 0.5H), 4.25-4.17 (m, 1H), 4.12-4.04 (m, 0.5H), 4.00 (s, 3H, OCH$_3$), 3.75-3.67 (m, 0.5H), 3.27-3.15 (m, 1H), 3.07-2.98 (m, 0.5H), 2.31-2.21 (m, 1H), 2.17-2.09 (m, 1H), 1.98-1.89 (m, 1H), 1.67-1.52 (m, 1H).

Example 44: N-[[4-[4-Amino-1-[(3R)-1-prop-2-enoyl-3-piperidyl]pyrazolo-[3,4-d]pyrimidin-3-yl]phenyl]methyl]-2-fluoro-3-(trifluoromethyl)benzamide

[4-[[[2-Fluoro-3-(trifluoromethyl)benzoyl]amino]methyl]phenyl]boronic acid

Following general procedure B, [4-(aminomethyl)phenyl]boronic acid hydrochloride (300 mg, 1.6 mmol) and 2-Fluoro-3-(trifluoromethyl)benzoyl chloride (398.5 mg, 1.76 mmol) gave [4-[[[2-fluoro-3-(trifluoromethyl)benzoyl]amino]methyl]phenyl]boronic acid (484.9 mg, 1.07 mmol, 67% yield) as an off-white gum.

UPLC-MS (ES$^+$, Short acidic): 1.47 min, m/z 341.8 [M+H]$^+$ tert-Butyl (3R)-3-[4-amino-3-[4-[[[2-fluoro-3-(trifluoromethyl)benzoyl]amino]methyl]-phenyl]pyrazolo[3,4-d]pyrimidin-1-yl]piperidine-1-carboxylate Following general procedure D, [4-[[[2-fluoro-3-(trifluoromethyl)benzoyl]amino]methyl]-phenyl]boronic acid (484 mg, 1.42 mmol) and tert-butyl (3R)-3-(4-amino-3-iodo-pyrazolo[3,4-d]pyrimidin-1-yl)piperidine-1-carboxylate (240 mg, 0.54 mmol) gave tert-butyl (3R)-3-[4-amino-3-[4-[[[2-fluoro-3-(trifluoromethyl)benzoyl]amino]methyl]phenyl]pyrazolo-[3,4-d]pyrimidin-1-yl]piperidine-1-carboxylate (501 mg, 0.53 mmol, 98% yield) as a brown foam.

UPLC-MS (ES$^+$, Short acidic): 1.80 min, m/z 614.5 [M+H]$^+$

N-[[4-[4-Amino-1-[(3R)-3-piperidyl]pyrazolo[3,4-d]pyrimidin-3-yl]phenyl]methyl]-2-fluoro-3-(trifluoromethyl)benzamide Following general procedure E, tert-butyl (3R)-3-[4-amino-3-[4-[[[2-fluoro-3-(trifluoromethyl)benzoyl]amino]methyl]phenyl]pyrazolo[3,4-d]pyrimidin-1-yl]piperidine-1-carboxylate (501 mg, 0.53 mmol) afforded N-[[4-[4-amino-1-[(3R)-3-piperidyl]pyrazolo[3,4-d]pyrimidin-3-yl]phenyl]methyl]-2-fluoro-3-(trifluoromethyl)benzamide (195.6 mg, 0.36 mmol, 68% yield) as an off-white foam.

UPLC-MS (ES$^+$, Short acidic): 1.24 min, m/z 514.3 [M+H]$^+$

N-[[4-[4-Amino-1-[(3R)-1-prop-2-enoyl-3-piperidyl]pyrazolo[3,4-d]pyrimidin-3-yl]phenyl]-methyl]-2-fluoro-3-(trifluoromethyl)benzamide Following general procedure F, N-[[4-[4-amino-1-[(3R)-3-piperidyl]pyrazolo[3,4-d]pyrimidin-3-yl]phenyl]methyl]-2-fluoro-3-(trifluoromethyl)benzamide (195.6 mg, 0.38 mmol) gave N-[[4-[4-amino-1-[(3R)-1-prop-2-enoyl-3-piperidyl]pyrazolo[3,4-d]pyrimidin-3-yl]phenyl]methyl]-2-fluoro-3-(trifluoromethyl)benzamide (44.2 mg, 0.07 mmol, 19% yield) as an off-white foam.

UPLC-MS (ES$^+$, Short acidic): 1.50 min, m/z 568.4 [M+H]$^+$

UPLC-MS (ES$^+$, Long acidic): 3.40 min, m/z 568.4 [M+H]$^+$ $^1$H-NMR (400 MHz, DMSO-d$_6$) δ (ppm, 1:1 mixture of conformers) 9.22 (t, J 6.0 Hz, 1H, NH), 8.27 (s, 1H, ArH), 8.00-7.90 (m, 2H, ArH), 7.67 (d, $^3J$ 8.0 Hz, 2H, ArH), 7.57-7.49 (m, 3H, ArH), 6.87 (dd, $^3J_{trans}$ 16.4, $^3J_{cis}$ 10.4 Hz, 0.5H), 6.72 (dd, $^3J_{trans}$ 16.4, $^3J_{cis}$ 10.4 Hz, 0.5H), 6.14 (d, $^3J_{trans}$ 16.4 Hz, 0.5H), 6.07 (d, $^3J_{trans}$ 16.4 Hz, 0.5H), 5.71 (d, $^3J_{cis}$ 10.4 Hz, 0.5H), 5.59 (d, $^3J_{cis}$ 10.4 Hz, 0.5H), 4.78-4.66 (m, 1H), 4.58 (d, J 6.0 Hz, 2H, CH$_2$), 4.56-4.50 (m, 0.5H), 4.26-4.16 (m, 1H), 4.12-4.06 (m, 0.5H), 3.77-3.66 (m, 0.5H), 3.28-3.15 (m, 1H), 3.08-2.97 (m, 0.5H), 2.31-2.21 (m, 1H), 2.18-2.08 (m, 1H), 1.98-1.89 (m, 1H), 1.68-1.51 (m, 1H).

Example 45: N-[[4-[4-Amino-1-[(3R)-1-prop-2-enoyl-3-piperidyl]pyrazolo-[3,4-d]pyrimidin-3-yl]phenyl]methyl]-5-chloro-2-methoxy-benzamide

[4-[[(5-Chloro-2-methoxy-benzoyl)amino]methyl]phenyl]boronic acid

Following general procedure A, [4-(aminomethyl)phenyl]boronic acid hydrochloride (386.7 mg, 2.06 mmol) and 5-chloro-2-methoxybenzoic acid (350.0 mg, 1.88 mmol) gave [4-[[(5-chloro-2-methoxy-benzoyl)amino]methyl]phenyl]boronic acid (259.0 mg, 0.53 mmol, 28% yield as a yellow oil.

UPLC-MS (ES$^+$, Short acidic): 1.45 min, m/z 319.8 [M+H]$^+$ tert-Butyl (3R)-3-[4-amino-3-[4-[[(5-chloro-2-methoxy-benzoyl)amino]methyl]phenyl]-pyrazolo[3,4-d]pyrimidin-1-yl]piperidine-1-carboxylate Following general procedure D, [4-[[(5-chloro-2-methoxy-benzoyl)amino]methyl]phenyl]-boronic acid (458.1 mg, 0.93 mmol) and tert-butyl (3R)-3-(4-amino-3-iodo-pyrazolo[3,4-d]pyrimidin-1-yl)piperidine-1-carboxylate (230.0 mg, 0.52 mmol) gave tert-butyl (3R)-3-[4-amino-3-[4-[[(5-chloro-2-methoxy-benzoyl)amino]methyl]phenyl]pyrazolo[3,4-d]pyrimidin-1-yl]piperidine-1-carboxylate (452.0 mg, 0.50 mmol, 96% yield) as a brown foam.

UPLC-MS (ES$^+$, Short acidic): 1.79 min, m/z 593.1 [M+H]$^+$

N-[[4-[4-Amino-1-[(3R)-3-piperidyl]pyrazolo[3,4-d]pyrimidin-3-yl]phenyl]methyl]-5-chloro-2-methoxy-benzamide Following general procedure E, tert-butyl (3R)-3-[4-amino-3-[4-[[(5-chloro-2-methoxy-benzoyl)amino]methyl]phenyl]pyrazolo[3,4-d]pyrimidin-1-yl]piperidine-1-carboxylate (452.0 mg, 0.50 mmol) afforded N-[[4-[4-amino-1-[(3R)-3-piperidyl]pyrazolo[3,4-d]pyrimidin-3-yl]phenyl]methyl]-5-chloro-2-methoxy-benzamide (103.0 mg, 0.16 mmol, 32% yield) as a brown foam.

UPLC-MS (ES$^+$, Short acidic): 1.23 min, m/z 492.2 [M+H]$^+$

N-[[4-[4-Amino-1-[(3R)-1-prop-2-enoyl-3-piperidyl] pyrazolo[3,4-d]pyrimidin-3-yl]phenyl]-methyl]-5-chloro-2-methoxy-benzamide Following general procedure F, N-[[4-[4-amino-1-[(3R)-3-piperidyl]pyrazolo[3,4-d]-pyrimidin-3-yl]phenyl]methyl]-5-chloro-2-methoxy-benzamide (103.0 mg, 0.21 mmol) gave N-[[4-[4-amino-1-[(3R)-1-prop-2-enoyl-3-piperidyl]pyrazolo[3,4-d]pyrimidin-3-yl]phenyl]methyl]-5-chloro-2-methoxy-benzamide (15.0 mg, 0.03 mmol, 12% yield) as an off-white foam.

UPLC-MS (ES$^+$, Short acidic): 1.49 min, m/z 547.0 [M+H]$^+$

UPLC-MS (ES$^+$, Long acidic): 3.37 min, m/z 547.0 [M+H]$^+$ $^1$H-NMR (400 MHz, DMSO-d$_6$) δ (ppm, 1:1 mixture of conformers) 8.86 (t, J 6.0 Hz, 1H, NH), 8.27 (s, 1H, ArH), 7.71 (d, J 2.8 Hz, 1H, ArH), 7.65 (d, J 8.0 Hz, 2H, ArH), 7.56-7.48 (m, 3H, ArH), 7.21 (d, J 9.2 Hz 1H, ArH), 6.87 (dd, $^3J_{trans}$ 16.4 $^3J_{cis}$ 10.4 Hz, 0.5H), 6.72 (dd, $^3J_{trans}$ 16.4, $^3J_{cis}$ 10.4 Hz, 0.5H), 6.14 (d, $^3J_{trans}$ 16.4 Hz, 0.5H), 6.07 (d, $^3J_{trans}$ 16.4 Hz, 0.5H), 5.71 (d, $^3J_{cis}$ 10.4 Hz, 0.5H), 5.59 (d, $^3J_{cis}$ 10.4 Hz, 0.5H), 4.78-4.64 (m, 1H), 4.58 (d, J 6.0 Hz, 2H, CH$_2$), 4.56-4.51 (m, 0.5H), 4.26-4.16 (m, 1H), 4.12-4.04 (m, 0.5H), 3.92 (s, 3H, OCH$_3$), 3.76-3.66 (m, 0.5H), 3.27-3.14 (m, 1H), 3.06-2.97 (m, 0.5H), 2.31-2.21 (m, 1H), 2.18-2.09 (m, 1H), 1.98-1.88 (m, 1H), 1.68-1.51 (m, 1H).

Example 46: N-[[4-[4-Amino-1-[(3R)-1-prop-2-enoyl-3-piperidyl]pyrazolo-[3,4-d]pyrimidin-3-yl]phenyl]methyl]-3-(trifluoromethoxy)benzamide

[4-[[[3-(Trifluoromethoxy)benzoyl]amino]methyl]phenyl]boronic acid

Following general procedure B, [4-(aminomethyl)phenyl]boronic acid hydrochloride (300 mg, 1.60 mmol) and 3-(trifluoromethoxy)benzoyl chloride (395.4 mg, 1.76 mmol) gave [4-[[[3-(trifluoromethoxy)benzoyl]amino]methyl]phenyl]boronic acid (565.3 mg, 1.25 mmol, 78% yield) as an off-white solid.

UPLC-MS (ES$^+$, Short acidic): 1.51 min, m/z 339.8 [M+H]$^+$ tert-Butyl (3R)-3-[4-amino-3-[4-[[[3-(trifluoromethoxy)benzoyl]amino]methyl]phenyl]-pyrazolo[3,4-d]pyrimidin-1-yl]piperidine-1-carboxylate Following general procedure D, [4-[[[3-(trifluoromethoxy)benzoyl]amino]methyl]phenyl]-boronic acid (448.9 mg, 0.99 mmol) and tert-butyl (3R)-3-(4-amino-3-iodo-pyrazolo[3,4-d]pyrimidin-1-yl)piperidine-1-carboxylate (245 mg, 0.55 mmol) gave tert-butyl (3R)-3-[4-amino-3-[4-[[[3-(trifluoromethoxy)benzoyl]amino]methyl]phenyl]pyrazolo[3,4-d]pyrimidin-1-yl]piperidine-1-carboxylate (452.0 mg, 0.48 mmol, 87% yield) as a brown foam.

LC-MS (ES$^+$, Short acidic): 2.35 min, m/z 612.3 [M+H]$^+$

N-[[4-[4-Amino-1-[(3R)-3-piperidyl]pyrazolo[3,4-d]pyrimidin-3-yl]phenyl]methyl]-3-(trifluoromethoxy)benzamide Following general procedure E, tert-butyl (3R)-3-[4-amino-3-[4-[[[3-(trifluoromethoxy)-benzoyl]amino]methyl]phenyl]pyrazolo[3,4-d]pyrimidin-1-yl]piperidine-1-carboxylate (580 mg, 0.62 mmol) afforded N-[[4-[4-amino-1-[(3R)-3-piperidyl]pyrazolo[3,4-d]pyrimidin-3-yl]phenyl]methyl]-3-(trifluoromethoxy)benzamide (192.0 mg, 0.36 mmol, 58% yield) as an off-white/brown foam.

LC-MS (ES$^+$, Short acidic): 1.30 min, m/z 512.2 [M+H]$^+$

N-[[4-[4-Amino-1-[(3R)-1-prop-2-enoyl-3-piperidyl]pyrazolo[3,4-d]pyrimidin-3-yl]phenyl]-methyl]-3-(trifluoromethoxy)benzamide Following general procedure F, N-[[4-[4-amino-1-[(3R)-3-piperidyl]pyrazolo[3,4-d]-pyrimidin-3-yl]phenyl]methyl]-3-(trifluoromethoxy)benzamide (173 mg, 0.34 mmol) and acrylic acid (0.02 mL, 0.34 mmol) gave N-[[4-[4-amino-1-[(3R)-1-prop-2-enoyl-3-piperidyl]pyrazolo[3,4-d]pyrimidin-3-yl]phenyl]methyl]-3-(trifluoromethoxy)benzamide (42.8 mg, 0.07 mmol, 21% yield) as an off-white foam.

UPLC-MS (ES$^+$, Short acidic): 1.54 min, m/z 566.3 [M+H]$^+$

UPLC-MS (ES$^+$, Long acidic): 3.49 min, m/z 566.3 [M+H]$^+$ $^1$H-NMR (400 MHz, DMSO-d$_6$) δ (ppm, 1:1 mixture of conformers) 9.30 (t, J 6.0 Hz, 1H, NH), 8.27 (s, 1H, ArH), 7.98 (d, J 7.6 Hz, 1H, ArH), 7.90-7.86 (m, 1H, ArH), 7.70-7.62 (m, 3H, ArH), 7.58 (d, J 8.0 Hz, 1H, ArH), 7.51 (d, J 8.0 Hz, 2H, ArH), 6.87 (dd, $^3J_{trans}$ 16.4, $^3J_{cis}$ 10.4 Hz, 0.5H), 6.72 (dd, $^3J_{trans}$ 16.4, $^3J_{cis}$ 10.4 Hz, 0.5H), 6.13 (d, $^3J_{trans}$ 16.4 Hz, 0.5H), 6.06 (d, $^3J_{trans}$ 16.4 Hz, 0.5H), 5.71 (d, $^3J_{cis}$ 10.4 Hz, 0.5H), 5.59 (d, $^3J_{cis}$ 10.4 Hz, 0.5H), 4.78-4.64 (m, 1H), 4.59 (d, J 6.0 Hz, 2H, CH$_2$), 4.56-4.50 (m, 0.5H), 4.26-4.16 (m, 1H), 4.12-4.03 (m, 0.5H), 3.76-3.67 (m, 0.5H), 3.27-3.14 (m, 1H), 3.08-2.97 (m, 0.5H), 2.31-2.21 (m, 1H), 2.18-2.07 (m, 1H), 1.98-1.89 (m, 1H), 1.69-1.51 (m, 1H).

Example 47: N-[[3-[4-Amino-1-[(3R)-1-prop-2-enoyl-3-piperidyl]pyrazolo[3,4-d]pyrimidin-3-yl]phenyl]methyl]-5-fluoro-2-methoxy-benzamide

[3-[[(5-Fluoro-2-methoxy-benzoyl)amino]methyl]phenyl]boronic acid

Following general procedure A, 5-fluoro-2-methoxybenzoic acid (200.0 mg, 1.18 mmol) and [3-(aminomethyl)phenyl]boronic acid (195.2 mg, 1.29 mmol) afforded [3-[[(5-fluoro-2-methoxy-benzoyl)amino]methyl]phenyl]boronic acid (250.0 mg, 0.82 mmol, 70% yield) as a yellow oil.

UPLC-MS (ES$^+$, Short acidic): 1.37 min, m/z 303.8 [M+H]$^+$ tert-Butyl (3R)-3-[4-amino-3-[3-[[(5-fluoro-2-methoxy-benzoyl)amino]methyl]phenyl]pyrazolo[3,4-d]pyrimidin-1-yl]piperidine-1-carboxylate Following general procedure D, [3-[[(5-fluoro-2-methoxy-benzoyl)amino]methyl]phenyl]boronic acid (204.6 mg, 0.68 mmol), and tert-butyl (3R)-3-(4-amino-3-iodo-pyrazolo[3,4-d]pyrimidin-1-yl)piperidine-1-carboxylate (200.0 mg, 0.45 mmol) gave tert-butyl (3R)-3-[4-amino-3-[3-[[(5-fluoro-2-methoxy-benzoyl)amino]methyl]phenyl]pyrazolo[3,4-d]pyrimidin-1-yl]piperidine-1-carboxylate (250.0 mg, 0.43 mmol, 96% yield) as a brown solid.

UPLC-MS (ES$^+$, Short acidic): 1.75 min, m/z 576.5 [M+H]$^+$

N-[[3-[4-Amino-1-[(3R)-3-piperidyl]pyrazolo[3,4-d]pyrimidin-3-yl]phenyl]methyl]-5-fluoro-2-methoxy-benzamide Following general procedure E, tert-butyl (3R)-3-[4-amino-3-[3-[[(5-fluoro-2-methoxy-benzoyl)amino]methyl]phenyl]pyrazolo[3,4-d]pyrimidin-1-yl]piperidine-1-carboxylate (250.0 mg, 0.43 mmol) gave N-[[3-[4-amino-1-[(3R)-3-piperidyl]pyrazolo[3,4-d]pyrimidin-3-yl]phenyl]methyl]-5-fluoro-2-methoxy-benzamide (90.0 mg, 0.18 mmol, 43% yield) as a brown solid.

UPLC-MS (ES+, Short acidic): 1.19 min, m/z 476.4 [M+H]+

N-[[3-[4-amino-1-[(3R)-1-prop-2-enoyl-3-piperidyl]pyrazolo[3,4-d]pyrimidin-3-yl]phenyl]methyl]-5-fluoro-2-methoxy-benzamide Following general procedure F, N-[[3-[4-amino-1-[(3R)-3-piperidyl]pyrazolo[3,4-d]pyrimidin-3-yl]phenyl]methyl]-5-fluoro-2-methoxy-benzamide (90.0 mg, 0.19 mmol) afforded N-[[3-[4-amino-1-[(3R)-1-prop-2-enoyl-3-piperidyl]pyrazolo[3,4-d]pyrimidin-3-yl]phenyl]methyl]-5-fluoro-2-methoxy-benzamide (26.0 mg, 0.02 mmol, 26% yield) as a colourless gum.

UPLC-MS (ES+, Short acidic): 1.45 min, m/z 530.3 [M+H]+

UPLC-MS (ES+, Long acidic): 3.23 min, m/z 530.4 [M+H]+

$^1$H-NMR (400 MHz, DMSO-$d_6$) δ (ppm, 1:1 mixture of conformers): 8.91 (t, $^3$J 7.6 Hz, 1H, NH), 8.27 (s, 1H, ArH), 7.66 (br. s, 1H, ArH), 7.57-7.44 (m, 4H, ArH), 7.35-7.30 (m, 1H, ArH), 7.19-7.15 (m, 1H, ArH), 6.86 (dd, $^3$J$_{trans}$ 16.2, $^3$J$_{cis}$ 10.5 Hz, 0.5H), 6.73 (dd, $^3$J$_{trans}$ 16.2, $^3$J$_{cis}$ 10.5 Hz, 0.5H), 6.13 (d, $^3$J$_{trans}$ 16.2 Hz, 0.5H), 6.07 (d, $^3$J$_{trans}$ 16.2 Hz, 0.5H), 5.70 (d, $^3$J$_{cis}$ 10.5 Hz, 0.5H), 5.59 (d, $^3$J$_{cis}$ 10.5 Hz, 0.5H), 4.76-4.66 (m, 1H), 4.59 (d, $^3$J 6.0 Hz, 2H, CH$_2$), 4.58-4.51 (m, 0.5H), 4.29-4.17 (m, 1H), 4.12-4.04 (m, 0.5H), 3.87 (s, 3H, OCH$_3$), 3.72-3.64 (m, 0.5H), 3.25-3.15 (m, 1H), 3.02-2.92 (m, 0.5H), 2.32-2.22 (m, 1H), 2.16-2.08 (m, 1H), 1.96-1.88 (m, 1H), 1.65-1.51 (m, 1H).

Example 48: N-[[3-[4-Amino-1-[(3R)-1-prop-2-enoyl-3-piperidyl]pyrazolo[3,4-d]pyrimidin-3-yl]phenyl]methyl]-4-fluoro-2-methoxy-benzamide

[3-[[(4-Fluoro-2-methoxy-benzoyl)amino]methyl]phenyl]boronic acid

Following general procedure A, 4-fluoro-2-methoxybenzoic acid (200.0 mg, 1.18 mmol) and [3-(aminomethyl)phenyl]boronic acid (195.2 mg, 1.29 mmol) gave [3-[[(4-fluoro-2-methoxy-benzoyl)amino]methyl]phenyl]boronic acid (250.0 mg, 0.82 mmol, 70% yield) as a yellow oil.

UPLC-MS (ES+, Short acidic): 1.37 min, m/z 303.9 [M+H]+ tert-Butyl (3R)-3-[4-amino-3-[3-[[(4-fluoro-2-methoxy-benzoyl)amino]methyl]phenyl]pyrazolo[3,4-d]pyrimidin-1-yl]piperidine-1-carboxylate Following general procedure D, [3-[[(4-fluoro-2-methoxy-benzoyl)amino]methyl]phenyl]boronic acid (204.7 mg, 0.68 mmol), and tert-butyl (3R)-3-(4-amino-3-iodo-pyrazolo[3,4-d]pyrimidin-1-yl)piperidine-1-carboxylate (200.0 mg, 0.45 mmol) gave tert-butyl (3R)-3-[4-amino-3-[3-[[(4-fluoro-2-methoxy-benzoyl)amino]methyl]phenyl]pyrazolo[3,4-d]pyrimidin-1-yl]piperidine-1-carboxylate (204.0 mg, 0.35 mmol, 78% yield).

UPLC-MS (ES+, Short acidic): 1.76 min, m/z 576.4 [M+H]+

N-[[3-[4-Amino-1-[(3R)-3-piperidyl]pyrazolo[3,4-d]pyrimidin-3-yl]phenyl]methyl]-4-fluoro-2-methoxy-benzamide Following general procedure E, tert-butyl (3R)-3-[4-amino-3-[3-[[(4-fluoro-2-methoxy-benzoyl)amino]methyl]phenyl]pyrazolo[3,4-d]pyrimidin-1-yl]piperidine-1-carboxylate (204.0 mg, 0.35 mmol) gave N-[[3-[4-amino-1-[(3R)-3-piperidyl]pyrazolo[3,4-d]pyrimidin-3-yl]phenyl]methyl]-4-fluoro-2-methoxy-benzamide (150 mg, 0.32 mmol, 89% yield) as a brown solid.

UPLC-MS (ES+, Short acidic): 1.19 min, m/z 476.3 [M+H]+

N-[[3-[4-Amino-1-[(3R)-1-prop-2-enoyl-3-piperidyl]pyrazolo[3,4-d]pyrimidin-3-yl]phenyl]methyl]-4-fluoro-2-methoxy-benzamide Following general procedure F, N-[[3-[4-amino-1-[(3R)-3-piperidyl]pyrazolo[3,4-d]pyrimidin-3-yl]phenyl]methyl]-4-fluoro-2-methoxy-benzamide (150.0 mg, 0.32 mmol) afforded N-[[3-[4-amino-1-[(3R)-1-prop-2-enoyl-3-piperidyl]pyrazolo[3,4-d]pyrimidin-3-yl]phenyl]methyl]-4-fluoro-2-methoxy-benzamide (33.0 mg, 0.06 mmol, 20% yield) as a colourless gum.

UPLC-MS (ES+, Short acidic): 1.44 min, m/z 530.4 [M+H]+

UPLC-MS (ES+, Long acidic): 3.23 min, m/z 530.3 [M+H]+

$^1$H-NMR (400 MHz, DMSO-$d_6$) δ (ppm, 1:1 mixture of conformers): 8.76 (t, $^3$J 6.0 Hz, 1H, NH), 8.26 (s, 1H, ArH), 7.83 (dd, J 8.6, J 7.2 Hz, 1H, ArH), 7.64 (br. s, 1H, ArH), 7.56-7.43 (m, 3H, ArH), 7.07-7.04 (m, 1H, ArH), 6.88-6.83 (m, 1H, ArH), 6.89-6.80 (m, 0.5H), 6.72 (dd, $^3$J$_{trans}$ 16.2, $^3$J$_{cis}$ 10.5 Hz, 0.5H), 6.13 (d, $^3$J$_{trans}$ 16.2 Hz, 0.5H), 6.07 (d, $^3$J$_{trans}$ 16.2 Hz, 0.5H), 5.70 (d, $^3$J$_{cis}$ 10.5 Hz, 0.5H), 5.59 (d, $^3$J$_{cis}$ 10.5 Hz, 0.5H), 4.76-4.66 (m, 1H), 4.58 (d, $^3$J 6.0 Hz, 2H, CH$_2$), 4.58-4.52 (m, 0.5H), 4.28-4.17 (m, 1H), 4.11-4.03 (m, 0.5H), 3.89 (s, 3H, OCH$_3$), 3.73-3.64 (m, 0.5H), 3.25-3.17 (m, 1H), 3.00-2.92 (m, 0.5H), 2.32-2.22 (m, 1H), 2.15-2.08 (m, 1H), 1.96-1.87 (m, 1H), 1.63-1.53 (m, 1H).

Example 49: N-[[4-[4-Amino-1-[(3R)-1-prop-2-enoyl-3-piperidyl]pyrazolo[3,4-d]pyrimidin-3-yl]phenyl]methyl]-3,5-bis(trifluoromethyl)benzamide

[4-[[[3,5-Bis-trifluoromethylbenzoyl]amino]methyl]phenyl]boronic acid

To a solution of 3,5-bis(trifluoromethyl)benzoyl chloride (276 mg, 1.00 mmol) in THF (2 mL) under a nitrogen atmosphere at 0° C. was added potassium phosphate (584.0 mg, 2.75 mmol), followed by 4-aminomethylphenylboronic acid hydrochloride (187 mg, 1.00 mmol). The reaction was allowed to return to rt and stirred overnight. Water was added, and the reaction mixture extracted with EtOAc (3×). The combined organics extracts were dried over anhydrous sodium sulfate, filtered, and concentrated in vacuo to afford [4-[[[(3,5-bis(trifluoromethyl)benzoyl]amino]methyl]phenyl]boronic acid (378 mg, 0.97 mmol, 97% yield) as an off-white solid.

UPLC-MS (ES+, short acidic): 1.68 min, m/z 392.0 [M+H]+ tert-Butyl (3R)-3-[4-amino-3-[4-[[[3,5-bis(trifluoromethyl)benzoyl]amino]methyl]phenyl]pyrazolo[3,4-d]pyrimidin-1-yl]piperidine-1-carboxylate Following general procedure D, (using [1,1'-bis(di-tert-butylphosphino)ferrocene]dichloropalladium(II) as the catalyst), [4-[[[3,5-bis(trifluoromethyl)benzoyl]amino]methyl]phenyl]boronic acid (234 mg, 0.6 mmol) and tert-butyl (3R)-3-(4-amino-3-iodo-pyrazolo[3,4-d]pyrimidin-1-yl)piperidine-1-carboxylate (177.7 mg, 0.40 mmol) gave tert-butyl (3R)-3-[4-amino-3-[4-[[[3,5-bis(trifluoromethyl)benzoyl]amino]methyl]phenyl]pyrazolo[3,4-d]pyrimidin-1-yl]piperidine-1-carboxylate (125 mg, 0.19 mmol, 47% yield).

UPLC-MS (ES+, short acidic): 1.98 min, m/z 664.4 [M+H]+

N-[[4-[4-Amino-1-[(3R)-3-piperidyl]pyrazolo[3,4-d]pyrimidin-3-yl]phenyl]methyl]-3,5-bis(trifluoromethyl)benzamide Following general procedure E, tert-butyl (3R)-3-[4-amino-3-[4-[[[3,5-bis(trifluoromethyl)benzoyl]amino]methyl]phenyl]pyrazolo[3,4-d]pyrimidin-1-yl]piperidine-1-carboxylate (176 mg, 0.27 mmol) afforded N-[[4-[4-amino-1-[(3R)-3-piperidyl]pyrazolo[3,4-d]pyrimidin-3-yl]phenyl]methyl]-3,5-bis(trifluoromethyl)benzamide (151 mg, 0.27 mmol, 100% yield) as a white solid.

UPLC-MS (ES+, Short acidic): 1.48 min, m/z 564.1 [M+H]+

N-[[4-[4-Amino-1-[(3R)-1-prop-2-enoyl-3-piperidyl]pyrazolo[3,4-d]pyrimidin-3-yl]phenyl]methyl]-3,5-bis(trifluoromethyl)benzamide Following general procedure F, N-[[4-[4-amino-1-[(3R)-3-piperidyl]pyrazolo[3,4-d]pyrimidin-3-yl]phenyl]methyl]-3,5-bis(trifluoromethyl)benzamide (151 mg, 0.27 mmol) afforded N-[[4-[4-amino-1-[(3R)-1-prop-2-enoyl-3-piperidyl]pyrazolo[3,4-d]pyrimidin-3-yl]phenyl]methyl]-3,5-bis(trifluoromethyl)benzamide (11 mg, 0.02 mmol, 6% yield) as a white solid.

UPLC-MS (ES+, Short acidic): 1.70 min, m/z 618.4 [M+H]+

UPLC-MS (ES+, Long acidic): 3.92 min, m/z 618.3 [M+H]+

$^1$H NMR (400 MHz, DMSO-$d_6$): δ (ppm, 1:1 mixture of conformers): 9.60 (t, $^3J$ 6.0 Hz, 1H, NH), 8.59 (s, 2H, ArH), 8.36 (s, 1H, ArH), 8.27 (s, 1H, ArH), 7.66 (d, J 7.9 Hz, 2H, ArH), 7.54 (d, J 7.9 Hz, 2H, ArH), 6.87 (dd, $^3J_{trans}$ 16.2, $^3J_{cis}$ 10.5 Hz, 0.5H), 6.71 (dd, $^3J_{trans}$ 16.2, $^3J_{cis}$ 10.5 Hz, 0.5H), 6.13 (d, $^3J_{trans}$ 16.2 Hz, 0.5H), 6.06 (d, $^3J_{trans}$ 16.2 Hz, 0.5H), 5.71 (d, $^3J_{cis}$ 10.5 Hz, 0.5H), 5.58 (d, $^3J_{cis}$ 10.5 Hz, 0.5H), 4.76-4.66 (m, 1H), 4.63 (d, $^3J$ 6.0 Hz, 2H, CH$_2$), 4.58-4.51 (m, 0.5H), 4.24-4.15 (m, 1H), 4.12-4.03 (m, 0.5H), 3.76-3.66 (m, 0.5H), 3.25-3.17 (m, 1H), 3.08-2.99 (m, 0.5H), 2.33-2.20 (m, 1H), 2.15-2.08 (m, 1H), 1.99-1.88 (m, 1H), 1.65-1.53 (m, 1H).

Example 50: N-[[4-[4-Amino-1-[(3R)-1-prop-2-enoyl-3-piperidyl]pyrazolo[3,4-d]pyrimidin-3-yl]phenyl]methyl]-2-methoxy-6-methylbenzamide

[4-[[[2-Methoxy-6-methylbenzoyl]amino]methyl]phenyl]boronic acid

2-Methoxy-6-methylbenzoic acid (166 mg, 1.00 mmol) was refluxed in thionyl chloride (1 mL) for 3 h. The cooled mixture was concentrated under reduced pressure, and traces of thionyl chloride were removed by co-evaporating (twice) with DCM under reduced pressure. To the residue under a nitrogen atmosphere at 0° C. was added potassium phosphate (584.0 mg; 2.75 mmol), followed by 4-aminomethylphenylboronic acid hydrochloride (187 mg, 1.00 mmol). The reaction was allowed to return to rt and stirred overnight. Water was added, and the reaction mixture extracted with EtOAc (3×). The combined organics extracts were dried over anhydrous sodium sulfate, filtered, and concentrated in vacuo to afford [4-[[[2-methoxy-6-methylbenzoyl]amino]methyl]phenyl]boronic acid (267 mg, 0.89 mmol, 89% yield) as an off-white solid.

UPLC-MS (ES+, Short acidic): 1.25 min, m/z 299.8 [M+H]+ tert-Butyl (3R)-3-[4-amino-3-[4-[[[2-methoxy-6-methylbenzoyl]amino]methyl]phenyl]pyrazolo[3,4-d]pyrimidin-1-yl]piperidine-1-carboxylate Following general procedure D, [4-[[[2-methoxy-6-methylbenzoyl]amino]methyl]phenyl]boronic acid (252 mg, 0.84 mmol) and tert-butyl (3R)-3-(4-amino-3-iodo-pyrazolo[3,4-d]pyrimidin-1-yl)piperidine-1-carboxylate (250 mg, 0.56 mmol) gave tert-butyl (3R)-3-[4-amino-3-[4-[[[2-methoxy-6-methylbenzoyl]amino]methyl]phenyl]pyrazolo[3,4-d]pyrimidin-1-yl]piperidine-1-carboxylate (216 mg, 0.38 mmol, 67% yield).

UPLC-MS (ES+, Short acidic): 1.66 min, m/z 572.5 [M+H]+

N-[[4-[4-Amino-1-[(3R)-3-piperidyl]pyrazolo[3,4-d]pyrimidin-3-yl]phenyl]methyl]-2-methoxy-6-methylbenzamide Following general procedure E, tert-butyl (3R)-3-[4-amino-3-[4-[[[2-methoxy-6-methyl benzoyl]amino]methyl]phenyl]pyrazolo[3,4-d]pyrimidin-1-yl]piperidine-1-carboxylate (216 mg, 0.38 mmol) afforded N-[[4-[4-amino-1-[(3R)-3-piperidyl]pyrazolo[3,4-d]pyrimidin-3-yl]phenyl]methyl]-2-methoxy-6-methylbenzamide (172 mg, 0.36 mmol, 96% yield) as an off-white solid.

UPLC-MS (ES+, Short acidic): 0.99 min, m/z 472.2 [M+H]+

N-[[4-[4-Amino-1-[(3R)-1-prop-2-enoyl-3-piperidyl]pyrazolo[3,4-d]pyrimidin-3-yl]phenyl]methyl]-2-methoxy-6-methyl benzamide Following general procedure F (but with two further additions of the co-reagents to ensure complete conversion), N-[[4-[4-amino-1-[(3R)-3-piperidyl]pyrazolo[3,4-d]pyrimidin-3-yl]phenyl]methyl]-2-methoxy-6-methylbenzamide (151 mg, 0.27 mmol) afforded N-[[4-[4-amino-1-[(3R)-1-prop-2-enoyl-3-piperidyl]pyrazolo[3,4-d]pyrimidin-3-yl]phenyl]methyl]-2-methoxy-6-methylbenzamide (24 mg, 0.05 mmol, 22% yield) as a white solid.

UPLC-MS (ES+, Short acidic): 1.35 min, m/z 526.4 [M+H]+

UPLC-MS (ES+, Long acidic): 3.05 min, m/z 526.4 [M+H]+

$^1$H NMR (400 MHz, DMSO-$d_6$): δ (ppm, 1:1 mixture of conformers): 8.77 (t, $^3J$ 6.0 Hz, 1H, NH), 8.27 (s, 1H, ArH), 7.66 (d, J 7.9 Hz, 2H, ArH), 7.55 (d, J 7.9 Hz, 2H, ArH), 7.25 (t, J 7.9 Hz, 1H, ArH), 6.93-6.80 (m, 2H, ArH), 6.90-6.79 (m, 0.5H), 6.74 (dd, $^3J_{trans}$ 16.2, $^3J_{cis}$ 10.5 Hz, 0.5H), 6.14 (d, $^3J_{trans}$ 16.2 Hz, 0.5H), 6.08 (d, $^3J_{trans}$ 16.2 Hz, 0.5H), 5.72 (d, $^3J_{cis}$ 10.5 Hz, 0.5H), 5.60 (d, $^3J_{cis}$ 10.5 Hz, 0.5H), 4.77-4.66 (m, 1H), 4.60-4.50 (m, 0.5H), 4.53 (d, $^3J$ 6.0 Hz, 2H, CH$_2$), 4.27-4.15 (m, 1H), 4.13-4.04 (m, 0.5H), 3.79 (s, 3H, OCH$_3$), 3.76-3.68 (m, 0.5H), 3.29-3.17 (m, 1H), 3.08-2.97 (m, 0.5H), 2.34-2.22 (m, 1H), 2.21 (s, 3H, CH$_3$), 2.17-2.09 (m, 1H), 1.99-1.88 (m, 1H), 1.66-1.52 (m, 1H).

Example 51: N-[[4-[4-Amino-1-[(3R)-1-cyano-3-piperidyl]pyrazolo[3,4-d]pyrimidin-3-yl]phenyl]methyl]-5-fluoro-2-methoxybenzamide Following general procedure G, N-[[4-[4-amino-1-[(3R)-3-piperidyl]pyrazolo[3,4-d]pyrimidin-3-yl]phenyl]methyl]-5-fluoro-2-methoxybenzamide (59 mg, 0.12 mmol) afforded N-[[4-[4-amino-1-[(3R)-1-cyano-3-piperidyl]pyrazolo[3,4-d]pyrimidin-3-yl]phenyl]methyl]-5-fluoro-2-methoxybenzamide (41 mg, 0.08 mmol, 66%).

UPLC-MS (ES$^+$, Short acidic): 1.44 min, m/z 501.3 [M+H]$^+$

UPLC-MS (ES$^+$, Long acidic): 3.28 min, m/z 501.4 [M+H]$^+$ $^1$H-NMR (400 MHz, DMSO-d$_6$) δ (ppm) 8.87 (t, J 6.1 Hz, 1H, NH), 8.28 (s, 1H, ArH), 7.65 (d, J 8.2 Hz, 2H, ArH), 7.53 (dd, J 9.1, J 3.3 Hz, 1H, ArH), 7.51 (d, J 8.2 Hz, 2H, ArH), 7.38-7.32 (m, 1H, ArH), 7.20 (dd, J 9.1, J 4.3 Hz, 1H, ArH), 4.91-4.83 (m, 1H), 4.59 (d, J 6.1 Hz, 2H, CH$_2$), 3.91 (s, 3H, CH$_3$), 3.64 (dd, $^2$J 12.4, $^3$J 4.2 Hz, 1H), 3.53 (dd, $^2$J 12.4, $^3$J 10.3 Hz, 1H), 3.44-3.36 (m, 1H), 3.21-3.12 (m, 1H), 2.24-2.05 (m, 2H), 1.96-1.74 (m, 2H).

Example 52: N-[[4-[4-Amino-1-[(3R)-1-prop-2-enoyl-3-piperidyl]pyrazolo[3,4-d]pyrimidin-3-yl]phenyl]methyl]-4-(trifluoromethyl)benzamide

[4-[[[4-(Trifluoromethyl)benzoyl]amino]methyl]phenyl]boronic acid

To a solution of 4-(aminomethyl)phenyl]boronic acid (250.0 mg, 1.66 mmol) in water (2 mL) was added 50% aqueous potassium hydroxide (1 mL), followed by 4-(trifluoromethyl)benzoyl chloride (0.3 mL, 1.99 mmol). The reaction mixture was stirred for 16 h, acidified with 1 M HCl. The filtrate was then washed with water to afford [4-[[[4-(trifluoromethyl)benzoyl]amino]methyl]phenyl]boronic acid (300.0 mg, 0.93 mmol, 56% yield) as a white solid.

UPLC-MS (ES$^+$, Short acidic): 1.47 min, m/z 323.8 [M+H]$^+$ tert-Butyl (3R)-3-[4-amino-3-[4-[[[4-(trifluoromethyl)benzoyl]amino]methyl]phenyl]pyrazolo[3,4-d]pyrimidin-1-yl]piperidine-1-carboxylate Following general procedure D, [4-[[[4-(trifluoromethyl)benzoyl]amino]methyl]phenyl]boronic acid (305.4 mg, 0.95 mmol) and tert-butyl (3R)-3-(4-amino-3-iodo-pyrazolo[3,4-d]pyrimidin-1-yl)piperidine-1-carboxylate (280.0 mg, 0.63 mmol) gave tert-butyl (3R)-3-[4-amino-3-[4-[[[4-(trifluoromethyl)benzoyl]amino]methyl]phenyl]pyrazolo[3,4-d]pyrimidin-1-yl]piperidine-1-carboxylate (200.0 mg, 0.34 mmol, 53% yield) as a brown foam.

UPLC-MS (ES$^+$, Short acidic): 1.77 min, m/z 596.5 [M+H]$^+$ tert-Butyl (3R)-3-[4-amino-3-[4-[[[4-(trifluoromethyl)benzoyl]amino]methyl]phenyl]pyrazolo[3,4-d]pyrimidin-1-yl]piperidine-1-carboxylate Following general procedure E, tert-butyl (3R)-3-[4-amino-3-[4-[[[4-(trifluoromethyl)benzoyl]amino]methyl]phenyl]pyrazolo[3,4-d]pyrimidin-1-yl]piperidine-1-carboxylate (200.0 mg, 0.34 mmol) gave N-[[4-[4-amino-1-[(3R)-3-piperidyl]pyrazolo[3,4-d]pyrimidin-3-yl]phenyl]methyl]-4-(trifluoromethyl)benzamide (140.0 mg, 0.28 mmol, 84% yield) as an off white solid.

UPLC-MS (ES$^+$, Short acidic): 1.23 min, m/z 496.3 [M+H]$^+$

N-[[4-[4-Amino-1-[(3R)-3-piperidyl]pyrazolo[3,4-d]pyrimidin-3-yl]phenyl]methyl]-4-(trifluoromethyl)benzamide Following general procedure F, N-[[4-[4-amino-1-[(3R)-3-piperidyl]pyrazolo[3,4-d]pyrimidin-3-yl]phenyl]methyl]-4-(trifluoromethyl)benzamide (140.0 mg, 0.28 mmol) gave N-[[4-[4-amino-1-[(3R)-1-prop-2-enoyl-3-piperidyl]pyrazolo[3,4-d]pyrimidin-3-yl]phenyl]methyl]-4-(trifluoromethyl)benzamide (11.0 mg, 0.015 mmol, 5% yield).

UPLC-MS (ES$^+$, Short acidic): 1.49 min, m/z 550.3 [M+H]$^+$ $^1$H NMR (400 MHz, DMSO-d$_6$) δ (ppm, 1:1 mixture of conformers): 9.36 (t, $^3$J 7.1 Hz, 1H, NH), 8.27 (s, 1H, ArH), 8.12 (d, $^3$J 8.9 Hz, 2H, ArH), 7.89 (d, $^3$J 8.9 Hz, 2H, ArH), 7.65 (d, $^3$J 8.9 Hz, 2H, ArH), 7.52 (d, $^3$J 8.9 Hz, 2H, ArH), 6.86 (dd, $^3$J$_{trans}$ 16.0, $^3$J$_{cis}$ 10.6 Hz, 0.5H), 6.72 (dd, $^3$J$_{trans}$ 16.0, $^3$J$_{cis}$ 10.6 Hz, 0.5H), 6.13 (d, $^3$J$_{trans}$ 16.0 Hz, 0.5H), 6.06 (d, $^3$J$_{trans}$ 16.0 Hz, 0.5H), 5.71 (d, $^3$J$_{cis}$ 10.6 Hz, 0.5H), 5.58 (d, $^3$J$_{cis}$ 10.6 Hz, 0.5H), 4.76-4.67 (m, 1H, CH), 4.60 (d, 2H, $^3$J 7.1 Hz, CH$_2$), 4.58-4.43 (m, 0.5H, 0.5×CH), 4.23-4.18 (m, 1H), 4.10-4.06 (m, 0.5H), 3.74-3.68 (m, 0.5H), 3.25-3.16 (m, 1H), 3.06-2.99 (m, 0.5H), 2.31-2.22 (m, 1H), 2.16-2.10 (m, 1H), 1.96-1.91 (m, 1H), 1.66-1.55 (m, 1H).

Example 53: N-[[4-[4-Amino-1-[(3R)-1-prop-2-enoyl-3-piperidyl]pyrazolo[3,4-d]pyrimidin-3-yl]phenyl]methyl]-2,3-difluoro-benzamide

[4-[[(2,3-Difluorobenzoyl)amino]methyl]phenyl]boronic acid

Following general procedure B, 4-(aminomethyl)phenyl]boronic acid hydrochloride (300 mg, 1.60 mmol) and 2,3-difluorobenzoyl chloride (0.22 mL, 1.76 mmol) afforded crude [4-[[(2,3-difluorobenzoyl)amino]methyl]phenyl]boronic acid (445 mg, 0.99 mmol, 62% yield) as an off-white solid.

UPLC-MS (ES$^+$, Short acidic): 1.29 min, m/z 292.1 [M+H]$^+$ tert-Butyl (3R)-3-[4-amino-3-[4-[[(2,3-difluorobenzoyl)amino]methyl]phenyl]pyrazolo[3,4-d]pyrimidin-1-yl]piperidine-1-carboxylate Following general procedure D, tert-butyl (3R)-3-(4-amino-3-iodo-pyrazolo[3,4-d]pyrimidin-1-yl)piperidine-1-carboxylate (200 mg, 0.45 mmol) and 2,3-difluoro-N-[[4-(4,4,5,5-tetramethyl-1,3,2-dioxaborolan-2-yl)phenyl]methyl]benzamide (252 mg, 0.68 mmol) gave tert-butyl (3R)-3-[4-amino-3-[4-[[(2,3-difluorobenzoyl)amino]methyl]phenyl]pyrazolo[3,4-d]pyrimidin-1-yl]piperidine-1-carboxylate (230 mg, 0.41 mmol, 91% yield) as an orange solid.

UPLC-MS (ES$^+$, Short acidic): 1.68 min, m/z 564.4 [M+H]$^+$

N-[[4-[4-Amino-1-[(3R)-3-piperidyl]pyrazolo[3,4-d]pyrimidin-3-yl]phenyl]methyl]-2,3-difluoro-benzamide Following general procedure E, tert-butyl (3R)-3-[4-amino-3-[4-[[(2,3-difluorobenzoyl)amino]methyl]phenyl]pyrazolo[3,4-d]pyrimidin-1-yl]piperidine-1-carboxylate (230 mg, 0.41 mmol) gave the title compound (160 mg, 0.35 mmol, 85% yield) as a yellow foam.

UPLC-MS (ES+, Short acidic): 1.11 min, m/z 464.2 [M+H]+

N-[[4-[4-amino-1-[(3R)-1-prop-2-enoyl-3-piperidyl]pyrazolo[3,4-d]pyrimidin-3-yl]phenyl]methyl]-2,3-difluoro-benzamide Following general procedure F, N-[[4-[4-amino-1-[(3R)-3-piperidyl]pyrazolo[3,4-d]pyrimidin-3-yl]phenyl]methyl]-2,3-difluoro-benzamide (160 mg, 0.35 mmol) and acrylic acid (24 µL, 0.35 mmol) gave N-[[4-[4-amino-1-[(3R)-1-prop-2-enoyl-3-piperidyl]pyrazolo[3,4-d]pyrimidin-3-yl]phenyl]methyl]-2,3-difluoro-benzamide (50 mg, 0.09 mmol, 25% yield) as a white powder.

UPLC-MS (ES+, Short acidic): 1.40 min, m/z 518.4 [M+H]+

UPLC-MS (ES+, Long acidic): 3.13 min, m/z 518.3 [M+H]+

$^1$H NMR (400 MHz, DMSO-$d_6$) δ (ppm, 1:1 mixture of conformers) 9.12 (t, J 6.0 Hz, 1H, NH), 8.32 (s, 1H, ArH), 7.69-7.63 (m, 2H, ArH), 7.63-7.54 (m, 1H), 7.52 (d, J 8.1 Hz, 2H, ArH), 7.49-7.43 (m, 1H, ArH), 7.35-7.27 (m, 1H, ArH), 6.93-6.63 (m, 1H), 6.19-6.01 (m, 1H), 5.75-5.53 (m, 1H), 4.82-4.65 (m, 1H), 4.57 (d, J 6.0 Hz, 2H), 4.61-4.50 (m, 1H), 4.25-4.14 (m, 1H), 4.12-4.02 (m, 0.5H), 3.78-3.64 (m, 0.5H), 3.29-3.14 (m, 1H), 3.09-2.97 (m, 0.5H), 2.29-2.20 (m, 1H), 2.18-2.07 (m, 1H), 1.99-1.88 (m, 1H), 1.69-1.50 (m, 1H).

Example 54: N-[[4-[4-amino-1-[(3R)-1-prop-2-enoyl-3-piperidyl]pyrazolo[3,4-d]pyrimidin-3-yl]phenyl]methyl]-3,5-difluoro-benzamide

[4-[[(3,5-Difluorobenzoyl)amino]methyl]phenyl]boronic acid

Following general procedure B, 4-(aminomethyl)phenylboronic acid hydrochloride (187 mg, 1.00 mmol) and 3,5-difluorobenzoyl chloride (0.12 mL, 1.00 mmol) gave [4-[[(3,5-difluorobenzoyl)amino]methyl]phenyl]boronic acid (171 mg, 0.59 mmol, 59% yield) as a white solid.

UPLC-MS (ES+, Short acidic): 1.36 min, m/z 293.2 [M+2]+ tert-Butyl (3R)-3-[4-amino-3-[4-[[(3,5-difluorobenzoyl)amino]methyl]phenyl]pyrazolo[3,4-d]pyrimidin-1-yl]piperidine-1-carboxylate Following general procedure D, [4-[[(3,5-difluorobenzoyl)amino]methyl]phenyl]boronic acid (172 mg, 0.59 mmol) and tert-butyl (3R)-3-(4-amino-3-iodo-pyrazolo[3,4-d]pyrimidin-1-yl)piperidine-1-carboxylate (175 mg, 0.39 mmol) afforded tert-butyl (3R)-3-[4-amino-3-[4-[[(3,5-difluorobenzoyl)amino]methyl]phenyl]pyrazolo[3,4-d]pyrimidin-1-yl]piperidine-1-carboxylate (190 mg, 0.34 mmol, 86% yield) as a brown foam.

UPLC-MS (ES+, Short acidic): 1.22 min, m/z 464.2 [M+H]+

N-[[4-[4-amino-1-[(3R)-3-piperidyl]pyrazolo[3,4-d]pyrimidin-3-yl]phenyl]methyl]-3,5-difluoro-benzamide Following general procedure E, tert-butyl (3R)-3-[4-amino-3-[4-[[(3,5-difluorobenzoyl)amino]methyl]phenyl]pyrazolo[3,4-d]pyrimidin-1-yl]piperidine-1-carboxylate (190 mg, 0.34 mmol) gave N-[[4-[4-amino-1-[(3R)-3-piperidyl]pyrazolo[3,4-d]pyrimidin-3-yl]phenyl]methyl]-3,5-difluoro-benzamide (132 mg, 0.29 mmol, 85% yield) as an off-white foam.

UPLC-MS (ES+, Short acidic): 1.74 min, m/z 564.5 [M+H]+

N-[[4-[4-Amino-1-[(3R)-1-prop-2-enoyl-3-piperidyl]pyrazolo[3,4-d]pyrimidin-3-yl]phenyl]methyl]-3,5-difluoro-benzamide Following general procedure F, N-[[4-[4-amino-1-[(3R)-3-piperidyl]pyrazolo[3,4-d]pyrimidin-3-yl]phenyl]methyl]-3,5-difluoro-benzamide (83 mg, 0.18 mmol) gave N-[[4-[4-amino-1-[(3R)-1-prop-2-enoyl-3-piperidyl]pyrazolo[3,4-d]pyrimidin-3-yl]phenyl]methyl]-3,5-difluoro-benzamide (28 mg, 0.05 mmol, 30% yield).

UPLC-MS (ES+, Long acidic): 3.23 min, m/z 518.3 [M+H]+

$^1$H NMR (400 MHz, DMSO-$d_6$) δ (ppm, 1:1 mixture of conformers) 9.28 (t, J 5.9 Hz, 1H, NH), 8.26 (s, 1H, ArH), 7.69-7.58 (m, 4H, ArH), 7.54-7.44 (m, 3H, ArH), 6.93-6.63 (m, 1H), 6.17-6.00 (m, 1H), 5.74-5.54 (m, 1H), 4.78-4.62 (m, 1H), 4.57 (d, J 5.9 Hz, 2H), 4.55-4.51 (m, 1H), 4.26-4.14 (m, 1H), 4.12-4.01 (m, 0.5H), 3.75-3.65 (m, 0.5H), 3.25-3.14 (m, 1H), 3.07-2.96 (m, 0.5H), 2.31-2.18 (m, 1H), 2.17-2.08 (m, 1H), 2.00-1.89 (m, 1H), 1.68-1.49 (m, 1H).

Example 55: N-[[4-[4-Amino-1-[(3R)-1-prop-2-enoyl-3-piperidyl]pyrazolo[3,4-d]pyrimidin-3-yl]phenyl]methyl]-2-fluoro-5-methoxy-benzamide

[4-[[(2-Fluoro-5-methoxy-benzoyl)amino]methyl]phenyl]boronic acid

Following general procedure A, 4-aminomethylphenylboronic acid hydrochloride (303 mg, 1.62 mmol) and 2-fluoro-5-methoxybenzoic acid (250 mg, 1.47 mmol) gave [4-[[(2-fluoro-5-methoxy-benzoyl)amino]methyl]phenyl]boronic acid (334 mg, 1.10 mmol, 75% yield) as a pale yellow solid.

UPLC-MS (ES+, Short acidic): 1.31 min, m/z 303.9 [M+H]+ tert-Butyl (3R)-3-[4-amino-3-[4-[[(2-fluoro-5-methoxy-benzoyl)amino]methyl]phenyl]pyrazolo[3,4-d]pyrimidin-1-yl]piperidine-1-carboxylate Following general procedure D, [4-[[(2-fluoro-5-methoxy-benzoyl)amino]methyl]phenyl]boronic acid (205 mg, 0.68 mmol) and tert-butyl (3R)-3-(4-amino-3-iodo-pyrazolo[3,4-d]pyrimidin-1-yl)piperidine-1-carboxylate (200 mg, 0.45 mmol) gave tert-butyl (3R)-3-[4-amino-3-[4-[[(2-fluoro-5-methoxy-benzoyl)amino]methyl]phenyl]pyrazolo[3,4-d]pyrimidin-1-yl]piperidine-1-carboxylate (305 mg, 0.53 mmol, assumed quantitative) as a yellow foam.

UPLC-MS (ES+, Short acidic): 1.70 min, m/z 576.5 [M+H]+

N-[[4-[4-Amino-1-[(3R)-3-piperidyl]pyrazolo[3,4-d]pyrimidin-3-yl]phenyl]methyl]-2-fluoro-5-methoxybenzamide Following general procedure E, tert-butyl (3R)-3-[4-amino-3-[4-[[(2-fluoro-5-methoxy-benzoyl)amino]methyl]phenyl]pyrazolo[3,4-d]pyrimidin-1-yl]piperidine-1-carboxylate (305 mg, 0.53 mmol) gave N-[[4-[4-amino-1-[(3R)-3-piperidyl]pyrazolo[3,4-d]pyrimidin-3-yl]phenyl]methyl]-2-fluoro-5-methoxy-benzamide (230 mg, 0.48 mmol, 91% yield) as a light brown foam.

UPLC-MS (ES+, Short acidic): 1.13 min, m/z 476.4 [M+H]+

N-[[4-[4-Amino-1-[(3R)-1-prop-2-enoyl-3-piperidyl]pyrazolo[3,4-d]pyrimidin-3-yl]phenyl]methyl]-2-fluoro-5-methoxy-benzamide Following general procedure F, N-[[4-[4-amino-1-[(3R)-3-piperidyl]pyrazolo[3,4-d]pyrimidin-3-yl]phenyl]methyl]-2-fluoro-5-methoxy-benzamide (230 mg, 0.48 mmol) afforded N-[[4-[4-amino-1-[(3R)-1-prop-2-enoyl-3-piperidyl]pyrazolo[3,4-d]pyrimidin-3-yl]phenyl]methyl]-2-fluoro-5-methoxy-benzamide (37 mg, 0.07 mmol, 15% yield) as a white solid.

UPLC-MS (ES+, Short acidic): 1.40 min, m/z 530.4 [M+H]+

UPLC-MS (ES+, Long acidic): 3.14 min, m/z 530.4 [M+H]+

$^1$H NMR (400 MHz, DMSO-d$_6$) δ (ppm, 1:1 mixture of conformers) 8.95-8.88 (m, 1H, NH), 8.26 (s, 1H, ArH), 7.68-7.61 (m, 2H, ArH), 7.54-7.48 (m, 2H, ArH), 7.25 (dd, J 10.2, 8.9 Hz, 1H, ArH), 7.17 (dd, J 5.5, 3.2 Hz, 1H, ArH), 7.11-7.05 (m, 1H, ArH), 6.92-6.635 (m, 1H), 6.18-6.01 (m, 1H), 5.75-5.55 (m, 1H), 4.78-4.63 (m, 1H), 4.58-4.51 (m, 0.5H), 4.55 (d, J 5.9 Hz, 2H), 4.26-4.14 (m, 1H), 4.13-4.02 (m, 1H), 3.78 (s, 3H), 3.74-3.65 (m, 0.5H), 3.26-3.14 (m, 1H), 3.07-2.96 (m, 0.5H), 2.32-2.20 (m, 1H), 2.16-2.07 (m, 1H), 1.97-1.87 (m, 1H), 1.66-1.51 (m, 1H).

Example 56: N-[[4-[4-Amino-1-[(3R)-1-prop-2-enoyl-3-piperidyl]pyrazolo[3,4-d]pyrimidin-3-yl]phenyl]methyl]-2-fluoro-6-(trifluoromethyl)benzamide

[4-[[[2-Fluoro-6-(trifluoromethyl)benzoyl]amino]methyl]phenyl]boronic acid

Following general procedure B, 2-fluoro-6-(trifluoromethyl)benzoyl chloride (0.17 mL, 1.10 mmol) and 4-aminomethylphenylboronic acid hydrochloride (207 mg, 1.10 mmol) afforded crude [4-[[[2-fluoro-6-(trifluoromethyl)benzoyl]amino]methyl]phenyl]boronic acid (467 mg, 1.10 mmol, assumed quantitative) as a white solid.

UPLC-MS (ES+, Short acidic): 1.34 min, m/z 341.9 [M+H]+ tert-Butyl (3R)-3-[4-amino-3-[4-[[[2-fluoro-6-(trifluoromethyl)benzoyl]amino]methyl]phenyl]pyrazolo[3,4-d]pyrimidin-1-yl]piperidine-1-carboxylate Following general procedure D, [4-[[[2-fluoro-6-(trifluoromethyl)benzoyl]amino]methyl]phenyl]boronic acid (230 mg, 0.68 mmol) and tert-butyl (3R)-3-(4-amino-3-iodopyrazolo[3,4-d]pyrimidin-1-yl)piperidine-1-carboxylate (200 mg, 0.45 mmol) gave tert-butyl (3R)-3-[4-amino-3-[4-[[[2-fluoro-6-(trifluoromethyl)benzoyl]amino]methyl]phenyl]pyrazolo[3,4-d]pyrimidin-1-yl]piperidine-1-carboxylate (251 mg, 0.41 mmol, 91% yield) as a yellow film.

UPLC-MS (ES+, Short acidic): 1.71 min, m/z 614.5 [M+H]+

N-[[4-[4-amino-1-[(3R)-3-piperidyl]pyrazolo[3,4-d]pyrimidin-3-yl]phenyl]methyl]-2-fluoro-6-(trifluoromethyl)benzamide Following general procedure E, tert-butyl (3R)-3-[4-amino-3-[4-[[[2-fluoro-6-(trifluoromethyl)benzoyl]amino]methyl]phenyl]pyrazolo[3,4-d]pyrimidin-1-yl]piperidine-1-carboxylate (251 mg, 0.41 mmol) gave crude N-[[4-[4-amino-1-[(3R)-3-piperidyl]pyrazolo[3,4-d]pyrimidin-3-yl]phenyl]methyl]-2-fluoro-6-(trifluoromethyl)benzamide (229 mg, 0.41 mmol, assumed quantitative) as a yellow foam.

UPLC-MS (ES+, Short acidic): 1.16 min, m/z 514.3 [M+H]+

N-[[4-[4-Amino-1-[(3R)-1-prop-2-enoyl-3-piperidyl]pyrazolo[3,4-d]pyrimidin-3-yl]phenyl]methyl]-2-fluoro-6-(trifluoromethyl)benzamide Following general procedure F, N-[[4-[4-amino-1-[(3R)-3-piperidyl]pyrazolo[3,4-d]pyrimidin-3-yl]phenyl]methyl]-2-fluoro-6-(trifluoromethyl)benzamide (229 mg, 0.41 mmol) afforded N-[[4-[4-amino-1-[(3R)-1-prop-2-enoyl-3-piperidyl]pyrazolo[3,4-d]pyrimidin-3-yl]phenyl]methyl]-2-fluoro-6-(trifluoromethyl)benzamide (51 mg, 0.09 mmol, 20% yield) as a white solid.

UPLC-MS (ES+, Short acidic): 1.42 min, m/z 568.3 [M+H]+

UPLC-MS (ES+, Long acidic): 3.20 min, m/z 568.3 [M+H]+

$^1$H NMR (400 MHz, DMSO-d$_6$) δ (ppm, 1:1 mixture of conformers) 9.33 (t, J 6.0 Hz, 1H, NH), 8.27 (s, 1H, ArH), 7.75-7.62 (m, 5H, ArH), 7.54-7.48 (m, 2H, ArH), 6.93-6.66 (m, 1H), 6.18-6.01 (m, 1H), 5.75-5.55 (m, 1H), 4.79-4.64 (m, 1H), 4.57 (d, J 6.0 Hz, 2H), 4.56-4.50 (m, 0.5H), 4.26-4.16 (m, 1H), 4.12-4.03 (m, 0.5H), 3.77-3.66 (m, 0.5H), 3.28-3.15 (m, 1H), 3.08-2.95 (m, 0.5H), 2.31-2.21 (m, 1H), 2.18-2.06 (m, 1H), 1.98-1.88 (m, 1H), 1.67-1.51 (m, 1H).

Example 57: N-[[4-[4-amino-1-[(3R)-1-prop-2-enoyl-3-piperidyl]pyrazolo[3,4-d]pyrimidin-3-yl]phenyl]methyl]-4-fluoro-3-(trifluoromethyl)benzamide

[4-[[[4-Fluoro-3-(trifluoromethyl)benzoyl]amino]methyl]phenyl]boronic acid

Following general procedure B, 4-fluoro-3-(trifluoromethyl)benzoyl chloride (227 mg, 1.00 mmol) and 4-aminomethylphenylboronic acid hydrochloride (187 mg, 1.00 mmol) gave [4-[[[4-fluoro-3-(trifluoromethyl)benzoyl]amino]methyl]phenyl]boronic acid (245 mg, 0.72 mmol, 72% yield) as a white solid.

UPLC-MS (ES+, Short acidic): 1.51 min, m/z 341.8 [M+H]+ tert-Butyl (3R)-3-[4-amino-3-[4-[[[4-fluoro-3-(trifluoromethyl)benzoyl]amino]methyl]phenyl]pyrazolo[3,4-d]pyrimidin-1-yl]piperidine-1-carboxylate Following general procedure D, [4-[[[4-fluoro-3-(trifluoromethyl)benzoyl]amino]methyl]phenyl]boronic acid (230 mg, 0.68 mmol) and tert-butyl (3R)-3-(4-amino-3-iodo-pyrazolo[3,4-d]pyrimidin-1-)piperidine-1-carboxylate (200 mg, 0.45 mmol) gave tert-butyl (3R)-3-[4-amino-3-[4-[[[4-fluoro-3-(trifluoromethyl)benzoyl]amino]methyl]phenyl] pyrazolo[3,4-d]pyrimidin-1-yl]piperidine-1-carboxylate (194 mg, 0.32 mmol, 70% yield) as a light brown film.

UPLC-MS (ES+, Short acidic): 1.84 min, m/z 614.5 [M+H]+

N-[[4-[4-Amino-1-[(3R)-3-piperidyl]pyrazolo[3,4-d] pyrimidin-3-yl]phenyl]methyl]-4-fluoro-3-(trifluoromethyl)benzamide Following general procedure E, tert-butyl (3R)-3-[4-amino-3-[4-[[[4-fluoro-3-(trifluoromethyl)benzoyl]amino] methyl]phenyl]pyrazolo[3,4-d]pyrimidin-1-yl]piperidine-1-carboxylate (194 mg, 0.32 mmol) gave N-[[4-[4-amino-1-[(3R)-3-piperidyl]pyrazolo[3,4-d]pyrimidin-3-yl]phenyl] methyl]-4-fluoro-3-(trifluoromethyl)benzamide (155 mg, 0.30 mmol, 95% yield) as a pale yellow film.

UPLC-MS (ES+, Short acidic): 1.30 min, m/z 514.3 [M+H]+

N-[[4-[4-Amino-1-[(3R)-1-prop-2-enoyl-3-piperidyl] pyrazolo[3,4-d]pyrimidin-3-y]phenyl]methyl]-4-fluoro-(trifluoromethyl)benzamide Following general procedure F, N-[[4-[4-amino-1-[(3R)-3-piperidyl]pyrazolo[3,4-d]pyrimidin-3-yl]phenyl]methyl]-4-fluoro-3-(trifluoromethyl)benzamide (155 mg, 0.30 mmol) afforded N-[[4-[4-amino-1-[(3R)-1-prop-2-enoyl-3-piperidyl]pyrazolo[3,4-d]pyrimidin-3-yl]phenyl]methyl]-4-fluoro-3-(trifluoromethyl)benzamide (19 mg, 0.03 mmol, 11% yield) as a white solid.

UPLC-MS (ES+, Short acidic): 1.57 min, m/z 568.3 [M+H]+

UPLC-MS (ES+, Long acidic): 3.54 min, m/z 568.3 [M+H]+

$^1$H NMR (400 MHz, DMSO-$d_6$) δ (ppm, 1:1 mixture of conformers) 9.38 (t, J 6.0 Hz, 1H, NH), 8.36-8.28 (m, 2H, ArH), 8.26 (s, 1H, ArH), 7.71-7.61 (m, 3H, ArH), 7.54-7.48 (m, 2H, ArH), 6.92-6.63 (m, 1H), 6.17-6.00 (m, 1H), 5.74-5.54 (m, 1H), 4.79-4.63 (m, 1H), 4.59 (d, J 6.0 Hz, 2H), 4.58-4.50 (m, 1H), 4.25-4.14 (m, 1H), 4.12-4.02 (m, 0.5H), 3.75-3.65 (m, 0.5H), 3.25-3.15 (m, 1H), 3.07-2.97 (m, 0.5H), 2.30-2.19 (m, 1H), 2.16-2.06 (m, 1H), 1.99-1.87 (m, 1H), 1.68-1.51 (m, 1H).

Example 58: N-[[4-[4-Amino-1-[(3R)-1-prop-2-enoyl-3-piperidyl]pyrazolo[3,4-d]pyrimidin-3-yl] phenyl]methyl]-2-fluoro-4-methoxy-benzamide

[4-[[(2-Fluoro-4-methoxy-benzoyl)amino]methyl] phenyl]boronic acid

Following general procedure B, [4-(aminomethyl)phenyl] boronic acid hydrochloride (300 mg, 1.60 mmol) and 2-fluoro-4-methoxybenzoyl chloride (332 mg, 1.76 mmol) gave [4-[[(2-fluoro-4-methoxy-benzoyl)amino]methyl]phenyl]boronic acid (253 mg, 0.67 mmol, 42% yield) as an off-white solid.

UPLC-MS (ES+, Short acidic): 1.31 min, m/z 303.9 [M+H]+ tert-Butyl (3R)-3-[4-amino-3-[4-[[(2-fluoro-4-methoxy-benzoyl)amino]methyl]phenyl]pyrazolo[3, 4-d]pyrimidin-1-yl]piperidine-1-carboxylate Following general procedure D, [4-[[(2-fluoro-4-methoxy-benzoyl)amino]methyl]phenyl]boronic acid (205 mg, 0.68 mmol) and tert-butyl (3R)-3-(4-amino-3-iodo-pyrazolo[3,4-d]pyrimidin-1-yl)piperidine-1-carboxylate (200 mg, 0.45 mmol) gave, after further purification by flash column chromatography (DCM/MeOH 100:0 to 90:10), tert-butyl (3R)-3-[4-amino-3-[4-[[(2-fluoro-4-methoxy-benzoyl)amino]methyl]phenyl]pyrazolo[3,4-d]pyrimidin-1-yl] piperidine-1-carboxylate (235 mg, 0.33 mmol, 72% yield) as a pale yellow solid.

UPLC-MS (ES+, Short acidic): 2.14 min, m/z 576.3 [M+H]+

N-[[4-[4-Amino-1-[(3R)-3-piperidyl]pyrazolo[3,4-d] pyrimidin-3-yl]phenyl]methyl]-2-fluoro-4-methoxybenzamide Following general procedure E, tert-butyl (3R)-3-[4-amino-3-[4-[[(2-fluoro-4-methoxy-benzoyl)amino]methyl] phenyl]pyrazolo[3,4-d]pyrimidin-1-yl]piperidine-1-carboxylate (235 mg, 0.41 mmol) gave, after further purification by flash column chromatography (DCM/7N NH$_3$ in MeOH 100:0 to 90:10), N-[[4-[4-amino-1-[(3R)-3-piperidyl]pyrazolo[3,4-d]pyrimidin-3-yl]phenyl]methyl]-2-fluoro-4-methoxy- benzamide (176 mg, 0.33 mmol, 82% yield) as a white solid.

UPLC-MS (ES+, Short acidic): 1.12 min, m/z 476.4 [M+H]+

N-[[4-[4-Amino-1-[(3R)-1-prop-2-enoyl-3-piperidyl] pyrazolo[3,4-d]pyrimidin-3-yl]phenyl]methyl]-2-fluoro-4-methoxy-benzamide Following general procedure F, N-[[4-[4-amino-1-[(3R)-3-piperidyl]pyrazolo[3,4-d]pyrimidin-3-yl]phenyl]methyl]-2-fluoro-4-methoxy-benzamide (176 mg, 0.37 mmol) gave, purification by flash column chromatography (DCM/MeOH 100:0 to 90:10), N-[[4-[4-amino-1-[(3R)-1-prop-2-enoyl-3-piperidyl]pyrazolo[3,4-d]pyrimidin-3-yl]phenyl]methyl]-2-fluoro-4-methoxy-benzamide (40 mg, 0.07 mmol, 18% yield) as a white solid.

UPLC-MS (ES+, Short acidic): 1.39 min, m/z 530.5 [M+H]+

UPLC-MS (ES+, Long acidic): 3.14 min, m/z 530.4 [M+H]+

$^1$H NMR (400 MHz, DMSO-$d_6$) δ (ppm, 1:1 mixture of conformers) 8.73-8.66 (m, 1H, NH), 8.26 (s, 1H, ArH), 7.70 (d, J 8.7 Hz, 1H, ArH), 7.67-7.61 (m, 2H, ArH), 7.53-7.46 (m, 2H, ArH), 6.93 (dd, J 13.0, 2.4 Hz, 1H, ArH), 6.87 (dd, J 8.7, 2.4 Hz, 1H, ArH), 6.90-6.66 (m, 1H), 6.17-6.02 (m, 1H), 5.74-5.54 (m, 1H), 4.77-4.63 (m, 1H), 4.57 (d, J 5.9 Hz, 2H), 4.59-4.49 (m, 0.5H), 4.25-4.15 (m, 1H), 4.11-4.02 (m, 0.5H), 3.82 (s, 3H), 3.75-3.65 (m, 0.5H), 3.27-3.13 (m, 1H), 3.06-2.94 (m, 0.5H), 2.32-2.19 (m, 1H), 2.17-2.06 (m, 1H), 1.97-1.87 (m, 1H), 1.67-1.49 (m, 1H).

Example 59: N-[[4-[4-Amino-1-[(3R)-1-prop-2-enoyl-3-piperidyl]pyrazolo[3,4-d]pyrimidin-3-yl] phenyl]methyl]-2-methyl-benzamide

[4-[[(2-Methylbenzoyl)amino]methyl]phenyl]boronic acid

Following general procedure B, o-toluoylchloride (247 mg, 1.60 mmol) and [4-(aminomethyl)phenyl]boronic acid hydrochloride (300 mg, 1.60 mmol) afforded the title compound (290 mg, 1.08 mmol, 67% yield).

UPLC-MS (ES⁺, Short acidic): 1.26 min, m/z 269.8 [M+H]⁺ tert-Butyl (3R)-3-[4-amino-3-[4-[[(2-methylbenzoyl)amino]methyl]phenyl]pyrazolo[3,4-d]pyrimidin-1-yl]piperidine-1-carboxylate Following general procedure D, [4-[[(2-methylbenzoyl)amino]methyl]phenyl]boronic acid (290 mg, 1.08 mmol) and tert-butyl (3R)-3-(4-amino-3-iodo-pyrazolo[3,4-d]pyrimidin-1-yl)piperidine-1-carboxylate (200 mg, 0.45 mmol) afforded the title compound (160 mg, 0.30 mmol, 66% yield) as an orange-red solid.

UPLC-MS (ES⁺, Short acidic): 1.66 min, m/z 542.5 [M+H]⁺

N-[[4-[4-Amino-1-[(3R)-3-piperidyl]pyrazolo[3,4-d]pyrimidin-3-yl]phenyl]methyl]-2-methyl-benzamide Following general procedure E, tert-butyl (3R)-3-[4-amino-3-[4-[[(2-methylbenzoyl)amino]methyl]phenyl]pyrazolo[3,4-d]pyrimidin-1-yl]piperidine-1-carboxylate (160 mg, 0.30 mmol) afforded the title compound (118 mg, 0.27 mmol, 58% yield) as an off-white solid.

UPLC-MS (ES⁺, Short acidic): 1.11 min, m/z 442.3 [M+H]⁺

N-[[4-[4-Amino-1-[(3R)-1-prop-2-enoyl-3-piperidyl]pyrazolo[3,4-d]pyrimidin-3-yl]phenyl]methyl]-2-methyl-benzamide Following general procedure F, N-[[4-[4-amino-1-[(3R)-3-piperidyl]pyrazolo[3,4-d]pyrimidin-3-yl]phenyl]methyl]-2-methyl-benzamide (118 mg, 0.27 mmol) afforded the title compound (13 mg, 0.03 mmol, 9% yield) as a colourless solid.

UPLC-MS (ES⁺, Short acidic): 1.37 min, m/z 496.4 [M+H]⁺

UPLC-MS (ES⁺, Long acidic): 3.04 min, m/z 496.5 [M+H]⁺

¹H NMR (400 MHz, DMSO-d₆) δ (ppm, 1:1 mixture of conformers) 8.86 (t, J 6.0 Hz, 1H, NH), 8.27 (s, 1H, ArH), 7.69-7.62 (m, 2H, ArH), 7.54-7.49 (m, 2H, ArH), 7.43-7.38 (m, 1H, ArH), 7.37-7.31 (m, 1H, ArH), 7.28-7.22 (m, 2H, ArH), 6.92-6.66 (m, 1H), 6.18-6.01 (m, 1H), 5.75-5.55 (m, 1H), 4.79-4.64 (m, 1H), 4.60-4.49 (m, 0.5H), 4.53 (d, J 6.0 Hz, 2H), 4.27-4.14 (m, 1H), 4.12-4.03 (m, 0.5H), 3.76-3.65 (m, 0.5H), 3.26-3.14 (m, 1H), 3.06-2.95 (m, 0.5H), 2.36 (s, 3H), 2.30-2.19 (m, 1H), 2.18-2.06 (m, 1H), 2.00-1.87 (m, 1H), 1.68-1.49 (m, 1H).

Example 60: N-[[4-[4-amino-1-[(3R)-1-prop-2-enoyl-3-piperidyl]pyrazolo[3,4-d]pyrimidin-3-yl]phenyl]methyl]-2-methoxy-5-methyl-benzamide

[3-[[(2-Methoxy-5-methyl-benzoyl)amino]methyl]phenyl]boronic acid

Following general procedure A, [3-(aminomethyl)phenyl]boronic acid hydrochloride (248 mg, 1.32 mmol) and 2-methoxy-5-methylbenzoic acid (200 mg, 1.20 mmol) gave [3-[[(2-methoxy-5-methyl-benzoyl)amino]methyl]phenyl]boronic acid (284 mg, 0.95 mmol, 79% yield) as a pale yellow foam.

UPLC-MS (ES⁺, Short acidic): 1.42 min, m/z 299.9 [M+H]⁺ tert-Butyl (3R)-3-[4-amino-3-[3-[[(2-methoxy-5-methyl-benzoyl)amino]methyl]phenyl]pyrazolo[3,4-d]pyrimidin-1-yl]piperidine-1-carboxylate Following general procedure D, [4-[[[4-fluoro-3-(trifluoromethyl)benzoyl]amino]methyl]phenyl]boronic acid (230 mg, 0.68 mmol) and tert-butyl (3R)-3-(4-amino-3-iodo-pyrazolo[3,4-d]pyrimidin-1-yl)piperidine-1-carboxylate (200 mg, 0.45 mmol) gave tert-butyl (3R)-3-[4-amino-3-[3-[[(2-methoxy-5-methyl-benzoyl)amino]methyl]phenyl]pyrazolo[3,4-d]pyrimidin-1-yl]piperidine-1-carboxylate (260 mg, 0.45 mmol, quantitative) as a pale yellow foam.

UPLC-MS (ES⁺, Short acidic): 1.80 min, m/z 572.5 [M+H]⁺

N-[[3-[4-Amino-1-[(3R)-3-piperidyl]pyrazolo[3,4-d]pyrimidin-3-yl]phenyl]methyl]-2-methoxy-5-methyl-benzamide Following general procedure E, tert-butyl (3R)-3-[4-amino-3-[3-[[(2-methoxy-5-methyl-benzoyl)amino]methyl]phenyl]pyrazolo[3,4-d]pyrimidin-1-yl]piperidine-1-carboxylate (260 mg, 0.46 mmol) gave N-[[3-[4-amino-1-[(3R)-3-piperidyl]pyrazolo[3,4-d]pyrimidin-3-yl]phenyl]methyl]-2-methoxy-5-methyl-benzamide (202 mg, 0.43 mmol, 94% yield) as a yellow foam.

UPLC-MS (ES⁺, Short acidic): 1.22 min, m/z 472.4 [M+H]⁺

N-[[3-[4-Amino-1-[(3R)-1-prop-2-enoyl-3-piperidyl]pyrazolo[3,4-d]pyrimidin-3-yl]phenyl]methyl]-2-methoxy-5-methyl-benzamide Following general procedure F, N-[[3-[4-amino-1-[(3R)-3-piperidyl]pyrazolo[3,4-d]pyrimidin-3-yl]phenyl]methyl]-2-methoxy-5-methyl-benzamide (202 mg, 0.43 mmol) afforded N-[[3-[4-amino-1-[(3R)-1-prop-2-enoyl-3-piperidyl]pyrazolo[3,4-d]pyrimidin-3-yl]phenyl]methyl]-2-methoxy-5-methyl-benzamide (52 mg, 0.10 mmol, 23% yield) as a white solid.

UPLC-MS (ES⁺, Short acidic): 1.49 min, m/z 526.4 [M+H]⁺

UPLC-MS (ES⁺, Long acidic): 3.35 min, m/z 526.4 [M+H]⁺

¹H NMR (400 MHz, DMSO-d₆) δ (ppm, 1:1 mixture of conformers) 8.76 (t, J 6.0 Hz, 1H, NH), 8.26 (s, 1H, ArH), 7.70-7.42 (m, 5H, ArH), 7.29-7.23 (m, 1H, ArH), 7.03 (d, J 8.4 Hz, 1H, ArH), 6.91-6.66 (m, 1H), 6.17-6.01 (m, 1H), 5.74-5.54 (m, 1H), 4.78-4.63 (m, 1H), 4.57 (d, J 6.0 Hz, 2H), 4.58-4.49 (m, 0.5H), 4.31-4.15 (m, 1H), 4.14-4.03 (m, 0.5H), 3.84 (s, 3H), 3.73-3.62 (m, 0.5H), 3.25-3.10 (m, 1H), 3.01-2.90 (m, 0.5H), 2.30-2.19 (m, 1H), 2.25 (s, 3H), 2.17-2.07 (m, 1H), 1.96-1.87 (m, 1H), 1.67-1.50 (m, 1H).

Example 61: N-[[4-[4-Amino-1-[(3R)-1-prop-2-enoyl-3-piperidyl]pyrazolo[3,4-d]pyrimidin-3-yl]phenyl]methyl]-4-ethoxy-3-(trifluoromethyl)benzamide

[4-[[[4-Ethoxy-3-(trifluoromethyl)benzoyl]amino]methyl]phenyl]boronic acid

Following general procedure B, 4-aminomethylphenylboronic acid hydrochloride (186 mg, 1.00 mmol) and 4-ethoxy-3-(trifluoromethyl)benzoyl chloride (253 mg, 1.00 mmol) gave [4-[[[4-ethoxy-3-(trifluoromethyl)benzoyl]amino]methyl]phenyl]boronic acid (340 mg, 0.93 mmol, 93% yield) as a white solid.

UPLC-MS (ES⁺, Short acidic): 1.57 min, m/z 367.9 [M+H]⁺ tert-Butyl (3R)-3-[4-amino-3-[4-[[[4-ethoxy-3-(trifluoromethyl)benzoyl]amino]methyl]phenyl]pyrazolo[3,4-d]pyrimidin-1-yl]piperidine-1-carboxylate Following general procedure D, [4-[[[4-ethoxy-3-(trifluoromethyl)benzoyl]amino]methyl]phenyl]boronic acid (248 mg, 0.68 mmol) and tert-butyl (3R)-3-(4-amino-3-iodo-pyrazolo[3,4-d]pyrimidin-1-yl)piperidine-1-carboxylate (200 mg, 0.45 mmol) gave tert-butyl (3R)-3-[4-amino-3-[4-[[[4-ethoxy-3-(trifluoromethyl)benzoyl]amino]methyl]phenyl]pyrazolo[3,4-d]pyrimidin-1-yl]piperidine-1-carboxylate (174 mg, 0.27 mmol, 60% yield) as a yellow solid.

UPLC-MS (ES⁺, Short acidic): 1.86 min, m/z 640.5 [M+H]⁺

N-[[4-[4-Amino-1-[(3R)-3-piperidyl]pyrazolo[3,4-d]pyrimidin-3-yl]phenyl]methyl]-4-ethoxy-3-(trifluoromethyl)benzamide Following general procedure E, tert-butyl (3R)-3-[4-amino-3-[4-[[[4-ethoxy-3-(trifluoromethyl)benzoyl]amino]methyl]phenyl]pyrazolo[3,4-d]pyrimidin-1-yl]piperidine-1-carboxylate (174 mg, 0.27 mmol) gave N-[[4-[4-amino-1-[(3R)-3-piperidyl]pyrazolo[3,4-d]pyrimidin-3-yl]phenyl]methyl]-4-ethoxy-3-(trifluoromethyl)benzamide (118 mg, 0.22 mmol, 80% yield) as a yellow film.

UPLC-MS (ES⁺, Short acidic): 1.36 min, m/z 540.3 [M+H]⁺

N-[[4-[4-Amino-1-[(3R)-1-prop-2-enoyl-3-piperidyl]pyrazolo[3,4-d]pyrimidin-3-yl]phenyl]methyl]-4-ethoxy-3-(trifluoromethyl)benzamide Following general procedure F, N-[[4-[4-amino-1-[(3R)-3-piperidyl]pyrazolo[3,4-d]pyrimidin-3-yl]phenyl]methyl]-3-methyl-benzenesulfonamide (126 mg, 0.26 mmol) afforded N-[[4-[4-amino-1-[(3R)-1-prop-2-enoyl-3-piperidyl]pyrazolo[3,4-d]pyrimidin-3-yl]phenyl]methyl]-4-ethoxy-3-(trifluoromethyl)benzamide (7 mg, 0.01 mmol, 5% yield) as a white solid.

UPLC-MS (ES⁺, Short acidic): 1.61 min, m/z 594.5 [M+H]⁺

UPLC-MS (ES⁺, Long acidic): 3.67 min, m/z 594.4 [M+H]⁺

$^1$H NMR (400 MHz, DMSO-d$_6$) δ (ppm, 1:1 mixture of conformers) 9.21 (t, J 5.9 Hz, 1H, NH), 8.26 (s, 1H, ArH), 8.22-8.17 (m, 2H, ArH), 7.67-7.60 (m, 2H, ArH), 7.52-7.47 (m, 2H, ArH), 7.39-7.34 (m, 1H, ArH), 6.88-6.63 (m, 1H), 6.17-6.00 (m, 1H), 5.75-5.53 (m, 1H), 4.77-4.63 (m, 1H), 4.57 (d, J 5.9 Hz, 2H), 4.55-4.48 (m, 0.5H), 4.29-4.14 (m, 1H), 4.25 (q, J 7.0 Hz, 2H), 4.12-4.02 (m, 0.5H), 3.76-3.63 (m, 0.5H), 3.26-3.14 (m, 1H), 3.07-2.94 (m, 0.5H), 2.30-2.18 (m, 1H), 2.17-2.05 (m, 1H), 1.99-1.88 (m, 1H), 1.67-1.47 (m, 1H), 1.36 (t, J 7.1 Hz, 3H).

Example 62: N-[[4-[4-Amino-1-[(3R)-1-prop-2-enoyl-3-piperidyl]pyrazolo[3,4-d]pyrimidin-3-yl]-2-fluoro-phenyl]methyl]-2,6-difluoro-benzamide

[4-[[(2,6-Difluorobenzoyl)amino]methyl]-3-fluoro-phenyl]boronic acid

Following general procedure B, 2,6-difluorobenzoyl chloride (0.18 mL, 1.41 mmol) and [4-(aminomethyl)-3-fluoro-phenyl]boronic acid (250 mg, 1.48 mmol) afforded [4-[[(2,6-difluorobenzoyl)amino]methyl]-3-fluoro-phenyl]boronic acid (351 mg, 1.14 mmol, 77% yield) as a brown film.

UPLC-MS (ES⁺, Short acidic): 1.39 min, m/z 310.1 [M+H]⁺ tert-Butyl (3R)-3-[4-amino-3-[4-[[(2,6-difluorobenzoyl)amino]methyl]-3-fluoro-phenyl]pyrazolo[3,4-d]pyrimidin-1-yl]piperidine-1-carboxylate Following general procedure C, [4-[[(2,6-difluorobenzoyl)amino]methyl]-3-fluoro-phenyl]boronic acid (312 mg, 1.01 mmol) and tert-butyl (3R)-3-(4-amino-3-iodo-pyrazolo[3,4-d]pyrimidin-1-yl)piperidine-1-carboxylate (200 mg, 0.45 mmol) afforded tert-butyl (3R)-3-[4-amino-3-[4-[[(2,6-difluorobenzoyl)amino]methyl]-3-fluoro-phenyl]pyrazolo[3,4-d]pyrimidin-1-yl]piperidine-1-carboxylate (166 mg, 0.29 mmol, 63% yield) as a dark yellow film.

UPLC-MS (ES⁺, Short acidic): 2.14 min, m/z 582.3 [M+H]⁺

N-[[4-[4-Amino-1-[(3R)-3-piperidyl]pyrazolo[3,4-d]pyrimidin-3-yl]-2-fluoro-phenyl]methyl]-2,6-difluoro-benzamide Following general procedure E, tert-butyl (3R)-3-[4-amino-3-[4-[[(2,6-difluorobenzoyl)amino]methyl]-3-fluoro-phenyl]pyrazolo[3,4-d]pyrimidin-1-yl]piperidine-1-carboxylate (166 mg, 0.29 mmol) afforded N-[[4-[4-amino-1-[(3R)-3-piperidyl]pyrazolo[3,4-d]pyrimidin-3-yl]-2-fluoro-phenyl]methyl]-2,6-difluoro-benzamide (130 mg, 0.27 mmol, 95% yield) as a pale brown foam.

UPLC-MS (ES⁺, Short acidic): 0.98 min, m/z 482.2 [M+H]⁺

N-[[4-[4-Amino-1-[(3R)-1-prop-2-enoyl-3-piperidyl]pyrazolo[3,4-d]pyrimidin-3-yl]-2-fluoro-phenyl]methyl]-2,6-difluoro-benzamide Following general procedure F, N-[[4-[4-amino-1-[(3R)-3-piperidyl]pyrazolo[3,4-d]pyrimidin-3-yl]-2-fluoro-phenyl]methyl]-2,6-difluoro-benzamide (130 mg, 0.27 mmol) afforded N-[[4-[4-amino-1-[(3R)-1-prop-2-enoyl-3-piperidyl]pyrazolo[3,4-d]pyrimidin-3-yl]-2-fluoro-phenyl]methyl]-2,6-difluoro-benzamide (22 mg, 0.04 mmol, 15% yield) as a white powder.

UPLC-MS (ES⁺, Short acidic): 1.39 min, m/z 536.3 [M+H]⁺

UPLC-MS (ES⁺, Long acidic): 3.10 min, m/z 536.4 [M+H]⁺

$^1$H NMR (400 MHz, DMSO-d$_6$) δ (ppm, 1:1 mixture of conformers) 9.34 (t, J 5.9 Hz, 1H, NH), 8.29 (s, 1H, ArH), 7.59-7.49 (m, 3H, ArH), 7.49-7.42 (m, 1H, ArH), 7.24-7.16 (m, 1H, ArH), 6.92-6.63 (m, 1H), 6.18-6.00 (m, 1H), 5.75-5.53 (m, 1H), 4.81-4.65 (m, 1H), 4.58 (d, J 5.9 Hz, 2H), 4.57-4.47 (m, 1H), 4.23-4.11 (m, 1H), 4.11-3.99 (m, 0.5H), 3.78-3.68 (m, 0.5H), 3.36-3.16 (m, 1H), 3.12-3.00 (m, 0.5H), 2.29-2.18 (m, 1H), 2.17-2.05 (m, 1H), 1.99-1.87 (m, 1H), 1.68-1.50 (m, 1H).

Example 63: N-[[4-[4-Amino-1-[(3R)-1-prop-2-enoyl-3-piperidyl]pyrazolo[3,4-d]pyrimidin-3-yl]-2-fluoro-phenyl]methyl]-4-fluoro-2-methoxy-benzamide

[3-Fluoro-4-[[(4-fluoro-2-methoxy-benzoyl)amino]methyl]phenyl]boronic acid

Following general procedure A, [4-(aminomethyl)-3-fluoro-phenyl]boronic acid (250 mg, 1.48 mmol) and 4-fluoro-2-methoxybenzoic acid (239 mg, 1.41 mmol) afforded [3-fluoro-4-[[(4-fluoro-2-methoxy-benzoyl)amino]methyl]phenyl]boronic acid (318 mg, 0.99 mmol, 67% yield) as a dark yellow film.

UPLC-MS (ES+, Short acidic): 1.69 min, m/z 322.0 [M+H]+ tert-Butyl (3R)-3-[4-amino-3-[3-fluoro-4-[[(4-fluoro-2-methoxy-benzoyl)amino]methyl]phenyl]pyrazolo[3,4-d]pyrimidin-1-yl]piperidine-1-carboxylate Following general procedure C, [3-fluoro-4-[[(4-fluoro-2-methoxy-benzoyl)amino]methyl]phenyl]boronic acid (324 mg, 1.01 mmol) and tert-butyl (3R)-3-(4-amino-3-iodo-pyrazolo[3,4-d]pyrimidin-1-yl)piperidine-1-carboxylate (200 mg, 0.45 mmol) afforded tert-butyl (3R)-3-[4-amino-3-[3-fluoro-4-[[(4-fluoro-2-methoxy-benzoyl)amino]methyl]phenyl]pyrazolo[3,4-d]pyrimidin-1-yl]piperidine-1-carboxylate (260 mg, 0.44 mmol, 97% yield) as a light brown film.

UPLC-MS (ES+, Short acidic): 2.34 min, m/z 594.3 [M+H]+

N-[[4-[4-Amino-1-[(3R)-3-piperidyl]pyrazolo[3,4-d]pyrimidin-3-yl]-2-fluoro-phenyl]methyl]-4-fluoro-2-methoxy-benzamide Following general procedure E, tert-butyl (3R)-3-[4-amino-3-[3-fluoro-4-[[(4-fluoro-2-methoxy-benzoyl)amino]methyl]phenyl]pyrazolo[3,4-d]pyrimidin-1-yl]piperidine-1-carboxylate (261 mg, 0.44 mmol) afforded N-[[4-[4-amino-1-[(3R)-3-piperidyl]pyrazolo[3,4-d]pyrimidin-3-yl]-2-fluoro-phenyl]methyl]-4-fluoro-2-methoxy-benzamide (217 mg, 0.44 mmol, 100% yield) as a brown film.

UPLC-MS (ES+, Short acidic): 1.16 min, m/z 494.2 [M+H]+

N-[[4-[4-Amino-1-[(3R)-1-prop-2-enoyl-3-piperidyl]pyrazolo[3,4-d]pyrimidin-3-yl]-2-fluoro-phenyl]methyl]-4-fluoro-2-methoxy-benzamide Following general procedure F, N-[[4-[4-amino-1-[(3R)-3-piperidyl]pyrazolo[3,4-d]pyrimidin-3-yl]-2-fluoro-phenyl]methyl]-4-fluoro-2-methoxy-benzamide (217 mg, 0.44 mmol) afforded N-[[4-[4-amino-1-[(3R)-1-prop-2-enoyl-3-piperidyl]pyrazolo[3,4-d]pyrimidin-3-yl]-2-fluoro-phenyl]methyl]-4-fluoro-2-methoxy-benzamide (63 mg, 0.12 mmol, 26% yield) as a white crystalline powder.

UPLC-MS (ES+, Short acidic): 1.49 min, m/z 548.4 [M+H]+

UPLC-MS (ES+, Long acidic): 3.37 min, m/z 548.4 [M+H]+

$^1$H NMR (400 MHz, DMSO-$d_6$) δ (ppm, 1:1 mixture of conformers) 8.71 (t, J 5.9 Hz, 1H, NH), 8.27 (s, 1H, ArH), 7.84 (dd, J 8.7, 7.2 Hz, 1H), 7.56-7.40 (m, 3H, ArH), 7.09 (dd, J 11.4, 2.4 Hz, 1H), 6.92-6.64 (m, 2H), 6.18-6.00 (m, 1H), 5.75-5.52 (m, 1H), 4.81-4.64 (m, 1H), 4.61 (d, J 5.9 Hz, 2H), 4.56-4.58 (m, 1H), 4.23-4.11 (m, 1H), 4.10-4.00 (m, 0.5H), 3.94 (s, 3H), 3.77-3.66 (m, 0.5H), 3.30-3.15 (m, 1H), 3.12-2.98 (m, 0.5H), 2.34-2.19 (m, 1H), 2.16-2.06 (m, 1H), 1.98-1.85 (m, 1H), 1.68-1.49 (m, 1H).

Example 64: N-[[4-[4-amino-1-[(3R)-1-prop-2-enoyl-3-piperidyl]pyrazolo[3,4-d]pyrimidin-3-yl]-2-fluoro-phenyl]methyl]-3-cyano-benzamide

[N-[[(3-Cyanobenzoyl)amino]methyl]-3-fluoro-phenyl]boronic acid

Following general procedure A, 3-cyanobenzoic acid (207 mg, 1.41 mmol) and [4-(aminomethyl)-3-fluoro-phenyl]boronic acid (250 mg, 1.48 mmol) afforded [4-[[(3-cyanobenzoyl)amino]methyl]-3-fluoro-phenyl]boronic acid (307 mg, 1.03 mmol, 70% yield) as a brown film.

UPLC-MS (ES+, Short acidic): 1.42 min, m/z 340.0 [M+MeCN+H]+ tert-Butyl (3R)-3-[4-amino-3-[4-[[(3-cyanobenzoyl)amino]methyl]-3-fluoro-phenyl]pyrazolo[3,4-d]pyrimidin-1-yl]piperidine-1-carboxylate Following general procedure C, [4-[[(3-cyanobenzoyl)amino]methyl]-3-fluoro-phenyl]boronic acid (301 mg, 1.01 mmol) and tert-butyl (3R)-3-(4-amino-3-iodo-pyrazolo[3,4-d]pyrimidin-1-yl)piperidine-1-carboxylate (200 mg, 0.45 mmol) afforded tert-butyl (3R)-3-[4-amino-3-[4-[[(3-cyanobenzoyl)amino]methyl]-3-fluoro-phenyl]pyrazolo[3,4-d]pyrimidin-1-yl]piperidine-1-carboxylate (171 mg, 0.30 mmol, 67% yield) as a light brown film.

UPLC-MS (ES+, Short acidic): 2.15 min, m/z 571.3 [M+H]+

N-[[4-[4-Amino-1-[(3R)-3-piperidyl]pyrazolo[3,4-d]pyrimidin-3-yl]-2-fluoro-phenyl]methyl]-3-cyano-benzamide Following general procedure E, tert-butyl (3R)-3-[4-amino-3-[4-[[(3-cyanobenzoyl)amino]methyl]-3-fluoro-phenyl]pyrazolo[3,4-d]pyrimidin-1-yl]piperidine-1-carboxylate (171 mg, 0.30 mmol) afforded N-[[4-[4-amino-1-[(3R)-3-piperidyl]pyrazolo[3,4-d]pyrimidin-3-yl]-2-fluoro-phenyl]methyl]-3-cyano-benzamide (141 mg, 0.30 mmol, 100% yield) as a brown film.

UPLC-MS (ES+, Short acidic): 1.04 min, m/z 471.2 [M+H]+

N-[[4-[4-Amino-1-[(3R)-1-prop-2-enoyl-3-piperidyl]pyrazolo[3,4-d]pyrimidin-3-yl]-2-fluoro-phenyl]methyl]-3-cyano-benzamide Following general procedure F, N-[[4-[4-amino-1-[(3R)-3-piperidyl]pyrazolo[3,4-d]pyrimidin-3-yl]-2-fluoro-phenyl]methyl]-3-cyano-benzamide (141 mg, 0.30 mmol) afforded N-[[4-[4-amino-1-[(3R)-1-prop-2-enoyl-3-piperidyl]pyrazolo[3,4-d]pyrimidin-3-yl]-2-fluoro-phenyl]methyl]-3-cyano-benzamide (23 mg, 0.04 mmol, 15% yield) as a white powder.

UPLC-MS (ES+, Short acidic): 1.39 min, m/z 525.4 [M+H]+

UPLC-MS (ES+, Long acidic): 3.10 min, m/z 525.4 [M+H]+

$^1$H NMR (400 MHz, DMSO-$d_6$) δ (ppm, 1:1 mixture of conformers) 9.30 (t, J 5.9 Hz, 1H, NH), 8.36-8.33 (m, 1H), 8.26 (s, 1H, ArH), 8.24-8.19 (m, 1H, ArH), 8.06-8.01 (m, 1H, ArH), 7.75-7.70 (m, 1H, ArH), 7.60-7.54 (m, 1H, ArH), 7.51-7.40 (m, 2H, ArH), 6.93-6.62 (m, 1H), 6.19-5.99 (m, 1H), 5.75-5.52 (m, 1H), 4.81-4.65 (m, 1H), 4.61 (d, J 5.9 Hz, 2H), 4.56-4.47 (m, 1H), 4.22-4.10 (m, 1H), 4.10-4.00 (m, 0.5H), 3.77-3.65 (m, 0.5H), 3.33-3.14 (m, 1H), 3.11-3.01 (m, 0.5H), 2.30-2.18 (m, 1H), 2.17-2.07 (m, 1H), 1.98-1.87 (m, 1H), 1.66-1.49 (m, 1H).

Example 65: N-[[4-[4-amino-1-(1-prop-2-enoyl-3-piperidyl)pyrazolo[3,4-d]pyrimidin-3-yl]-2-fluoro-phenyl]methyl]-2-methoxy-benzamide (1E)-4-Bromo-2-fluoro-benzaldehyde oxime Following general procedure G, 4-bromo-2-fluoro-benzaldehyde oxime (1.00 g, 4.93 mmol) afforded (1E)-4-bromo-2-fluoro-benzaldehyde oxime (1.02 g, 4.69 mmol, 95% yield) as a white crystalline powder.
UPLC-MS (ES+, Short acidic): 1.59 min, m/z 219.8 [M+H]+

[3-Fluoro-4-[(E)-hydroxyiminomethyl]phenyl]boronic acid

Following general procedure I, (1E)-4-bromo-2-fluoro-benzaldehyde oxime (4.00 g, 18.4 mmol) afforded [3-fluoro-4-[(E)-hydroxyiminomethyl]phenyl]boronic acid (3.04 g, 16.6 mmol, 91% yield) as an white solid.
UPLC-MS (ES−, Short acidic): 0.87 min, m/z 182.0 [M−H]−

[4-(Aminomethyl)-3-fluoro-phenyl]boronic acid

Following general procedure J, [3-fluoro-4-[(E)-hydroxyiminomethyl]phenyl]boronic acid (4.90 g, 26.8 mmol) afforded [4-(aminomethyl)-3-fluoro-phenyl]boronic acid (0.93 g, 5.52 mmol, 21% yield) as an off-white solid.
$^1$H NMR (400 MHz, MeOD-$d_4$) 7.71-7.34 (m, 3H, ArH), 4.20 (s, 2H)

[3-Fluoro-4-[[(2-methoxybenzoyl)amino]methyl]phenyl]boronic acid

Following general procedure A, [4-(aminomethyl)-3-fluoro-phenyl]boronic acid (250 mg, 1.48 mmol) and 2-methoxybenzoic acid (214 mg, 1.41 mmol) afforded [3-fluoro-4-[[(2-methoxybenzoyl)amino]methyl]phenyl]boronic acid (306 mg, 1.01 mmol, 68.3% yield) as a brown film.
UPLC-MS (ES+, Short acidic): 1.56 min, m/z 304.1 [M+H]+
tert-Butyl (3R)-3-[4-amino-3-[3-fluoro-4-[[(2-methoxybenzoyl)amino]methyl]phenyl]pyrazolo[3,4-d]pyrimidin-1-yl]piperidine-1-carboxylate
Following general procedure C, [3-fluoro-4-[[(2-methoxybenzoyl)amino]methyl]phenyl]boronic acid (306 mg, 1.01 mmol) and tert-butyl (3R)-3-(4-amino-3-iodo-pyrazolo[3,4-d]pyrimidin-1-yl)piperidine-1-carboxylate (200 mg, 0.45 mmol) afforded tert-butyl (3R)-3-[4-amino-3-[3-fluoro-4-[[(2-methoxybenzoyl)amino]methyl]phenyl]pyrazolo[3,4-d]pyrimidin-1-yl]piperidine-1-carboxylate (210 mg, 0.37 mmol, 81% yield) as a brown film.
UPLC-MS (ES+, Short acidic): 2.26 min, m/z 576.3 [M+H]+

N-[[4-[4-amino-1-[(3R)-3-piperidyl]pyrazolo[3,4-d]pyrimidin-3-yl]-2-fluoro-phenyl]methyl]-2-methoxy-benzamide Following general procedure E, tert-butyl (3R)-3-[4-amino-3-[3-fluoro-4-[[(2-methoxybenzoyl)amino]methyl]phenyl]pyrazolo[3,4-d]pyrimidin-1-yl]piperidine-1-carboxylate (210 mg, 0.36 mmol) afforded N-[[4-[4-amino-1-[(3R)-3-piperidyl]pyrazolo[3,4-d]pyrimidin-3-yl]-2-fluoro-phenyl]methyl]-2-methoxy-benzamide (159 mg, 0.33 mmol, 92% yield) as a brown foam.
UPLC-MS (ES+, Short acidic): 1.14 min, m/z 476.2 [M+H]+

N-[[4-[4-amino-1-[(3R)-1-prop-2-enoyl-3-piperidyl]pyrazolo[3,4-d]pyrimidin-3-yl]-2-fluoro-phenyl]methyl]-2-methoxy-benzamide Following general procedure F, N-[[4-[4-amino-1-(3-piperidyl)pyrazolo[3,4-d]pyrimidin-3-yl]-2-fluoro-phenyl]methyl]-2-methoxy-benzamide (159 mg, 0.33 mmol) afforded N-[[4-[4-amino-1-[(3R)-1-prop-2-enoyl-3-piperidyl]pyrazolo[3,4-d]pyrimidin-3-yl]-2-fluoro-phenyl]methyl]-2-methoxy-benzamide (24 mg, 0.05 mmol, 14% yield) as a white powder.
UPLC-MS (ES+, Short acidic): 1.45 min, m/z 530.4 [M+H]+
UPLC-MS (ES+, Long acidic): 3.28 min, m/z 530.4 [M+H]+
$^1$H NMR (400 MHz, DMSO-$d_6$) δ (ppm, 1:1 mixture of conformers) 8.76 (t, J 6.0 Hz, 1H, NH), 8.28 (s, 1H, ArH), 7.77 (dd, J 7.6, 1.7 Hz, 1H), 7.58-7.40 (m, 4H, ArH), 7.20-7.15 (m, 1H, ArH), 7.08-7.02 (m, 1H, ArH), 6.92-6.62 (m, 1H), 6.18-6.00 (m, 1H), 5.76-5.53 (m, 1H), 4.84-4.64 (m, 1H), 4.61 (d, J 6.0 Hz, 2H), 4.57-4.45 (m, 1H), 4.24-4.12 (m, 1H), 4.10-4.00 (m, 0.5H), 3.91 (s, 3H), 3.77-3.66 (m, 0.5H), 3.34-3.14 (m, 1H), 3.11-2.99 (m, 0.5H), 2.31-2.19 (m, 1H), 2.17-2.06 (m, 1H), 1.99-1.87 (m, 1H), 1.68-1.49 (m, 1H).

Example 66: N-[[4-[4-amino-1-[(3R)-1-prop-2-enoyl-3-piperidyl]-pyrazolo[3,4-d]pyrimidin-3-yl]phenyl]methyl]-2-fluoro-N-methyl-benzamide

[4-[[(2-Fluorobenzoyl)amino]methyl]phenyl]boronic acid

Following general procedure A, [4-(aminomethyl)phenyl]boronic acid hydrochloride (403 mg, 2.15 mmol) and 2-fluorobenzoic acid (274 mg, 1.96 mmol) gave [4-[[(2-fluorobenzoyl)amino]methyl]phenyl]boronic acid (430 mg, 1.2 mmol, 60% yield) as an off-white solid.
UPLC-MS (ES+, Short acidic): 1.32 min, m/z 274.1 [M+H]+

4-[[(2-Fluorobenzoyl)-methyl-amino]methyl]phenyl]boronic acid

To a solution of [4-[[(2-fluorobenzoyl)amino]methyl]phenyl]boronic acid (430 mg, 1.57 mmol) in DMF (11 mL) was added sodium hydride (195 mg, 4.88 mmol). The solution was stirred at room temperature for 1 h under a nitrogen atmosphere. After this time, iodomethane (0.3 mL, 4.88 mmol) was added, and the mixture was stirred overnight at room temperature. The reaction was diluted with saturated ammonium chloride (100 mL) before being extracted using ethyl acetate (2×100 mL). The combined organic layers were then washed with 0.1 M NaOH (100 mL), water (100 mL) and brine (2×100 mL). The yellow/brown solution was then dried over $Na_2SO_4$ and concentrated under reduced pressure to afford [4-[[(2-fluorobenzoyl)-methyl-amino]methyl]phenyl]boronic acid (390 mg, 0.95 mmol, 60% yield) as a yellow oil that solidified upon standing.

UPLC-MS: (ES+, Short acidic): 1.44 min, 288.1 m/z [M+H]+ tert-Butyl (3R)-3-[4-amino-3-[4-[[(2-fluorobenzoyl)-N-methylformamino]methyl]phenyl]-pyrazolo[3,4-d]pyrimidin-1-yl]piperidine-1-carboxylate Following general procedure D, [4-[[(2-fluorobenzoyl)amino]methyl]phenyl]boronic acid (337 mg, 0.86 mmol) and tert-butyl (3R)-3-(4-amino-3-iodo-pyrazolo[3,4-d]pyrimidin-1-yl)piperidine-1-carboxylate (240 mg, 0.54 mmol) gave tert-butyl (3R)-3-[4-amino-3-[4-[[(2-fluorobenzoyl)-N-methylformamido]methyl]phenyl]pyrazolo[3,4-d]pyrimidin-1-yl]-piperidine-1-carboxylate (299 mg, 0.51 mmol, 94% yield) as a dark brown foam.

UPLC-MS (ES+, Short acidic): 2.16 min, m/z 560.3 [M+H]+

N-[[4-[4-Amino-1-[(3R)-3-piperidyl]pyrazolo[3,4-d]pyrimidin-3-yl]phenyl]methyl]-2-fluoro-N-methyl-benzamide Following general procedure E, tert-butyl (3R)-3-[4-amino-3-[4-[[(2-fluorobenzoyl)-methyl-amino]methyl]phenyl]pyrazolo[3,4-d]pyrimidin-1-yl]piperidine-1-carboxylate (299 mg, 0.53 mmol) afforded N-[[4-[4-amino-1-[(3R)-3-piperidyl]pyrazolo[3,4-d]pyrimidin-3-yl]-phenyl]methyl]-2-fluoro-N-methyl-benzamide (215 mg, 0.44 mmol, 83% yield) as a brown foam.

UPLC-MS (ES+, Short acidic): 1.11 min, m/z 460.4 [M+H]+

N-[[4-[4-Amino-1-[(3R)-1-prop-2-enoyl-3-piperidyl]pyrazolo[3,4-d]pyrimidin-3-yl]-phenyl]-methyl]-2-fluoro-N-methyl-benzamide Following general procedure F, N-[[4-[4-amino-1-[(3R)-3-piperidyl]pyrazolo[3,4-d-]pyrimidin-3-yl]phenyl]methyl]-2-fluoro-N-methyl-benzamide (215 mg, 0.47 mmol) gave N-[[4-[4-amino-1-[(3R)-1-prop-2-enoyl-3-piperidyl]pyrazolo[3,4-d]pyrimidin-3-yl]phenyl]methyl]-2-fluoro-N-methyl-benzamide (42 mg, 0.08 mmol, 17% yield) as an off-white foam.

UPLC-MS (ES+, Short acidic): 1.41 min, m/z 514.4 [M+H]+

UPLC-MS (ES+, Long acidic): 3.17 min, m/z 514.5 [M+H]+

$^1$H NMR (400 MHz, DMSO-d$_6$) δ (ppm, 1:1 mixture of conformers) 8.30-8.24 (m, 1H, ArH), 7.73-7.67 (m, 1H, ArH), 7.66-7.61 (m, 1H, ArH), 7.57-7.46 (m, 3H, ArH), 7.38-7.26 (m, 3H, ArH), 6.93-6.63 (m, 1H), 6.19-6.00 (m, 1H), 5.76-5.52 (m, 1H), 4.81 (s, 1.2H), 4.78-4.64 (m, 1H), 4.60-4.51 (m, 1H), 4.49 (s, 0.8H), 4.26-4.15 (m, 1H), 4.13-4.03 (m, 0.5H), 3.76-3.65 (m, 0.5H), 3.28-3.14 (m, 1H), 3.06-3.00 (m, 0.5H), 2.99 (s, 1.2H), 2.83 (s, 1.8H), 2.31-2.20 (m, 1H), 2.18-2.08 (m, 1H), 1.98-1.89 (m, 1H), 1.68-1.51 (m, 1H).

Example 67: N-[[4-[4-Amino-1-[(3R)-1-prop-2-enoyl-3-piperidyl]pyrazolo[3,4-d]pyrimidin-3-yl]phenyl]methyl]-3-methoxy-benzamide

[4-[[(3-Methoxybenzyl)amino]methyl]phenyl]boronic acid

Following general procedure B, [4-(aminomethyl)phenyl]boronic acid hydrochloride (300 mg, 1.60 mmol) and 3-methoxybenzoyl chloride (0.25 mL, 1.76 mmol) gave [4-[[(3-methoxybenzoyl)amino]methyl]phenyl]boronic acid (435 mg, 1.07 mmol, 68% yield) as an off-white solid.

UPLC-MS (ES+, Short acidic): 1.27 min, m/z 285.8 [M+H]+ tert-Butyl (3R)-3-[4-amino-3-[4-[[(3-methoxybenzoyl)amino]methyl]phenyl]pyrazolo[3,4-d]pyrimidin-1-yl]piperidine-1-carboxylate Following general procedure D, [4-[[(3-methoxybenzoyl)amino]methyl]phenyl]boronic acid (144 mg, 0.51 mmol) and tert-butyl (3R)-3-(4-amino-3-iodo-pyrazolo[3,4-d]pyrimidin-1-yl)piperidine-1-carboxylate (150 mg, 0.36 mmol) gave tert-butyl (3R)-3-[4-amino-3-[4-[[(3-methoxybenzoyl)amino]methyl]phenyl]pyrazolo[3,4-d]pyrimidin-1-yl]piperidine-1-carboxylate (149 mg, 0.28 mmol, 79% yield) as a yellow solid.

UPLC-MS (ES+, Short acidic): 1.64 min, m/z 558.5 [M+H]+

N-[[4-[4-Amino-1-[(3R)-3-piperidyl]pyrazolo[3,4-d]pyrimidin-3-yl]phenyl]methyl]-3-methoxy-benzamide Following general procedure E, tert-butyl (3R)-3-[4-amino-3-[4-[[(3-methoxybenzoyl)amino]methyl]phenyl]pyrazolo[3,4-d]pyrimidin-1-yl]piperidine-1-carboxylate (149 mg, 0.27 mmol) afforded N-[[4-[4-amino-1-[(3R)-3-piperidyl]pyrazolo[3,4-d]pyrimidin-3-yl]phenyl]methyl]-3-methoxy-benzamide (69 mg, 0.16 mmol, 56% yield) as a yellow oil.

UPLC-MS (ES+, Short acidic): 1.10 min, m/z 458.3 [M+H]+

N-[[4-[4-Amino-1-[(3R)-1-prop-2-enoyl-3-piperidyl]pyrazolo[3,4-d]pyrimidin-3-yl]phenyl]methyl]-3-methoxy-benzamide Following general procedure F, N-[[4-[4-amino-1-[(3R)-3-piperidyl]pyrazolo[3,4-d]pyrimidin-3-yl]phenyl]methyl]-3-methoxy-benzamide (69 mg, 0.15 mmol) gave N-[[4-[4-amino-1-[(3R)-1-prop-2-enoyl-3-piperidyl]pyrazolo[3,4-d]pyrimidin-3-yl]phenyl]methyl]-3-methoxy-benzamide (10 mg, 0.02 mmol, 13% yield) as a white solid.

UPLC-MS (ES+, Short acidic): 1.37 min, m/z 512.4 [M+H]+

UPLC-MS (ES+, Long acidic): 3.05 min, m/z 512.4 [M+H]+

$^1$H NMR (400 MHz, DMSO-d$_6$) δ (ppm, 1:1 mixture of conformers) 9.10 (t, J 6.0 Hz, 1H, NH), 8.26 (s, 1H, ArH), 7.67-7.60 (m, 2H, ArH), 7.53-7.45 (m, 4H, ArH), 7.40 (dd, J 8.0, 7.8 Hz, 1H 7.11 (ddd, J 8.0, 2.7, 1.0 Hz, 1H 6.93-6.63 (m, 1H), 6.17-6.00 (m, 1H), 5.75-5.54 (m, 1H), 4.79-4.62 (m, 1H), 4.56 (d, J 6.0 Hz, 2H), 4.55-4.50 (m, 0.5H), 4.25-4.15 (m, 1H), 4.12-4.02 (m, 0.5H), 3.81 (s, 3H), 3.75-3.62 (m, 0.5H), 3.25-3.12 (m, 1H), 3.07-2.94 (m, 0.5H), 2.30-2.20 (m, 1H), 2.16-2.06 (m, 1H), 1.98-1.86 (m, 1H), 1.67-1.50 (m, 1H).

Example 68: N-[[3-[4-amino-1-[(3R)-1-prop-2-enoyl-3-piperidyl]pyrazolo[3,4-d]pyrimidin-3-yl]phenyl]methyl]-2,6-difluoro-benzamide

[3-[[(2,6-Difluorobenzoyl)amino]methyl]phenyl]boronic acid

Following general procedure B, 2,6-difluorobenzoyl chloride (0.14 mL, 1.13 mmol) and (3-(aminomethyl)phenyl)

boronic acid hydrochloride (212 mg, 1.13 mmol) afforded [3-[[(2,6-difluorobenzoyl)amino]methyl]phenyl]boronic acid (143 mg, 0.49 mmol, 43% yield) as a white solid.

UPLC-MS (ES+, Short acidic): 1.24 min, m/z 291.8 [M+H]+ tert-Butyl (3R)-3-[4-amino-3-[3-[[(2,6-difluorobenzoyl)amino]methyl]phenyl]pyrazolo[3,4-d]pyrimidin-1-yl]piperidine-1-carboxylate Following general procedure D, [3-[[(2,6-difluorobenzoyl)amino]methyl]phenyl]boronic acid (147 mg, 0.51 mmol) and tert-butyl (3R)-3-(4-amino-3-iodo-pyrazolo[3,4-d]pyrimidin-1-yl)piperidine-1-carboxylate (150 mg, 0.34 mmol) gave tert-butyl (3R)-3-[4-amino-3-[3-[[(2,6-difluorobenzoyl)amino]methyl]phenyl]pyrazolo[3,4-d]pyrimidin-1-yl]piperidine-1-carboxylate (170 mg, 0.30 mmol, 89% yield) as an off-white foam.

UPLC-MS (ES+, Short acidic): 1.64 min, m/z 564.5 [M+H]+

N-[[3-[4-Amino-1-[(3R)-3-piperidyl]pyrazolo[3,4-d]pyrimidin-3-yl]phenyl]methyl]-2,6-difluoro-benzamide Following general procedure E, tert-butyl (3R)-3-[4-amino-3-[3-[[(2,6-difluorobenzoyl)amino]methyl]phenyl]pyrazolo[3,4-d]pyrimidin-1-yl]piperidine-1-carboxylate (170 mg, 0.30 mmol) gave N-[[3-[4-amino-1-[(3R)-3-piperidyl]pyrazolo[3,4-d]pyrimidin-3-yl]phenyl]methyl]-2,6-difluoro-benzamide (141 mg, 0.30 mmol, quantitative) as a dark yellow foam.

UPLC-MS (ES+, Short acidic): 1.08 min, m/z 464.3 [M+H]+

N-[[3-[4-Amino-1-[(3R)-1-prop-2-enoyl-3-piperidyl]pyrazolo[3,4-d]pyrimidin-3-yl]phenyl]methyl]-2,6-difluoro-benzamide Following general procedure F, N-[[3-[4-amino-1-[(3R)-3-piperidyl]pyrazolo[3,4-d]pyrimidin-3-yl]phenyl]methyl]-2,6-difluoro-benzamide (141 mg, 0.30 mmol) afforded N-[[3-[4-amino-1-[(3R)-1-prop-2-enoyl-3-piperidyl]pyrazolo[3,4-d]pyrimidin-3-yl]phenyl]methyl]-2,6-difluoro-benzamide (47 mg, 0.09 mmol, 30% yield) as a white solid.

UPLC-MS (ES+, Short acidic): 1.35 min, m/z 518.4 [M+H]+

UPLC-MS (ES+, Long acidic): 2.98 min, m/z 518.4 [M+H]+

$^1$H NMR (400 MHz, DMSO-d$_6$) δ (ppm, 1:1 mixture of conformers) 9.32 (t, J 6.0 Hz, 1H, NH), 8.27 (s, 1H, ArH), 7.68-7.63 (m, 1H, ArH), 7.59-7.48 (m, 3H, ArH), 7.47-7.42 (m, 1H, ArH), 7.21-7.13 (m, 2H, ArH), 6.93-6.66 (m, 1H), 6.20-6.01 (m, 1H), 5.76-5.55 (m, 1H), 4.81-4.64 (m, 1H), 4.62-4.47 (m, 2.5H), 4.31-4.18 (m, 1H), 4.13-4.05 (m, 0.5H), 3.74-3.65 (m, 0.5H), 3.25-3.13 (m, 1H), 3.03-2.88 (m, 0.5H), 2.35-2.20 (m, 1H), 2.18-2.06 (m, 1H), 1.98-1.88 (m, 1H), 1.69-1.51 (m, 1H).

Example 69: N-[[4-[4-Amino-1-[(3R)-1-prop-2-enoyl-3-piperidyl]pyrazolo[3,4-d]pyrimidin-3-yl]phenyl]methyl]-2-(trifluoromethyl)benzamide

[4-[[[2-(Trifluoromethyl)benzoyl]amino]methyl]phenyl]boronic acid

Following general procedure B, [4-(aminomethyl)phenyl]boronic acid hydrochloride (300 mg, 1.6 mmol) and 2-(trifluoromethyl)benzoyl chloride (0.26 mL, 1.76 mmol) afforded the title compound (348 mg, 1.08 mmol, 67% yield).

UPLC-MS (ES+, short acidic): 1.32 min, m/z 324.0 [M+H]+ tert-Butyl (3R)-3-[4-amino-3-[4-[[[2-(trifluoromethyl)benzoyl]amino]methyl]phenyl]pyrazolo[3,4-d]pyrimidin-1-yl]piperidine-1-carboxylate Following general procedure D, [4-[[[2-(trifluoromethyl)benzoyl]amino]methyl]phenyl]boronic acid (348 mg, 1.08 mmol) afforded the title compound (310 mg, 0.52 mmol, 92% yield) as an orange solid.

UPLC-MS (ES+, Short acidic): 2.17 min, m/z 596.3 [M+H]+

N-[[4-[4-Amino-1-[(3R)-3-piperidyl]pyrazolo[3,4-d]pyrimidin-3-yl]phenyl]methyl]-2-(trifluoromethyl)benzamide Following general procedure E, tert-butyl (3R)-3-[4-amino-3-[4-[[[2-(trifluoromethyl)benzoyl]amino]methyl]phenyl]pyrazolo[3,4-d]pyrimidin-1-yl]piperidine-1-carboxylate (310 mg, 0.52 mmol) afforded the title compound (210 mg, 0.42 mmol, 81% yield) as an off-white solid.

UPLC-MS (ES+, Short acidic): 1.11 min, m/z 496.3 [M+H]+

N-[[4-[4-Amino-1-[(3R)-1-prop-2-enoyl-3-piperidyl]pyrazolo[3,4-d]pyrimidin-3-yl]phenyl]methyl]-2-(trifluoromethyl)benzamide Following general procedure F, N-[[4-[4-amino-1-[(3R)-3-piperidyl]pyrazolo[3,4-d]pyrimidin-3-yl]phenyl]methyl]-2-(trifluoromethyl)benzamide (210 mg, 0.42 mmol) afforded the title compound (54 mg, 0.10 mmol, 23% yield) as a white powder.

UPLC-MS (ES+, Short acidic): 1.41 min, m/z 550.4 [M+H]+

UPLC-MS (ES+, Long acidic): 3.14 min, m/z 550.4 [M+H]+

$^1$H NMR (400 MHz, DMSO-d$_6$) δ (ppm, 1:1 mixture of conformers) 9.11 (t, J 5.9 Hz, 1H, NH), 8.27 (s, 1H, ArH), 7.83-7.78 (m, 1H, ArH), 7.78-7.72 (m, 1H, ArH), 7.70-7.58 (m, 4H, ArH), 7.55-7.48 (m, 2H, ArH), 6.92-6.65 (m, 1H), 6.18-6.00 (m, 1H), 5.73-5.53 (m, 1H), 4.79-4.62 (m, 1H), 4.61-4.47 (m, 2.5H), 4.28-4.15 (m, 1H), 4.12-4.01 (m, 0.5H), 3.78-3.64 (m, 0.5H), 3.28-3.12 (m, 1H), 3.07-2.95 (m, 0.5H), 2.36-2.19 (m, 1H), 2.19-2.06 (m, 1H), 1.98-1.86 (m, 1H), 1.67-1.50 (m, 1H).

Example 70: N-[[4-[4-Amino-1-[(3R)-1-prop-2-enoyl-3-piperidyl]pyrazolo[3,4-d]pyrimidin-3-yl]phenyl]methyl]-2-methoxy-N-methyl-benzamide

[4-[[(2-Methoxybenzoyl)amino]methyl]phenyl]boronic acid

Following general procedure A, 2-methoxybenzoic acid (0.25 mL, 1.76 mmol) and [4-(aminomethyl)phenyl]boronic acid hydrochloride (300 mg, 1.60 mmol) afforded the title compound (370 mg, 1.3 mmol, 81%).

UPLC-MS (ES+, short acidic): 1.31 min, m/z 285.9 [M+H]+

[4-[[(2-Methoxybenzoyl)-methyl-amino]methyl] phenyl]boronic acid

To a solution of [4-[[(2-methoxybenzoyl)amino]methyl] phenyl]boronic acid (370 mg, 1.3 mmol) in DMF (15 mL) was added sodium hydride (160 mg, 4.00 mmol). The solution was stirred at 0° C. for 1 h under nitrogen. Iodomethane (0.3 mL, 4.00 mmol) was then added, and the mixture was stirred overnight at room temperature. The reaction was diluted with saturated ammonium chloride (100 mL) before being extracted with EtOAc (2×100 mL). The combined organic layers were then washed with 0.1 M NaOH (100 mL), water (100 mL) and brine (100 mL). The light yellow solution was then dried over $Na_2SO_4$ and concentrated in vacuo to the title compound (167 mg, 0.60 mmol, 43% yield) as a light yellow solid.

UPLC-MS (ES$^+$, short acidic): 1.45 min, 300.1 m/z [M+H]$^+$ tert-Butyl (3R)-3-[4-amino-3-[4-[[(2-methoxybenzoyl)-methyl-amino]methyl]phenyl]pyrazolo[3,4-d]pyrimidin-1-yl]piperidine-1-carboxylate Following general procedure D, [4-[[(2-methoxybenzoyl)-methyl-amino]methyl]phenyl]boronic acid (167 mg, 0.56 mmol) afforded the title compound (79 mg, 0.14 mmol, 31% yield) as an orange solid.

UPLC-MS (ES$^+$, Short acidic): 2.14 min, m/z 572.3 [M+H]$^+$

N-[[4-[4-Amino-1-[(3R)-3-piperidyl]pyrazolo[3,4-d] pyrimidin-3-yl]phenyl]methyl]-2-methoxy-N-methyl-benzamide Following general procedure E, tert-butyl (3R)-3-[4-amino-3-[4-[[(2-methoxybenzoyl)-methyl-amino]methyl] phenyl]pyrazolo[3,4-d]pyrimidin-1-yl]piperidine-1-carboxylate (79.0 mg, 0.14 mmol) afforded the title compound (60 mg, 0.13 mmol, 92% yield) as an off-white solid.

UPLC-MS (ES$^+$, Short acidic): 1.16 min, m/z 472.3 [M+H]$^+$

N-[[4-[4-Amino-1-[(3R)-1-prop-2-enoyl-3-piperidyl] pyrazolo[3,4-d]pyrimidin-3-yl]phenyl]methyl]-2-methoxy-N-methyl-benzamide Following general procedure F, N-[[4-[4-amino-1-[(3R)-3-piperidyl]pyrazolo[3,4-d]pyrimidin-3-yl]phenyl]methyl]-2-methoxy-N-methyl-benzamide (60 mg, 0.13 mmol afforded the title compound (2 mg, 0.01 mmol, 3% yield) as a white solid.

UPLC-MS (ES$^+$, Short acidic): 1.41 min, m/z 526.4 [M+H]$^+$

UPLC-MS (ES$^+$, Long acidic): 3.16 min, m/z 526.5 [M+H]$^+$ $^1$H NMR (400 MHz, DMSO-d$_6$) δ (ppm, mixture of conformers) 8.30-8.25 (m, 1H, ArH), 7.73-7.67 (m, 1H, ArH), 7.66-7.59 (m, 1H, ArH), 7.55-7.49 (m, 1H, ArH), 7.46-7.36 (m, 1H, ArH), 7.35-7.30 (m, 1H, ArH), 7.30-7.24 (m, 1H, ArH), 7.15-6.96 (m, 2H, ArH), 6.92-6.66 (m, 1H), 6.20-6.00 (m, 1H), 5.74-5.54 (m, 1H), 4.99-4.87 (m, 0.5H), 4.79-4.49 (m, 2.5H), 4.57 (d, J 5.9 Hz, 2H), 4.39 (s, 0.8H), 4.27-4.13 (m, 1H), 4.13-4.01 (m, 0.5H), 3.86 (s, 2H), 3.81 (s, 1H), 3.75-3.66 (m, 0.5H), 3.25-3.14 (m, 1H), 3.07-2.96 (m, 0.5H), 2.93 (s, 1.2H), 2.73 (s, 2H), 2.31-2.19 (m, 1H), 2.18-2.07 (m, 1H), 1.99-1.88 (m, 1H), 1.67-1.51 (m, 1H).

Example 71: N-[[4-[4-amino-1-[(3R)-1-prop-2-enoyl-3-piperidyl]pyrazolo[3,4-d]pyrimidin-3-yl] phenyl]methyl]-2-methoxy-benzamide

[3-[[[(2-Methoxybenzoyl)amino]methyl]phenyl] boronic acid

Following general procedure A, [3-(aminomethyl)phenyl] boronic acid hydrochloride (271 mg, 1.45 mmol) and 2-methoxybenzoic acid (200 mg, 1.31 mmol) gave [3-[[(2-methoxybenzoyl)amino]methyl]phenyl]boronic acid (286 mg, 1.00 mmol, 76% yield) as a pale yellow foam.

UPLC-MS (ES$^+$, Short acidic): 1.32 min, m/z 285.8 [M+H]$^+$ tert-Butyl (3R)-3-[4-amino-3-[3-[[(2-methoxybenzoyl)amino]methyl]phenyl]pyrazolo[3,4-d]pyrimidin-1-yl]piperidine-1-carboxylate Following general procedure D, [4-[[[4-fluoro-3-(trifluoromethyl)benzoyl]amino]methyl]phenyl]boronic acid (230 mg, 0.68 mmol) and tert-butyl (3R)-3-(4-amino-3-iodopyrazolo[3,4-d]pyrimidin-1-yl)piperidine-1-carboxylate (200 mg, 0.45 mmol), gave tert-butyl (3R)-3-[4-amino-3-[3-[[(2-methoxybenzoyl)amino]methyl]phenyl]pyrazolo[3,4-d]pyrimidin-1-yl]piperidine-1-carboxylate (236 mg, 0.42 mmol, 94% yield) as a yellow film.

UPLC-MS (ES$^+$, Short acidic): 1.70 min, m/z 558.5 [M+H]$^+$

N-[[3-[4-Amino-1-[(3R)-3-piperidyl]pyrazolo[3,4-d] pyrimidin-3-yl]phenyl]methyl]-2-methoxy-benzamide Following general procedure E, tert-butyl (3R)-3-[4-amino-3-[3-[[(2-methoxybenzoyl)amino]methyl]phenyl] pyrazolo[3,4-d]pyrimidin-1-yl]piperidine-1-carboxylate (236 mg, 0.42 mmol) gave crude N-[[3-[4-amino-1-[(3R)-3-piperidyl]pyrazolo[3,4-d]pyrimidin-3-yl]phenyl]methyl]-2-methoxy-benzamide (196 mg, 0.42 mmol, quantitative) as a pale yellow foam.

UPLC-MS (ES$^+$, Short acidic): 1.16 min, m/z 458.3 [M+H]$^+$

N-[[3-[4-Amino-1-[(3R)-1-prop-2-enoyl-3-piperidyl] pyrazolo[3,4-d]pyrimidin-3-yl]phenyl]methyl]-2-methoxy-benzamide Following general procedure F, N-[[3-[4-amino-1-[(3R)-3-piperidyl]pyrazolo[3,4-d]pyrimidin-3-yl]phenyl]methyl]-2-methoxy-benzamide (196 mg, 0.43 mmol) afforded N-[[3-[4-amino-1-[(3R)-1-prop-2-enoyl-3-piperidyl]pyrazolo[3,4-d]pyrimidin-3-yl]phenyl]methyl]-2-methoxy-benzamide (112 mg, 0.22 mmol, 51% yield) as a white solid.

UPLC-MS (ES$^+$, Short acidic): 1.41 min, m/z 512.4 [M+H]$^+$

UPLC-MS (ES$^+$, Long acidic): 3.14 min, m/z 512.4 [M+H]$^+$ $^1$H NMR (400 MHz, DMSO-d$_6$) δ (ppm, 1:1 mixture of conformers) 8.79 (t, J 6.0 Hz, 1H, NH), 8.27 (s, 1H, ArH), 7.76 (dd, J 7.7, 1.8 Hz, 1H, ArH), 7.67-7.62 (m, 1H, ArH), 7.57-7.43 (m, 4H, ArH), 7.17-7.12 (m, 1H, ArH), 7.02 (dt, J 7.5, 1.0 Hz, 1H, ArH), 6.91-6.67 (m, 1H), 6.17-6.01 (m, 1H), 5.74-5.55 (m, 1H), 4.78-4.64 (m, 1H), 4.58 (d, J 6.0 Hz, 2H), 4.55-4.51 (m, 0.5H), 4.30-4.16 (m, 1H), 4.13-4.03 (m, 0.5H), 3.87 (s, 3H), 3.72-3.62 (m, 0.5H), 3.25-3.10 (m, 1H), 3.03-2.91 (m, 0.5H), 2.31-2.19 (m, 1H), 2.17-2.07 (m, 1H), 1.98-1.87 (m, 1H), 1.68-1.50 (m, 1H).

Example 72: N-[[3-[4-amino-1-[(3R)-1-prop-2-enoyl-3-piperidyl]pyrazolo[3,4-d]pyrimidin-3-yl]phenyl]methyl]-3-cyano-benzamide N-[3-[[(3-Cyanobenzoyl)amino]methyl]phenyl]boronic acid Following general procedure A, 3-cyanobenzoic acid (200 mg, 1.36 mmol) and [3-(aminomethyl)phenyl]boronic acid hydrochloride (280 mg, 1.50 mmol) gave crude [3-[[(3-cyanobenzoyl)amino]methyl]phenyl]boronic acid (461 mg, 1.65 mmol, assumed quantitative) as a pale yellow foam.
UPLC-MS (ES$^+$, Short acidic): 1.25 min, m/z 280.9 [M+H]$^+$ tert-Butyl (3R)-3-[4-amino-3-[3-[[(3-cyanobenzoyl)amino]methyl]phenyl]pyrazolo[3,4-d]pyrimidin-1-yl]piperidine-1-carboxylate Following general procedure D, [3-[[(3-cyanobenzoyl)amino]methyl]phenyl]boronic acid (236 mg, 0.84 mmol) and tert-butyl (3R)-3-(4-amino-3-iodo-pyrazolo[3,4-d]pyrimidin-1-yl)piperidine-1-carboxylate (250 mg, 0.56 mmol) gave tert-butyl (3R)-3-[4-amino-3-[3-[[(3-cyanobenzoyl)amino]methyl]phenyl]pyrazolo[3,4-d]pyrimidin-1-yl]piperidine-1-carboxylate (255 mg, 0.46 mmol, 82% yield) as a yellow foam
UPLC-MS (ES$^+$, Short acidic): 1.64 min, m/z 553.5 [M+H]$^+$ N-[[3-[4-Amino-1-[(3R)-3-piperidyl]pyrazolo[3,4-d]pyrimidin-3-yl]phenyl]methyl]-3-cyano-benzamide Following general procedure E, tert-butyl (3R)-3-[4-amino-3-[3-[[(3-cyanobenzoyl)amino]methyl]phenyl]pyrazolo[3,4-d]pyrimidin-1-yl]piperidine-1-carboxylate (255 mg, 0.46 mmol) gave N-[[3-[4-amino-1-[(3R)-3-piperidyl]pyrazolo[3,4-d]pyrimidin-3-yl]phenyl]methyl]-3-cyano-benzamide (197 mg, 0.44 mmol, 94% yield) as a yellow film.
UPLC-MS (ES$^+$, Short acidic): 1.07 min, m/z 453.4 [M+H]$^+$ N-[[3-[4-Amino-1-[(3R)-1-prop-2-enoyl-3-piperidyl]pyrazolo[3,4-d]pyrimidin-3-yl]phenyl]methyl]-3-cyano-benzamide Following general procedure F, N-[[3-[4-amino-1-[(3R)-3-piperidyl]pyrazolo[3,4-d]pyrimidin-3-yl]phenyl]methyl]-3-cyano-benzamide (197 mg, 0.44 mmol) afforded N-[[3-[4-amino-1-[(3R)-1-prop-2-enoyl-3-piperidyl]pyrazolo[3,4-d]pyrimidin-3-yl]phenyl]methyl]-3-cyano-benzamide (51.2 mg, 0.10 mmol, 23% yield) as a white solid.
UPLC-MS (ES$^+$, Short acidic): 1.36 min, m/z 507.5 [M+H]$^+$
UPLC-MS (ES$^+$, Long acidic): 3.00 min, m/z 507.4 [M+H]$^+$
$^1$H NMR (400 MHz, DMSO-d$_6$) δ (ppm, 1:1 mixture of conformers) 9.33 (t, J 5.6 Hz, 1H, NH), 8.34-8.32 (m, 1H), 8.26 (s, 1H, ArH), 8.23-8.19 (m, 1H, ArH), 8.04-8.00 (m, 1H, ArH), 7.74-7.68 (m, 1H, ArH), 7.66-7.61 (m, 1H, ArH), 7.59-7.43 (m, 3H, ArH), 6.91-6.64 (m, 1H), 6.17-5.99 (m, 1H), 5.74-5.52 (m, 1H), 4.79-4.62 (m, 1H), 4.61-4.47 (m, 2.5H), 4.27-4.14 (m, 1H), 4.12-4.02 (m, 0.5H), 3.73-3.62 (m, 0.5H), 3.25-3.11 (m, 1H), 3.05-2.93 (m, 0.5H), 2.30-2.19 (m, 1H), 2.16-2.06 (m, 1H), 1.98-1.87 (m, 1H), 1.67-1.51 (m, 1H).

Example 73: N-[[3-[4-amino-1-[(3R)-1-prop-2-enoyl-3-piperidyl]pyrazolo[3,4-d]pyrimidin-3-yl]phenyl]methyl]-2,5-difluoro-benzamide

[3-[[(2,5-Difluorobenzoyl)amino]methyl]phenyl]boronic acid

Following general procedure B, (3-(aminomethyl)phenyl) boronic acid hydrochloride (318 mg, 1.70 mmol) and 2,5-difluorobenzoyl chloride (0.21 mL, 1.70 mmol) afforded [3-[[(2,5-difluorobenzoyl)amino]methyl]phenyl]boronic acid (112 mg, 0.39 mmol, 23% yield) as a white solid.
UPLC-MS (ES$^+$, Short acidic): 1.33 min, m/z 291.8 [M+H]$^+$ tert-Butyl (3R)-3-[4-amino-3-[3-[[(2,5-difluorobenzoyl)amino]methyl]phenyl]pyrazolo[3,4-d]pyrimidin-1-yl]piperidine-1-carboxylate Following general procedure D, tert-butyl (3R)-3-(4-amino-3-iodo-pyrazolo[3,4-d]pyrimidin-1-yl)piperidine-1-carboxylate (170 mg, 0.38 mmol) and [3-[[(2,5-difluorobenzoyl)amino]methyl]phenyl]boronic acid (167 mg, 0.57 mmol) afforded tert-butyl (3R)-3-[4-amino-3-[3-[[(2,5-difluorobenzoyl)amino]methyl]phenyl]pyrazolo[3,4-d]pyrimidin-1-yl]piperidine-1-carboxylate (135 mg, 0.24 mmol, 63% yield) as a yellow film.
UPLC-MS (ES$^+$, Short acidic): 1.72 min, m/z 564.5 [M+H]$^+$ N-[[3-[4-Amino-1-[(3R)-3-piperidyl]pyrazolo[3,4-d]pyrimidin-3-yl]phenyl]methyl]-2,5-difluoro-benzamide Following general procedure E, tert-butyl (3R)-3-[4-amino-3-[3-[[(2,5-difluorobenzoyl)amino]methyl]phenyl]pyrazolo[3,4-d]pyrimidin-1-yl]piperidine-1-carboxylate (135 mg, 0.24 mmol) gave N-[[3-[4-amino-1-[(3R)-3-piperidyl]pyrazolo[3,4-d]pyrimidin-3-yl]phenyl]methyl]-2,5-difluoro-benzamide (98 mg, 0.21 mmol, 89% yield) as a yellow film.
UPLC-MS (ES$^+$, Short acidic): 1.14 min, m/z 464.3 [M+H]$^+$ N-[[3-[4-Amino-1-[(3R)-1-prop-2-enoyl-3-piperidyl]pyrazolo[3,4-d]pyrimidin-3-yl]phenyl]methyl]-2,5-difluoro-benzamide Following general procedure F, N-[[3-[4-amino-1-[(3R)-3-piperidyl]pyrazolo[3,4-d]pyrimidin-3-yl]phenyl]methyl]-2,5-difluoro-benzamide (98 mg, 0.21 mmol) afforded N-[[3-[4-amino-1-[(3R)-1-prop-2-enoyl-3-piperidyl]pyrazolo[3,4-d]pyrimidin-3-yl]phenyl]methyl]-2,5-difluoro-benzamide (29 mg, 0.06 mmol, 26% yield) as a white solid.
UPLC-MS (ES$^+$, Short acidic): 1.42 min, m/z 518.3 [M+H]$^+$
UPLC-MS (ES$^+$, Long acidic): 3.15 min, m/z 518.3 [M+H]$^+$
$^1$H NMR (400 MHz, DMSO-d$_6$) δ (ppm, 1:1 mixture of conformers) 9.07-8.99 (m, 1H, NH), 8.27 (s, 1H, ArH), 7.67-7.60 (m, 1H, ArH), 7.59-7.31 (m, 6H, ArH), 6.92-6.67 (m, 1H), 6.17-6.02 (m, 1H), 5.75-5.55 (m, 1H), 4.78-4.64 (m, 1H), 4.59-4.50 (m, 2.5H), 4.30-4.16 (m, 1H), 4.13-4.03

(m, 0.5H), 3.75-3.63 (m, 0.5H), 3.25-3.10 (m, 1H), 3.03-2.91 (m, 0.5H), 2.31-2.19 (m, 1H), 2.17-2.07 (m, 1H), 1.98-1.87 (m, 1H), 1.67-1.49 (m, 1H).

Example 74: N-[[4-[4-amino-1-[(3R)-1-[[(2R)-oxiran-2-yl]methyl]-3-piperidyl]pyrazolo[3,4-d]pyrimidin-3-yl]phenyl]methyl]-2-methoxy-benzamide To a solution of N-[[4-[4-amino-1-[(3R)-3-piperidyl]pyrazolo[3,4-d]pyrimidin-3-yl]phenyl]methyl]-2-methoxy-benzamide (110 mg, 0.24 mmol) in DMF (1 mL) were added successively N,N-diisopropylethylamine (0.05 mL, 0.26 mmol) and (S)-glycidyl nosylate (69 mg, 0.26 mmol). The mixture was stirred at room temperature for 2 days, quenched with an aqueous sodium bicarbonate solution (20 mL) and then extracted (×3) with EtOAc. The combined organics were dried over $Na_2SO_4$, filtered and concentrated. Further purification by flash column chromatography (1-10% 1N $NH_3$ in MeOH/EtOAc) gave N-[[4-[4-amino-1-[(3R)-1-[[(2R)-oxiran-2-yl]methyl]-3-piperidyl]pyrazolo[3,4-d]pyrimidin-3-yl]phenyl]methyl]-2-methoxy-benzamide (15 mg, 0.03 mmol, 12% yield) as an off-white solid.

UPLC-MS (ES$^+$, Short acidic): 1.23 min, m/z 514.2 [M+H]$^+$

UPLC-MS (ES$^+$, Long acidic): 2.55 min, m/z 514.3 [M+H]$^+$ $^1$H NMR (400 MHz, DMSO-d$_6$) δ (ppm, 1:1 mixture of conformers) 8.77 (t, J 6.1 Hz, 1H, NH), 8.25 (s, 1H, ArH), 7.77 (dd, J 7.6, 1.7 Hz, 1H, ArH), 7.66-7.60 (m, 2H, ArH), 7.54-7.45 (m, 3H, ArH), 7.18-7.13 (m, 1H, ArH), 7.04 (dt, J 7.6, 1.0 Hz, 1H, ArH), 4.93-4.72 (m, 1H), 4.58 (d, J 6.1 Hz, 2H), 3.90 (s, 3H), 3.21-2.68 (m, 5H), 2.46-1.91 (m, 6H), 1.89-1.77 (m, 1H), 1.76-1.59 (m, 1H).

Example 75: N-[[3-[4-amino-1-[(3R)-1-prop-2-enoyl-3-piperidyl]pyrazolo[3,4-d]pyrimidin-3-yl]phenyl]methyl]-3-(trifluoromethyl)benzamide N-[[3-(4,4,5,5-tetramethyl-1,3,2-dioxaborolan-2-yl)phenyl]methyl]-3-(trifluoromethyl)benzamide Under $N_2$, a stirred solution of sodium hydride (60% dispersed in mineral oil) (54 mg, 1.35 mmol) in THF (6 mL) was cooled to 0° C. using an ice bath before 3-(trifluoromethyl)benzamide (153 mg, 0.81 mmol) was added. The resulting solution was stirred at this temperature for 1 h30 before 2-[3-(bromomethyl)phenyl]-4,4,5,5-tetramethyl-1,3,2-dioxaborolane (200 mg, 0.67 mmol) was added and the solution allowed to warm to room temperature and was stirred overnight. The solution was diluted with EtOAc (20 mL) and quenched with a saturated ammonium chloride solution (20 mL) before being partitioned. The aqueous layer was washed with EtOAc (3×10 mL) before the combined organics were washed with water (30 mL) and brine (30 mL). The combined organics were dried ($Na_2SO_4$), filtered and concentrated to dryness in vacuo to afford crude N-[[3-(4,4,5,5-tetramethyl-1,3,2-dioxaborolan-2-yl)phenyl]methyl]-3-(trifluoromethyl)benzamide (400 mg, 0.56 mmol, 84% yield) as a clear oil that crystallised upon standing.

UPLC-MS (ES$^+$, Short acidic): 1.99 min, m/z 406 [M+H]$^+$ tert-Butyl (3R)-3-[4-amino-3-[3-[[[3-(trifluoromethyl)benzoyl]amino]methyl]phenyl]pyrazolo[3,4-d]pyrimidin-1-yl]piperidine-1-carboxylate Following general procedure D, N-[[3-(4,4,5,5-tetramethyl-1,3,2-dioxaborolan-2-yl)phenyl]methyl]-3-(trifluoromethyl)benzamide (274 mg, 0.68 mmol) and tert-butyl (3R)-3-(4-amino-3-iodo-pyrazolo[3,4-d]pyrimidin-1-yl)piperidine-1-carboxylate (200 mg, 0.45 mmol) gave tert-butyl (3R)-3-[4-amino-3-[3-[[[3-(trifluoromethyl)benzoyl]amino]methyl]phenyl]pyrazolo[3,4-d]pyrimidin-1-yl]piperidine-1-carboxylate (129 mg, 0.22 mmol, 48% yield) as a dark yellow foam.

UPLC-MS (ES$^+$, Short acidic): 1.84 min, m/z 596.5 [M+H]$^+$

N-[[3-[4-Amino-1-[(3R)-3-piperidyl]pyrazolo[3,4-d]pyrimidin-3-yl]phenyl]methyl]-3-(trifluoromethyl)benzamide Following general procedure E, tert-butyl (3R)-3-[4-amino-3-[3-[[[3-(trifluoromethyl)benzoyl]amino]methyl]phenyl]pyrazolo[3,4-d]pyrimidin-1-yl]piperidine-1-carboxylate (129 mg, 0.22 mmol) gave N-[[3-[4-amino-1-[(3R)-3-piperidyl]pyrazolo[3,4-d]pyrimidin-3-yl]phenyl]methyl]-3-(trifluoromethyl)benzamide (99 mg, 0.20 mmol, 92% yield) as a yellow film.

UPLC-MS (ES$^+$, Short acidic): 1.30 min, m/z 496.4 [M+H]$^+$

N-[[3-[4-Amino-1-[(3R)-1-prop-2-enoyl-3-piperidyl]pyrazolo[3,4-d]pyrimidin-3-yl]phenyl]methyl]-3-(trifluoromethyl)benzamide Following general procedure F, N-[[3-[4-amino-1-[(3R)-3-piperidyl]pyrazolo[3,4-d]pyrimidin-3-yl]phenyl]methyl]-3-(trifluoromethyl)benzamide (99 mg, 0.20 mmol) afforded N-[[3-[4-amino-1-[(3R)-1-prop-2-enoyl-3-piperidyl]pyrazolo[3,4-d]pyrimidin-3-yl]phenyl]methyl]-3-(trifluoromethyl)benzamide (39 mg, 0.07 mmol, 36% yield) as a white solid.

UPLC-MS (ES$^+$, Short acidic): 1.54 min, m/z 550.4 [M+H]$^+$

UPLC-MS (ES$^+$, Long acidic): 3.47 min, m/z 550.4 [M+H]$^+$ $^1$H NMR (400 MHz, DMSO-d$_6$) δ (ppm, 1:1 mixture of conformers) 9.37 (t, J 5.4 Hz, 1H, NH), 8.31-8.17 (m, 3H, ArH), 7.95-7.90 (m, 1H, ArH), 7.78-7.68 (m, 1H, ArH), 7.67-7.62 (m, 1H, ArH), 7.59-7.43 (m, 3H, ArH), 6.92-6.64 (m, 1H), 6.17-6.01 (m, 1H), 5.74-5.54 (m, 1H), 4.80-4.63 (m, 1H), 4.61-4.49 (m, 2.5H), 4.29-4.15 (m, 1H), 4.12-4.01 (m, 0.5H), 3.72-3.61 (m, 0.5H), 3.25-3.11 (m, 1H), 3.05-2.91 (m, 0.5H), 2.32-2.19 (m, 1H), 2.17-2.06 (m, 1H), 1.97-1.87 (m, 1H), 1.67-1.49 (m, 1H).

Example 76: N-[[5-[4-amino-1-[(3R)-1-prop-2-enoyl-3-piperidyl]pyrazolo[3,4-d]pyrimidin-3-yl]-2-fluoro-phenyl]methyl]-2,5-difluoro-benzamide

[3-[[(2,5-Difluorobenzoyl)amino]methyl]-4-fluoro-phenyl]boronic acid

Following general procedure A, [3-(aminomethyl)-4-fluoro-phenyl]boronic acid (200 mg, 1.18 mmol) and 2,5-difluorobenzoyl chloride (0.14 mL, 1.12 mmol) afforded [3-[[(2,5-difluorobenzoyl)amino]methyl]-4-fluoro-phenyl]boronic acid (341 mg, 1.10 mmol, 93% yield) as a pale yellow film.

UPLC-MS (ES$^+$, Short acidic): 1.63 min, m/z 310.1 [M+H]$^+$ tert-Butyl (3R)-3-[4-amino-3-[3-[[(2,5-difluorobenzoyl)amino]methyl]-4-fluoro-phenyl]pyrazolo[3,4-d]pyrimidin-1-yl]piperidine-1-carboxylate Following general procedure D, tert-butyl (3R)-3-(4-amino-3-iodo-pyrazolo[3,4-d]pyrimidin-1-yl)piperidine-1-carboxylate (200 mg, 0.45 mmol) and [3-[[(2,5-difluorobenzoyl)amino]methyl]-4-fluoro-phenyl]boronic acid (209 mg, 0.68 mmol) afforded tert-butyl (3R)-3-[4-amino-3-[[(2,5-difluorobenzoyl)amino]methyl]-4-fluoro-phenyl]pyrazolo[3,4-d]pyrimidin-1-yl]piperidine-1-carboxylate (252 mg, 0.43 mmol, 96% yield) as a light brown film.

UPLC-MS (ES$^+$, Short acidic): 2.25 min, m/z 582.3 [M+H]$^+$

N-[[5-[4-Amino-1-[(3R)-3-piperidyl]pyrazolo[3,4-d]pyrimidin-3-yl]-2-fluoro-phenyl]methyl]-2,5-difluoro-benzamide Following general procedure E, tert-butyl (3R)-3-[4-amino-3-[3-[[(2,5-difluorobenzoyl)amino]methyl]-4-fluoro-phenyl]pyrazolo[3,4-d]pyrimidin-1-yl]piperidine-1-carboxylate (255 mg, 0.44 mmol) gave N-[[5-[4-amino-1-[(3R)-3-piperidyl]pyrazolo[3,4-d]pyrimidin-3-yl]-2-fluoro-phenyl]methyl]-2,5-difluoro-benzamide (48 mg, 0.10 mmol, 23% yield) as a pale brown foam.

UPLC-MS (ES$^+$, Short acidic): 1.27 min, m/z 482.2 [M+H]$^+$

N-[[5-[4-Amino-1-[(3R)-1-prop-2-enoyl-3-piperidyl]pyrazolo[3,4-d]pyrimidin-3-yl]-2-fluoro-phenyl]methyl]-2,5-difluoro-benzamide Following general procedure F, N-[[5-[4-amino-1-[(3R)-3-piperidyl]pyrazolo[3,4-d]pyrimidin-3-yl]-2-fluoro-phenyl]methyl]-2,5-difluoro-benzamide (155 mg, 0.32 mmol) afforded N-[[5-[4-amino-1-[(3R)-1-prop-2-enoyl-3-piperidyl]pyrazolo[3,4-d]pyrimidin-3-yl]-2-fluoro-phenyl]methyl]-2,5-difluoro-benzamide (59 mg, 0.11 mmol, 34% yield) as a white solid.

UPLC-MS (ES$^+$, Short acidic): 1.46 min, m/z 536.4 [M+H]$^+$

UPLC-MS (ES$^+$, Long acidic): 3.27 min, m/z 536.3 [M+H]$^+$ $^1$H NMR (400 MHz, DMSO-d$_6$) δ (ppm, 1:1 mixture of conformers) 9.05-8.99 (m, 1H, NH), 8.25 (s, 1H, ArH), 7.74-7.67 (m, 1H, ArH), 7.64-7.55 (m, 1H, ArH), 7.49-7.42 (m, 1H, ArH), 7.42-7.32 (m, 3H, ArH), 6.91-6.63 (m, 1H), 6.17-6.01 (m, 1H), 5.74-5.54 (m, 1H), 4.77-4.63 (m, 1H), 4.61-4.49 (m, 2.5H), 4.30-4.14 (m, 1H), 4.12-4.04 (m, 0.5H), 3.72-3.61 (m, 0.5H), 3.25-3.10 (m, 1H), 3.04-2.90 (m, 0.5H), 2.30-2.18 (m, 1H), 2.16-2.06 (m, 1H), 1.97-1.85 (m, 1H), 1.68-1.50 (m, 1H).

Example 77: N-[[5-[4-amino-1-[(3R)-1-prop-2-enoyl-3-piperidyl]pyrazolo[3,4-d]pyrimidin-3-yl]-2-fluoro-phenyl]methyl]-2-methoxy-benzamide

[4-Fluoro-3-[[(2-methoxybenzoyl)amino]methyl]phenyl]boronic acid

Following general procedure A, [3-(aminomethyl)-4-fluoro-phenyl]boronic acid (200 mg, 1.18 mmol) and 2-methoxybenzoic acid (0.12 mL, 1.12 mmol) afforded [4-fluoro-3-[[(2-methoxybenzoyl)amino]methyl]phenyl]boronic acid (269 mg, 0.18 mmol, 15% yield) as a colourless film.

UPLC-MS (ES$^+$, Short acidic): 1.60 min, m/z 304.0 [M+H]$^+$ tert-Butyl (3R)-3-[4-amino-3-[4-fluoro-3-[[(2-methoxybenzoyl)amino]methyl]phenyl]pyrazolo[3,4-d]pyrimidin-1-yl]piperidine-1-carboxylate Following general procedure D, tert-butyl (3R)-3-(4-amino-3-iodo-pyrazolo[3,4-d]pyrimidin-1-yl)piperidine-1-carboxylate (200 mg, 0.45 mmol) and [3-[[(2,5-difluorobenzoyl)amino]methyl]-4-fluoro-phenyl]boronic acid (209 mg, 0.68 mmol) afforded tert-butyl (3R)-3-[4-amino-3-[4-fluoro-3-[[(2-methoxybenzoyl)amino]methyl]phenyl]pyrazolo[3,4-d]pyrimidin-1-yl]piperidine-1-carboxylate (69 mg, 0.12 mmol, 27% yield) as a light brown film.

UPLC-MS (ES$^+$, Short acidic): 2.24 min, m/z 576.3 [M+H]$^+$

N-[[5-[4-Amino-1-[(3R)-3-piperidyl]pyrazolo[3,4-d]pyrimidin-3-yl]-2-fluoro-phenyl]methyl]-2-methoxy-benzamide Following general procedure E, tert-butyl (3R)-3-[4-amino-3-[4-fluoro-3-[[(2-methoxybenzoyl)amino]methyl]phenyl]pyrazolo[3,4-d]pyrimidin-1-yl]piperidine-1-carboxylate (69 mg, 0.12 mmol) afforded N-[[5-[4-amino-1-[(3R)-3-piperidyl]pyrazolo[3,4-d]pyrimidin-3-yl]-2-fluoro-phenyl]methyl]-2-methoxy-benzamide (48 mg, 0.10 mmol, 84% yield) as a pale brown foam.

UPLC-MS (ES$^+$, Short acidic): 1.18 min, m/z 476.2 [M+H]$^+$

N-[[5-[4-amino-1-[(3R)-1-prop-2-enoyl-3-piperidyl]pyrazolo[3,4-d]pyrimidin-3-yl]-2-fluoro-phenyl]methyl]-2-methoxy-benzamide Following general procedure F, N-[[5-[4-amino-1-[(3R)-3-piperidyl]pyrazolo[3,4-d]pyrimidin-3-yl]-2-fluoro-phenyl]methyl]-3-methoxy-benzamide (48 mg, 0.10 mmol) afforded N-[[5-[4-amino-1-[(3R)-1-prop-2-enoyl-3-piperidyl]pyrazolo[3,4-d]pyrimidin-3-yl]-2-fluoro-phenyl]methyl]-2-methoxy-benzamide (20 mg, 0.04 mmol, 36% yield) as a white solid.

UPLC-MS (ES$^+$, Short acidic): 1.45 min, m/z 530.4 [M+H]$^+$

UPLC-MS (ES$^+$, Long acidic): 3.27 min, m/z 530.4 [M+H]$^+$ $^1$H NMR (400 MHz, DMSO-d$_6$) δ (ppm, 1:1 mixture of conformers) 8.77 (t, J 5.9 Hz, 1H, NH), 8.24 (s, 1H, ArH), 7.74 (dd, J 7.7, 1.8 Hz, 1H, ArH), 7.71-7.65 (m, 1H, ArH), 7.60-7.54 (m, 1H, ArH), 7.50-7.43 (m, 1H, ArH), 7.40-7.33 (m, 1H, ArH), 7.16-7.11 (m, 1H, ArH), 7.05-6.99 (m, 1H, ArH), 6.90-6.65 (m, 1H), 6.16-6.00 (m, 1H), 5.74-5.53 (m, 1H), 4.75-4.46 (m, 4H), 4.30-4.14 (m, 1H), 4.12-4.01 (m, 0.5H), 3.84 (s, 3H), 3.70-3.59 (m, 0.5H), 3.23-3.09 (m, 1H), 2.99-2.86 (m, 0.5H), 2.30-2.17 (m, 1H), 2.15-2.05 (m, 1H), 1.96-1.84 (m, 1H), 1.68-1.48 (m, 1H).

Example 78: N-[[4-[4-amino-1-[(3R)-1-prop-2-enoyl-3-piperidyl]pyrazolo[3,4-d]pyrimidin-3-yl]phenyl]methyl]-2-fluoro-3-methyl-benzamide

[N-[[(2-Fluoro-3-methyl-benzoyl)amino]methyl]phenyl]boronic acid

Following general procedure A, [4-(aminomethyl)phenyl]boronic acid hydrochloride (107 mg, 0.57 mmol) and 2-fluoro-3-methylbenzoic acid (0.08 mL, 0.52 mmol) gave the title compound (67 mg, 0.23 mmol, 45% yield) as a yellow solid.

UPLC-MS (ES+, Short acidic): 1.35 min, m/z 287.8 [M+H]+ tert-Butyl (3R)-3-[4-amino-3-[4-[[(2-fluoro-3-methyl-benzoyl)amino]methyl]phenyl]pyrazolo[3,4-d]pyrimidin-1-yl]piperidine-1-carboxylate Following general procedure D, tert-butyl (3R)-3-(4-amino-3-iodo-pyrazolo[3,4-d]pyrimidin-1-yl)piperidine-1-carboxylate (200 mg, 0.45 mmol) and 2-fluoro-3-methyl-N-[[4-(4,4,5,5-tetramethyl-1,3,2-dioxaborolan-2-yl)phenyl]methyl]benzamide (249 mg, 0.68 mmol) gave the title compound (243 mg, 0.43 mmol, 96% yield) as a pale yellow foam.

UPLC-MS (ES+, Short acidic): 1.73 min, m/z 560.4 [M+H]+

N-[[4-[4-Amino-1-[(3R)-3-piperidyl]pyrazolo[3,4-d]pyrimidin-3-yl]phenyl]methyl]-2-fluoro-3-methyl-benzamide Following general procedure E, tert-butyl (3R)-3-[4-amino-3-[4-[[(2-fluoro-3-methyl-benzoyl)amino]methyl]phenyl]pyrazolo[3,4-d]pyrimidin-1-yl]piperidine-1-carboxylate (243 mg, 0.43 mmol) gave the title compound (177 mg, 0.39 mmol, 89% yield) as a yellow foam.

UPLC-MS (ES+, Short acidic): 1.17 min, m/z 460.3 [M+H]+

N-[[4-[4-Amino-1-[(3R)-1-prop-2-enoyl-3-piperidyl]pyrazolo[3,4-d]pyrimidin-3-yl]phenyl]methyl]-2-fluoro-3-methyl-benzamide Following general procedure F, N-[[4-[4-amino-1-[(3R)-3-piperidyl]pyrazolo[3,4-d]pyrimidin-3-yl]phenyl]methyl]-2-fluoro-3-methyl-benzamide (177 mg, 0.39 mmol) and acrylic acid (26 µL, 0.39 mmol) gave the title compound (5 mg, 0.09 mmol, 2% yield) as a white solid.

UPLC-MS (ES+, Short acidic): 1.44 min, m/z 514.3 [M+H]+

UPLC-MS (ES+, Long acidic): 3.23 min, m/z 514.4 [M+H]+

$^1$H NMR (400 MHz, DMSO-$d_6$) δ (ppm, 1:1 mixture of conformers) 8.96-8.88 (m, 1H, NH), 8.27 (s, 1H, ArH), 7.69-7.58 (m, 2H, ArH), 7.54-7.38 (m, 4H, ArH), 7.23-7.13 (m, 1H, ArH), 6.90-6.63 (m, 1H), 6.16-6.01 (m, 1H), 5.75-5.54 (m, 1H), 4.78-4.63 (m, 1H), 4.60-4.48 (m, 2.5H), 4.26-4.13 (m, 1H), 4.12-4.01 (m, 0.5H), 3.76-3.63 (m, 0.5H), 3.28-3.14 (m, 1H), 3.07-2.96 (m, 0.5H), 2.31-2.20 (m, 1H), 2.16-2.07 (m, 1H), 2.00-1.86 (m, 1H), 1.67-1.45 (m, 1H).

Example 79: N-[[4-[4-amino-1-[(3R)-1-propanoyl-3-piperidyl]pyrazolo[3,4-d]pyrimidin-3-yl]phenyl]methyl]-2-methoxy-benzamide

N-[[4-[4-Amino-1-[(3R)-1-propanoyl-3-piperidyl]pyrazolo[3,4-d]pyrimidin-3-yl]phenyl]methyl]-2-methoxy-benzamide Following general procedure F, N-[[4-[4-amino-1-[(3R)-3-piperidyl]pyrazolo[3,4-d]pyrimidin-3-yl]phenyl]methyl]-2-methoxy-benzamide (150 mg, 0.33 mmol) and propionic acid (0.02 mL, 0.33 mmol) gave, after further purification by flash column chromatography (DCM/MeOH 100:0 to 90:10), N-[[4-[4-amino-1-[(3R)-1-propanoyl-3-piperidyl]pyrazolo[3,4-d]pyrimidin-3-yl]phenyl]methyl]-2-methoxy-benzamide (80 mg, 0.14 mmol, 43% yield) as a yellow solid.

UPLC-MS (ES+, Short acidic): 1.42 min, m/z 514.4 [M+H]+

UPLC-MS (ES+, Long acidic): 3.18 min, m/z 514.4 [M+H]+

$^1$H NMR (400 MHz, DMSO-$d_6$) δ (ppm, 1:1 mixture of conformers) 8.77 (t, J 6.1 Hz, 1H, NH), 8.26 (d, J 9.9 Hz, 1H, ArH), 7.77 (dd, J 7.6, 1.8 Hz, 1H, ArH), 7.67-7.60 (m, 2H, ArH), 7.54-7.45 (m, 3H, ArH), 7.18-7.14 (m, 1H, ArH), 7.05 (td, J 7.6, 1.0 Hz, 1H, ArH), 4.79-4.68 (m, 0.5H), 4.67-4.46 (m, 4H), 4.27-4.18 (m, 0.5H), 4.05-3.98 (m, 0.5H), 3.94-3.81 (m, 4.5H), 3.61-3.51 (m, 0.5H), 3.14-3.05 (m, 1H), 2.88-2.79 (m, 0.5H), 2.43-2.17 (m, 4H), 2.16-2.05 (m, 1H), 1.94-1.82 (m, 1H), 1.69-1.43 (m, 1H), 1.06-0.90 (m, 3H).

Example 80: N-[[4-[4-amino-1-[(3R)-1-(2-cyano-acetyl)-3-piperidyl]pyrazolo[3,4-d]pyrimidin-3-yl]phenyl]methyl]-2-methoxy-benzamide Following general procedure F, N-[[4-[4-amino-1-[(3R)-3-piperidyl]pyrazolo[3,4-d]pyrimidin-3-yl]phenyl]methyl]-2-methoxy-benzamide (150 mg, 0.33 mmol) and cyanoacetic acid (28 mg, 0.33 mmol gave N-[[4-[4-amino-1-[(3R)-1-(2-cyanoacetyl)-3-piperidyl]pyrazolo[3,4-d]pyrimidin-3-yl]phenyl]methyl]-2-methoxy-benzamide (49 mg, 0.08 mmol, 25% yield) as a yellow solid.

UPLC-MS (ES+, Short acidic): 1.37 min, m/z 525.4 [M+H]+

UPLC-MS (ES+, Long acidic): 3.03 min, m/z 525.3 [M+H]+

$^1$H NMR (400 MHz, DMSO-$d_6$) δ (ppm, 1:1 mixture of conformers) 8.78 (t, J 6.1 Hz, 1H, NH), 8.26 (t, J 7.2 Hz, 1H, ArH), 7.77 (dd, J 7.7, 1.8 Hz, 1H, ArH), 7.67-7.61 (m, 2H, ArH), 7.54-7.45 (m, 3H, ArH), 7.19-7.14 (m, 1H, ArH), 7.05 (td, J 7.6, 1.0 Hz, 1H, ArH), 4.91-4.54 (m, 1H), 4.59 (d, J 6.1 Hz, 2H), 4.46-4.38 (m, 0.5H), 4.18-3.85 (m, 6H), 3.78-3.63 (m, 1H), 3.25-3.11 (m, 1H), 3.03-2.92 (m, 1H), 2.28-2.04 (m, 2H), 1.94-1.46 (m, 2H).

Example 81: N-[[4-[4-amino-1-[(3R)-1-prop-2-enoyl-3-piperidyl]pyrazolo[3,4-d]pyrimidin-3-yl]phenyl]methyl]-2,5-difluoro-N-methyl-benzamide

[1-[[(2,5-Difluorobenzoyl)amino]methyl]phenyl]boronic acid

Following general procedure B, [4-(aminomethyl)phenyl]boronic acid hydrochloride (300 mg, 1.60 mmol) and 2,5-difluorobenzoyl chloride (0.22 mL, 1.76 mmol) afforded the title compound (390 mg, 1.07 mmol, 67% yield) as a white solid.

UPLC-MS (ES+, Short acidic): 1.31 min, m/z 291.8 [M+H]+

[4-[[(2,5-Difluorobenzoyl)-methyl-amino]methyl]phenyl]boronic acid

To a solution of sodium hydride (188 mg, 4.69 mmol) in DMF (13 mL) was added [4-[[(2,5-difluorobenzoyl)amino]methyl]phenyl]boronic acid (390 mg, 1.34 mmol) and was stirred at room temperature for 1 h under nitrogen. Iodomethane (0.25 mL, 4.02 mmol) was added, and the mixture was stirred for 3 h at room temperature then diluted with saturated ammonium chloride (100 mL) and extracted with ethyl acetate (2×100 mL). The combined organics were then washed with 0.1 M NaOH (100 mL), water (100 mL) and brine (2×100 mL), dried over $Na_2SO_4$, filtered, and concentrated to yield the title compound (201 mg, 0.66 mmol, 49% yield) as a yellow solid.

UPLC-MS (ES$^+$, Short acidic): 1.35 min, m/z 305.9 $[M+H]^+$ tert-Butyl (3R)-3-[4-amino-3-[4-[[(2,5-difluorobenzoyl)-methyl-amino]methyl]phenyl]pyrazolo[3,4-d]pyrimidin-1-yl]piperidine-1-carboxylate Following general procedure D, [4-[[(2,5-difluorobenzoyl)-methyl-amino]methyl]phenyl]boronic acid (0.17 mL, 0.68 mmol) and tert-butyl (3R)-3-(4-amino-3-iodo-pyrazolo[3,4-d]pyrimidin-1-yl)piperidine-1-carboxylate (200 mg, 0.45 mmol) gave the title compound (248 mg, 0.43 mmol, 95% yield) as an orange foam.

UPLC-MS (ES$^+$, Short acidic): 1.74 min, m/z 578.5 $[M+H]^+$

N-[[4-[4-amino-1-[(3R)-3-piperidyl]pyrazolo[3,4-d]pyrimidin-3-yl]phenyl]methyl]-2,5-difluoro-N-methyl-benzamide Following general procedure E, tert-butyl (3R)-3-[4-amino-3-[4-[[(2-fluoro-5-methyl-benzoyl)amino]methyl]phenyl]pyrazolo[3,4-d]pyrimidin-1-yl]piperidine-1-carboxylate (229 mg, 0.41 mmol) gave the title compound (138 mg, 0.29 mmol, 65% yield) as a white foam.

UPLC-MS (ES$^+$, Short acidic): 1.20 min, m/z 478.2 $[M+H]^+$

N-[[4-[4-amino-1-[(3R)-1-prop-2-enoyl-3-piperidyl]pyrazolo[3,4-d]pyrimidin-3-yl]phenyl]methyl]-2,5-difluoro-N-methyl-benzamide Following general procedure F, N-[[4-[4-amino-1-[(3R)-3-piperidyl]pyrazolo[3,4-d]pyrimidin-3-yl]phenyl]methyl]-2,5-difluoro-N-methyl-benzamide (138 mg, 0.29 mmol) and acrylic acid (0.02 mL, 0.29 mmol) gave N-[[4-[4-amino-1-[(3R)-1-prop-2-enoyl-3-piperidyl]pyrazolo[3,4-d]pyrimidin-3-yl]phenyl]methyl]-2,5-difluoro-N-methyl-benzamide (88 mg, 0.15 mmol, 52% yield) as a white powder.

UPLC-MS (ES$^+$, Short acidic): 1.44 min, m/z 532.4 $[M+H]^+$

UPLC-MS (ES$^+$, Long acidic): 3.25 min, m/z 532.4 $[M+H]^+$ $^1$H NMR (400 MHz, DMSO-$d_6$) δ (ppm, mixture of conformers) 8.27 (s, 1H, ArH), 7.72-7.59 (m, 2H, ArH), 7.53-7.47 (m, 1H, ArH), 7.47-7.29 (m, 4H, ArH), 6.92-6.62 (m, 1H), 6.18-6.00 (m, 1H), 5.73-5.53 (m, 1H), 4.79 (s, 1.2H), 4.77-4.62 (m, 1H), 4.60-4.50 (m, 0.5H), 4.49 (s, 0.8H), 4.26-4.15 (m, 1H), 4.12-4.02 (m, 0.5H), 3.77-3.64 (m, 0.5H), 3.27-3.12 (m, 1H), 3.07-2.93 (m, 1.7H), 2.85-2.78 (m, 2H), 2.31-2.20 (m, 1H), 2.17-2.07 (m, 1H), 1.98-1.87 (m, 1H), 1.67-1.48 (m, 1H).

Example 82: N-[[4-[4-amino-1-[(3R)-1-(cyanomethyl)-3-piperidyl]pyrazolo[3,4-d]pyrimidin-3-yl]phenyl]methyl]-2-methoxy-benzamide N-[[4-[4-Amino-1-[(3R)-1-(cyanomethyl)-3-piperidyl]pyrazolo[3,4-d]pyrimidin-3-yl]phenyl]methyl]-2-methoxy-benzamide To a stirred solution of N-[[4-[4-amino-1-[(3R)-3-piperidyl]pyrazolo[3,4-d]pyrimidin-3-yl]phenyl]methyl]-2-methoxy-benzamide (150 mg, 0.33 mmol) and N,N-diisopropylethylamine (0.07 mL, 0.39 mmol) in MeCN (5 mL) at 0° C. was added bromoacetonitrile (0.02 mL, 0.33 mmol). The reaction mixture was then stirred at 0-10° C. for 1.5 h under a nitrogen atmosphere. The reaction mixture was then diluted with DCM, washed with $H_2O$ (2×10 mL), dried through a phase separator cartridge and concentrated under reduced pressure. Further purification by flash column chromatography (DCM/MeOH 100:0 to 90:10) gave N-[[4-[4-amino-1-[(3R)-1-(cyanomethyl)-3-piperidyl]pyrazolo[3,4-d]pyrimidin-3-yl]phenyl]methyl]-2-methoxy-benzamide (66 mg, 0.12 mmol, 37% yield) as a pale brown solid.

UPLC-MS (ES$^+$, Short acidic): 1.44 min, m/z 497.4 $[M+H]^+$

UPLC-MS (ES$^+$, Long acidic): 3.19 min, m/z 497.4 $[M+H]^+$ $^1$H NMR (400 MHz, DMSO-$d_6$) δ (ppm, 1:1 mixture of conformers) 8.77 (t, J 6.1 Hz, 1H, NH), 8.25 (s, 1H, ArH), 7.77 (dd, J 7.7, 1.8 Hz, 1H, ArH), 7.68-7.62 (m, 2H, ArH), 7.53-7.48 (m, 3H, ArH), 7.18-7.14 (m, 1H, ArH), 7.04 (td, J 7.7, 1.0 Hz, 1H, ArH), 4.87-4.76 (m, 1H), 4.59 (d, J 6.1 Hz, 2H), 3.91 (s, 3H), 3.84 (d, J 17.1 Hz, 1H), 3.78 (d, J 17.1 Hz, 1H), 3.07-2.97 (m, 1H), 2.89-2.79 (m, 1H), 2.70-2.59 (m, 1H), 2.28-2.16 (m, 1H), 2.04-1.94 (m, 2H), 1.91-1.82 (m, 1H), 1.77-1.61 (m, 1H).

Example 83: N-[[4-[4-amino-1-[(3R)-1-(2-cyanoethyl)-3-piperidyl]pyrazolo[3,4-d]pyrimidin-3-yl]phenyl]methyl]-2-methoxy-benzamide N-[[4-[4-Amino-1-[(3R)-1-(2-cyanoethyl)-3-piperidyl]pyrazolo[3,4-d]pyrimidin-3-yl]phenyl]methyl]-2-methoxy-benzamide To a stirred solution of N-[[4-[4-amino-1-[(3R)-3-piperidyl]pyrazolo[3,4-d]pyrimidin-3-yl]phenyl]methyl]-2-methoxy-benzamide (150 mg, 0.33 mmol) and N,N-diisopropylethylamine (0.17 mL, 0.98 mmol) in DCM (5 mL) was added 3-bromopropionitrile (0.03 mL, 0.33 mmol). The reaction was then stirred at room temperature for 48 h under a nitrogen atmosphere. The reaction mixture was then diluted with DCM, washed with $H_2O$ (2×10 mL), dried through a phase separator cartridge and concentrated under reduced pressure. Further purification by flash column chromatography (DCM/MeOH 100:0 to 90:10) gave N-[[4-[4-amino-1-[(3R)-1-(2-cyanoethyl)-3-piperidyl]pyrazolo[3,4-d]pyrimidin-3-yl]phenyl]methyl]-2-methoxy-benzamide (37 mg, 0.06 mmol, 20% yield) as a brown solid.

UPLC-MS (ES$^+$, Short acidic): 1.23 min, m/z 511.3 $[M+H]^+$

UPLC-MS (ES$^+$, Long acidic): 2.60 min, m/z 511.3 $[M+H]^+$ $^1$H NMR (400 MHz, DMSO-$d_6$) δ (ppm, 1:1 mixture of conformers) 8.77 (t, J 6.1 Hz, 1H, NH), 8.25 (s, 1H, ArH), 7.77 (dd, J 7.6, 1.8 Hz, 1H, ArH), 7.65-7.61 (m, 2H, ArH), 7.53-7.45 (m, 3H, ArH), 7.18-7.14 (m, 1H, ArH), 7.04 (td, J 7.6, 0.9 Hz, 1H, ArH), 4.84-4.73 (m, 1H), 4.59 (d, J 6.1 Hz, 2H), 3.91 (s, 3H), 3.10-3.01 (m, 1H), 2.97-2.88 (m, 1H), 2.72-2.43 (m, 5H), 2.12-1.94 (m, 3H), 1.87-1.77 (m, 1H), 1.72-1.58 (m, 1H).

Example 84: N-[[4-[4-amino-1-[(3R)-1-prop-2-enoyl-3-piperidyl]pyrazolo[3,4-d]pyrimidin-3-yl]phenyl]methyl]-2-fluoro-5-methyl-benzamide tert-Butyl (3R)-3-[4-amino-3-[4-[[(2-fluoro-5-methyl-benzoyl)amino]methyl]phenyl]pyrazolo[3,4-d]pyrimidin-1-yl]piperidine-1-carboxylate Following general procedure D, [4-[[(2-fluoro-5-methyl-benzoyl)amino]methyl]phenyl]boronic acid (194 mg, 0.68 mmol) and tert-butyl (3R)-3-(4-amino-3-iodo-pyrazolo[3,4-d]pyrimidin-1-yl)piperidine-1-carboxylate (200 mg, 0.45 mmol) gave the title compound (108 mg, 0.19 mmol, 43% yield) as an orange foam.

UPLC-MS (ES+, Short acidic): 2.00 min, m/z 560.5 [M+H]+

N-[[4-[4-Amino-1-[(3R)-3-piperidyl]pyrazolo[3,4-d]pyrimidin-3-yl]phenyl]methyl]-2-fluoro-5-methyl-benzamide

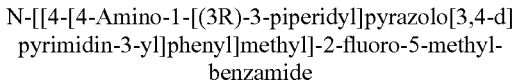

Following general procedure E, tert-butyl (3R)-3-[4-amino-3-[4-[[(2-fluoro-5-methyl-benzoyl)amino]methyl]phenyl]pyrazolo[3,4-d]pyrimidin-1-yl]piperidine-1-carboxylate (229 mg, 0.41 mmol) gave the title compound (88 mg, 0.19 mmol, 99% yield) as a white foam.

UPLC-MS (ES+, Short acidic): 1.18 min, m/z 460.2 [M+H]+

N-[[4-[4-Amino-1-[(3R)-1-prop-2-enoyl-3-piperidyl]pyrazolo[3,4-d]pyrimidin-3-yl]phenyl]methyl]-2-fluoro-5-methyl-benzamide Following general procedure F, N-[[4-[4-amino-1-[(3R)-3-piperidyl]pyrazolo[3,4-d]pyrimidin-3-yl]phenyl]methyl]-2-fluoro-5-methyl-benzamide (88 mg, 0.19 mmol) and acrylic acid (13 μL, 0.19 mmol) gave the title compound (55 mg, 0.10 mmol, 53% yield) as a white solid.

UPLC-MS (ES+, Short acidic): 3.24 min, m/z 514.5 [M+H]+

UPLC-MS (ES+, Long acidic): 1.46 min, m/z 514.4 [M+H]+

$^1$H NMR (400 MHz, DMSO-$d_6$) δ (ppm, 1:1 mixture of conformers) 8.95-8.85 (m, 1H, NH), 8.26 (s, 1H, ArH), 7.69-7.61 (m, 2H, ArH), 7.53-7.45 (m, 3H, ArH), 7.36-7.30 (m, 1H, ArH), 7.19 (dd, J 10.5, 8.4 Hz, 1H, ArH), 6.92-6.63 (m, 1H), 6.18-5.99 (m, 1H), 5.75-5.51 (m, 1H), 4.78-4.62 (m, 1H), 4.61-4.44 (m, 2.5H), 4.26-4.12 (m, 1H), 4.12-4.00 (m, 0.5H), 3.79-3.63 (m, 0.5H), 3.27-3.11 (m, 1H), 3.08-2.93 (m, 0.5H), 2.32 (s, 3H), 2.31-2.20 (m, 1H), 2.17-2.05 (m, 1H), 2.01-1.85 (m, 1H), 1.69-1.49 (m, 1H).

Example 85: N-[[4-[4-Amino-1-[(3R)-3-piperidyl]pyrazolo[3,4-d]pyrimidin-3-yl]phenyl]methyl]-4-fluoro-2-(trifluoromethoxy)benzamide

[4-[[[4-Fluoro-2-(trifluoromethoxy)benzoyl]amino]methyl]phenyl]boronic acid

Following procedure A, [4-(aminomethyl)phenyl]boronic acid hydrochloride (230 mg, 1.23 mmol) and 4-fluoro-2-(trifluoromethoxy)benzoic acid (0.24 mL, 1.12 mmol) afforded the title compound (300 mg, 0.42 mmol, 38% yield) as a yellow solid.

UPLC-MS (ES+, Short acidic): 1.71 min, m/z 358.0 [M+H]+ tert-Butyl (3R)-3-[4-amino-3-[4-[[[4-fluoro-2-(trifluoromethoxy)benzoyl]amino]methyl]phenyl]pyrazolo[3,4-d]pyrimidin-1-yl]piperidine-1-carboxylate Following general procedure D, [4-[[[4-fluoro-2-(trifluoromethoxy)benzoyl]amino]methyl]phenyl]boronic acid (0.11 mL, 0.34 mmol) and tert-butyl (3R)-3-(4-amino-3-iodo-pyrazolo[3,4-d]pyrimidin-1-yl)piperidine-1-carboxylate (100 mg, 0.23 mmol) gave the title compound (114 mg, 0.18 mmol, 80% yield) as an orange foam.

UPLC-MS (ES+, Short acidic): 1.83 min, m/z 630[M+H]+

N-[[4-[4-Amino-1-[(3R)-3-piperidyl]pyrazolo[3,4-d]pyrimidin-3-yl]phenyl]methyl]-4-fluoro-2-(trifluoromethoxy)benzamide

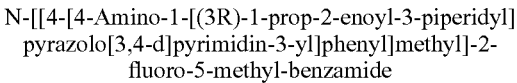

Following general procedure E, tert-butyl (3R)-3-[4-amino-3-[4-[[(2-fluoro-5-methyl-benzoyl)amino]methyl]phenyl]pyrazolo[3,4-d]pyrimidin-1-yl]piperidine-1-carboxylate (229 mg, 0.41 mmol) gave the title compound (93 mg, 0.18 mmol, 97% yield) as a white foam.

UPLC-MS (ES+, Short acidic): 1.30 min, m/z 530.2 [M+H]+

N-[[4-[4-Amino-1-[(3R)-1-prop-2-enoyl-3-piperidyl]pyrazolo[3,4-d]pyrimidin-3-yl]phenyl]methyl]-4-fluoro-2-(trifluoromethoxy)benzamide Following general procedure F, N-[[4-[4-amino-1-[(3R)-3-piperidyl]pyrazolo[3,4-d]pyrimidin-3-yl]phenyl]methyl]-4-fluoro-2-(trifluoromethoxy)benzamide (107 mg, 0.20 mmol) and acrylic acid (0.01 mL, 0.20 mmol) gave the title compound (13 mg, 0.02 mmol, 10% yield)

UPLC-MS (ES+, Short acidic): 1.51 min, m/z 584.2 [M+H]+

UPLC-MS (ES+, Long acidic): 3.39 min, m/z 584.3 [M+H]+

$^1$H NMR (400 MHz, DMSO-$d_6$) δ (ppm, 1:1 mixture of conformers) 9.08 (t, J 6.0 Hz, 1H, NH), 8.27 (s, 1H, ArH), 7.73 (dd, J 8.5, 6.5 Hz, 1H, ArH), 7.67-7.61 (m, 2H, ArH), 7.53-7.46 (m, 3H, ArH), 7.40 (td, J 8.5, 2.5 Hz, 1H, ArH), 6.93-6.65 (m, 1H), 6.18-6.01 (m, 1H), 5.74-5.54 (m, 1H), 4.80-4.64 (m, 1H), 4.60-4.47 (m, 2.5H), 4.25-4.14 (m, 1H), 4.11-4.01 (m, 0.5H), 3.77-3.65 (m, 0.5H), 3.28-3.14 (m, 1H), 3.08-2.95 (m, 0.5H), 2.31-2.21 (m, 1H), 2.18-2.07 (m, 1H), 1.99-1.86 (m, 1H), 1.69-1.47 (m, 1H).

Example 86: N-[[4-[4-Amino-1-[(3R)-1-[(E)-4-(dimethylamino)but-2-enoyl]-3-piperidyl]pyrazolo[3,4-d]pyrimidin-3-yl]phenyl]methyl]-2-methoxy-benzamide To a solution of N-[[4-[4-amino-1-[(3R)-3-piperidyl]pyrazolo[3,4-d]pyrimidin-3-yl]phenyl]methyl]-2-methoxy-benzamide (50 mg, 0.11 mmol) in DCM (2 mL) was added triethylamine (0.05 mL, 0.33 mmol), followed by trans-4-dimethylaminocrotonic acid hydrochloride (22 mg, 0.13 mmol) and EDCI (31 mg, 0.16 mmol). The reaction mixture was then stirred at 25° C. for 16 h, quenched with a saturated solution of NH$_4$Cl and extracted with DCM. The combined organics were dried over Na$_2$SO$_4$ and concentrated in vacuo. Further purification by mass-direct preparative LC-MS yielded N-[[4-[4-amino-1-[(3R)-1-[(E)-4-(dimethylamino)but-2-enoyl]-3-piperidyl]pyrazolo[3,4-d]pyrimidin-3-yl]phenyl]methyl]-2-methoxy-benzamide (21 mg, 0.04 mmol, 33% yield) as a white solid.

UPLC-MS (ES+, Long acidic): 2.64 min, m/z 569.4 [M+H]+

$^1$H NMR (400 MHz, DMSO-$d_6$) δ (ppm, 1:1 mixture of conformers) 8.77 (t, J 6.2 Hz, 1H, NH), 8.25 (s, 1H, ArH), 7.77 (dd, J 7.6, 1.7 Hz, 1H, ArH), 7.66-7.61 (m, 2H, ArH), 7.53-7.45 (m, 3H, ArH), 7.18-7.14 (m, 1H, ArH), 7.05 (td, J 7.6, 1.0 Hz, 1H, ArH), 6.75-6.44 (m, 2H), 4.77-4.63 (m, 1H), 4.62-4.48 (m, 2.5H), 4.20-3.97 (m, 1.5H), 3.91 (s, 3H), 3.78-3.66 (m, 0.5H), 3.29-2.94 (m, 1.5H), 2.30-2.03 (m, 7H), 2.02-1.87 (m, 3H), 1.71-1.51 (m, 1H).

Example 87: N-[[4-[4-amino-1-[(3R)-1-[(E)-but-2-enoyl]-3-piperidyl]pyrazolo[3,4-d]pyrimidin-3-yl]phenyl]methyl]-2-methoxy-benzamide Following general procedure F, N-[[4-[4-amino-1-[(3R)-3-piperidyl]pyrazolo[3,4-d]pyrimidin-3-yl]phenyl]methyl]-2-methoxy-benzamide (50 mg, 0.11 mmol) gave N-[[4-[4-amino-1-[(3R)-1-[(E)-but-2-enoyl]-3-piperidyl]pyrazolo[3,4-d]pyrimidin-3-yl]phenyl]methyl]-2-methoxy-benzamide (21 mg, 0.04 mmol, 37% yield) as a white solid.

UPLC-MS (ES+, Long acidic): 3.25 min, m/z 526.5 [M+H]+

$^1$H NMR (400 MHz, DMSO-$d_6$) δ (ppm, 1:1 mixture of conformers) 8.77 (t, J 6.1 Hz, 1H, NH), 8.26 (s, 1H, ArH), 7.77 (dd, J 7.6, 1.7 Hz, 1H, ArH), 7.67-7.61 (m, 2H, ArH), 7.54-7.45 (m, 3H, ArH), 7.18-7.14 (m, 1H, ArH), 7.04 (td, J 7.6, 1.0 Hz, 1H, ArH), 6.76-6.49 (m, 2H), 6.47-6.31 (m, 0.5H), 4.76-4.62 (m, 1H), 4.62-4.46 (m, 2.5H), 4.24-4.02 (m, 1.5H), 3.91 (s, 3H), 3.78-3.64 (m, 0.5H), 3.23-3.08 (m, 1H), 3.04-2.92 (m, 0.5H), 2.29-2.19 (m, 1H), 2.16-2.06 (m, 1H), 1.96-1.89 (m, 1H), 1.89-1.67 (m, 3H), 1.64-1.47 (m, 1H).

Example 88: N-[[4-[4-amino-1-[(3R)-1-prop-2-enoyl-3-piperidyl]pyrazolo[3,4-d]pyrimidin-3-yl]phenyl]methyl]-5-fluoro-pyridine-2-carboxamide

[4-[[(5-Fluoropyridine-2-carbonyl)amino]methyl]phenyl]boronic acid

Following general procedure A, [4-(aminomethyl)phenyl]boronic acid hydrochloride (0.41 g, 2.20 mmol) and 5-fluoropyridine-2-carboxylic acid (0.27 mL, 2.00 mmol) gave [4-[[(5-fluoropyridine-2-carbonyl)amino]methyl]phenyl]boronic acid (0.31 g, 1.13 mmol, 57% yield) as an off-white solid.

UPLC-MS (ES+, Short acidic): 1.25 min, m/z 274.9 [M+H]+ tert-Butyl (3R)-3-[4-amino-3-[4-[[(5-fluoropyridine-2-carbonyl)amino]methyl]phenyl]pyrazolo[3,4-d]pyrimidin-1-yl]piperidine-1-carboxylate Following general procedure D, [4-[[(5-fluoropyridine-2-carbonyl)amino]methyl]phenyl]boronic acid (185 mg, 0.68 mmol) and tert-butyl (3R)-3-(4-amino-3-iodo-pyrazolo[3,4-d]pyrimidin-1-yl)piperidine-1-carboxylate (200 mg, 0.45 mmol) gave tert-butyl (3R)-3-[4-amino-3-[4-[[(5-fluoropyridine-2-carbonyl)amino]methyl]phenyl]pyrazolo[3,4-d]pyrimidin-1-yl]piperidine-1-carboxylate (333 mg, 0.61 mmol assumed quantitative) as a brown solid, which was used as such for the next step.

UPLC-MS (ES+, Short acidic): 2.04 min, m/z 547.3 [M+H]+

N-[[4-[4-amino-1-[(3R)-3-piperidyl]pyrazolo[3,4-d]pyrimidin-3-yl]phenyl]methyl]-5-fluoro-pyridine-2-carboxamide Following general procedure E, tert-butyl (3R)-3-[4-amino-3-[4-[[(5-fluoropyridine-2-carbonyl)amino]methyl]phenyl]pyrazolo[3,4-d]pyrimidin-1-yl]piperidine-1-carboxylate (333 mg, 0.61 mmol) gave N-[[4-[4-amino-1-[(3R)-3-piperidyl]pyrazolo[3,4-d]pyrimidin-3-yl]phenyl]methyl]-5-fluoro-pyridine-2-carboxamide (198 mg, 0.44 mmol, 72% yield) as a brown foam.

UPLC-MS (ES+, Short acidic): 1.12 min, m/z 447.2 [M+H]+

N-[[4-[4-Amino-1-[(3R)-1-prop-2-enoyl-3-piperidyl]pyrazolo[3,4-d]pyrimidin-3-yl]phenyl]methyl]-5-fluoro-pyridine-2-carboxamide Following general procedure F, N-[[4-[4-amino-1-[(3R)-3-piperidyl]pyrazolo[3,4-d]pyrimidin-3-yl]phenyl]methyl]-5-fluoro-pyridine-2-carboxamide (198 mg, 0.44 mmol) gave N-[[4-[4-amino-1-[(3R)-1-prop-2-enoyl-3-piperidyl]pyrazolo[3,4-d]pyrimidin-3-yl]phenyl]methyl]-5-fluoro-pyridine-2-carboxamide (47 mg, 0.09 mmol, 21% yield) as a white solid.

UPLC-MS (ES+, Long acidic): 3.02 min, m/z 501.3 [M+H]+

$^1$H NMR (400 MHz, DMSO-$d_6$) δ (ppm, 1:1 mixture of conformers) 9.40 (t, J 6.4 Hz, 1H, NH), 8.68 (d, J 2.8 Hz, 1H, ArH), 8.25 (s, 1H, ArH), 8.17-8.13 (m, 1H, ArH), 7.92 (td, J 8.8, 2.8 Hz, 1H, ArH), 7.65-7.59 (m, 2H, ArH), 7.52-7.47 (m, 2H, ArH), 6.93-6.64 (m, 1H), 6.18-6.00 (m, 1H), 5.74-5.53 (m, 1H), 4.78-4.63 (m, 1H), 4.62-4.48 (m, 2.5H), 4.25-4.12 (m, 1H), 4.11-4.00 (m, 0.5H), 3.75-3.65 (m, 0.5H), 3.25-3.12 (m, 1H), 3.06-2.94 (m, 0.5H), 2.31-2.19 (m, 1H), 2.16-2.06 (m, 1H), 1.97-1.86 (m, 1H), 1.67-1.50 (m, 1H).

Example 89: N-[[4-[4-amino-1-[(3R)-1-prop-2-enoyl-3-piperidyl]pyrazolo[3,4-d]pyrimidin-3-yl]phenyl]methyl]-3,5-dimethyl-benzamide

[4-[[(3,5-Dimethylbenzoyl)amino]methyl]phenyl]boronic acid

Following general procedure A, [4-(aminomethyl)phenyl]boronic acid hydrochloride (410 mg, 2.20 mmol) and 3,5-dimethylbenzoic acid (300 mg, 2.00 mmol) afforded [4-[[(3,5-dimethylbenzoyl)amino]methyl]phenyl]boronic acid (370 mg, 1.31 mmol, 65% yield) as a colourless solid.

UPLC-MS (ES+, Short acidic): 1.45 min, m/z 284.1 [M+H]+ tert-Butyl (3R)-3-[4-amino-3-[4-[[(3,5-dimethylbenzoyl)amino]methyl]phenyl]pyrazolo[3,4-d]pyrimidin-1-yl]piperidine-1-carboxylate Following general procedure D, [4-[[(,5-dimethylbenzoyl)amino]methyl]phenyl]boronic acid (0.18 mL, 0.68 mmol) and tert-butyl (3R)-3-(4-amino-3-iodo-pyrazolo[3,4-d]pyrimidin-1-yl)piperidine-1-carboxylate (200 mg, 0.45 mmol) afforded tert-butyl (3R)-3-[4-amino-3-[4-[[(3,5-dimethylbenzoyl)amino]methyl]phenyl]pyrazolo[3,4-d]pyrimidin-1-yl]piperidine-1-carboxylate (210 mg, 0.38 mmol, 83% yield) as an orange foam.

UPLC-MS (ES+, Short acidic): 1.81 min, m/z 556.6 [M+H]+

N-[[4-[4-Amino-1-[(3R)-3-piperidyl]pyrazolo[3,4-d]pyrimidin-3-yl]phenyl]methyl]-3,5-dimethyl-benzamide Following general procedure E, tert-butyl (3R)-3-[4-amino-3-[4-[[(3,5-dimethylbenzoyl)amino]methyl]phenyl]pyrazolo[3,4-d]pyrimidin-1-yl]piperidine-1-carboxylate (210 mg, 0.38 mmol) afforded N-[[4-[4-amino-1-[(3R)-3- piperidyl]pyrazolo[3,4-d]pyrimidin-3-yl]phenyl]methyl]-3,5-dimethyl-benzamide (160 mg, 0.35 mmol, 92% yield) as a brown solid.

UPLC-MS (ES+, Short acidic): 1.28 min, m/z 456.4 [M+H]+

N-[[4-[4-Amino-1-[(3R)-1-prop-2-enoyl-3-piperidyl]pyrazolo[3,4-d]pyrimidin-3-yl]phenyl]methyl]-3,5-dimethyl-benzamide

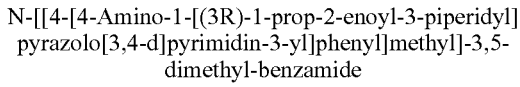

Following general procedure F, N-[[4-[4-amino-1-[(3R)-3-piperidyl]pyrazolo[3,4-d]pyrimidin-3-yl]phenyl]methyl]-3,5-dimethyl-benzamide (187 mg, 0.41 mmol) afforded N-[[4-[4-amino-1-[(3R)-1-prop-2-enoyl-3-piperidyl]pyrazolo[3,4-d]pyrimidin-3-yl]phenyl]methyl]-3,5-dimethyl-benzamide (35 mg, 0.07 mmol, 17%) as a white solid.

UPLC-MS (ES+, Short acidic): 1.51 min, 510.3 m/z M+H]+

UPLC-MS (ES+, Long acidic): 3.37 min, 510.4 m/z [M+H]+

$^1$H NMR (400 MHz, DMSO-$d_6$) δ (ppm, 1:1 mixture of conformers) 9.00 (t, J 6.0 Hz, 1H, NH), 8.26 (s, 1H, ArH), 7.67-7.61 (m, 2H, ArH), 7.56-7.45 (m, 4H, ArH), 7.17 (s, 1H, ArH), 6.92-6.65 (m, 1H), 6.18-6.01 (m, 1H), 5.75-5.54 (m, 1H), 4.79-4.62 (m, 1H), 4.60-4.48 (m, 2.5H), 4.26-4.14 (m, 1H), 4.12-4.01 (m, 0.5H), 3.76-3.63 (m, 0.5H), 3.27-3.12 (m, 1H), 3.07-2.94 (m, 0.5H), 2.32 (s, 6H), 2.30-2.19 (m, 1H), 2.16-2.06 (m, 1H), 1.97-1.87 (m, 1H), 1.68-1.48 (m, 1H).

Example 90: N-[[4-[4-Amino-1-(1-prop-2-enoyl-3-piperidyl)pyrazolo[3,4-d]pyrimidin-3-yl]phenyl]methyl]-2,5-difluoro-benzamide tert-Butyl 3-[4-amino-3-[4-[[(2,5-difluorobenzoyl)amino]methyl]phenyl]pyrazolo[3,4-d]pyrimidin-1-yl]piperidine-1-carboxylate Following general procedure D, tert-butyl 3-(4-amino-3-iodo-pyrazolo[3,4-d]pyrimidin-1-yl)piperidine-1-carboxylate (127 mg, 0.29 mmol) and [4-[[(2,5-difluorobenzoyl)amino]methyl]phenyl]boronic acid (129 mg, 0.43 mmol) gave tert-butyl 3-[4-amino-3-[4-[[(2,5-difluorobenzoyl)amino]methyl]phenyl]pyrazolo[3,4-d]pyrimidin-1-yl]piperidine-1-carboxylate (274 mg, 0.39 mmol, assumed quantitative) as a light beige foam.

LC-MS (ES+, Short acidic): 1.84 min, m/z 564.2 [M+H]+

N-[[4-[4-Amino-1-(3-piperidyl)pyrazolo[3,4-d]pyrimidin-3-yl]phenyl]methyl]-2,5-difluoro-benzamide Following general procedure E, tert-butyl 3-[4-amino-3-[4-[[(2,5-difluorobenzoyl)amino]methyl]phenyl]pyrazolo[3,4-d]pyrimidin-1-yl]piperidine-1-carboxylate (274 mg, 0.39 mmol) gave N-[[4-[4-amino-1-(3-piperidyl)pyrazolo[3,4-d]pyrimidin-3-yl]phenyl]methyl]-2,5-difluoro-benzamide (0.11 g, 0.25 mmol, 63% yield) as an off-white foam.

LC-MS (ES+, Short acidic): 0.90 min, m/z 464.1 [M+H]+

$^1$H NMR (400 MHz, DMSO-$d_6$): 9.08-9.01 (m, 1H), 8.24 (s, 1H), 7.67-7.61 (m, 2H), 7.53-7.46 (m, 3H), 7.44-7.35 (m, 1H), 4.73-4.63 (m, 1H), 4.55 (d, J 6.0 Hz, 2H), 3.12-3.03 (m, 1H), 2.99-2.87 (m, 2H), 2.61-2.38 (m, 2H), 2.16-2.06 (m, 1H), 2.06-1.97 (m, 1H), 1.80-1.71 (m, 1H). 1.63-1.50 (m, 1H).

N-[[4-[4-Amino-1-(1-prop-2-enoyl-3-piperidyl)pyrazolo[3,4-d]pyrimidin-3-yl]phenyl]methyl]-2,5-difluoro-benzamide

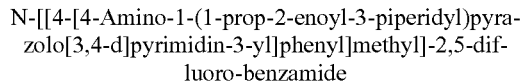

Following general procedure F, N-[[4-[4-amino-1-(3-piperidyl)pyrazolo[3,4-d]pyrimidin-3-yl]phenyl]methyl]-2,5-difluoro-benzamide (114 mg, 0.25 mmol) and acrylic acid (0.02 mL, 0.23 mmol) gave N-[[4-[4-amino-1-(1-prop-2-enoyl-3-piperidyl)pyrazolo[3,4-d]pyrimidin-3-yl]phenyl]methyl]-2,5-difluoro-benzamide (53 mg, 0.10 mmol, 42% yield).

UPLC-MS (ES+, Short acidic): 1.41 min, m/z 518.4 [M+H]+

UPLC-MS (ES+, Long acidic): 3.12 min, m/z 518.3 [M+H]+

$^1$H NMR (400 MHz, DMSO-$d_6$) δ (ppm, 1:1 mixture of conformers) 9.05 (t, J 5.7 Hz, 1H, NH), 8.26 (s, 1H, ArH), 7.65 (d, J 7.9 Hz, 2H, ArH), 7.51 (d, J 7.9 Hz, 2H), 7.52-7.46 (m, 1H, ArH), 7.44-7.35 (m, 2H, ArH), 6.87 (dd, J 16.5 Hz, J 10.5 Hz, 0.5H), 6.72 (dd, J 16.5 Hz, J 10.5 Hz, 0.5H), 6.13 (d, J 16.5 Hz, 0.5H), 6.06 (d, J 16.5 Hz, 0.5H), 5.71 (d, J 10.5 Hz, 0.5H), 5.58 (d, J 10.5 Hz, 0.5H), 4.80-4.63 (m, 1H), 4.56 (d, J 5.7 Hz, 2H), 4.62-4.48 (m, 0.5H), 4.27-4.14 (m, 1H), 4.12-4.01 (m, 0.5H), 3.78-3.64 (m, 0.5H), 3.28-3.12 (m, 1H), 3.08-2.95 (m, 0.5H), 2.34-2.19 (m, 1H), 2.18-2.06 (m, 1H), 1.99-1.87 (m, 1H), 1.69-1.50 (m, 1H).

Example 91: N-[[4-[4-amino-1-[(3R)-1-(2,3-dihydroxypropanoyl)-3-piperidyl]pyrazolo[3,4-d]pyrimidin-3-yl]phenyl]methyl]-2-methoxy-benzamide

N-[[4-[4-Amino-1-[(3R)-1-(2,3-dihydroxypropanoyl)-3-piperidyl]pyrazolo[3,4-d]pyrimidin-3-yl]phenyl]methyl]-2-methoxy-benzamide To a stirred solution of N-[[4-[4-amino-1-[(3R)-1-prop-2-enoyl-3-piperidyl]pyrazolo[3,4-d]pyrimidin-3-yl]phenyl]methyl]-2-methoxy-benzamide (119 mg, 0.23 mmol) in tert-butanol (3.2 mL) and pyridine (0.02 mL, 0.23 mmol) was added a 2.5 wt % osmium tetroxide solution (80 mg, 0.31 mmol). The reaction was placed under a nitrogen atmosphere and was left to stir at room temperature for 18 h, quenched with a saturated NaHSO$_3$ solution and was left to stir for an additional 1 h. The aqueous mixture was extracted with EtOAc (×3). The combined organic extracts were dried through a phase separator and the filtrate concentrated under reduced pressure. Further purification by flash column chromatography (DCM/MeOH 100:0 to 90:10) gave N-[[4-[4-amino-1-[(3R)-1-(2,3-dihydroxypropanoyl)-3-piperidyl]pyrazolo[3,4-d]pyrimidin-3-yl]phenyl]methyl]-2-methoxy-benzamide (17 mg, 0.03 mmol, 12% yield) as white solid.

UPLC-MS (ES+, Short acidic): 1.26 min, m/z 546.3 [M+H]+

UPLC-MS (ES+, Long acidic): 2.77 min, m/z 546.2 [M+H]+

$^1$H NMR (400 MHz, DMSO-$d_6$) δ (ppm, 1:1 mixture of conformers) 8.77 (t, J 6.1 Hz, 1H, NH), 8.28-8.24 (m, 1H, ArH), 7.77 (dd, J 7.7, 1.8 Hz, 1H, ArH), 7.67-7.62 (m, 2H, ArH), 7.54-7.45 (m, 3H, ArH), 7.18-7.13 (m, 1H, ArH), 7.05 (td, J 7.7, 1.0 Hz, 1H, ArH), 5.08-4.97 (m, 0.5H), 4.93-4.74 (m, 1H), 4.73-4.63 (m, 1H), 4.62-4.48 (m, 2.5H), 4.44-4.20 (m, 2H), 4.14-4.03 (m, 0.5H), 3.91 s, 3H), 3.65-3.36 (m, 3H), 3.20-3.02 (m, 1.5H), 2.86-2.69 (m, 0.5H), 2.30-2.15 (m, 1H), 2.16-2.05 (m, 1H), 1.94-1.79 (m, 1H), 1.74-1.44 (m, 1H).

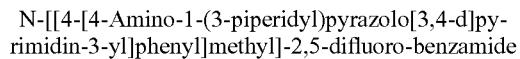

Example 92: N-[[4-[4-amino-1-[(3R)-1-but-2-ynoyl-3-piperidyl]pyrazolo[3,4-d]pyrimidin-3-yl]phenyl]methyl]-2-methoxy-benzamide Following general procedure F, N-[[4-[4-amino-1-[(3R)-3-piperidyl]pyrazolo[3,4-d]pyrimidin-3-yl]phenyl]methyl]-2-methoxy-benzamide (50 mg, 0.11 mmol) and but-2-ynoic acid (9 mg, 0.11 mmol) afforded N-[[4-[4-amino-1-[(3R)-1-but-2-ynoyl-3-piperidyl]pyrazolo[3,4-d]pyrimidin-3-yl]phenyl]methyl]-2-methoxy-benzamide (14 mg, 0.02 mmol, 23% yield).

UPLC-MS (ES$^+$, Short acidic): 1.43 min, m/z 524.4 [M+H]$^+$

UPLC-MS (ES$^+$, Long acidic): 3.23 min, m/z 524.4 [M+H]$^+$ $^1$H NMR (400 MHz, DMSO-d$_6$) δ (ppm, 1:1 mixture of conformers) 8.80-8.73 (m, 1H, NH), 8.26 (s, 0.5H, ArH), 8.25 (s, 0.5H, ArH), 7.79-7.74 (m, 1H, ArH), 7.67-7.62 (m, 2H, ArH), 7.54-7.44 (m, 3H, ArH), 7.19-7.13 (m, 1H, ArH), 7.08-7.01 (m, 1H, ArH), 4.84-4.74 (m, 0.5H), 4.71-4.62 (m, 0.5H), 4.59 (d, J 6.0 Hz, 2H), 4.45-4.37 (m, 0.5H), 4.34-4.28 (m, 0.5H), 4.26-4.18 (m, 0.5H), 4.05-3.97 (m, 0.5H), 3.91 (s, 3H), 3.84-3.77 (m, 0.5H), 3.32-3.24 (m, 2H), 3.14-3.06 (m, 0.5H), 2.30-2.19 (m, 1H), 2.17-2.08 (m, 1H), 2.05 (s, 1.5H), 2.01-1.92 (m, 1H), 1.84 (s, 1.5H), 1.71-1.48 (m, 1H).

Example 93: N-[[4-[4-amino-1-[(3R)-1-(oxetan-3-yl)-3-piperidyl]pyrazolo[3,4-d]pyrimidin-3-yl]phenyl]methyl]-2-methoxy-benzamide A three-neck flask, fitted with a condenser and a bleach (6% w/v) scrubber was charged with N-[[4-[4-amino-1-[(3R)-3-piperidyl]pyrazolo[3,4-d]pyrimidin-3-yl]phenyl]methyl]-2-methoxy-benzamide (50 mg, 0.11 mmol), methanol (2.2 mL), 3-oxetanone (0.01 mL, 0.12 mmol), zinc chloride (57 mg, 0.42 mmol) and sodium cyanoborohydride (25 mg, 0.39 mmol). The reaction mixture was heated to 50° C. and stirred at this temperature for 16 h, quenched with water (10 mL) and extracted with DCM (3×10 mL). The organics were passed through a phase separator and concentrated in vacuo. The residue was purified by flash column chromatography (0-15% MeOH in DCM) and filtration over SCX cartridge to afford N-[[4-[4-amino-1-[(3R)-1-(oxetan-3-yl)-3-piperidyl]pyrazolo[3,4-d]pyrimidin-3-yl]phenyl]methyl]-2-methoxy-benzamide (15 mg, 0.03 mmol, 27% yield).

UPLC-MS (ES$^+$, Short acidic): 1.16 min, m/z 514.3 [M+H]$^+$

UPLC-MS (ES$^+$, Long acidic): 2.59 min, m/z 514.3 [M+H]$^+$ $^1$H NMR (400 MHz, MeOH-d$_4$) δ (ppm) 8.24 (s, 1H, ArH), 7.91 (dd, J 7.8, 1.8 Hz, 1H, ArH), 7.67-7.63 (m, 2H, ArH), 7.58-7.47 (m, 3H, ArH), 7.18-7.14 (m, 1H, ArH), 7.07 (td, J 7.8, 1.0 Hz, 1H, ArH), 4.99-4.89 (m, 1H), 4.72-4.66 (m, 3H), 4.65-4.58 (m, 3H), 3.98 (s, 3H), 3.64-3.55 (m, 1H), 3.28-3.14 (m, 1H), 3.01-2.94 (m, 1H), 2.85-2.75 (m, 1H), 2.53-2.35 (m, 1H), 2.16-2.05 (m, 2H), 2.00-1.75 (m, 2H).

Example 94: N-[[4-[4-amino-1-[(3R)-1-methyl-3-piperidyl]pyrazolo[3,4-d]pyrimidin-3-yl]phenyl]methyl]-2-methoxy-benzamide

3-Iodo-1-[(3R)-3-piperidyl]pyrazolo[3,4-d]pyrimidin-4-amine

To a stirred solution of tert-butyl (3R)-3-(4-amino-3-iodo-pyrazolo[3,4-d]pyrimidin-1-yl)piperidine-1-carboxylate (500 mg, 1.13 mmol) in methanol (15 mL) was added hydrogen chloride in 1,4-dioxane (4 M, 0.78 mL, 22.51 mmol). The reaction was stirred at room temperature for 14 h then the solvent was removed under reduced pressure. Further purification by flash column chromatography (DCM/7 N NH$_3$ in MeOH 100:0 to 90:10) gave 3-iodo-1-[(3R)-3-piperidyl]pyrazolo[3,4-d]pyrimidin-4-amine (357 mg, 0.93 mmol, 83% yield) as a white solid.

UPLC-MS (ES$^+$, Short acidic): 0.74 min, m/z 345.0 [M+H]$^+$

3-Iodo-1-[(3R)-1-methyl-3-piperidyl]pyrazolo[3,4-d]pyrimidin-4-amine

To a stirred solution of 3-iodo-1-[(3R)-3-piperidyl]pyrazolo[3,4-d]pyrimidin-4-amine (357 mg, 1.04 mmol) and sodium triacetoxyborohydride (308 mg, 1.45 mmol) in DCM (30 mL) was added a formaldehyde solution (36.5-38%) in water (0.03 mL, 1.14 mmol). The reaction mixture was stirred at room temperature for 16 h. Additional formaldehyde solution (36.5-38%) in water (0.03 mL, 1.14 mmol) was added. The mixture was stirred at room temperature for another 2 h, quenched with a 5 M aqueous NaOH solution (10 mL) and concentrated under reduced pressure. The white residue was then partitioned between water (100 mL) and DCM (100 mL). The aqueous layer was extracted with DCM (3×100 mL). The combined organic extracts were then washed with brine (100 mL), dried over Na$_2$SO$_4$, filtered and concentrated under reduced pressure to afford 3-iodo-1-[(3R)-1-methyl-3-piperidyl]pyrazolo[3,4-d]pyrimidin-4-amine (315 mg, 0.79 mmol, 76% yield) as a white solid.

UPLC-MS (ES$^+$, Short acidic): 0.81 min, m/z 359.0 [M+H]$^+$

N-[[4-[4-Amino-1-[(3R)-1-methyl-3-piperidyl]pyrazolo[3,4-d]pyrimidin-3-yl]phenyl]methyl]-2-methoxy-benzamide Following general procedure D, 3-iodo-1-[(3R)-1-methyl-3-piperidyl]pyrazolo[3,4-d]pyrimidin-4-amine (100 mg, 0.28 mmol) and [4-[[(2-methoxybenzoyl)amino]methyl]phenyl]boronic acid (119 mg, 0.42 mmol) afforded N-[[4-[4-amino-1-[(3R)-1-methyl-3-piperidyl]pyrazolo[3,4-d]pyrimidin-3-yl]phenyl]methyl]-2-methoxy-benzamide (30 mg, 0.06 mmol, 20% yield) as a brown solid.

UPLC-MS (ES$^+$, Short acidic): 1.10 min, m/z 472.2 [M+H]$^+$

UPLC-MS (ES$^+$, Long acidic): 2.43 min, m/z 472.1 [M+H]$^+$ $^1$H NMR (400 MHz, DMSO-d$_6$) δ (ppm) 8.77 (t, J 6.0 Hz, 1H, NH), 8.24 (s, 1H, ArH), 7.77 (dd, J 7.75, 1.8 Hz, 1H, ArH), 7.66-7.60 (m, 2H, ArH), 7.53-7.45 (m, 3H, ArH), 7.18-7.14 (m, 1H, ArH), 7.40 (td, J 7.6, 1.0 Hz, 1H, ArH), 4.83-4.62 (m, 1H), 4.59 (d, J 6.0 Hz, 2H), 3.91 (s, 3H), 3.12-3.01 (m, 1H), 3.08-2.86 (m, 1H), 2.53-2.40 (m, 3H), 2.26-1.87 (m, 4H), 1.84-1.71 (m, 1H), 1.69-1.48 (m, 1H).

Example 95: N-[[4-[4-Amino-1-(1-prop-2-enoyl-4-piperidyl)pyrazolo[3,4-d]pyrimidin-3-yl]phenyl]methyl]-2-methoxy-benzamide tert-Butyl 4-(4-amino-3-iodo-pyrazolo[3,4-d]pyrimidin-1-yl)piperidine-1-carboxylate To a stirred solution of 3-iodo-1H-pyrazolo[3,4-d]pyrimidin-4-amine (5.61 g, 21.5 mmol) and tert-butyl 4-methylsulfonyloxypiperidine-1-carboxylate (6.61 g, 23.65 mmol) in DMF (80 mL) under a nitrogen atmosphere was added cesium carbonate (16.11 g, 49.44 mmol). The reaction mixture was heated to 70° C. and stirred further for 16 h at that temperature. The reaction mixture was cooled, concentrated under reduced pressure. The residue was taken up with EtOAc (100 mL) and water (200 mL) and sonicated for 25 min. The layers were partitioned. The aqueous layer was extracted with EtOAc (2×100 mL). The combined organic extracts were washed with brine (2×100 mL), dried over $Na_2SO_4$, filtered and concentrated under reduced pressure to give an orange solid. Further purification by flash column chromatography (DCM/EtOAc 1:1) gave tert-butyl 4-(4-amino-3-iodo-pyrazolo[3,4-d]pyrimidin-1-yl)piperidine-1-carboxylate (2.94 g, 6.62 mmol, 31% yield) as a pale orange solid.

$^1$H NMR (400 MHz, DMSO-$d_6$) δ (ppm) 8.20 (s, 1H, ArH), 4.87-4.75 (m, 1H), 4.14-3.98 (m, 2H), 3.07-2.80 (m, 2H), 1.98-1.80 (m, 2H).

tert-Butyl 4-[4-amino-3-[4-[[(2-methoxybenzoyl) amino]methyl]phenyl]pyrazolo[3,4-d]pyrimidin-1-yl]piperidine-1-carboxylate Following general procedure C, tert-butyl 4-(4-amino-3-iodo-pyrazolo[3,4-d]pyrimidin-1-yl)piperidine-1-carboxylate (2.92 g, 6.57 mmol) and [4-[[(2-methoxybenzoyl) amino]methyl]phenyl]boronic acid (2.90 g, 9.86 mmol) gave tert-butyl 4-[4-amino-3-[4-[[(2-methoxybenzoyl) amino]methyl]phenyl]pyrazolo[3,4-d]pyrimidin-1-yl]piperidine-1-carboxylate (2.63 g, 4.72 mmol, 72% yield) as a light beige foam.

LC-MS (ES$^+$, Short acidic): 3.42 min, m/z 558.3 [M+H]$^+$

N-[[4-[4-amino-1-(4-piperidyl)pyrazolo[3,4-d]pyrimidin-3-yl]phenyl]methyl]-2-methoxy-benzamide hydrochloride Following general procedure E, tert-butyl 4-[4-amino-3-[4-[[(2-methoxybenzoyl)amino]methyl]phenyl]pyrazolo[3,4-d]pyrimidin-1-yl]piperidine-1-carboxylate (2.63 g, 4.72 mmol) gave, after trituration with a mixture of MeOH/Et$_2$O, N-[[4-[4-amino-1-(4-piperidyl)pyrazolo[3,4-d]pyrimidin-3-yl]phenyl]methyl]-2-methoxy-benzamide hydrochloride (1.76 g, 3.56 mmol, 75% yield) as an off-white solid.

UPLC-MS (ES$^+$, Short acidic): 1.03 min, m/z 458.3 [M+H]$^+$

N-[[4-[4-Amino-1-(1-prop-2-enoyl-4-piperidyl)pyrazolo[3,4-d]pyrimidin-3-yl]phenyl]methyl]-2-methoxy-benzamide Following general procedure F, N-[[4-[4-amino-1-(4-piperidyl)pyrazolo[3,4-d]pyrimidin-3-yl]phenyl]methyl]-2-methoxy-benzamide (100 mg, 0.22 mmol) and acrylic acid (20 μL, 0.22 mmol) gave N-[[4-[4-amino-1-(1-prop-2-enoyl-4-piperidyl)pyrazolo[3,4-d]pyrimidin-3-yl]phenyl]methyl]-2-methoxy-benzamide (22 mg, 0.04 mmol, 19% yield) as a white powder.

UPLC-MS (ES$^+$, Short acidic): 1.28 min, m/z 512.3 [M+H]$^+$

UPLC-MS (ES$^+$, Long acidic): 2.93 min, m/z 512.3 [M+H]$^+$ $^1$H NMR (400 MHz, DMSO-$d_6$) δ (ppm, 1:1 cis and trans mixture) 8.76 (t, J 6.1 Hz, 1H, NH), 8.25 (s, 1H, ArH), 7.76 (dd, J 7.7, 1.8 Hz, 1H, ArH), 7.66-7.61 (m, 2H, ArH), 7.52-7.45 (m, 3H, ArH), 7.18-7.14 (m, 1H, ArH), 7.04 (td, J 7.7, 1.0 Hz, 1H, ArH), 6.87 (dd, J 16.6, 10.5 Hz, 1H), 6.13 (dd, J 16.6, 2.4 Hz, 1H), 5.69 (dd, J 10.5, 2.4 Hz, 1H), 5.06-4.96 (m, 1H), 4.58 (d, J 6.0 Hz, 2H), 4.57-4.50 (m, 1H), 4.26-4.15 (m, 1H), 3.91 (s, 3H), 2.99-2.85 (m, H), 2.13-1.93 (m, 4H).

Example 96: N-[[4-[4-Amino-1-(4-piperidyl)pyrazolo[3,4-d]pyrimidin-3-yl]phenyl]methyl]-2-methoxy-benzamide N-[[4-[4-Amino-1-(4-piperidyl)pyrazolo[3,4-d]pyrimidin-3-yl]phenyl]methyl]-2-methoxy-benzamide To a solution of N-[[4-[4-amino-1-(4-piperidyl)pyrazolo[3,4-d]pyrimidin-3-yl]phenyl]methyl]-2-methoxy-benzamide (96 mg, 0.21 mmol) in DCM (5 mL) was added a formaldehyde solution (36.5-38%) in water (0.03 mL, 0.23 mmol) and sodium triacetoxyborohydride (89 mg, 0.42 mmol). The reaction was placed under a nitrogen atmosphere and allowed to stir at room temperature overnight. NaOH (5 M, 15 mL) was added and the mixture stirred for 15 min. The mixture was concentrated to dryness. The solid residue was taken up in DCM and washed with water. The combined organic layer was dried over $Na_2SO_4$ and the solvent removed under reduced pressure. Further purification by flash chromatography afforded the title product as a white solid (35 mg, 0.07 mmol 34% yield).

LC-MS (ES$^+$, Short acidic): 2.37 min, m/z 472.1 [M+H]$^+$

LC-MS (ES$^+$, Short acidic): 2.42 min, m/z 472.1 [M+H]$^+$

UPLC-MS (ES$^+$, Long acidic): 2.34 min, m/z 472.1 [M+H]$^+$ $^1$H NMR (400 MHz, DMSO-$d_6$) δ (ppm) 8.77 (t, J 6.1 Hz, 1H, NH), 8.24 (s, 1H, ArH), 7.77 (dd, J 7.6, 1.7 Hz, 1H, ArH), 7.66-7.62 (m, 2H, ArH), 7.53-7.46 (m, 3H, ArH), 7.18-7.14 (m, 1H, ArH), 7.04 (td, J 7.6, 1.0 Hz, 1H, ArH), 4.70-4.61 (m, 1H), 4.58 (d, J 6.0 Hz, 2H), 3.91 (s, 3H), 3.00-2.88 (m, 2H), 2.28 (s, 3H), 2.25-2.08 (m, 4H), 1.94-1.86 (m, 2H).

Example 97: BTK Binding Affinity

BTK binding affinity of each compound tested was determined using a time-resolved fluorescence resonance energy transfer (TR-FRET) methodology. 2.5 nM Recombinant BTK kinase, varying concentrations of inhibitor, 2 nM LanthaScreen™ Eu anti-His Antibody and 15 nM Kinase Tracer 236 was incubated in 1× LanthaScreen™ Kinase Buffer A for five hours. Recombinant BTK kinase and all LanthaScreen™ components were purchased from Invitrogen. Measurements were performed in a reaction volume of 30 μL using half-area 96-well assay plates. The TR-FRET signal was read on a plate reader with an excitation wavelength of 340 nm and detection wavelengths of 615 and 665 nm. Binding affinity was determined for each compound by measuring TR-FRET signal at various concentrations of compound and plotting the relative fluorescence units against the inhibitor concentration to estimate the $IC_{50}$ from log[Inhibitor] vs response using the Variable Slope model in Graphpad prism from Graphpad software (San Diego, Calif.).

Results of the BTK Binding Affinity are shown below in Table 3.

Table 3 shows the BTK Binding affinity, as determined by the assay described above, for compounds of formula (I), categorised based on the BTK $IC_{50}$ value of the compound as "+", "++", "+++" and "++++". The category "+" refers to compounds with a BTK $IC_{50}$ of 10 nM to 100 nM. The category "++" refers to compounds with a BTK IC$_{50}$ of 1 nM to 10 nM. The category "+++" refers to compounds with a BTK IC$_{50}$ of 0.5 nM to 1 nM. The category "++++" refers to compounds with a BTK IC$_{50}$ of <0.5 nM.

Example 98: EGFR Binding Affinity

EGFR binding affinity was determined using a time-resolved fluorescence resonance energy transfer (TR-FRET) methodology. 2.5 nM Recombinant EGFR, varying concentrations of inhibitor, 2 nM LanthaScreen™ Eu anti-GST Antibody and 3 nM Kinase Tracer 199 was incubated in 1× LanthaScreen™ Kinase Buffer A for five hours. Recombinant EGFR and all LanthaScreen™ components were purchased from Invitrogen. Measurements were performed in a reaction volume of 30 μL using half-area 96-well assay plates. The TR-FRET signal was read on a plate reader with an excitation wavelength of 340 nm and detection wavelengths of 615 and 665 nm. Binding affinity was determined for each compound by measuring TR-FRET signal at various concentrations of compound and plotting the relative fluorescence units against the inhibitor concentration to estimate the IC$_{50}$ from log[Inhibitor] vs response using the Variable Slope model in Graphpad prism from Graphpad software (San Diego, Calif.).

Results of the EGFR binding affinity are shown in Table 3 below.

Table 1 shows the EGFR Binding Affinity, as determined by the assay described above, for compounds of formula (I), categorised based on the EGFR IC$_{50}$ value of the compound as "*", "" and "*". The category "*" refers to compounds with an EGFR IC$_{50}$ of >80 nM. The category "" refers to compounds with an EGFR IC$_{50}$ of 25 to 80 nM. The category "*" refers to compounds with an EGFR IC$_{50}$ of <25 nM. A cell containing "n.f." indicates that there was no fit for the compound in the assay.

Example 99: TMD8 Growth Assay

Compounds were assayed for effects on the growth of TMD8 human DLBCL cells that are dependent on NFκB signalling. TMD8 cells were grown in suspension in T225 flasks, centrifuged and re-suspended in 2.5% FBS containing media. Cells were then plated at 1.0×10$^4$ cells per well in 96-well plates in varying concentrations of compound and incubated for 72 hours at 37° C. An additional plate of cells to be used as the Day 0 read was seeded without compound addition, Resazurin was added to each well, incubated for 5 h and the fluorescence measured at 590 nm. After 72 h of compound treatment, Resazurin was added to each well of the compound treated plates, incubated for 5 hours and the fluorescence measured at 590 nm. The IC$_{50}$ was then calculated but subtracting the average Day 0 value from each well value from the treated plates, each treatment was then calculated as a percentage of the DMSO control and the percentages plotted against the inhibitor concentration to estimate the IC$_{50}$ from log[Inhibitor] vs response using the Variable Slope model in Graphpad prism from Graphpad software (San Diego, Calif.).

The results of the TMD8 growth assay are shown in Table 3 below.

Table 3 shows the TMD8 anti-proliferative activity, as determined by the assay described above, for compounds of formula (I), categorised based on the TMD8 IC$_{50}$ value of the compound as "x", "xx" and "xxx". The category "x" refers to compounds with a TMD8 IC$_{50}$ of 25 to 300 nM. The category "xx" refers to compounds with a TMD8 IC$_{50}$ of 5 to 25 nM. The category "xxx" refers to compounds with a TMD8 IC$_{50}$ of <5 nM. A "-" indicates that no testing has been carried out.

TABLE 3

| ID. No. | Name | BTK Binding IC50 (nM) | EGFR Binding IC50 (nM) | IC50 TMD8 (nM) |
|---|---|---|---|---|
| 1 | N-[[4-[4-amino-1-[(3R)-1-cyano-3-piperidyl]pyrazolo[3,4-d]pyrimidin-3-yl]phenyl]methyl]-2,5-difluoro-benzamide | ++ | n.f. | x |
| 2 | N-[[4-[4-amino-1-[(3R)-1-prop-2-enoyl-3-piperidyl]pyrazolo[3,4-d]pyrimidin-3-yl]phenyl]methyl]-4-fluoro-2-(trifluoromethyl)benzamide | ++ | * | xx |
| 3 | N-[[4-[4-amino-1-[(3R)-1-prop-2-enoyl-3-piperidyl]pyrazolo[3,4-d]pyrimidin-3-yl]phenyl]methyl]-2,4,5-trifluoro-benzamide | ++ | * | xx |
| 4 | N-[[4-[4-amino-1-[(3R)-1-prop-2-enoyl-3-piperidyl]pyrazolo[3,4-d]pyrimidin-3-yl]phenyl]methyl]-2-fluoro-4-methyl-benzamide | ++ | *** | xx |
| 5 | N-[[4-[4-amino-1-[(3R)-1-prop-2-enoyl-3-piperidyl]pyrazolo[3,4-d]pyrimidin-3-yl]phenyl]methyl]-2-(trifluoromethoxy)benzamide | ++++ | ** | xxx |
| 6 | N-[[4-[4-amino-1-[(3R)-1-prop-2-enoyl-3-piperidyl]pyrazolo[3,4-d]pyrimidin-3-yl]phenyl]methyl]-4-chloro-2-methoxy-benzamide | ++++ | *** | xxx |
| 7 | N-[[4-[4-amino-1-[(3R)-1-prop-2-enoyl-3-piperidyl]pyrazolo[3,4-d]pyrimidin-3-yl]phenyl]methyl]-4-chloro-benzamide | ++ | *** | xx |
| 8 | N-[[4-[4-amino-1-[(3R)-1-prop-2-enoyl-3-pipendyl]pyrazolo[3,4-d]pyrimidin-3-yl]phenyl]methyl]-2-methoxy-5-methyl-benzamide | ++++ | *** | xxx |
| 9 | N-[[4-[4-amino-1-[(3R)-1-prop-2-enoyl-3-pipendyl]pyrazolo[3,4-d]pyrimidin-3-yl]phenyl]methyl]-4-cyano-benzamide | ++ | *** | x |
| 10 | N-[[4-[4-amino-1-[(3R)-1-prop-2-enoyl-3-piperidyl]pyrazolo[3,4-d]pyrimidin-3-yl]phenyl]methyl]-3-(trifluoromethyl)benzamide | +++ | *** | xxx |

TABLE 3-continued

| ID. No. | Name | BTK Binding IC50 (nM) | EGFR Binding IC50 (nM) | IC50 TMD8 (nM) |
|---|---|---|---|---|
| 11 | N-[[4-[4-amino-1-[(3R)-1-prop-2-enoyl-3-piperidyl]pyrazolo[3,4-d]pyrimidin-3-yl]phenyl]methyl]-4-methyl-benzamide | ++ | *** | xx |
| 12 | N-[[4-[4-amino-1-[(3R)-1-prop-2-enoyl-3-piperidyl]pyrazolo[3,4-d]pyrimidin-3-yl]phenyl]methyl]-4-methoxy-benzamide | ++ | *** | xx |
| 13 | N-[[4-[4-amino-1-[(3R)-1-prop-2-enoyl-3-piperidyl]pyrazolo[3,4-d]pyrimidin-3-yl]phenyl]methyl]-3-cyano-benzamide | ++++ | ** | xxx |
| 14 | N-[[4-[4-amino-1-[(3R)-1-prop-2-enoyl-3-piperidyl]-pyrazolo[3,4-d]pyrimidin-3-yl]phenyl]methyl]-3-fluoro-2-methoxy-benzamide | ++++ | *** | xxx |
| 15 | N-[[4-[4-amino-1-[(3R)-1-prop-2-enoyl-3-piperidyl]pyrazolo[3,4-d]pyrimidin-3-yl]phenyl]methyl]-2-methoxy-4-methyl-benzamide | +++ | ** | xxx |
| 16 | N-[[4-[4-amino-1-[(3R)-1-prop-2-enoyl-3-piperidyl]pyrazolo[3,4-d]pyrimidin-3-yl]phenyl]methyl]-3-chloro-2-methoxy-benzamide | +++ | *** | xxx |
| 17 | N-[[4-[4-amino-1-[(3R)-1-cyano-3-piperidyl]pyrazolo[3,4-d]pyrimidin-3-yl]phenyl]methyl]-2-methoxy-benzamide | ++++ | n.d. | xxx |
| 18 | N-[[4-[4-amino-1-[(3R)-1-prop-2-enoyl-3-piperidyl]pyrazolo[3,4-d]pyrimidin-3-yl]phenyl]methyl]-3,5-dimethoxy-benzamide | ++ | * | x |
| 19 | N-[[4-[4-amino-1-[(3R)-1-prop-2-enoyl-3-piperidyl]pyrazolo[3,4-d]pyrimidin-3-yl]phenyl]methyl]-5-fluoro-2-methoxy-benzamide | ++++ | *** | xxx |
| 20 | N-[[4-[4-amino-1-[(3R)-1-prop-2-enoyl-3-piperidyl]pyrazolo[3,4-d]pyrimidin-3-yl]phenyl]methyl]-4-fluoro-2-methoxy-benzamide | +++ | ** | xxx |
| 21 | N-[[4-[4-amino-1-[(3R)-1-prop-2-enoyl-3-piperidyl]pyrazolo[3,4-d]pyrimidin-3-yl]phenyl]methyl]-2,6-difluoro-benzamide | ++++ | *** | xxx |
| 22 | N-[[4-[4-amino-1-[(3R)-1-prop-2-enoyl-3-piperidyl]pyrazolo[3,4-d]pyrimidin-3-yl]phenyl]methyl]-4-tert-butyl-benzamide | +++ | *** | xx |
| 23 | N-[[4-[4-amino-1-[(3R)-1-prop-2-enoyl-3-piperidyl]pyrazolo[3,4-d]pyrimidin-3-yl]phenyl]methyl]-2,5-difluoro-benzamide | ++++ | *** | xxx |
| 24 | N-[[4-[4-amino-1-[(3R)-1-prop-2-enoyl-3-piperidyl]pyrazolo[3,4-d]pyrimidin-3-yl]phenyl]methyl]-4-fluoro-benzamide | ++ | *** | xx |
| 25 | N-[[4-[4-amino-1-[(3R)-1-prop-2-enoyl-3-piperidyl]pyrazolo[3,4-d]pyrimidin-3-yl]phenyl]methyl]-2-fluoro-5-(trifluoromethyl)benzamide | +++ | ** | xxx |
| 26 | N-[[4-[4-amino-1-[(3R)-1-prop-2-enoyl-3-piperidyl]pyrazolo[3,4-d]pyrimidin-3-yl]phenyl]methyl]-2-methoxy-benzamide | ++++ | *** | xxx |
| 27 | N-[[4-[4-amino-1-[(3R)-1-prop-2-enoyl-3-piperidyl]pyrazolo[3,4-d]pyrimidin-3-yl]phenyl]methyl]-2,4-difluoro-benzamide | ++ | ** | x |
| 28 | N-[[4-[4-amino-1-[(3R)-1-prop-2-enoyl-3-piperidyl]pyrazolo[3,4-d]pyrimidin-3-yl]phenyl]methyl]benzamide | ++ | *** | xxx |
| 29 | N-[[4-[4-amino-1-[(3R)-1-prop-2-enoyl-3-piperidyl]pyrazolo[3,4-d]pyrimidin-3-yl]phenyl]methyl]-2-fluoro-benzamide | ++++ | *** | xxx |
| 30 | N-[[4-[4-Amino-1-[(3R)-1-prop-2-enoyl-3-piperidyl]pyrazolo[3,4-d]pyrimidin-3-yl]phenyl]methyl]-4-(trifluoromethoxy)benzamide | +++ | *** | x |
| 31 | N-[[4-[4-Amino-1-[(3R)-1-prop-2-enoyl-3-piperidyl]pyrazolo[3,4-d]pyrimidin-3-yl]phenyl]methyl]-3-methyl-benzamide | +++ | *** | xxx |
| 32 | N-[[4-[4-Amino-1-[(3R)-1-prop-2-enoyl-3-piperidyl]pyrazolo-[3,4-d]pyrimidin-3-yl]phenyl]methyl]-2-chloro-benzamide | +++ | *** | xxx |
| 33 | N-[[4-[4-amino-1-[(3R)-1-prop-2-enoyl-3-piperidyl]pyrazolo[3,4-d]pyrimidin-3-yl]phenyl]methyl]-2-fluoro-3-methoxy-benzamide | ++++ | ** | xxx |
| 34 | N-[[4-[4-amino-1-[(3R)-1-prop-2-enoyl-3-piperidyl]pyrazolo[3,4-d]pyrimidin-3-yl]phenyl]methyl]-3-fluoro-pyridine-2-carboxamide | +++ | *** | xx |
| 35 | N-[[4-[4-amino-1-[(3R)-1-prop-2-enoyl-3-piperidyl]pyrazolo[3,4-d]pyrimidin-3-yl]phenyl]methyl]-3-fluoro-pyridine-4-carboxamide | + | * | x |

TABLE 3-continued

| ID. No. | Name | BTK Binding IC50 (nM) | EGFR Binding IC50 (nM) | IC50 TMD8 (nM) |
|---|---|---|---|---|
| 36 | N-[[4-[4-amino-1-[(3R)-1-prop-2-enoyl-3-piperidyl]pyrazolo[3,4-d]pyrimidin-3-yl]phenyl]methyl]-2-fluoro-4-(trifluoromethyl)benzamide | ++ | *** | x |
| 37 | N-[[4-[4-amino-1-[(3R)-1-prop-2-enoyl-3-piperidyl]pyrazolo[3,4-d]pyrimidin-3-yl]phenyl]methyl]-3-chloro-benzamide | +++ | *** | xxx |
| 38 | N-[[4-[4-amino-1-[(3R)-1-prop-2-enoyl-3-piperidyl]pyrazolo[3,4-d]pyrimidin-3-yl]phenyl]methyl]-2-chloro-5-(trifluoromethyl)benzamide | ++ | ** | xxx |
| 39 | N-[[4-[4-amino-1-[(3R)-1-prop-2-enoyl-3-piperidyl]pyrazolo[3,4-d]pyrimidin-3-yl]phenyl]methyl]-2-methoxy-4-(trifluoromethyl)benzamide | ++ | *** | x |
| 40 | N-[[4-[4-amino-1-[(3R)-1-prop-2-enoyl-3-piperidyl]pyrazolo[3,4-d]pyrimidin-3-yl]phenyl]methyl]-3-fluoro-benzamide | +++ | *** | xxx |
| 41 | N-[[4-[4-amino-1-[(3R)-1-prop-2-enoyl-3-piperidyl]pyrazolo[3,4-d]pyrimidin-3-yl]phenyl]methyl]-2-fluoro-6-methoxybenzamide | ++ | * | xx |
| 42 | N-[[4-[4-amino-1-[(3R)-1-prop-2-enoyl-3-piperidyl]pyrazolo[3,4-d]pyrimidin-3-yl]phenyl]methyl]-2-methoxy-3-(trifluoromethyl)benzamide | ++ | * | x |
| 43 | N-[[4-[4-amino-1-[(3R)-1-prop-2-enoyl-3-piperidyl]pyrazolo[3,4-d]pyrimidin-3-yl]phenyl]methyl]-4-(trifluoromethyl)benzamide | ++ | *** | xx |
| 44 | N-[[4-[4-amino-1-[(3R)-1-cyano-3-piperidyl]pyrazolo[3,4-d]pyrimidin-3-yl]phenyl]methyl]-5-fluoro-2-methoxybenzamide | ++++ | * | xxx |
| 45 | N-[[4-[4-amino-1-[(3R)-1-prop-2-enoyl-3-piperidyl]pyrazolo[3,4-d]pyrimidin-3-yl]phenyl]methyl]-2-methoxy-6-methylbenzamide | ++ | * | xx |
| 46 | N-[[4-[4-amino-1-[(3R)-1-prop-2-enoyl-3-piperidyl]pyrazolo[3,4-d]pyrimidin-3-yl]phenyl]methyl]-3,5-bis(trifluoromethyl)benzamide | ++ | *** | xx |
| 47 | N-[[3-[4-amino-1-[(3R)-1-prop-2-enoyl-3-piperidyl]pyrazolo[3,4-d]pyrimidin-3-yl]phenyl]methyl]-4-fluoro-2-methoxy-benzamide | +++ | ** | xxx |
| 48 | N-[[3-[4-Amino-1-[(3R)-1-prop-2-enoyl-3-piperidyl]pyrazolo[3,4-d]pyrimidin-3-yl]phenyl]methyl]-5-fluoro-2-methoxy-benzamide | +++ | ** | xxx |
| 49 | N-[[4-[4-amino-1-[(3R)-1-prop-2-enoyl-3-piperidyl]pyrazolo-[3,4-d]pyrimidin-3-yl]phenyl]methyl]-3-(trifluoromethoxy)benzamide | +++ | *** | xxx |
| 50 | N-[[4-[4-Amino-1-[(3R)-1-prop-2-enoyl-3-piperidyl]pyrazolo-[3,4-d]pyrimidin-3-yl]phenyl]methyl]-5-chloro-2-methoxy-benzamide | ++++ | *** | xxx |
| 51 | N-[[4-[4-amino-1-[(3R)-1-prop-2-enoyl-3-piperidyl]pyrazolo-[3,4-d]pyrimidin-3-yl]phenyl]methyl]-2-fluoro-3-(trifluoromethyl)benzamide | ++ | *** | xxx |
| 52 | N-[[4-[4-amino-1-[(3R)-1-prop-2-enoyl-3-piperidyl]pyrazolo[3,4-d]pyrimidin-3-yl]phenyl]methyl]-2-methoxy-5-(trifluoromethyl)benzamide | ++++ | ** | xxx |
| 53 | N-[[4-[4-Amino-1-[(3R)-1-prop-2-enoyl-3-piperidyl]pyrazolo[3,4-d]pyrimidin-3-yl]phenyl]methyl]-3,5-difluoro-benzamide | +++ | ** | xxx |
| 54 | N-[[4-[4-Amino-1-[(3R)-1-prop-2-enoyl-3-piperidyl]pyrazolo[3,4-d]pyrimidin-3-yl]phenyl]methyl]-2,3-difluoro-benzamide | +++ | *** | xxx |
| 55 | N-[[4-[4-Amino-1-(4-piperidyl)pyrazolo[3,4-d]pyrimidin-3-yl]phenyl]methyl]-2-methoxy-benzamide | + | * | – |
| 56 | N-[[4-[4-Amino-1-(1-prop-2-enoyl-4-piperidyl)pyrazolo[3,4-d]pyrimidin-3-yl]phenyl]methyl]-2-methoxy-benzamide | ++ | * | – |
| 57 | N-[[4-[4-Amino-1-[(3R)-1-methyl-3-piperidyl]pyrazolo[3,4-d]pyrimidin-3-yl]phenyl]methyl]-2-methoxy-benzamide | ++ | * | – |
| 58 | N-[[4-[4-Amino-1-[(3R)-1-(oxetan-3-yl)-3-piperidyl]pyrazolo[3,4-d]pyrimidin-3-yl]phenyl]methyl]-2-methoxy-benzamide | + | * | – |
| 59 | N-[[4-[4-Amino-1-[(3R)-1-but-2-ynoyl-3-piperidyl]pyrazolo[3,4-d]pyrimidin-3-yl]phenyl]methyl]-2-methoxy-benzamide | +++ | * | – |
| 60 | N-[[4-[4-Amino-1-[(3R)-1-(2,3-dihydroxypropanoyl)-3-piperidyl]pyrazolo[3,4-d]pyrimidin-3-yl]phenyl]methyl]-2-methoxy-benzamide | ++ | * | – |
| 61 | N-[[4-[4-Amino-1-(1-prop-2-enoyl-3-piperidyl)pyrazolo[3,4-d]pyrimidin-3-yl]phenyl]methyl]-2,5-difluoro-benzamide | ++++ | ** | – |

TABLE 3-continued

| ID. No. | Name | BTK Binding IC50 (nM) | EGFR Binding IC50 (nM) | IC50 TMD8 (nM) |
|---|---|---|---|---|
| 62 | N-[[4-[4-Amino-1-[(3R)-1-prop-2-enoyl-3-piperidyl]pyrazolo[3,4-d]pyrimidin-3-yl]phenyl]methyl]-3,5-dimethyl-benzamide | ++ | *** | – |
| 63 | N-[[4-[4-Amino-1-[(3R)-1-prop-2-enoyl-3-piperidyl]pyrazolo[3,4-d]pyrimidin-3-yl]phenyl]methyl]-5-fluoro-pyridine-2-carboxamide | ++ | ** | – |
| 64 | N-[[4-[4-Amino-1-[(3R)-1-[(E)-but-2-enoyl]-3-piperidyl]pyrazolo[3,4-d]pyrimidin-3-yl]phenyl]methyl]-2-methoxy-benzamide | +++ | * | – |
| 65 | N-[[4-[4-Amino-1-[(3R)-1-[(E)-4-(dimethylamino)but-2-enoyl]-3-piperidyl]pyrazolo[3,4-d]pyrimidin-3-yl]phenyl]methyl]-2-methoxy-benzamide | ++++ | * | – |
| 66 | N-[[4-[4-Amino-1-[(3R)-1-prop-2-enoyl-3-piperidyl]pyrazolo[3,4-d]pyrimidin-3-yl]phenyl]methyl]-4-fluoro-2-(trifluoromethoxy)benzamide | ++ | * | – |
| 67 | N-[[4-[4-Amino-1-[(3R)-1-prop-2-enoyl-3-piperidyl]pyrazolo[3,4-d]pyrimidin-3-yl]phenyl]methyl]-2-fluoro-5-methyl-benzamide | +++ | ** | – |
| 68 | N-[[4-[4-Amino-1-[(3R)-1-(2-cyanoethyl)-3-piperidyl]pyrazolo[3,4-d]pyrimidin-3-yl]phenyl]methyl]-2-methoxy-benzamide | ++ | * | – |
| 69 | N-[[4-[4-Amino-1-[(3R)-1-(cyanomethyl)-3-piperidyl]pyrazolo[3,4-d]pyrimidin-3-yl]phenyl]methyl]-2-methoxy-benzamide | + | * | – |
| 70 | N-[[4-[4-Amino-1-[(3R)-1-prop-2-enoyl-3-piperidyl]pyrazolo[3,4-d]pyrimidin-3-yl]phenyl]methyl]-2,5-difluoro-N-methyl-benzamide | ++ | * | – |
| 71 | N-[[4-[4-Amino-1-[(3R)-1-(2-cyanoacetyl)-3-piperidyl]pyrazolo[3,4-d]pyrimidin-3-yl]phenyl]methyl]-2-methoxy-benzamide | ++ | * | – |
| 72 | N-[[4-[4-Amino-1-[(3R)-1-propanoyl-3-piperidyl]pyrazolo[3,4-d]pyrimidin-3-yl]phenyl]methyl]-2-methoxy-benzamide | ++ | * | – |
| 73 | N-[[4-[4-Amino-1-[(3R)-1-prop-2-enoyl-3-piperidyl]pyrazolo[3,4-d]pyrimidin-3-yl]phenyl]methyl]-2-fluoro-3-methyl-benzamide | ++ | ** | – |
| 74 | N-[[5-[4-Amino-1-[(3R)-1-prop-2-enoyl-3-piperidyl]pyrazolo[3,4-d]pyrimidin-3-yl]-2-fluoro-phenyl]methyl]-2-methoxy-benzamide | +++ | ** | – |
| 75 | N-[[5-[4-Amino-1-[(3R)-1-prop-2-enoyl-3-piperidyl]pyrazolo[3,4-d]pyrimidin-3-yl]-2-fluoro-phenyl]methyl]-2,5-difluoro-benzamide | ++ | *** | – |
| 76 | N-[[3-[4-Amino-1-[(3R)-1-prop-2-enoyl-3-piperidyl]pyrazolo[3,4-d]pyrimidin-3-yl]phenyl]methyl]-3-(trifluoromethyl)benzamide | ++++ | *** | – |
| 77 | N-[[4-[4-Amino-1-[(3R)-1-[[(2R)-oxiran-2-yl]methyl]-3-piperidyl]pyrazolo[3,4-d]pyrimidin-3-yl]phenyl]methyl]-2-methoxy-benzamide | ++ | ** | – |
| 78 | N-[[3-[4-Amino-1-[(3R)-1-prop-2-enoyl-3-piperidyl]pyrazolo[3,4-d]pyrimidin-3-yl]phenyl]methyl]-2,5-difluoro-benzamide | +++ | ** | – |
| 79 | N-[[3-[4-Amino-1-[(3R)-1-prop-2-enoyl-3-piperidyl]pyrazolo[3,4-d]pyrimidin-3-yl]phenyl]methyl]-3-cyano-benzamide | +++ | *** | – |
| 80 | N-[[3-[4-Amino-1-[(3R)-1-prop-2-enoyl-3-piperidyl]pyrazolo[3,4-d]pyrimidin-3-yl]phenyl]methyl]-2-methoxy-benzamide | ++++ | * | – |
| 81 | N-[[4-[4-Amino-1-[(3R)-1-prop-2-enoyl-3-piperidyl]pyrazolo[3,4-d]pyrimidin-3-yl]phenyl]methyl]-2-methoxy-N-methyl-benzamide | ++ | * | – |
| 82 | N-[[4-[4-Amino-1-[(3R)-1-prop-2-enoyl-3-piperidyl]pyrazolo[3,4-d]pyrimidin-3-yl]phenyl]methyl]-2-(trifluoromethyl)benzamide | ++ | * | – |
| 83 | N-[[3-[4-Amino-1-[(3R)-1-prop-2-enoyl-3-piperidyl]pyrazolo[3,4-d]pyrimidin-3-yl]phenyl]methyl]-2,6-difluoro-benzamide | ++ | *** | – |
| 84 | N-[[4-[4-Amino-1-[(3R)-1-prop-2-enoyl-3-piperidyl]pyrazolo[3,4-d]pyrimidin-3-yl]phenyl]methyl]-3-methoxy-benzamide | ++ | ** | – |
| 85 | N-[[4-[4-Amino-1-[(3R)-1-prop-2-enoyl-3-piperidyl]-pyrazolo[3,4-d]pyrimidin-3-yl]phenyl]methyl]-2-fluoro-N-methyl-benzamide | +++ | * | – |
| 86 | N-[[4-[4-Amino-1-(1-prop-2-enoyl-3-piperidyl)pyrazolo[3,4-d]pyrimidin-3-yl]-2-fluoro-phenyl]methyl]-2-methoxy-benzamide | +++ | *** | xxx |

TABLE 3-continued

| ID. No. | Name | BTK Binding IC50 (nM) | EGFR Binding IC50 (nM) | IC50 TMD8 (nM) |
|---|---|---|---|---|
| 87 | N-[[4-[4-Amino-1-[(3R)-1-prop-2-enoyl-3-piperidyl]pyrazolo[3,4-d]pyrimidin-3-yl]-2-fluoro-phenyl]methyl]-3-cyano-benzamide | ++ | *** | xx |
| 88 | N-[[4-[4-Amino-1-[(3R)-1-prop-2-enoyl-3-piperidyl]pyrazolo[3,4-d]pyrimidin-3-yl]-2-fluoro-phenyl]methyl]-4-fluoro-2-methoxy-benzamide | +++ | ** | xx |
| 89 | N-[[4-[4-Amino-1-[(3R)-1-prop-2-enoyl-3-piperidyl]pyrazolo[3,4-d]pyrimidin-3-yl]-2-fluoro-phenyl]methyl]-2,6-difluoro-benzamide | ++ | *** | xx |
| 90 | N-[[4-[4-Amino-1-[(3R)-1-prop-2-enoyl-3-piperidyl]pyrazolo[3,4-d]pyrimidin-3-yl]phenyl]methyl]-4-ethoxy-3-(trifluoromethyl)benzamide | ++ | *** | x |
| 91 | N-[[3-[4-Amino-1-[(3R)-1-prop-2-enoyl-3-piperidyl]pyrazolo[3,4-d]pyrimidin-3-yl]phenyl]methyl]-2-methoxy-5-methyl-benzamide | ++++ | ** | xxx |
| 92 | N-[[4-[4-Amino-1-[(3R)-1-prop-2-enoyl-3-piperidyl]pyrazolo[3,4-d]pyrimidin-3-yl]phenyl]methyl]-2-methyl-benzamide | +++ | *** | xxx |
| 93 | N-[[4-[4-Amino-1-[(3R)-1-prop-2-enoyl-3-piperidyl]pyrazolo[3,4-d]pyrimidin-3-yl]phenyl]methyl]-2-fluoro-4-methoxy-benzamide | ++ | *** | x |
| 94 | N-[[4-[4-Amino-1-[(3R)-1-prop-2-enoyl-3-piperidyl]pyrazolo[3,4-d]pyrimidin-3-yl]phenyl]methyl]-4-fluoro-3-(trifluoromethyl)benzamide | ++ | *** | x |
| 95 | N-[[4-[4-Amino-1-[(3R)-1-prop-2-enoyl-3-piperidyl]pyrazolo[3,4-d]pyrimidin-3-yl]phenyl]methyl]-2-fluoro-6-(trifluoromethyl)benzamide | +++ | ** | xxx |
| 96 | N-[[4-[4-Amino-1-[(3R)-1-prop-2-enoyl-3-piperidyl]pyrazolo[3,4-d]pyrimidin-3-yl]phenyl]methyl]-2-fluoro-5-methoxy-benzamide | +++ | * | xxx |

The following table, Table 4, provides values of the BTK binding efficacy of a selection of compounds of the invention.

TABLE 2

| ID. No. | Name | BTK Binding IC50 (nM) |
|---|---|---|
| 5 | N-[[4-[4-amino-1-[(3R)-1-prop-2-enoyl-3-piperidyl]pyrazolo[3,4-d]pyrimidin-3-yl]phenyl]methyl]-2-(trifluoromethoxy)benzamide | 0.4 |
| 6 | N-[[4-[4-amino-1-[(3R)-1-prop-2-enoyl-3-piperidyl]pyrazolo[3,4-d]pyrimidin-3-yl]phenyl]methyl]-4-chloro-2-methoxy-benzamide | 0.4 |
| 8 | N-[[4-[4-amino-1-[(3R)-1-prop-2-enoyl-3-piperidyl]pyrazolo[3,4-d]pyrimidin-3-yl]phenyl]methyl]-2-methoxy-5-methyl-benzamide | 0.2 |
| 13 | N-[[4-[4-amino-1-[(3R)-1-prop-2-enoyl-3-piperidyl]pyrazolo[3,4-d]pyrimidin-3-yl]phenyl]methyl]-3-cyano-benzamide | 0.4 |
| 15 | N-[[4-[4-amino-1-[(3R)-1-prop-2-enoyl-3-piperidyl]pyrazolo[3,4-d]pyrimidin-3-yl]phenyl]methyl]-2-methoxy-4-methyl-benzamide | 0.7 |
| 23 | N-[[4-[4-amino-1-[(3R)-1-prop-2-enoyl-3-piperidyl]pyrazolo[3,4-d]pyrimidin-3-yl]phenyl]methyl]-2,5-difluoro-benzamide | 0.4 |
| 26 | N-[[4-[4-amino-1-[(3R)-1-prop-2-enoyl-3-piperidyl]pyrazolo[3,4-d]pyrimidin-3-yl]phenyl]methyl]-2-methoxy-benzamide | 0.3 |
| 29 | N-[[4-[4-amino-1-[(3R)-1-prop-2-enoyl-3-piperidyl]pyrazolo[3,4-d]pyrimidin-3-yl]phenyl]methyl]-2-fluoro-benzamide | 0.4 |
| 48 | N-[[3-[4-Amino-1-[(3R)-1-prop-2-enoyl-3-piperidyl]pyrazolo[3,4-d]pyrimidin-3-yl]phenyl]methyl]-5-fluoro-2-methoxy-benzamide | 0.5 |
| 59 | N-[[4-[4-Amino-1-[(3R)-1-but-2-ynoyl-3-piperidyl]pyrazolo[3,4-d]pyrimidin-3-yl]phenyl]methyl]-2-methoxy-benzamide | 0.8 |

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A compound selected from the group consisting of:
   N-[[4-[4-amino-1-[(3R)-1-prop-2-enoyl-3-piperidyl]pyrazolo[3,4-d]pyrimidin-3-yl]phenyl]methyl]-2-fluoro-5-(trifluoromethyl)benzamide;
   N-[[4-[4-amino-1-[(3R)-1-prop-2-enoyl-3-piperidyl]pyrazolo[3,4-d]pyrimidin-3-yl]phenyl]methyl]-2-methoxy-4-methyl-benzamide;
   N-[[4-[4-amino-1-[(3R)-1-prop-2-enoyl-3-piperidyl]pyrazolo[3,4-d]pyrimidin-3-yl]phenyl]methyl]-2-methoxy-4-(trifluoromethyl)benzamide;
   N-[[4-[4-amino-1-[(3R)-1-prop-2-enoyl-3-piperidyl]pyrazolo-[3,4-d]pyrimidin-3-yl]phenyl]methyl]-2-fluoro-3-(trifluoromethyl)benzamide;
   N-[[3-[4-amino-1-[(3R)-1-prop-2-enoyl-3-piperidyl]pyrazolo[3,4-d]pyrimidin-3-yl]phenyl]methyl]-4-fluoro-2-methoxy-benzamide; and
   N-[[4-[4-amino-1-[(3R)-1-prop-2-enoyl-3-piperidyl]pyrazolo[3,4-d]pyrimidin-3-yl]phenyl]methyl]-4-(trifluoromethyl)benzamide;
   or a pharmaceutically acceptable salt thereof.

2. The compound of claim 1, wherein the compound is N-[[4-[4-amino-1-[(3R)-1-prop-2-enoyl-3-piperidyl]pyrazolo[3,4-d]pyrimidin-3-yl]phenyl]methyl]-2-fluoro-5-(trifluoromethyl)benzamide, or a pharmaceutically acceptable salt thereof.

3. The compound of claim 1, wherein the compound is N-[[4-[4-amino-1-[(3R)-1-prop-2-enoyl-3-piperidyl]pyrazolo[3,4-d]pyrimidin-3-yl]phenyl]methyl]-2-methoxy-4-methyl-benzamide, or a pharmaceutically acceptable salt thereof.

4. The compound of claim 1, wherein the compound is N-[[4-[4-amino-1-[(3R)-1-prop-2-enoyl-3-piperidyl]pyrazolo[3,4-d]pyrimidin-3-yl]phenyl]methyl]-2-methoxy-4-(trifluoromethyl)benzamide, or a pharmaceutically acceptable salt thereof.

5. The compound of claim 1, wherein the compound is N-[[4-[4-amino-1-[(3R)-1-prop-2-enoyl-3-piperidyl]pyrazolo-[3,4-d]pyrimidin-3-yl]phenyl]methyl]-2-fluoro-3-(trifluoromethyl)benzamide, or a pharmaceutically acceptable salt thereof.

6. The compound of claim 1, wherein the compound is N-[[3-[4-amino-1-[(3R)-1-prop-2-enoyl-3-piperidyl]pyrazolo[3,4-d]pyrimidin-3-yl]phenyl]methyl]-4-fluoro-2-methoxy-benzamide, or a pharmaceutically acceptable salt thereof.

7. The compound of claim 1, wherein the compound is N-[[4-[4-amino-1-[(3R)-1-prop-2-enoyl-3-piperidyl]pyrazolo[3,4-d]pyrimidin-3-yl]phenyl]methyl]-4-(trifluoromethyl)benzamide, or a pharmaceutically acceptable salt thereof.

8. The compound of claim 1, wherein the compound is selected from the group consisting of:
   N-[[4-[4-amino-1-[(3R)-1-prop-2-enoyl-3-piperidyl]pyrazolo[3,4-d]pyrimidin-3-yl]phenyl]methyl]-2-fluoro-5-(trifluoromethyl)benzamide;
   N-[[4-[4-amino-1-[(3R)-1-prop-2-enoyl-3-piperidyl]pyrazolo[3,4-d]pyrimidin-3-yl]phenyl]methyl]-2-methoxy-4-methyl-benzamide;
   N-[[4-[4-amino-1-[(3R)-1-prop-2-enoyl-3-piperidyl]pyrazolo[3,4-d]pyrimidin-3-yl]phenyl]methyl]-2-methoxy-4-(trifluoromethyl)benzamide;
   N-[[4-[4-amino-1-[(3R)-1-prop-2-enoyl-3-piperidyl]pyrazolo-[3,4-d]pyrimidin-3-yl]phenyl]methyl]-2-fluoro-3-(trifluoromethyl)benzamide;
   N-[[3-[4-amino-1-[(3R)-1-prop-2-enoyl-3-piperidyl]pyrazolo[3,4-d]pyrimidin-3-yl]phenyl]methyl]-4-fluoro-2-methoxy-benzamide; and
   N-[[4-[4-amino-1-[(3R)-1-prop-2-enoyl-3-piperidyl]pyrazolo[3,4-d]pyrimidin-3-yl]phenyl]methyl]-4-(trifluoromethyl)benzamide.

9. The compound of claim 1, wherein the compound is in the form of a pharmaceutically acceptable salt.

10. A pharmaceutical composition comprising a compound selected from the group consisting of:
    N-[[4-[4-amino-1-[(3R)-1-prop-2-enoyl-3-piperidyl]pyrazolo[3,4-d]pyrimidin-3-yl]phenyl]methyl]-2-fluoro-5-(trifluoromethyl)benzamide;
    N-[[4-[4-amino-1-[(3R)-1-prop-2-enoyl-3-piperidyl]pyrazolo[3,4-d]pyrimidin-3-yl]phenyl]methyl]-2-methoxy-4-methyl-benzamide;
    N-[[4-[4-amino-1-[(3R)-1-prop-2-enoyl-3-piperidyl]pyrazolo[3,4-d]pyrimidin-3-yl]phenyl]methyl]-2-methoxy-4-(trifluoromethyl)benzamide;
    N-[[4-[4-amino-1-[(3R)-1-prop-2-enoyl-3-piperidyl]pyrazolo-[3,4-d]pyrimidin-3-yl]phenyl]methyl]-2-fluoro-3-(trifluoromethyl)benzamide;
    N-[[3-[4-amino-1-[(3R)-1-prop-2-enoyl-3-piperidyl]pyrazolo[3,4-d]pyrimidin-3-yl]phenyl]methyl]-4-fluoro-2-methoxy-benzamide; and
    N-[[4-[4-amino-1-[(3R)-1-prop-2-enoyl-3-piperidyl]pyrazolo[3,4-d]pyrimidin-3-yl]phenyl]methyl]-4-(trifluoromethyl)benzamide;
    or a pharmaceutically acceptable salt thereof; and a pharmaceutically acceptable diluent or carrier.

11. The pharmaceutical composition of claim 10, wherein the compound is
    N-[[4-[4-amino-1-[(3R)-1-prop-2-enoyl-3-piperidyl]pyrazolo[3,4-d]pyrimidin-3-yl]phenyl]methyl]-2-fluoro-5-(trifluoromethyl)benzamide, or a pharmaceutically acceptable salt thereof.

12. The pharmaceutical composition of claim 10, wherein the compound is
    N-[[4-[4-amino-1-[(3R)-1-prop-2-enoyl-3-piperidyl]pyrazolo[3,4-d]pyrimidin-3-yl]phenyl]methyl]-2-methoxy-4-methyl-benzamide, or a pharmaceutically acceptable salt thereof.

13. The pharmaceutical composition of claim 10, wherein the compound is
    N-[[4-[4-amino-1-[(3R)-1-prop-2-enoyl-3-piperidyl]pyrazolo[3,4-d]pyrimidin-3-yl]phenyl]methyl]-2-methoxy-4-(trifluoromethyl)benzamide, or a pharmaceutically acceptable salt thereof.

14. The pharmaceutical composition of claim 10, wherein the compound is
    N-[[4-[4-amino-1-[(3R)-1-prop-2-enoyl-3-piperidyl]pyrazolo-[3,4-d]pyrimidin-3-yl]phenyl]methyl]-2-fluoro-3-(trifluoromethyl)benzamide, or a pharmaceutically acceptable salt thereof.

15. The pharmaceutical composition of claim 10, wherein the compound is

N-[[3-[4-amino-1-[(3R)-1-prop-2-enoyl-3-piperidyl] pyrazolo[3,4-d]pyrimidin-3-yl]phenyl]methyl]-4-fluoro-2-methoxy-benzamide, or a pharmaceutically acceptable salt thereof.

16. The pharmaceutical composition of claim 10, wherein the compound is

N-[[4-[4-amino-1-[(3R)-1-prop-2-enoyl-3-piperidyl] pyrazolo[3,4-d]pyrimidin-3-yl]phenyl]methyl]-4-(trifluoromethyl)benzamide, or a pharmaceutically acceptable salt thereof.

17. The pharmaceutical composition of claim 10, wherein the compound is selected from the group consisting of:

N-[[4-[4-amino-1-[(3R)-1-prop-2-enoyl-3-piperidyl] pyrazolo[3,4-d]pyrimidin-3-yl]phenyl]methyl]-2-fluoro-5-(trifluoromethyl)benzamide;

N-[[4-[4-amino-1-[(3R)-1-prop-2-enoyl-3-piperidyl] pyrazolo[3,4-d]pyrimidin-3-yl]phenyl]methyl]-2-methoxy-4-methyl-benzamide;

N-[[4-[4-amino-1-[(3R)-1-prop-2-enoyl-3-piperidyl] pyrazolo[3,4-d]pyrimidin-3-yl]phenyl]methyl]-2-methoxy-4-(trifluoromethyl)benzamide;

N-[[4-[4-amino-1-[(3R)-1-prop-2-enoyl-3-piperidyl] pyrazolo-[3,4-d]pyrimidin-3-yl]phenyl]methyl]-2-fluoro-3-(trifluoromethyl)benzamide;

N-[[3-[4-amino-1-[(3R)-1-prop-2-enoyl-3-piperidyl] pyrazolo[3,4-d]pyrimidin-3-yl]phenyl]methyl]-4-fluoro-2-methoxy-benzamide; and N-[[4-[4-amino-1-[(3R)-1-prop-2-enoyl-3-piperidyl] pyrazolo[3,4-d]pyrimidin-3-yl]phenyl]methyl]-4-(trifluoromethyl)benzamide.

18. The composition of claim 10, wherein the compound is in the form of a pharmaceutically acceptable salt.

* * * * *